(12) United States Patent
Seifert et al.

(10) Patent No.: US 11,780,926 B2
(45) Date of Patent: Oct. 10, 2023

(54) MULTIVALENT BINDING MOLECULES

(71) Applicant: UNIVERSITÄT STUTTGART, Stuttgart (DE)

(72) Inventors: Oliver Seifert, Stuttgart (DE); Roland Kontermann, Nürtingen (DE); Fabian Richter, Kirchheim unter Teck (DE)

(73) Assignee: UNIVERSITÄT STUTTGART, Stuttgart (DE)

(*) Notice: Subject to any disclaimer, the term of this patent is extended or adjusted under 35 U.S.C. 154(b) by 126 days.

(21) Appl. No.: 16/982,714

(22) PCT Filed: Mar. 22, 2018

(86) PCT No.: PCT/EP2018/057331
§ 371 (c)(1),
(2) Date: Sep. 21, 2020

(87) PCT Pub. No.: WO2019/179627
PCT Pub. Date: Sep. 26, 2019

(65) Prior Publication Data
US 2021/0002376 A1    Jan. 7, 2021

(51) Int. Cl.
*C07K 16/28* (2006.01)
*A61P 35/00* (2006.01)
*C07K 16/32* (2006.01)
*A61K 39/395* (2006.01)
*A61K 38/00* (2006.01)
*G01N 33/50* (2006.01)

(52) U.S. Cl.
CPC .... *C07K 16/2863* (2013.01); *A61K 39/39533* (2013.01); *A61P 35/00* (2018.01); *C07K 16/2878* (2013.01); *C07K 16/32* (2013.01); *A61K 38/00* (2013.01); *C07K 2317/30* (2013.01); *C07K 2317/526* (2013.01); *C07K 2317/60* (2013.01); *C07K 2317/62* (2013.01); *C07K 2317/64* (2013.01); *C07K 2317/66* (2013.01); *C07K 2317/73* (2013.01); *C07K 2317/75* (2013.01); *C07K 2317/92* (2013.01); *C07K 2317/94* (2013.01); *G01N 33/5091* (2013.01)

(58) Field of Classification Search
None
See application file for complete search history.

(56) References Cited

U.S. PATENT DOCUMENTS

2014/0213772 A1   7/2014  Ghayur et al.
2016/0289343 A1*  10/2016 Wu .......................... A61P 33/00
2017/0233472 A1*  8/2017  Barat ................. C07K 16/2803
                                                       424/136.1

FOREIGN PATENT DOCUMENTS

WO    2002/002781    1/2002
WO    2007/024715    3/2007
WO    2013/156148    10/2013

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Yu et al., Investigative Ophthalmology & Visual Science 49(2): 522-527 (Year: 2008).*
Piche-Nicholas et al., MABS 10(1): 81-94 (Year: 2018).*
Seifert et al., Molecular Cancer Ther 13(1): 101-111 (Year: 2013).*
Seifert et al., Protein Engineering, Design & Selection 25(10): 603-612, 2012 (Year: 2012).*
Alt et al., FEBS Letters 454: 90-94 (Year: 1999).*
The International Search Report (ISR) with Written Opinion for PCT/EP2018/057331 dated Sep. 28, 2018, pp. 1-26.
Spiess, Christoph et al. "Alternative molecular formats and therapeutic applications for bispecific antibodies" Molecular Immunology (2015) vol. 67(2) pp. 95-106.
Steinmetz, Anke et al. "CODV-Ig, a universal bispecific tetravalent and multifunctional immunoglobulin format for medical applications" MABS (2016) vol. 8(5), pp. 867-878.

* cited by examiner

*Primary Examiner* — Phuong Huynh
(74) *Attorney, Agent, or Firm* — McDonnell Boehnen Hulbert & Berghoff LLP

(57) ABSTRACT

The present invention relates to a modular multivalent antigen-binding protein complex, use of the antigen-binding protein complex in medicine and use of the antigen-binding protein complex in the prophylaxis, treatment or diagnosis of a disorder or disease.

Figure 1:
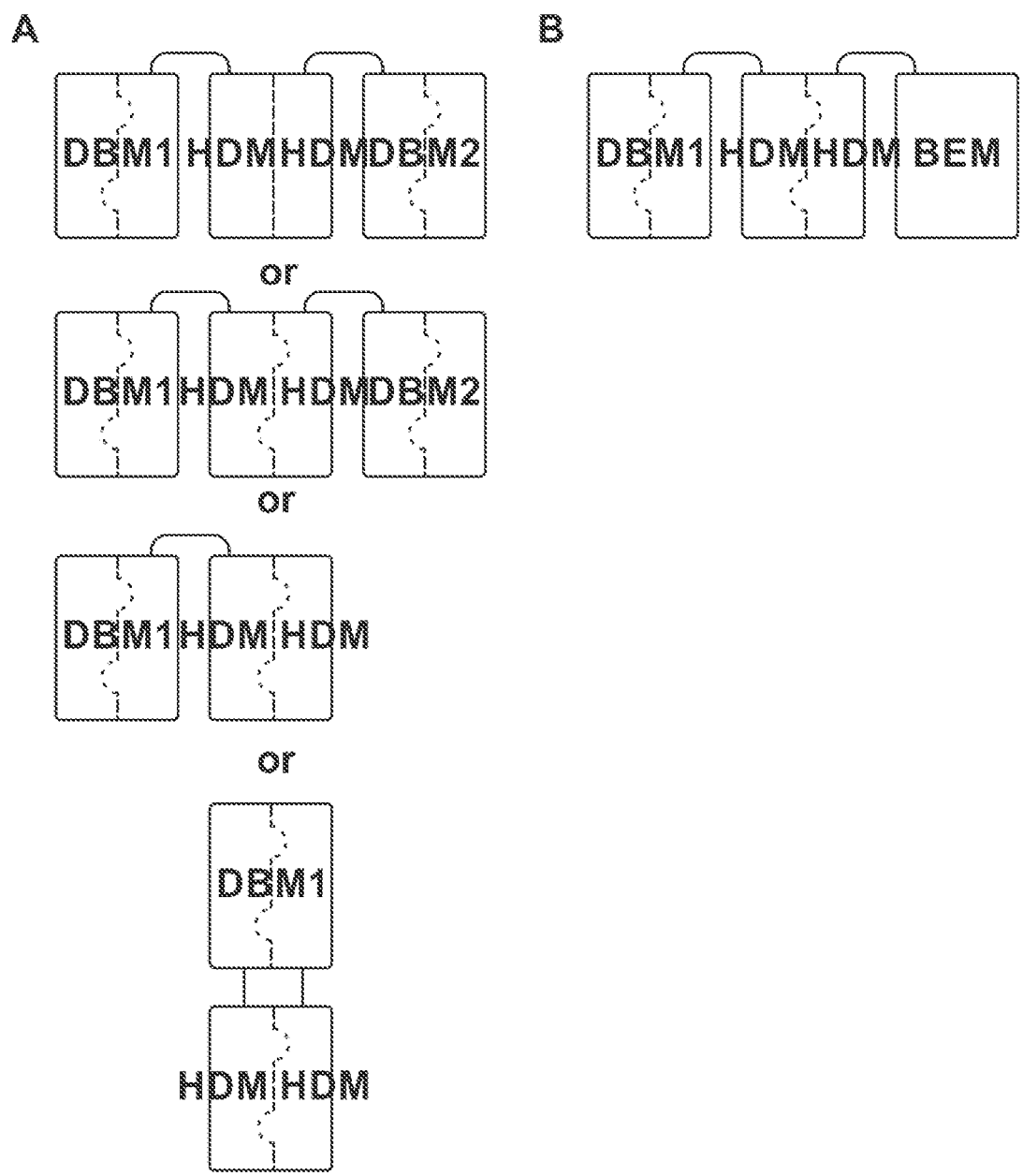

8 Claims, 112 Drawing Sheets
Specification includes a Sequence Listing.

monospecific bispecific bivalent

C

D

E

F

A

B

A

B

MULTIVALENT BINDING MOLECULES

CROSS REFERENCE TO RELATED APPLICATION

This application is a U.S. National Phase of International Application No. PCT/EP2018/057331, filed Mar. 22, 2018, which is incorporated by reference herein in its entirety.

The present invention relates to a modular multivalent antigen-binding protein complex use of the antigen-binding protein complex in medicine and use of the antigen-binding protein complex in the prophylaxis, treatment or diagnosis of a disorder or disease.

BACKGROUND OF THE INVENTION

Monoclonal antibodies have become an established treatment modality for a variety of diseases. Antibody engineering is routinely applied to adapt the composition and activity for therapeutic applications in humans, including a reduction of immunogenicity generating chimeric, humanized or fully human antibodies and the modification of Fc-mediated effector functions, e.g. increasing or abrogating ADCC (Presta, L G. 2008, Molecular engineering and design of therapeutic antibodies. Curr Opin. Immunol. 20, 460-470). Monoclonal antibodies possess a defined specificity for a single epitope of an antigen, thus can address only a singular target. However, complex diseases such as cancer or inflammatory disorders are usually multifactorial in nature. This is reflected by a redundancy of disease-mediating ligands and receptors as well as crosstalk between signal cascades. For example, several proinflammatory cytokines such as TNF, IL-1 and IL-6 have been identified as key players in inflammatory diseases. In cancer, tumor cells often upregulate different growth-promoting receptors, which can act either independently or crosstalk intracellulary through signaling networks. Of note, an acquisition of resistance to therapy is often associated with upregulation of alternative receptors as well as pathway switching between two receptors. Consequently, therapy with monoclonal antibodies targeting only a singular antigen has its limitations.

Bi- and multispecific antibodies find increasing interest for diagnostic and therapeutic applications (Kontermann, 2012, Dual targeting strategies with bispecific antibodies, mAbs 4, 182-197). Bispecific and multispecific antibodies recognize two or more different epitopes either on the same or on different antigens (Garber K. Bispecific antibodies rise again. Nat. Rev. Drug Discov. 2014; 13:799-801; Brinkmann & Kontermann, 2017, The making of bispecific antibodies, mAbs 9, 182-212).

Applications of bispecific antibodies cover a broad spectrum from diagnosis, imaging and therapy. Therapeutic applications include effector cell retargeting for cancer therapy, such as T-cells, which cannot be recruited to tumor cells by normal antibodies. Here, it is often necessary to bind monovalently to a trigger molecule on the effector cells, such as CD3 on T-cells, in order to avoid a systemic activation and induction of adverse effects (Segal et al., 1999, Bispecific antibodies in cancer therapy, Curr. Opin. Immunol. 11, 558-562). Furthermore, bispecific antibodies are used for dual targeting and pre-targeting strategies, half-life extension, and delivery through biological barriers such as the blood-brain barrier. Indications include cancer, chronic inflammatory diseases, autoimmunity, neurodegeneration, bleeding disorders, and infections (Kontermann & Brinkmann, 2015, Bispecific antibodies. Drug Discov. Today 20, 838-847).

Bispecific antibodies with defined specificities are artificial molecules, per se not found in nature. They have, therefore, to be generated by biochemical, molecular or genetic means. One approach is the chemical conjugation of two different antibodies or antibody fragments. Furthermore, fusing two antibody-producing cells, e.g. hybridomas, a hybrid cell line can be generated producing within the same cell two different heavy and two different light chains, which results besides various non-functional by-products in bispecific IgG molecules. The generation of bispecific IgG molecules faces two major problems due to the fact that the antigen-binding sites are built by the variable domains of the light and heavy chain ($V_L$, $V_H$). Firstly, a bispecific antibody requires two different heavy chains, and secondly, it requires also two different light chains. Bispecific IgG antibodies, thus exhibit asymmetry due to the presence of, at least, two different Fv regions. Promiscuous pairing of heavy and light chains of two antibodies expressed in one cell can theoretically result in 16 different combinations (10 different molecules), with only one being bispecific and the remaining pairings resulting in non-functional or monospecific molecules.

Recombinant bispecific antibodies can be classified according to format and composition. A main discrimination is the presence or absence of an Fc region. Fc-less bispecific antibodies will lack the Fc-mediated effector functions, such as ADCC, ADCP, complement fixation, and FcRn mediated recycling responsible for the long half-life of immunoglobulins. Fc-comprising bispecific antibodies can be further divided into those that exhibit a structure resembling that of an IgG molecule and those that contain additional binding sites, thus have an appended or modified Ig-like structure. The different bispecific antibodies will have either a symmetric or an asymmetric architecture. For example, the majority of bispecific IgG molecules are asymmetric, while IgG fusion proteins often are symmetric in their molecular composition. A further discriminating feature is the number of binding sites. In the simplest setting, e.g. utilized in IgG molecules, a bispecific antibody contains one binding site for each antigen (1+1), i.e. is bivalent. Adding an additional binding site to one of the chains of an IgG results in tetravalent molecules with a 2+2 stoichiometry. Other formats allow to generate 1+2 or 1+3 molecules, having one binding site for one antigen and 2 or 3 binding sites for the other antigen, respectively. This can be extended by further valencies, but also by implementing further specificities, e.g. to make tri- or tetraspecific molecules. Furthermore, the number of chains needed to produce the bispecific antibody can vary. Thus, most bispecific IgGs require normally four different polypeptide chains to be expressed. In some formats, a lower number of chains can be applied, requiring 3, 2 or only a single polypeptide chain. The different formats to generate bispecific antibodies has recently been summarized (Spiess et al., 2015, Alternative molecular formats and therapeutic applications for bispecific antibodies, Mol. Immunol. 67, 95-106; Brinkmann & Kontermann, 2017, The making of bispecific antibodies, mAbs 9, 182-212).

The available multivalent bi- or multispecific antibody formats face one or more of the following problems:
1) being small in size and are therefore rapidly cleared from circulation,
2) lack of a Fc region and therefore immune effector functions and FcRn-mediated recycling responsible for an extended plasma half-life,
3) require the use of peptide linker(s) of substantial lengths (>12 aa) for fusion of the antigen binding sites and their variable domains, 4) difficulties of one or more of the antigen-binding sites to access antigen for efficient binding,
5) require engineering to identify the best arrangement of the antigen-binding site for unaffected antigen-binding,
6) require engineering to identify the best length(s) and composition of the peptide linker sequences connecting the antigen-binding sites and variable domains within,
7) exceed a molecular mass of 200 kDa which might affect tissue penetration and biodistribution,
8) low stability and a tendency to form aggregates,
9) require a complex purification procedure to obtain a homogenous preparation,
10) lack of flexibility in varying valency and specificity,
11) potential immunogenicity of artificially introduced peptide linkers of substantial length,
12) post-translational modifications of the peptide linkers (e.g. glycosylation, phosphorylation) affecting homogeneity of therapeutic molecules.

The present invention provides a modular system composed of a dual-binding module (DBM) and a (hetero- or homo) dimerization module (HDM), which can further comprise a second DBM or one or more binding or effector modules (BEM), to generate multivalent bi- or multispecific antibodies with (i) only a minimal lengths of the peptide linker connecting the variable domains of the antigen-binding sites within the DBM (<12 aa, e.g. 10 or less, such as 5), (ii) providing unhindered access of the antigen-binding sites within an DBM to antigens without the need for identifying correct orientation and position of the antigen-binding sites, (iii) increased stability of the antigen-binding sites by use of homo- or heterodimerization domains in the DBM, (iv) further provides homo- or heterodimer formation through a dimerization module, (v) generation of novel multivalent antibodies from the variable domains of the parental antibodies without optimization of arrangement, (vi) allows the generation of various multivalent and multispecific antibodies, and (vii) allows the generation of symmetric and asymmetric molecule with a defined position of the respective antigen-binding site within the molecule.

SUMMARY OF THE INVENTION

In a first aspect, the present invention provides an antigen-binding protein complex comprising at least one dual binding module (DBM), and one homo- or hetero-dimerization module (HDM) and optionally a binding or effector module (BEM), wherein
a. a first DBM module (DBM1) comprises two polypeptides, wherein the first polypeptide (P1) comprises a first dimerization domain (DD1) and a first variable heavy chain ($V_H1$) and a first variable light chain ($V_L1$), wherein said $V_H1$ and $V_L1$ are connected by a peptide linker (L1), with a length preventing binding of $V_H1$ and $V_L1$ to each other, and the second polypeptide (P2) comprises a second dimerization domain (DD2) and a second variable heavy chain ($V_H2$) and a second variable light chain ($V_L2$), wherein said $V_H2$ and $V_L2$ are connected by a peptide linker (L2), with a length preventing binding of $V_H2$ and $V_L2$, to each other and wherein $V_H1$ binds to $V_L2$ and $V_L1$ binds to $V_H2$ and each variable domain pair forms a binding site, and wherein DD1 specifically binds to DD2;
b. a second DBM module (DBM2), when present comprises two polypeptides, wherein the first polypeptide (P1') comprises a first dimerization domain (DD1') and a first variable heavy chain ($V_H1'$) and a first variable light chain ($V_L1'$), wherein said $V_H1'$ and $V_L1'$ are connected by a peptide linker (L1'), with a length preventing binding of $V_H1'$ and $V_L1'$ to each other, and the second polypeptide (P2') comprises a second dimerization domain (DD2') and a second variable heavy chain ($V_H2'$) and a second variable light chain ($V_L2'$), wherein said $V_H2'$ and $V_L2'$ are connected by a peptide linker (L2'), with a length preventing binding of $V_H2'$ and $V_L2'$ to each other, and wherein $V_H1'$ binds to $V_L2'$ and $V_L1'$ binds to $V_H2'$ and each variable domain pair forms a binding site, wherein DD1' specifically binds to DD2';
c. the BEM module, when present, comprises two polypeptides, wherein the third polypeptide (P3) comprises a third dimerization domain (DD3) and a third variable heavy chain domain ($V_H3$) and the fourth polypeptide (P4) comprises a fourth dimerization domain (DD4) and a third variable light chain ($V_L3$) domain, wherein $V_H3$ binds $V_L3$ and forms a binding site, wherein DD3 specifically binds to DD4;
d. at least one HDM module comprises two polypeptides, wherein:
  (i) in case no DBM2 or BEM are present:
    (a) the fifth polypeptide (P5) is covalently linked to P1 of DBM1 and comprises a fifth dimerization domain (DD5) and the sixth polypeptide (P6) comprises a sixth dimerization domain (DD6), which specifically binds to DD5; or
    (b) fifth polypeptide (P5) is covalently linked to P1 of DBM1 and comprises a fifth dimerization domain (DD5) and the sixth polypeptide (P6) is covalently linked to P2 of DBM1 and comprises a sixth dimerization domain (DD6), which specifically binds to DD5; or
  (ii) in case DBM2 or BEM are present the fifth polypeptide (P5) is covalently linked to P1 or P2 of DBM1 and comprises a fifth dimerization domain (DD5) and the sixth polypeptide (P6) is covalently linked to either P1' or P2' of DBM2 or either to P3 or P4 of the BEM and comprises a sixth dimerization domain (DD6), which specifically binds to DD5.

In a second aspect, the present invention relates to the antigen-binding protein complex of the first aspect for use in medicine.

LIST OF FIGURES

In the following, the content of the figures comprised in this specification is described. In this context please also refer to the detailed description of the invention above and/or below.

FIG. 1: Schematic illustration of the modules used for the generation of multivalent and multispecific binding molecules. A: Fusion protein of DBM+HDM modules resulting in homodimer and heterodimer. B: Heterodimer of DBM+HDM module and HDM+BEM module.

Figure 2:
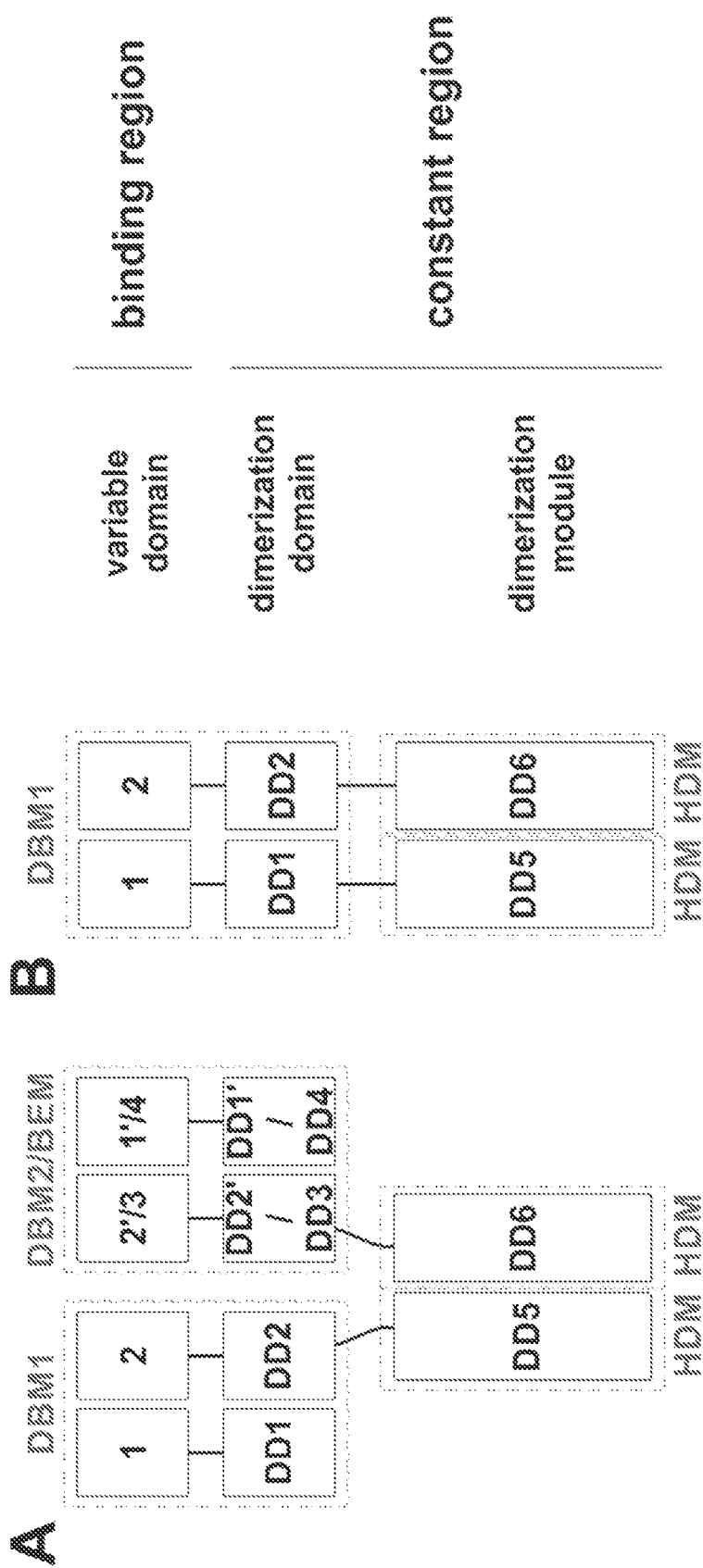

FIG. 2: Schematic overview of construction of the heavy and light chain of the Db-Ig platform. Heavy chain consists of variable domains 2 (2'/3), the dimerization domain DD2 (DD2'/DD3), and the Fc part DD5 (DD6). Light chain consist of the variable domain 1 (1'/4) and the dimerization domain DD1 (DD1'/DD4). Modules (DBM, HDM, BEM) described herein are encircled with a dotted line. A: Schematic construction of Db-Ig molecules comprising two heavy chains and two light chains. B: Schematic construction of Db-Ig molecules comprising two heavy chains.

Figure 3:
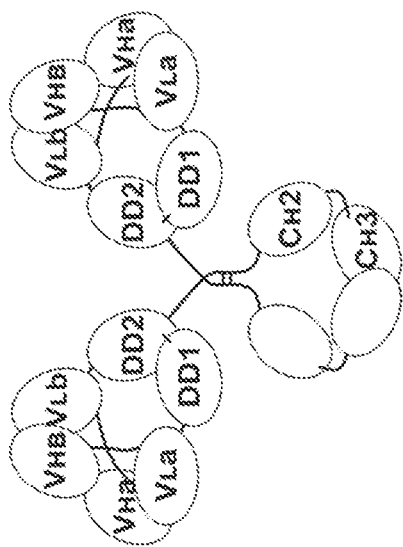
Figure 3:
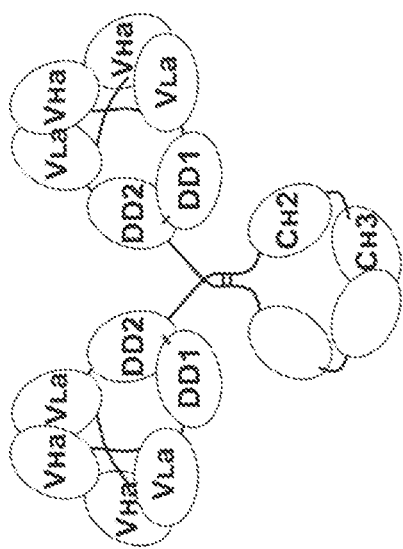
Figure 3:
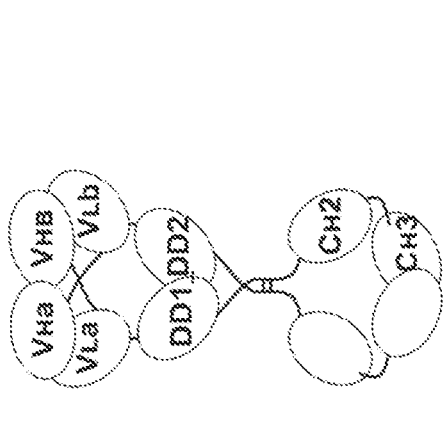
Figure 3:
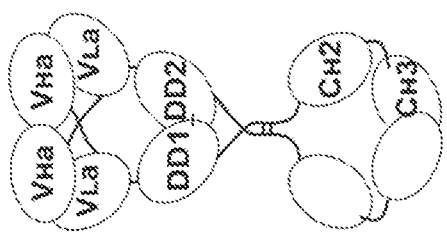

FIG. 3: Schematic overview of tetravalent, mono- and bispecific, and of bivalent, mono- and bispecific, Db-Ig molecules using homodimeric Fc part. Schematic illustration of the heavy and light chain of tetravalent, monospecific (4+0) or tetravalent, bispecific (2+2), and of the two heavy chain of a bivalent, monospecific (2+0) or bivalent, bispecific (1+1) Db-Ig molecules.

Figure 4:
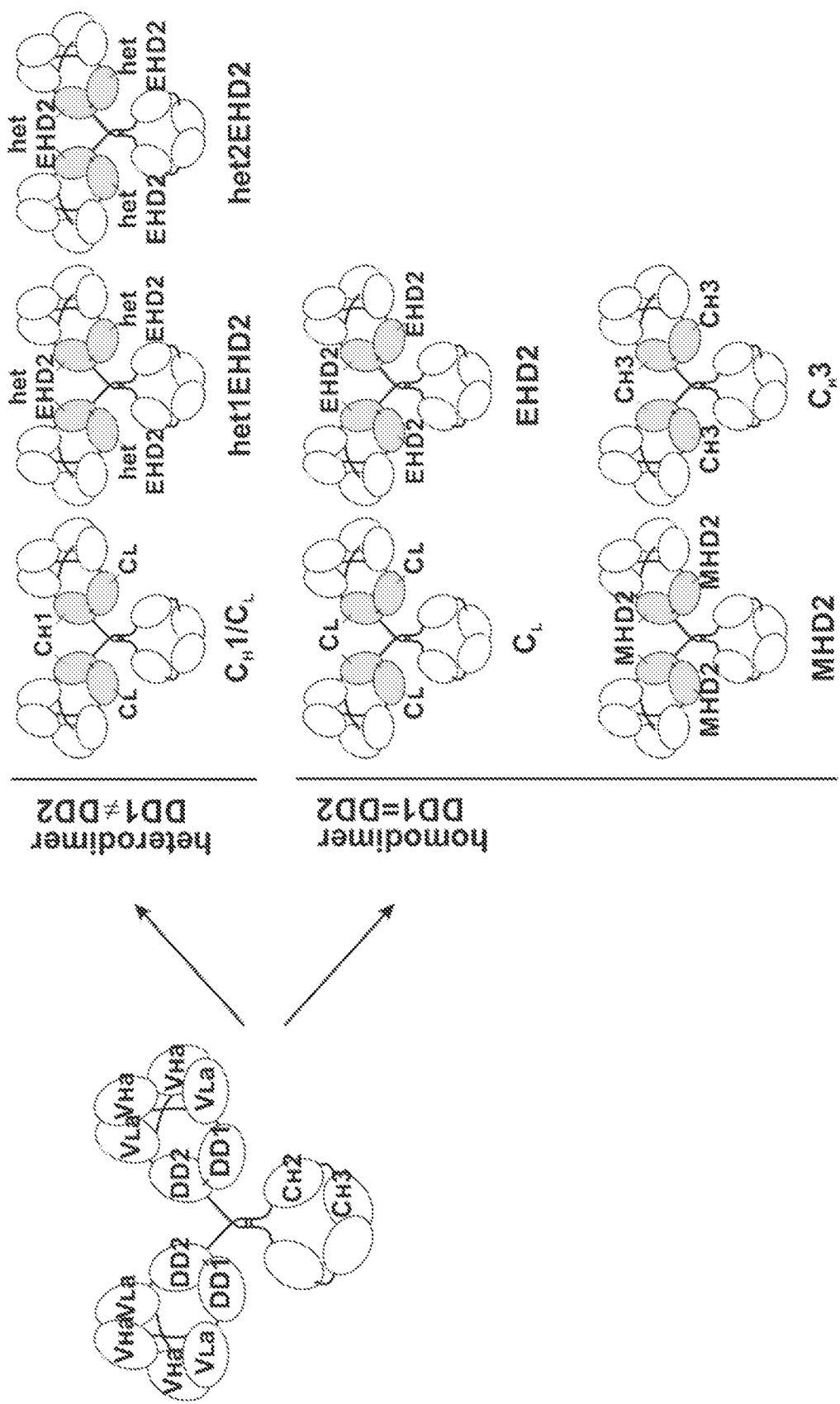

FIG. 4: Schematic overview of dimerization domains used for the generation of tetravalent, mono- and bispecific Db-Ig molecules using homodimeric Fc part. Dimerization modules are grouped according to heterodimer or homodimer. het1EHD2 contains a C247S mutation in the light chain and C337S mutation in the heavy chain, het2EHD2 contains a C337S in the light chain and C247S mutation in the heavy chain.

Figure 5:
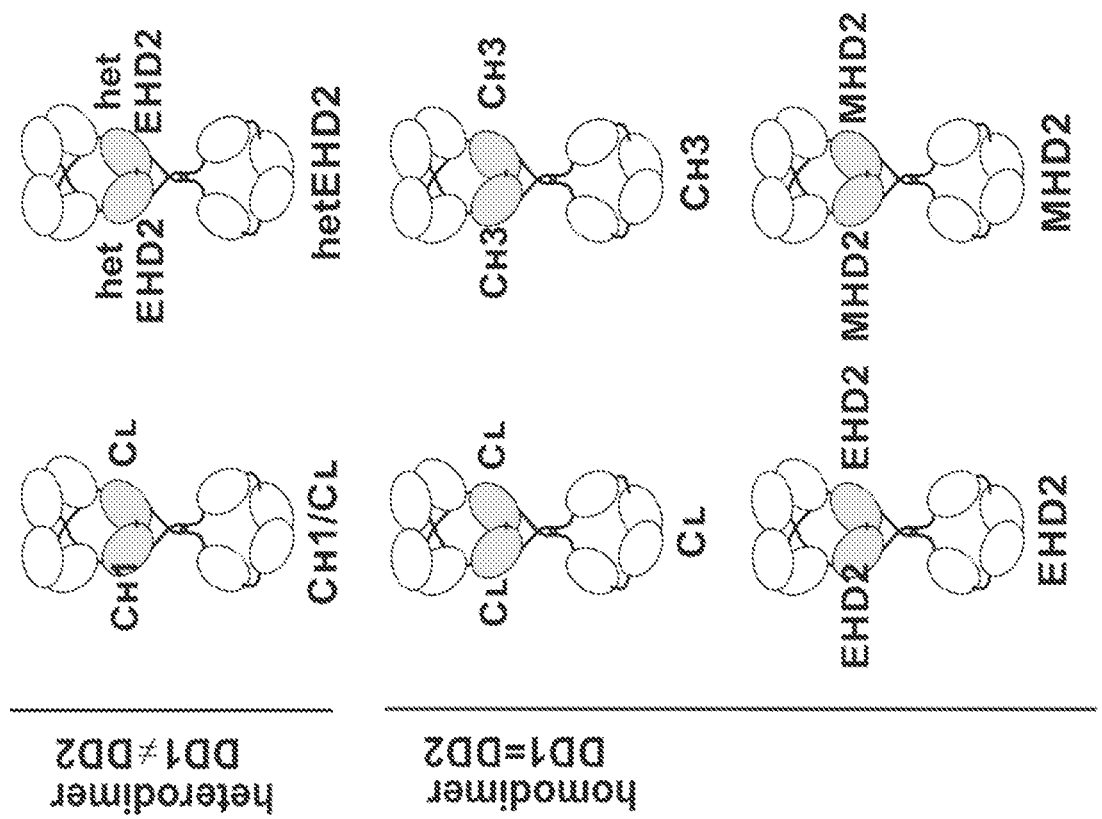
Figure 5:
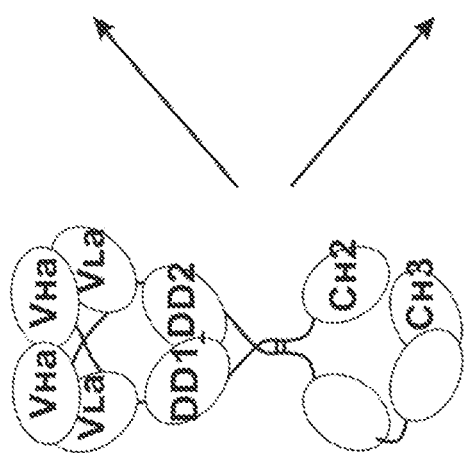

FIG. 5: Schematic overview of dimerization domains used for the generation of bivalent, monospecific Db-Ig molecules using homodimeric Fc part. Dimerization modules are grouped according to heterodimer or homodimer.

Figure 6:
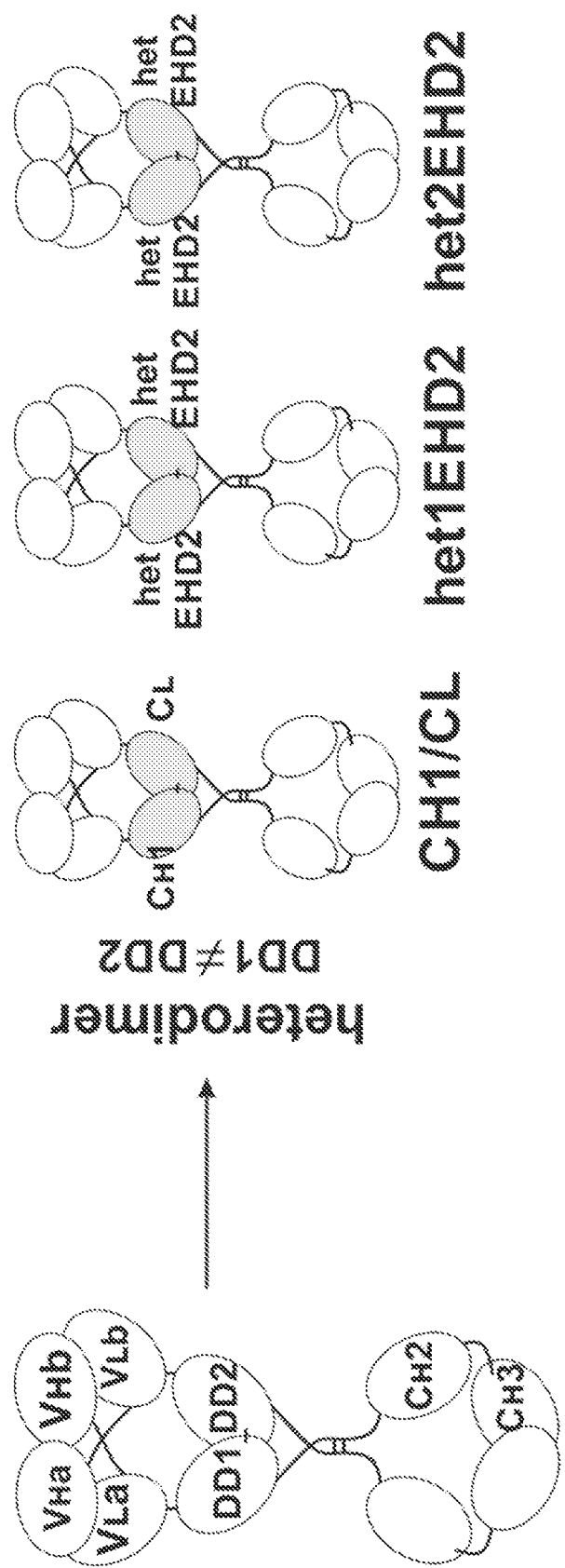

FIG. 6: Schematic overview of dimerization domains used for the generation of bivalent, bispecific Db-Ig molecules using homodimeric Fc part. Only dimerization domains, which form a heterodimer were used for the generation of bivalent, bispecific binding molecules. het1EHD2 contains a C247S mutation in the first heavy chain and C337S mutation in the second heavy chain, het2EHD2 contains C337S in the first heavy chain and C247S mutation in the second heavy chain.

Figure 7A:
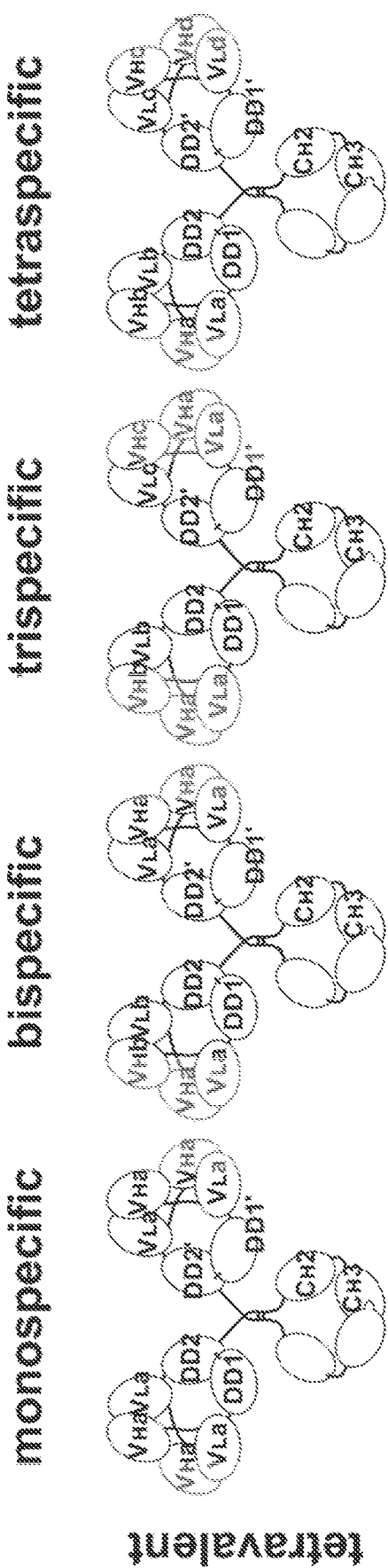
Figure 7B:
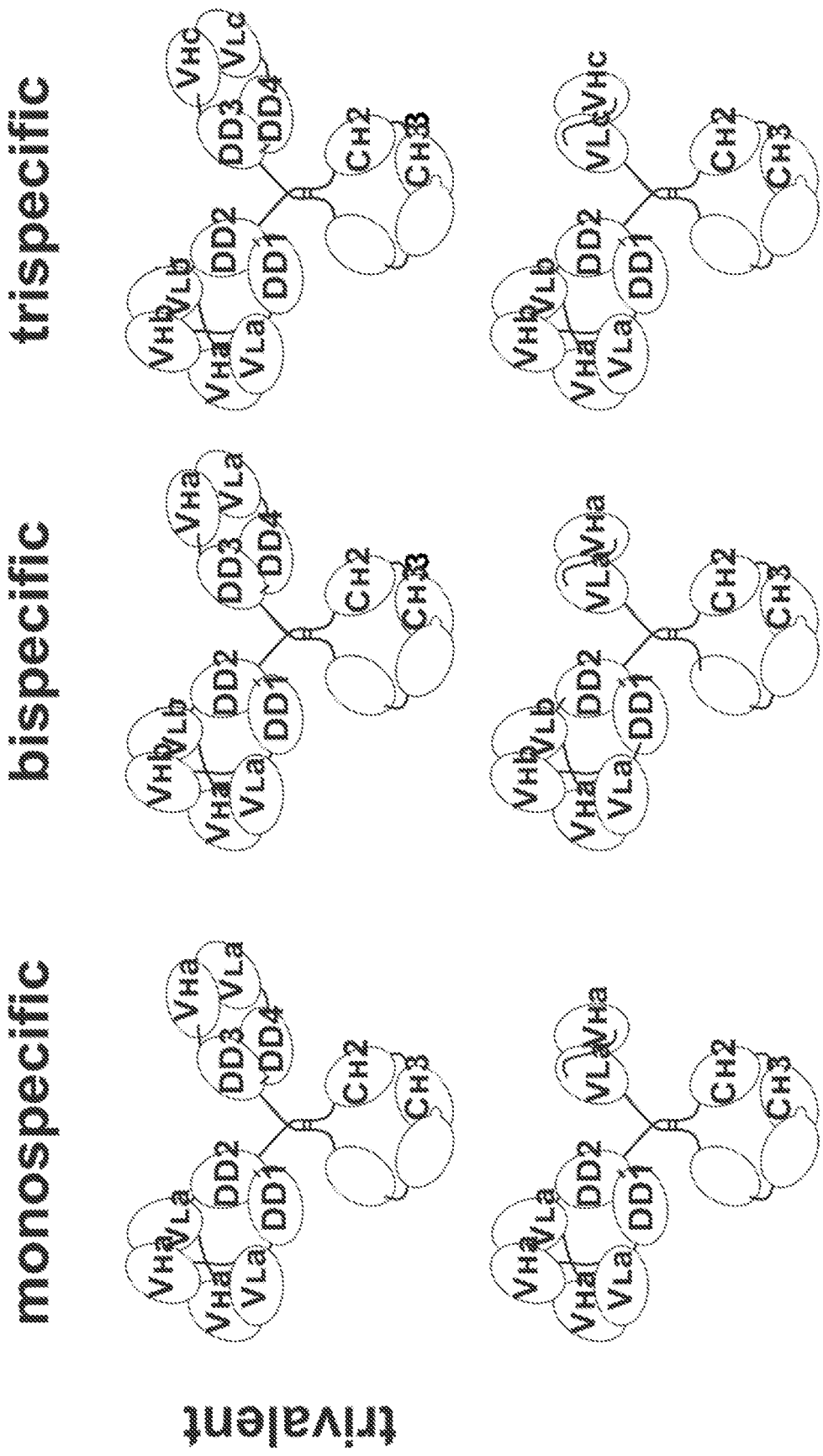
Figure 7C:
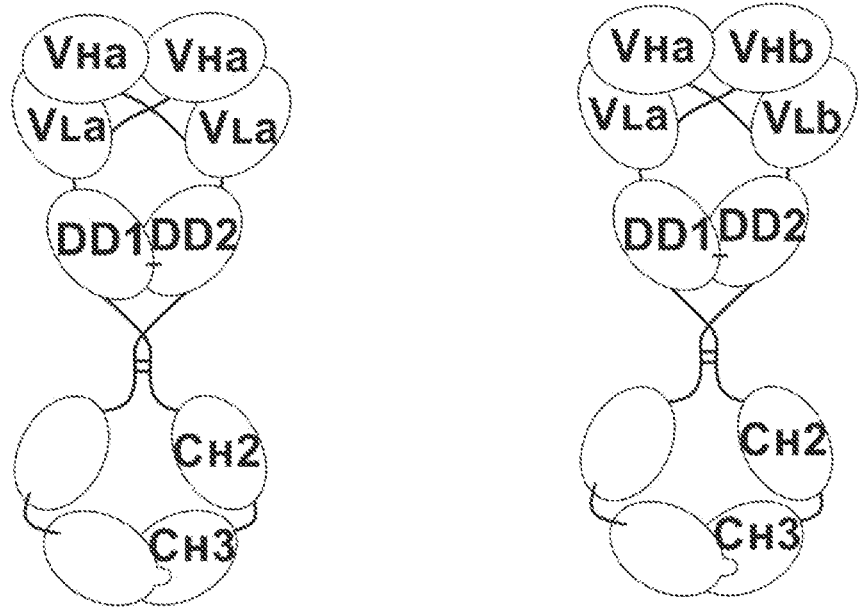

FIG. 7A-C: Schematic overview of tetra-, tri-, bivalent Db-Ig molecules using heterodimeric Fe part. Schematic illustration of the light and/or heavy chain of tetravalent (mono- (4+0), bi- (2+2, 3+1), tri- (2+1+1), and tetraspecific (1+1+1+1)), trivalent (mono-(3+0), bi- (2+1), and trispecific (1+1+1)), bivalent (mono- (2+0), and bispecific (1+1)) Db-Ig molecules.

Figure 8:
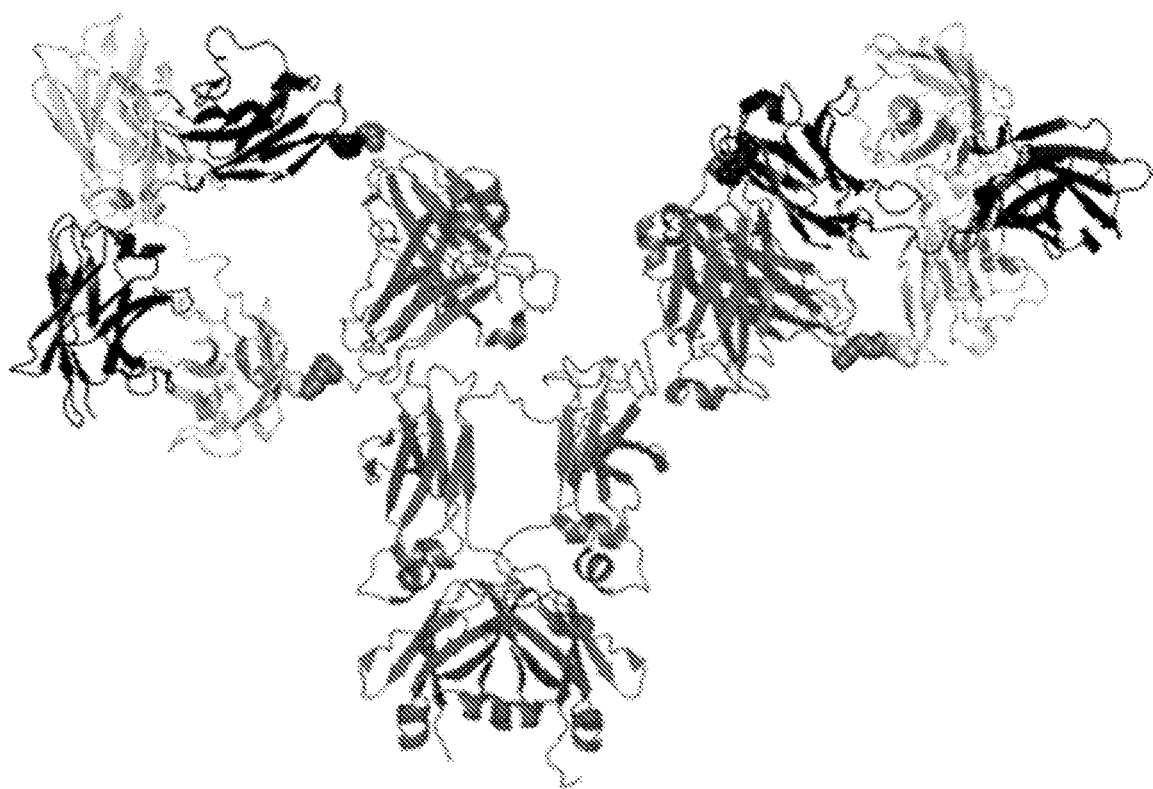

FIG. 8: Computational modeling of a diabody moiety and the constant domains of IgG. Both chains of the diabody are colored in black and light grey, whereas the constant domains of IgG are colored dark gray. Interface of diabody and constant domains are shown as spheres. Modeling was performed using PyMol (1HZH: human IgG; 1LMK: bivalent diabody).

Figure 9:
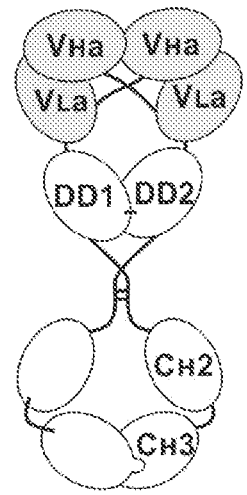
Figure 9:
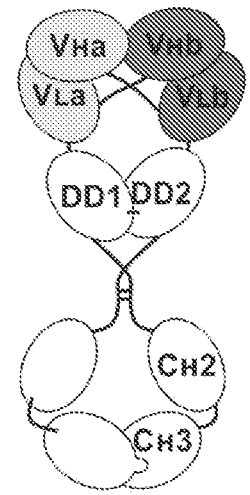
Figure 9:
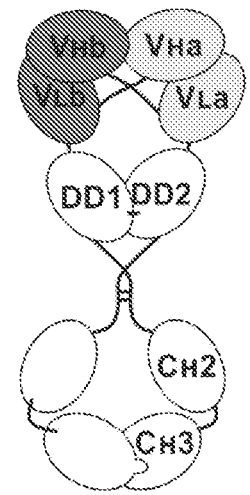

FIG. 9: Schematic overview of antigen-binding sites of bivalent Db-Ig molecules using a heterodimeric Fe part. Schematic illustration of the heavy chains of bivalent (mono-(2+0), and bispecific (1+1)) Db-Ig molecules. Specificities of the antigen-binding sites are colored as dark and light grey.

Figure 10:
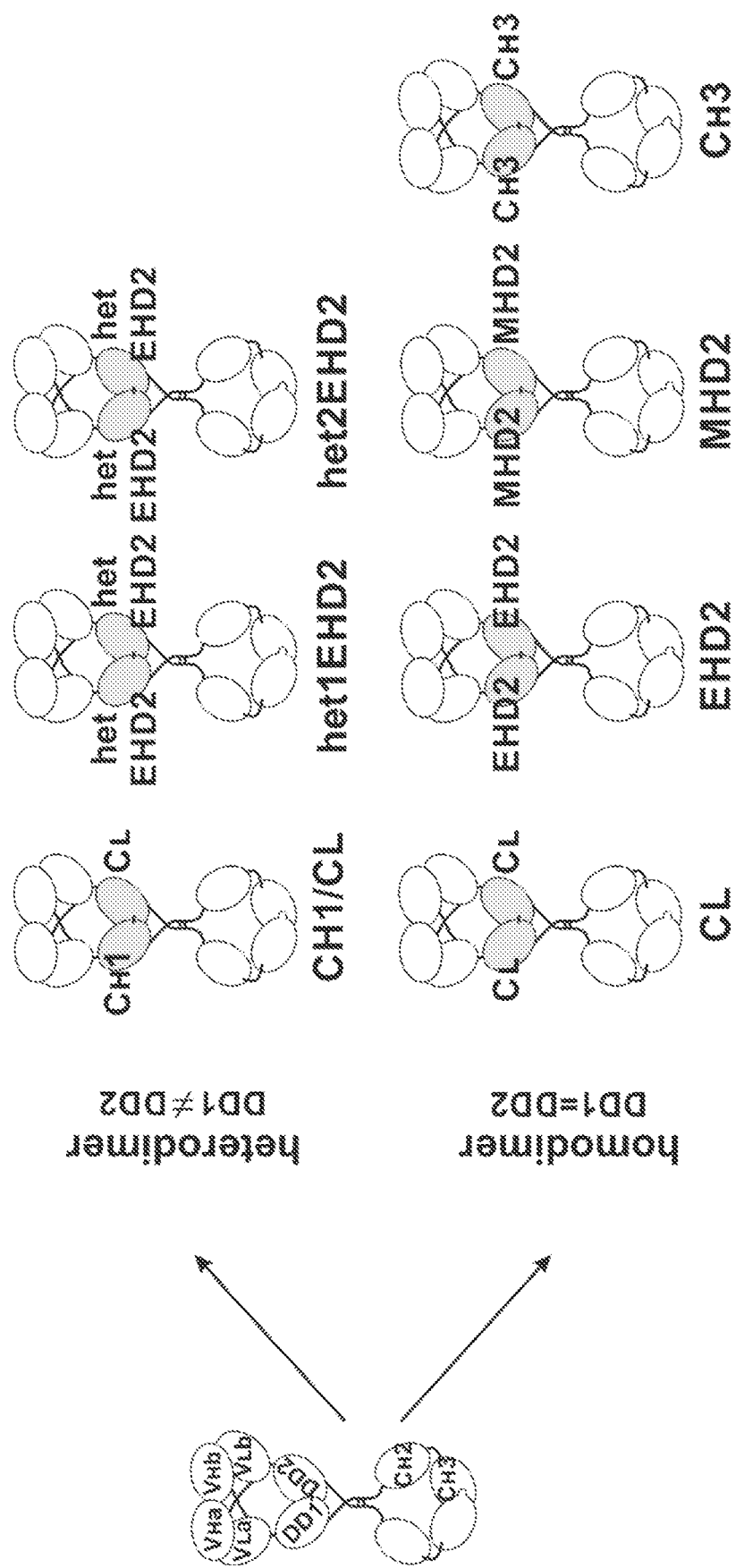

FIG. 10: Schematic overview of the different dimerization modules used for the generation of bivalent Db-Ig molecules using a heterodimeric Fc part. Dimerization modules are grouped according to heterodimer or homodimer.

Figure 11A:
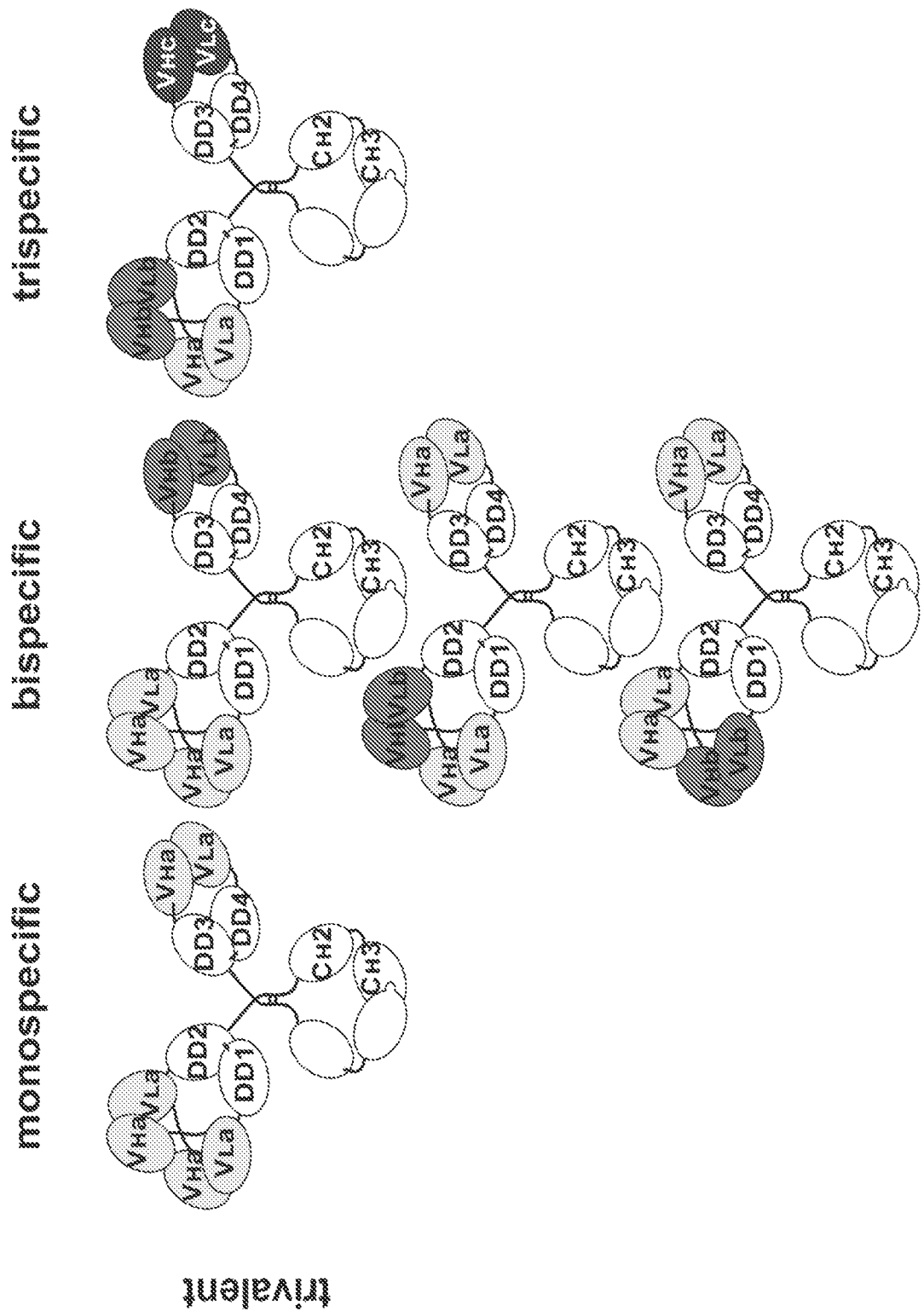
Figure 11B:
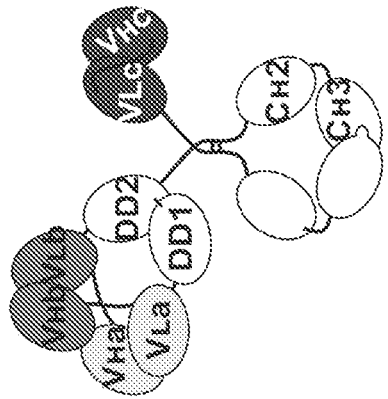
Figure 11B:
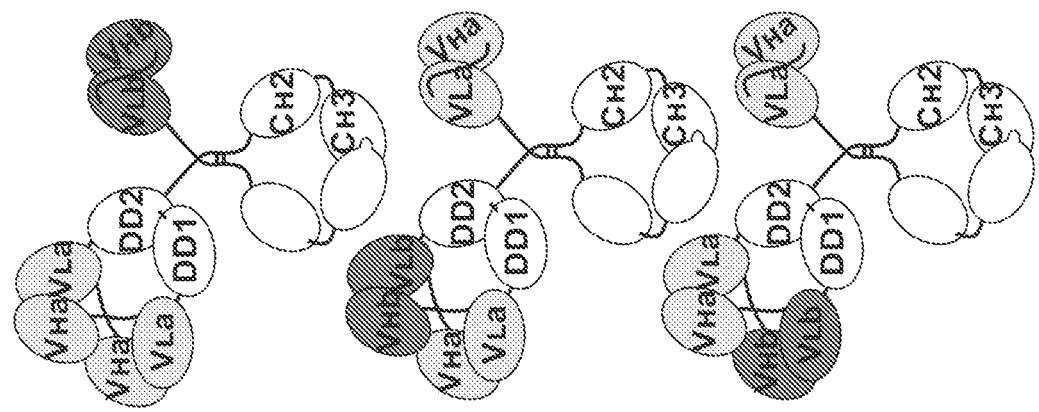
Figure 11B:
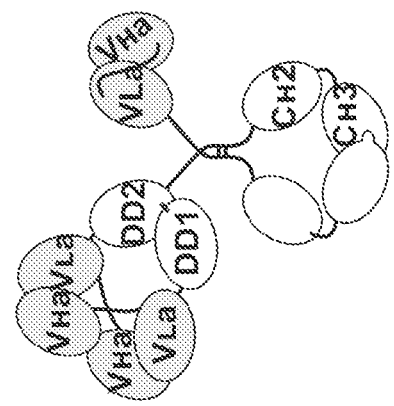

FIG. 11A-B: Schematic overview of the antigen-binding sites of trivalent Db-Ig molecules using a heterodimeric Fc part. Schematic illustration of the trivalent (mono- (3+0), bispecific (2+1), and trispecific (1+1+1)) Db-Ig molecules combining the diabody moiety either with a Fab fragment or a single-chain Fv (scFv). Specificities of the antigen-binding sites are colored with black, dark and light grey.

FIG. 12A-G: Schematic overview of hetero-dimerization modules (Fc$_{knob}$) used for the generation of trivalent db-Fab molecules using a heterodimeric Fc part. Combinatorial overview of dimerization modules used for the generation of trivalent db-Fab molecules using the example of a monospecific molecule. This is also true for trivalent, bi- or trispecific molecules. het1EHD2 contains a C247S mutation in the light chain and C337S mutation in the heavy chain, het2EHD2 contains a C337S in the light chain and C247S mutation in the heavy chain.

FIG. 13A-G: Schematic overview of homo-dimerization modules (Fc$_{knob}$) used for the generation of trivalent db-Fab molecules using a heterodimeric Fc part. Combinatorial overview of dimerization modules used for the generation of trivalent db-Fab molecules using the example of a monospecific molecule. This is also true for trivalent, bi- or trispecific molecules.

Figure 14:
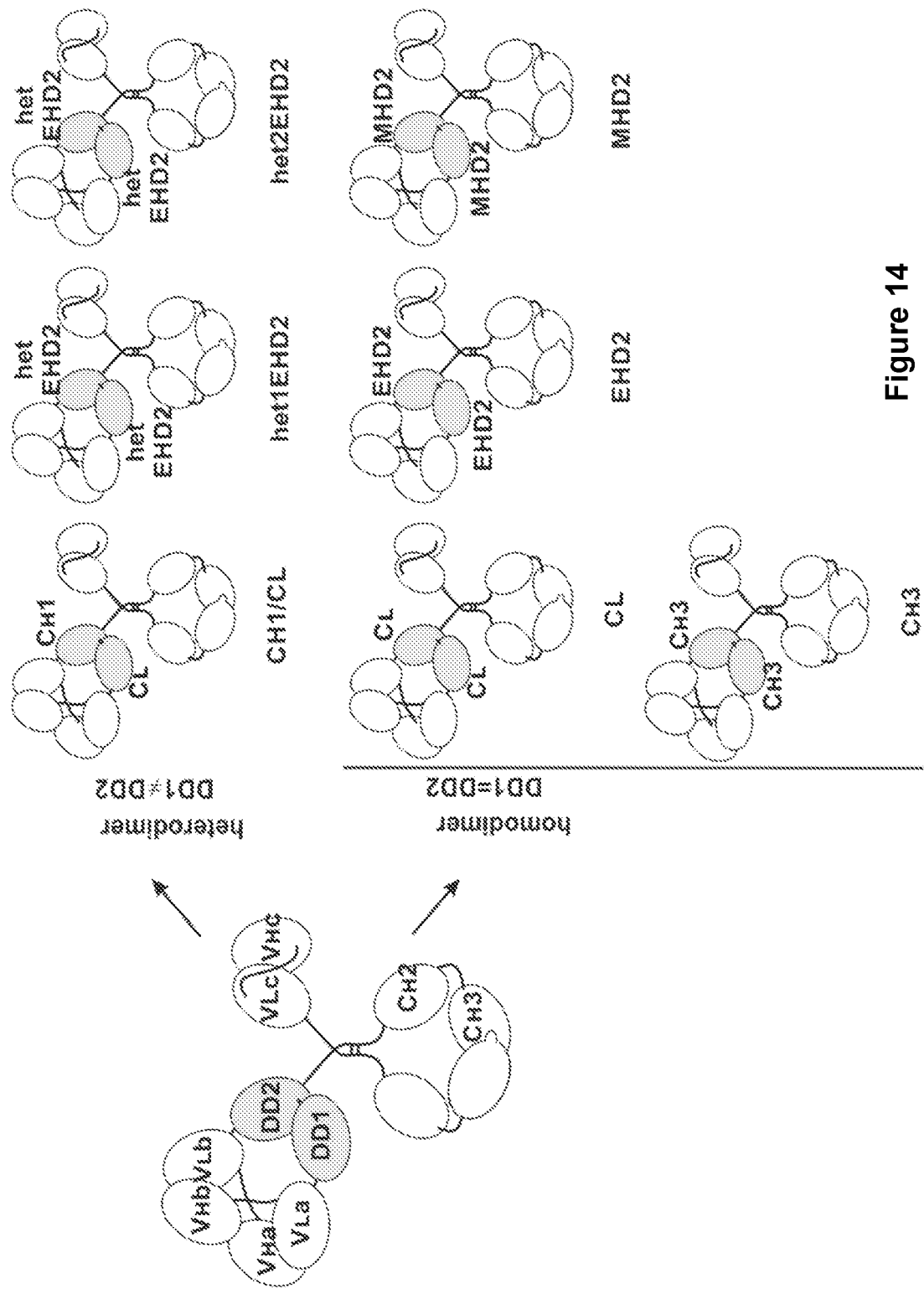
Figure 15A:
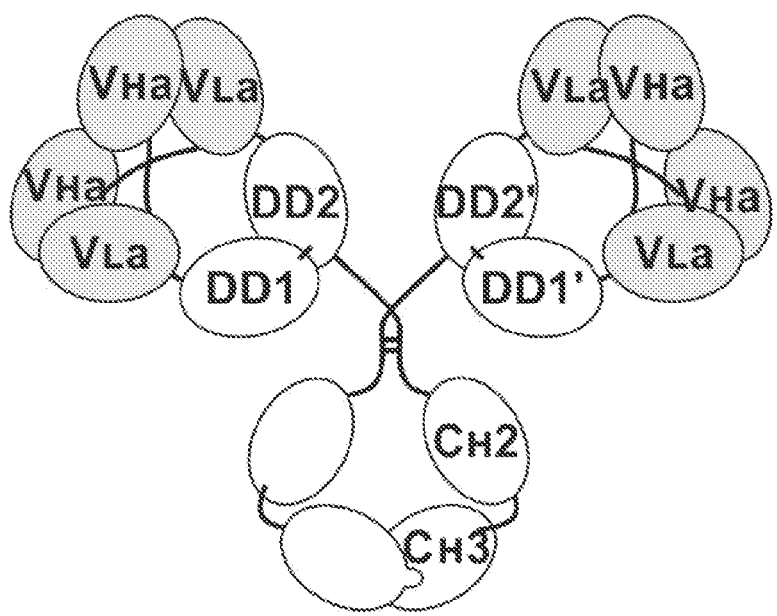
Figure 15B:
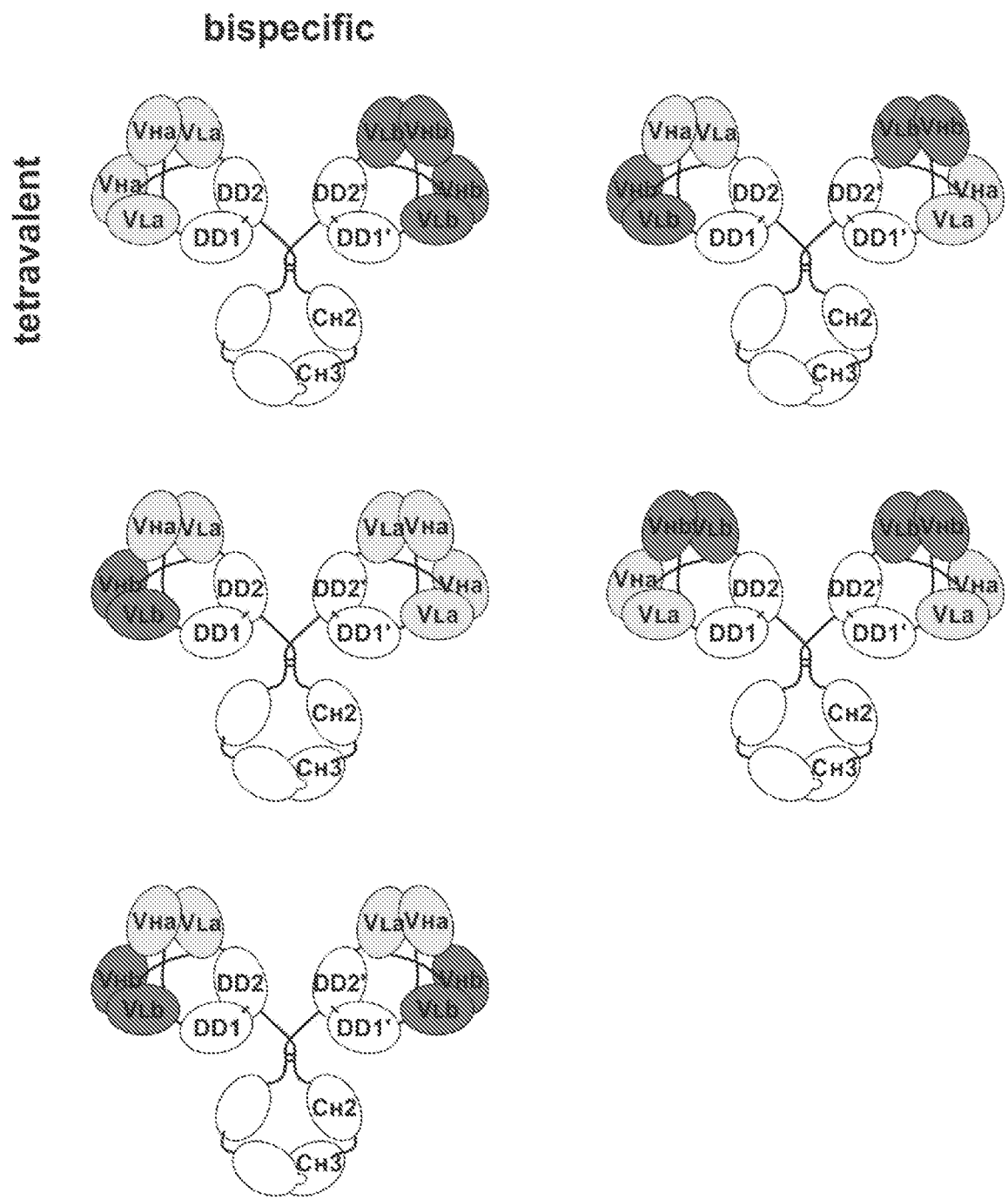
Figure 15C:
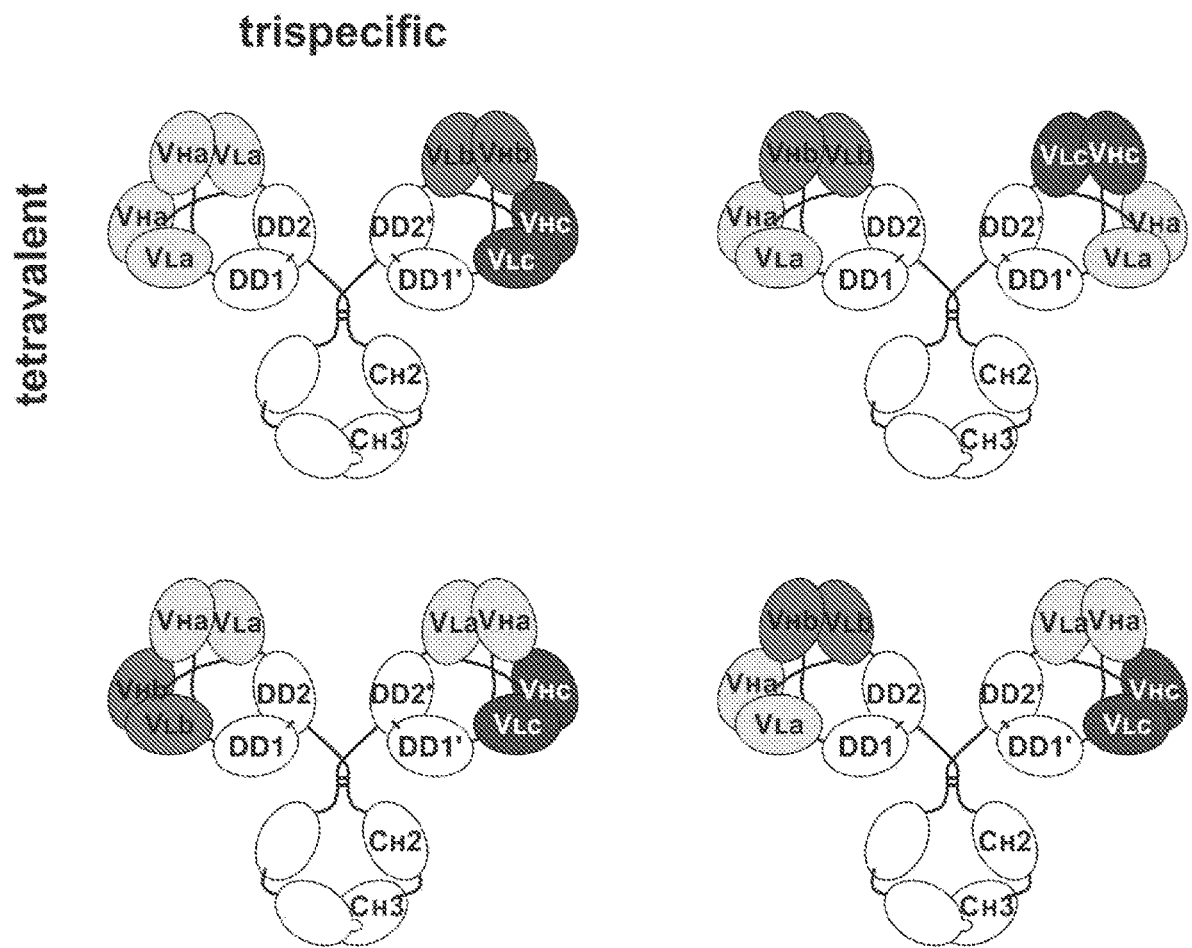
Figure 15D:
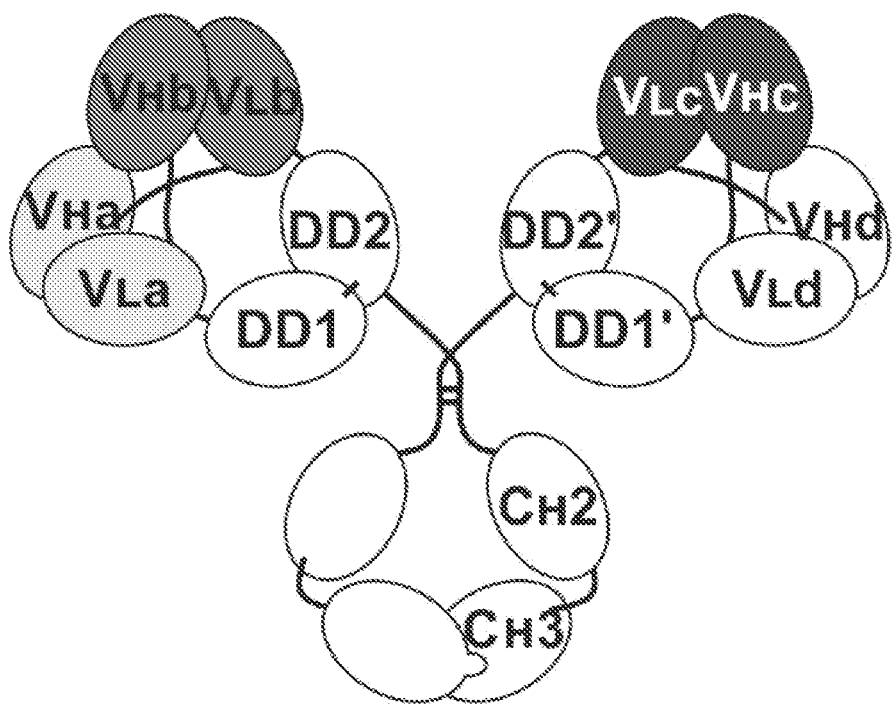
Figure 16:
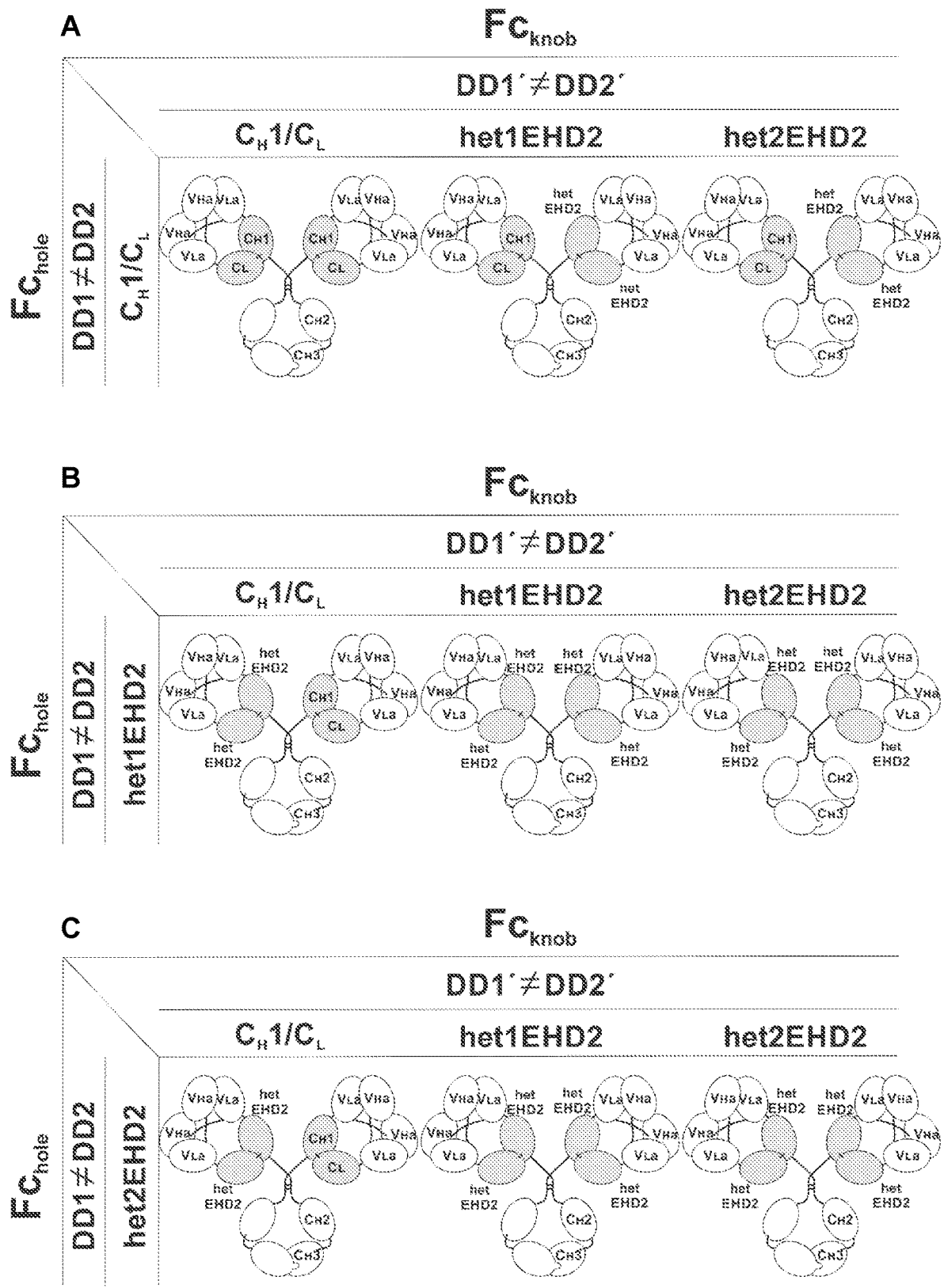
Figure 16:
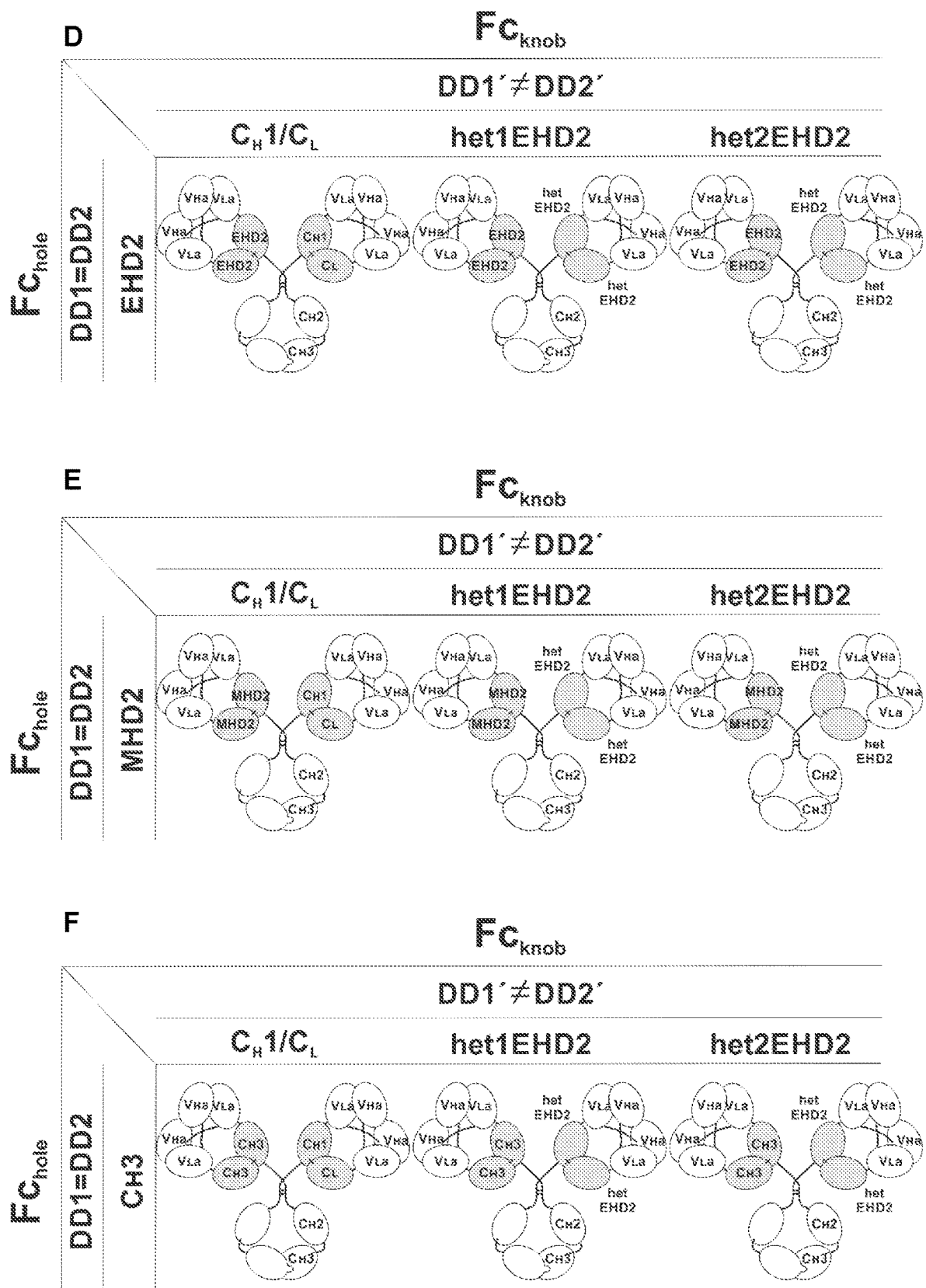
Figure 16:
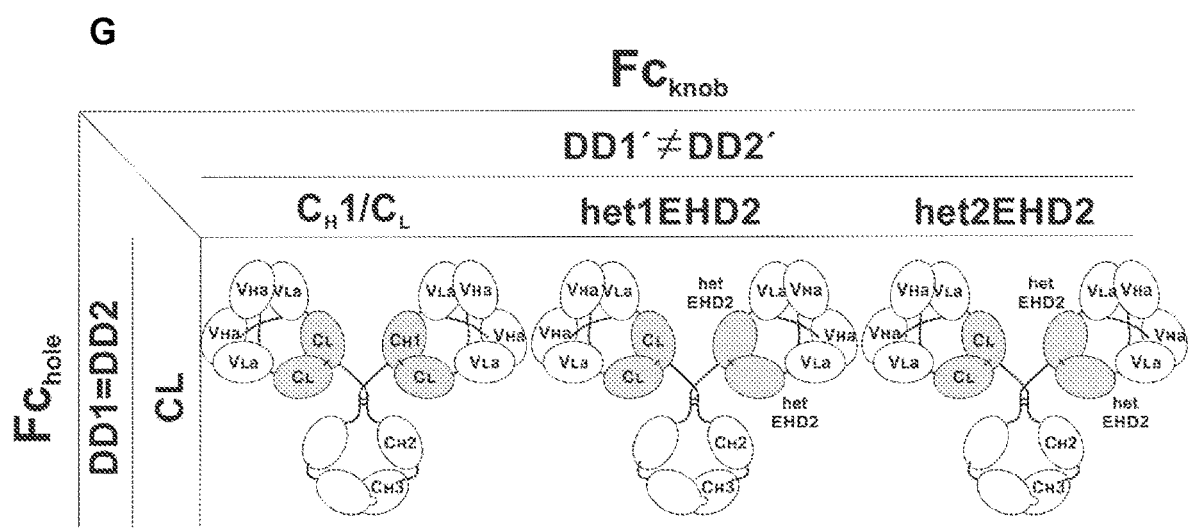
Figure 17A:
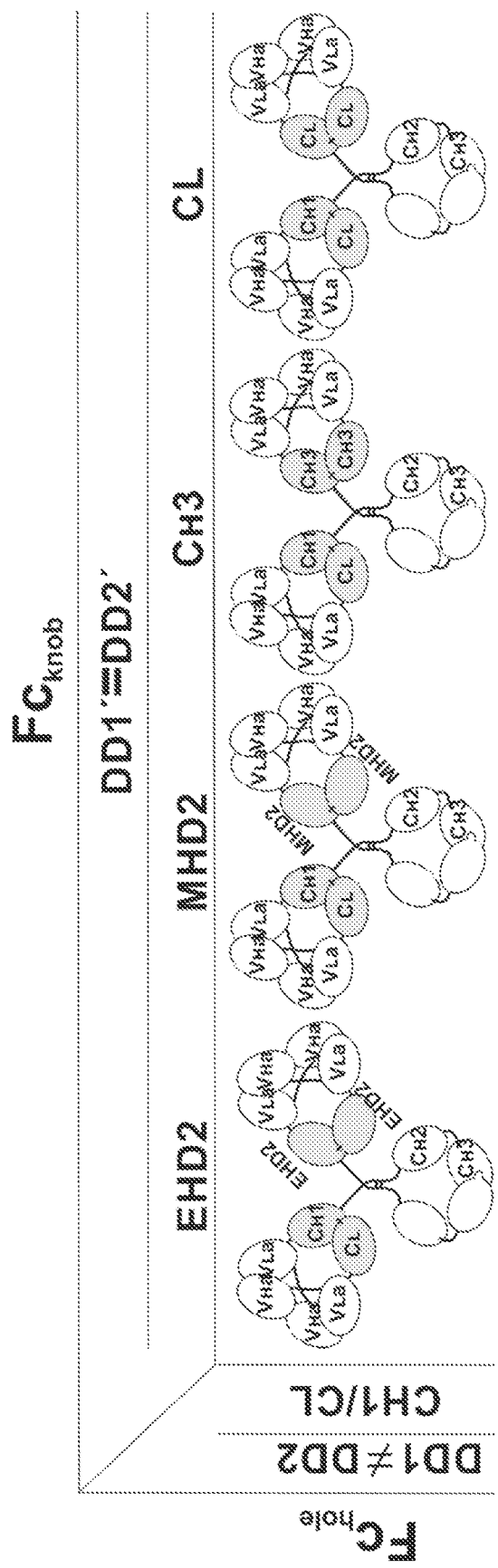
Figure 17B:
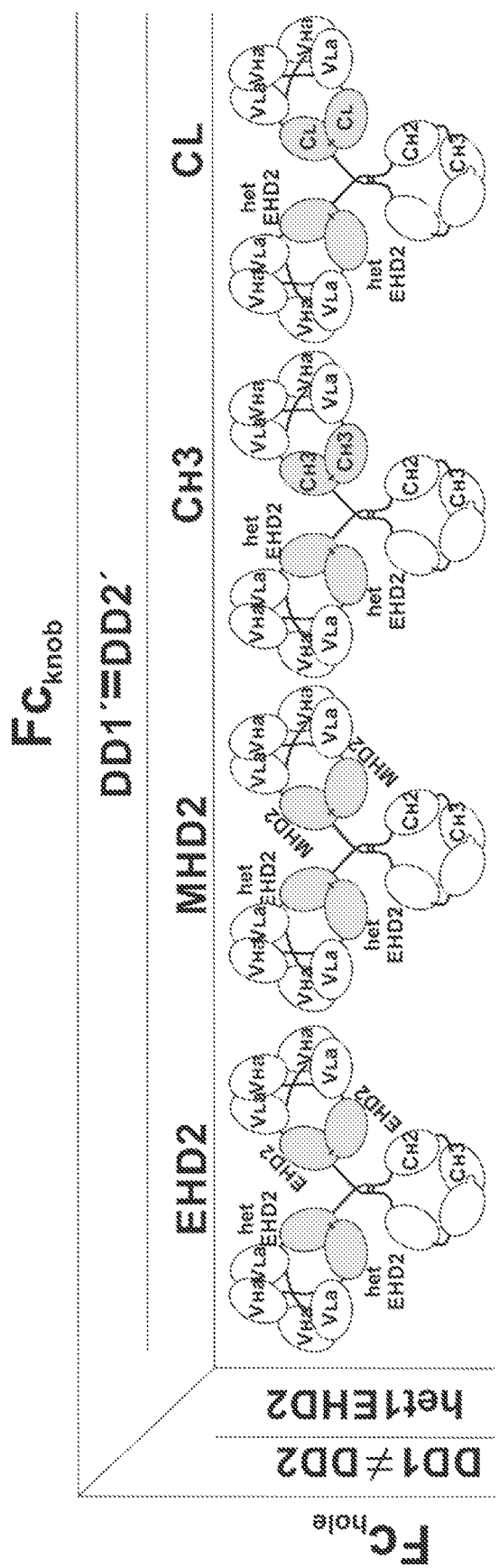
Figure 17C:
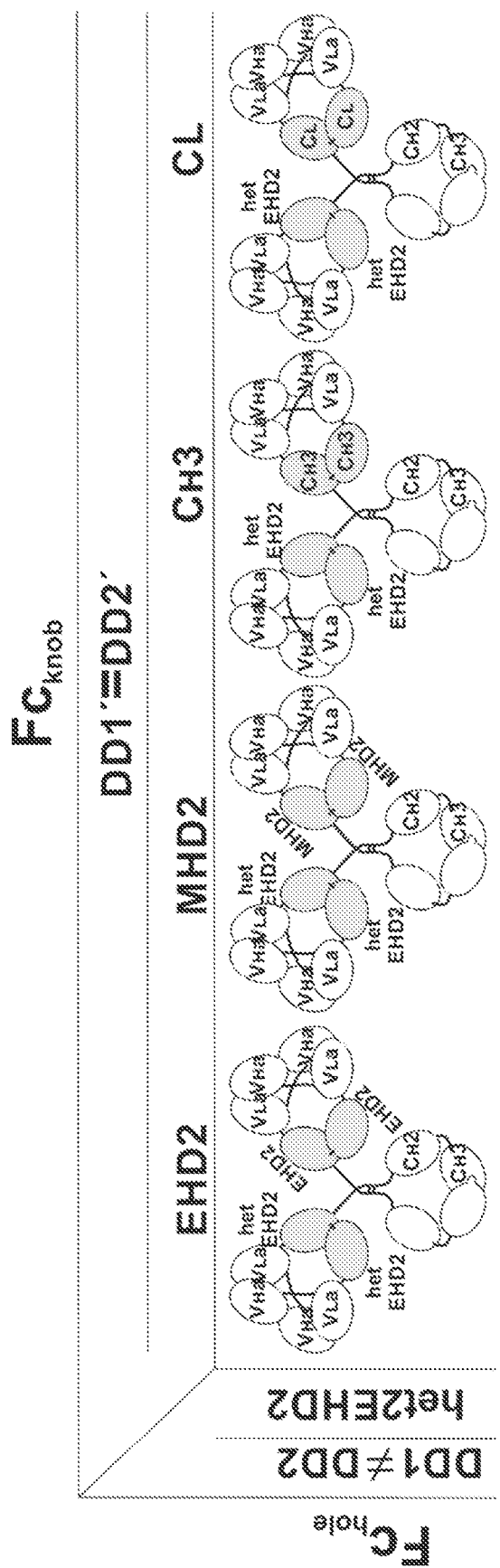
Figure 17D:
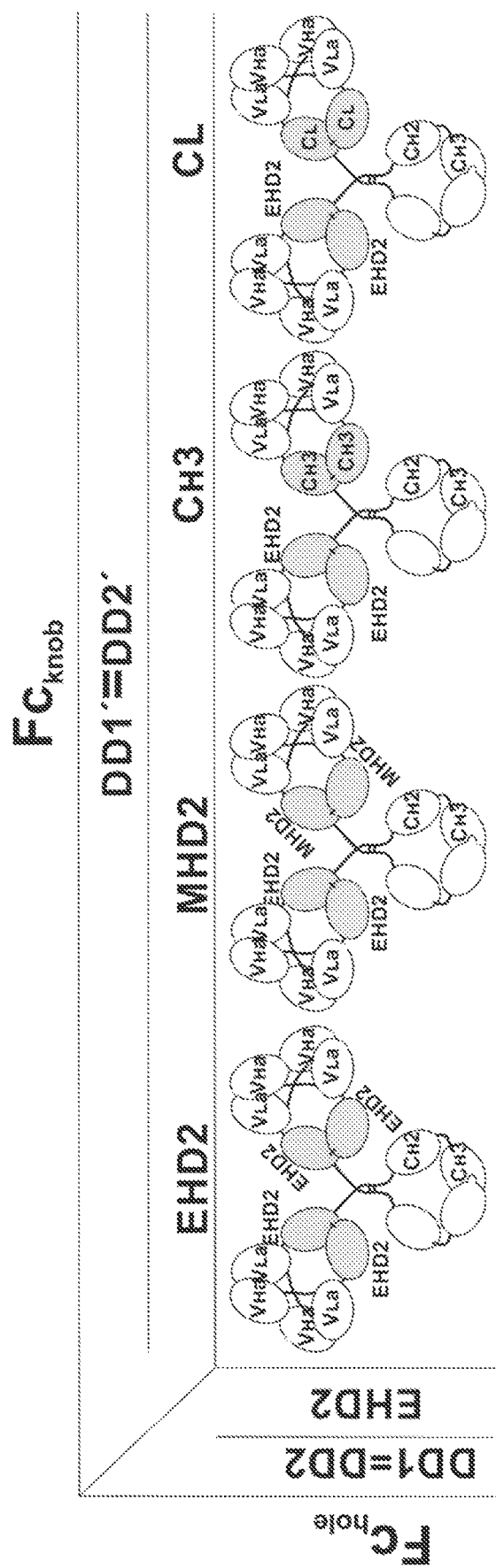
Figure 17E:
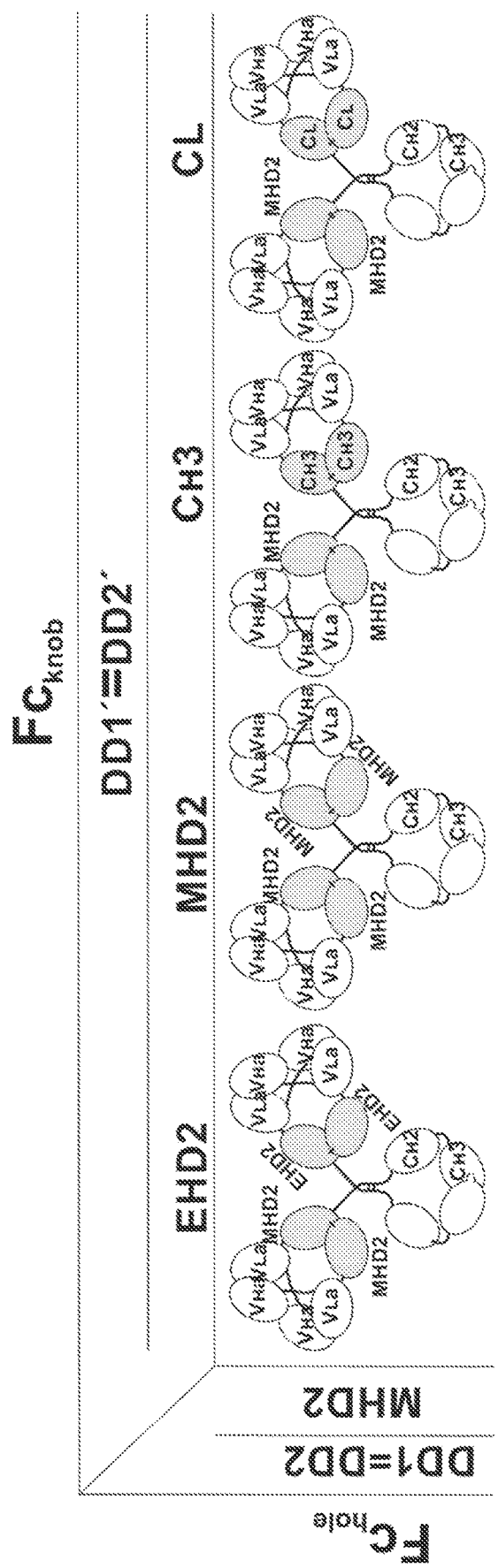
Figure 17F:
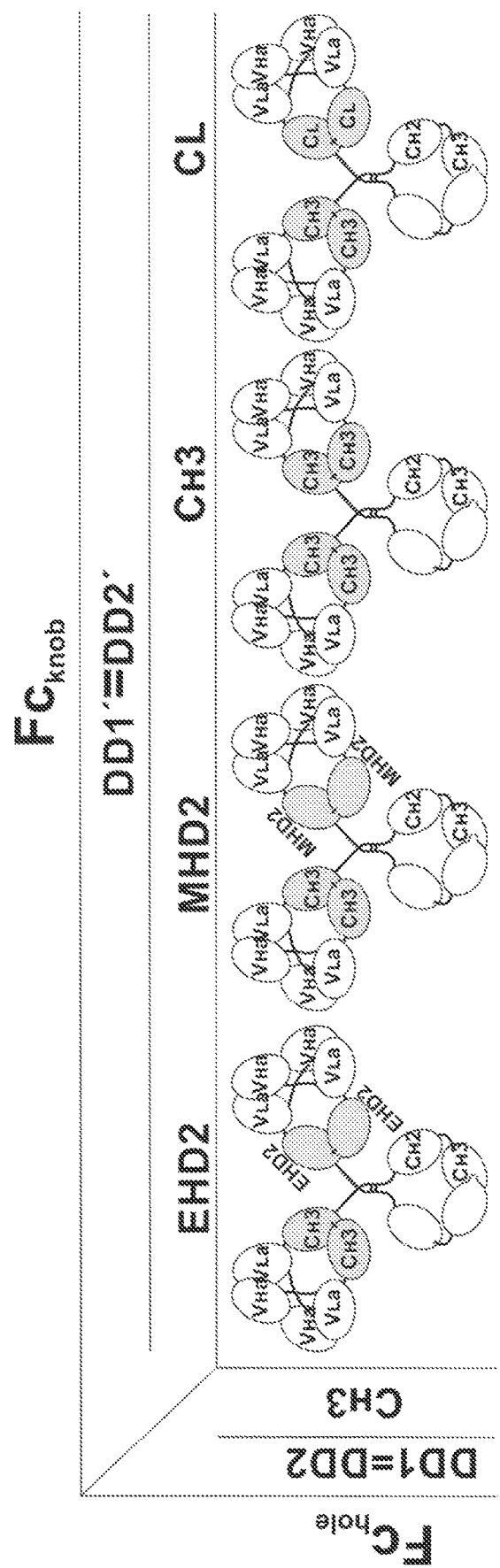
Figure 17G:
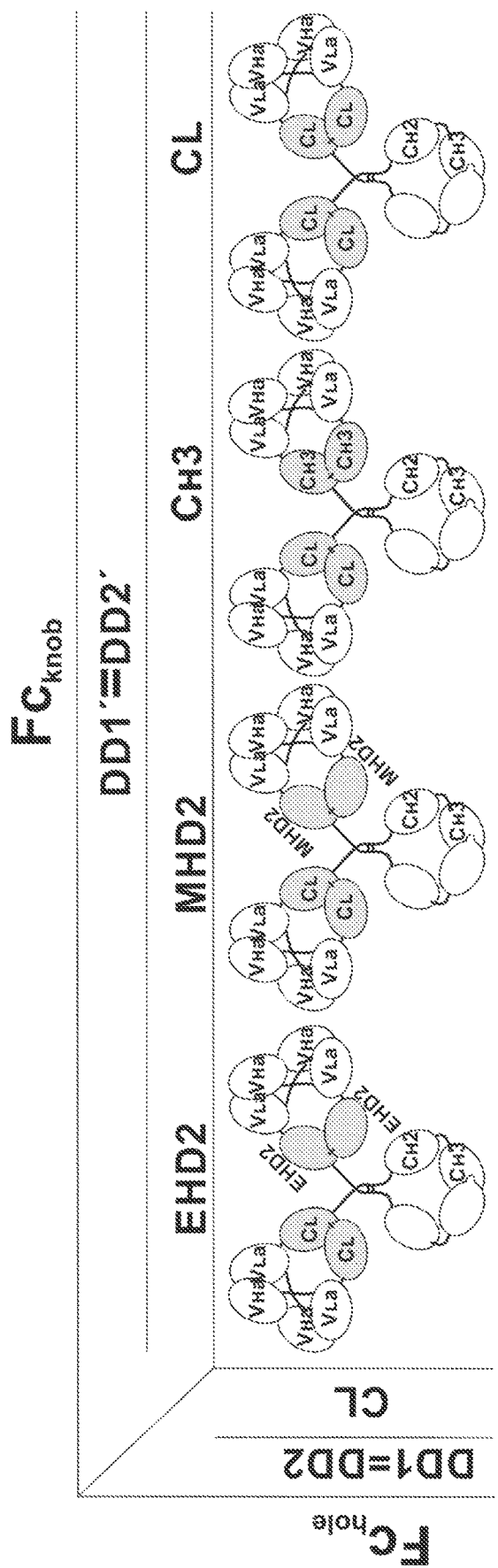
Figure 18:
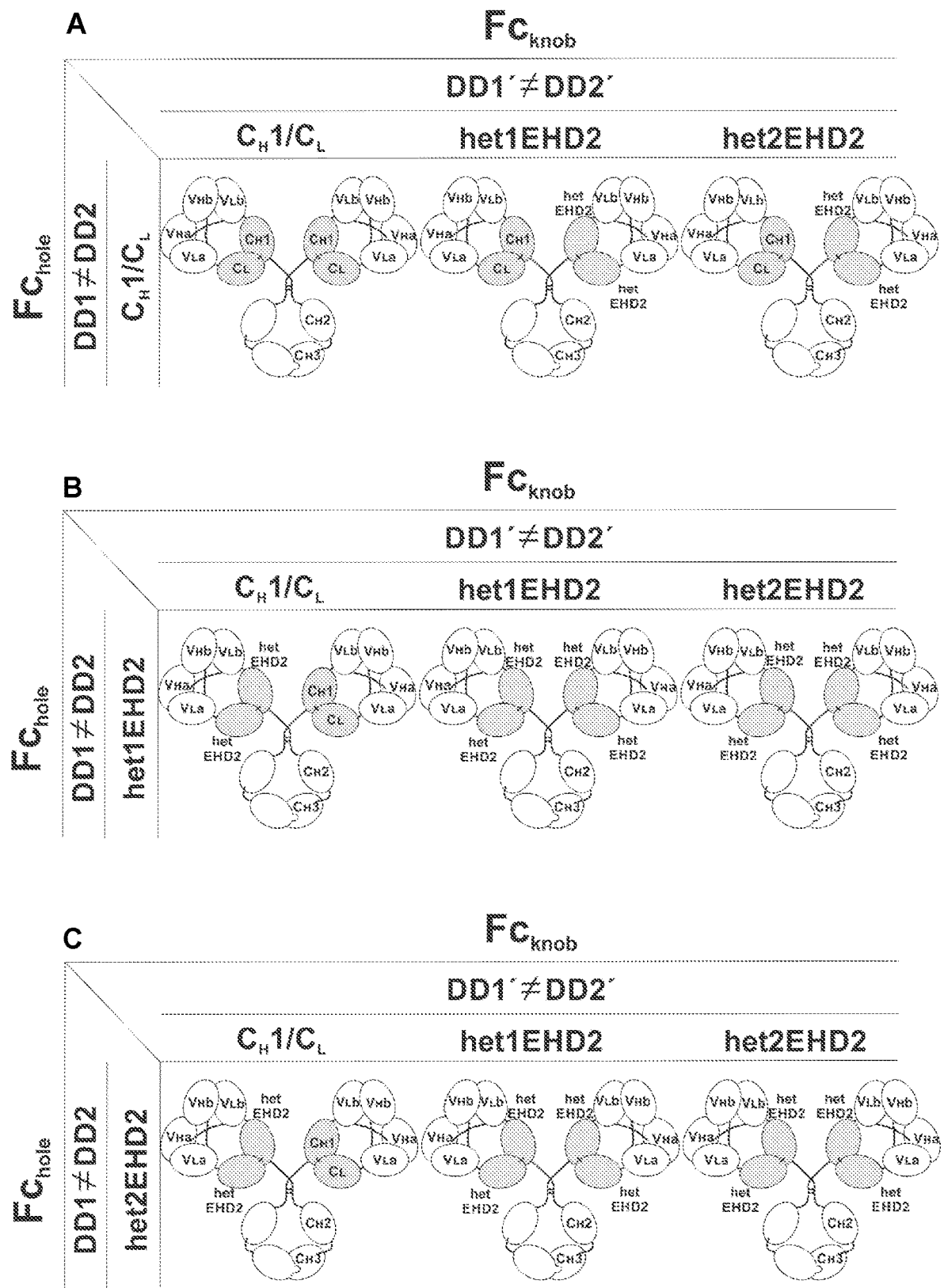
Figure 18:
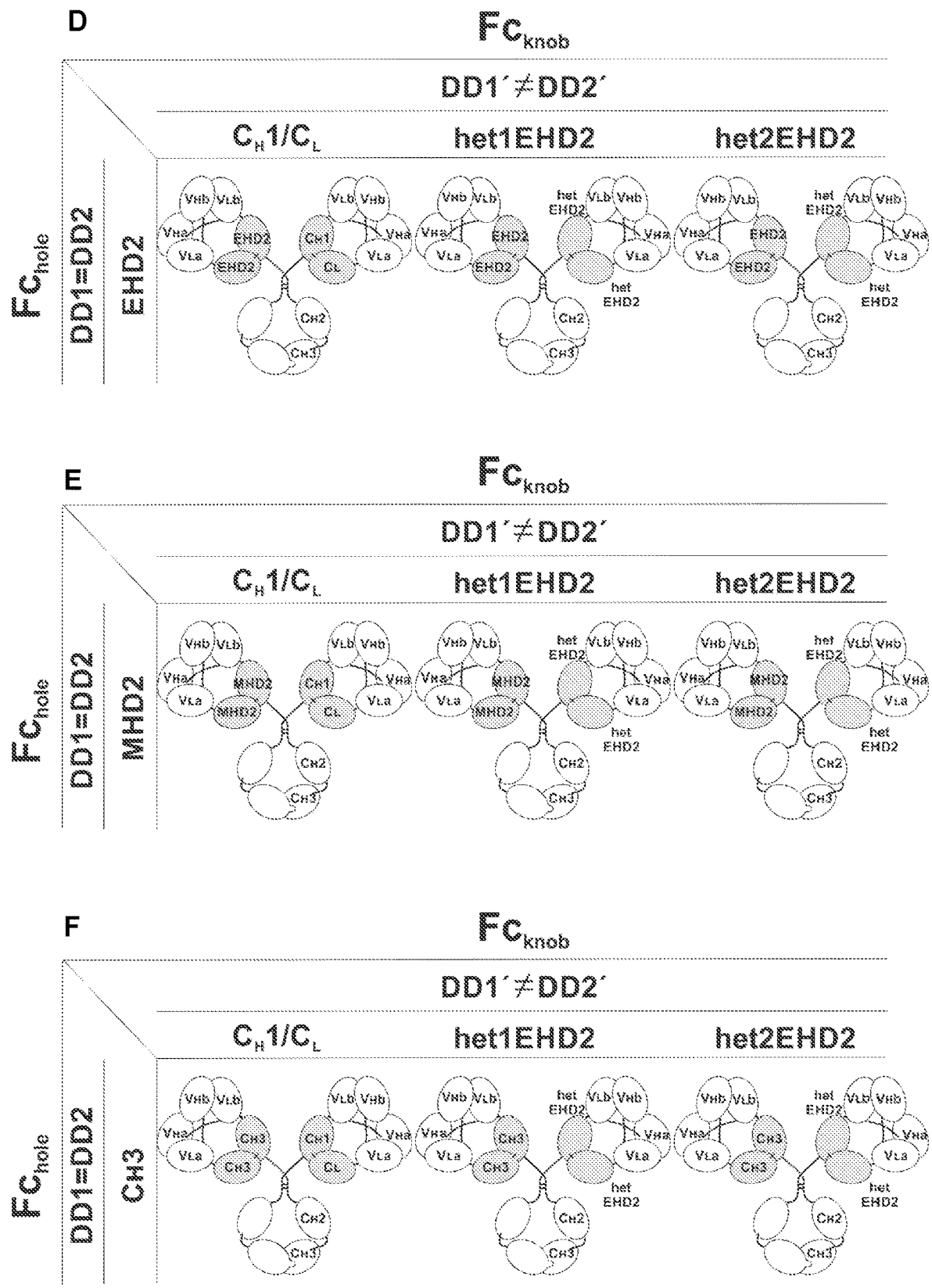
Figure 18:
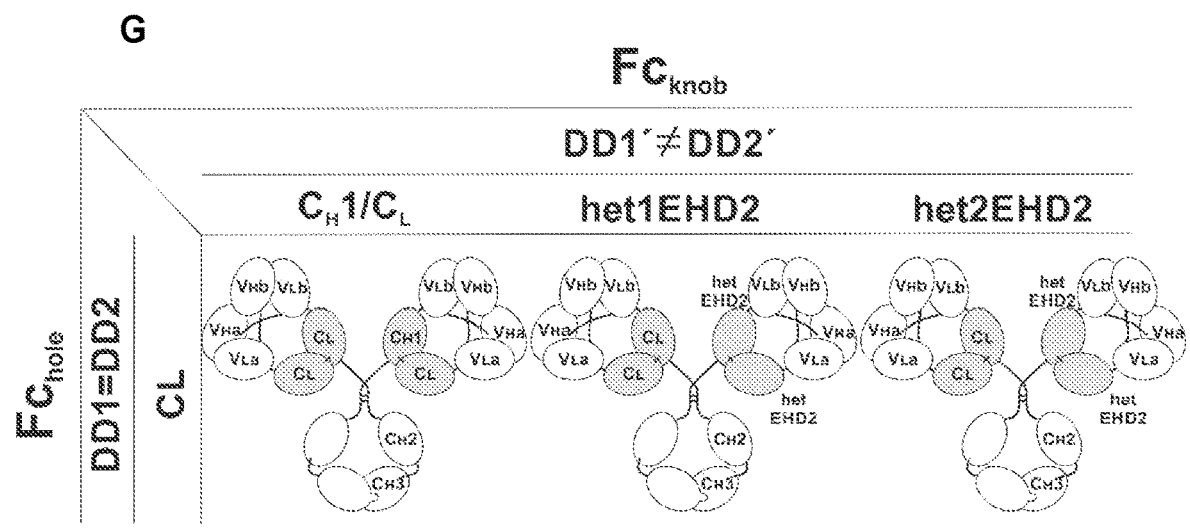
Figure 19A:
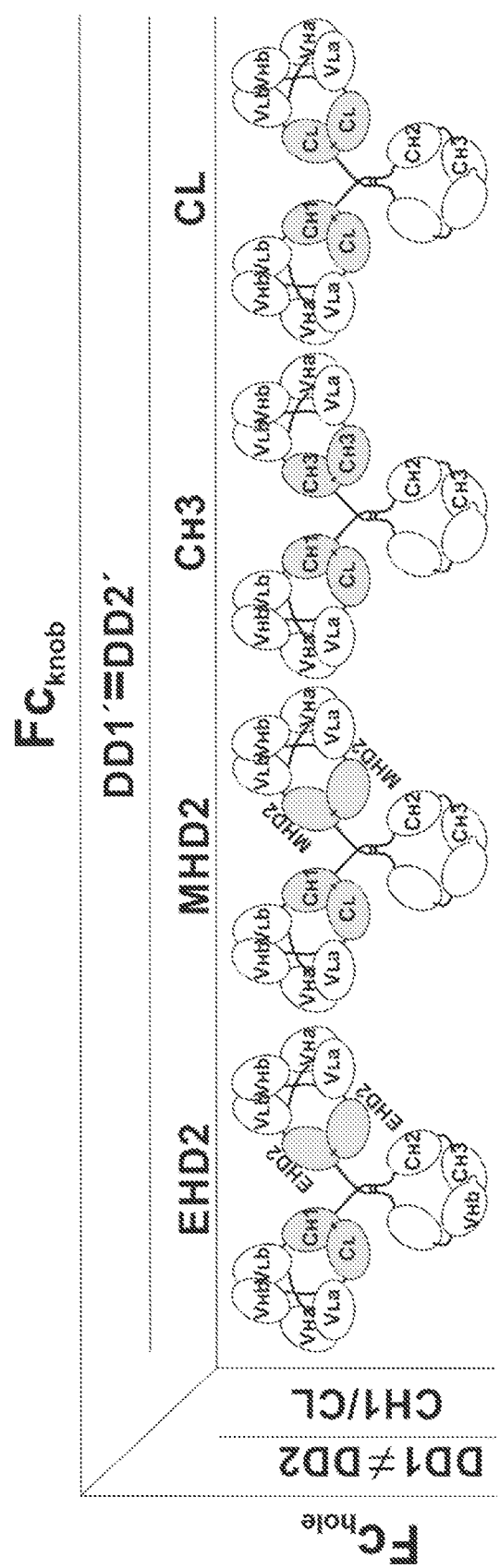
Figure 19B:
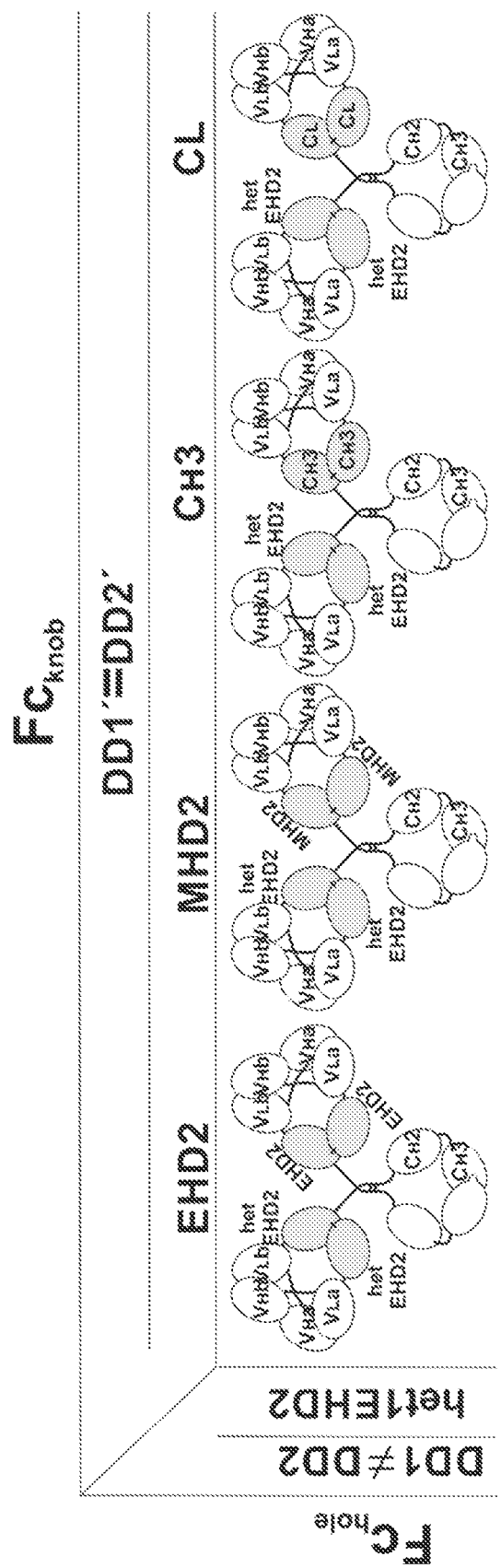
Figure 19C:
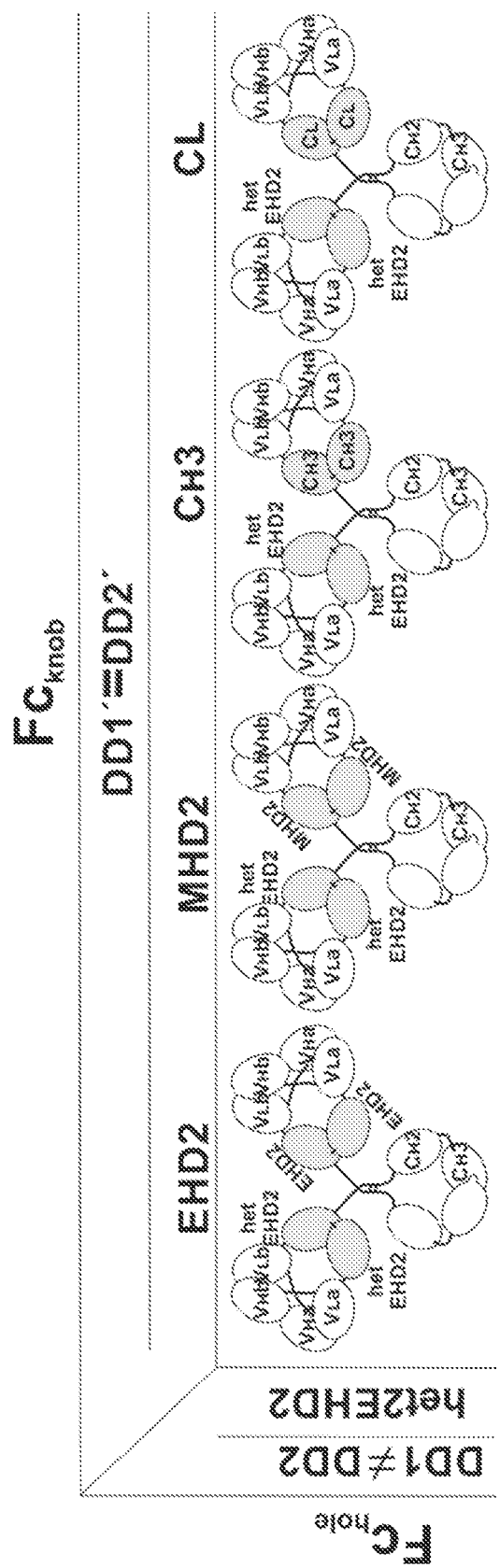
Figure 19D:
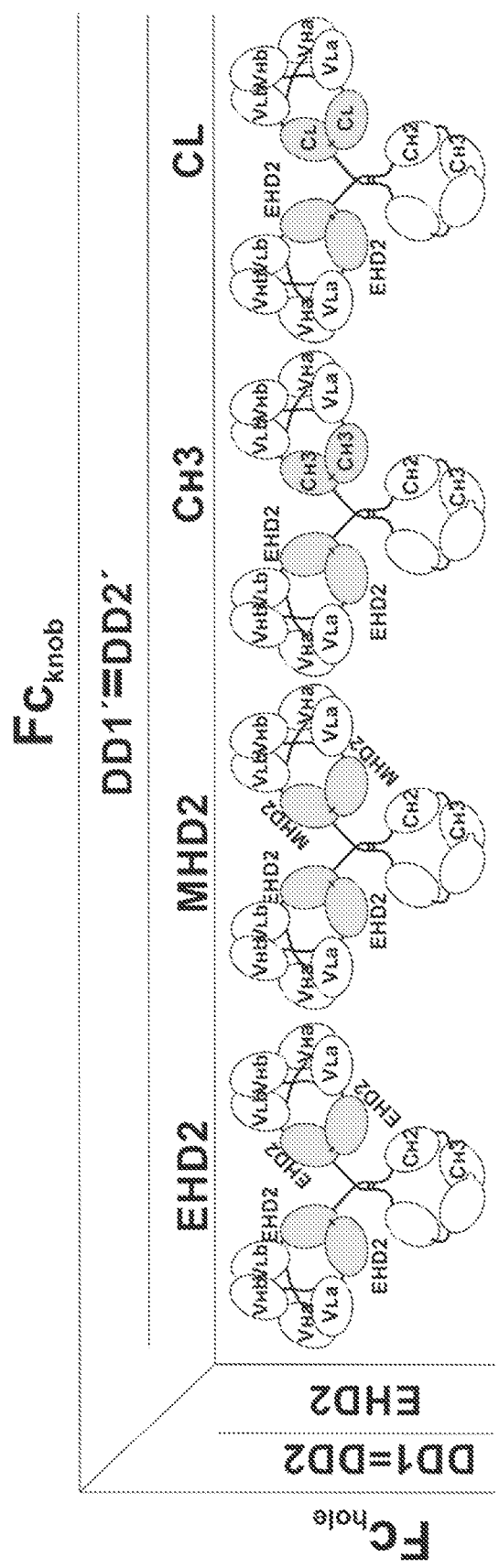
Figure 19E:
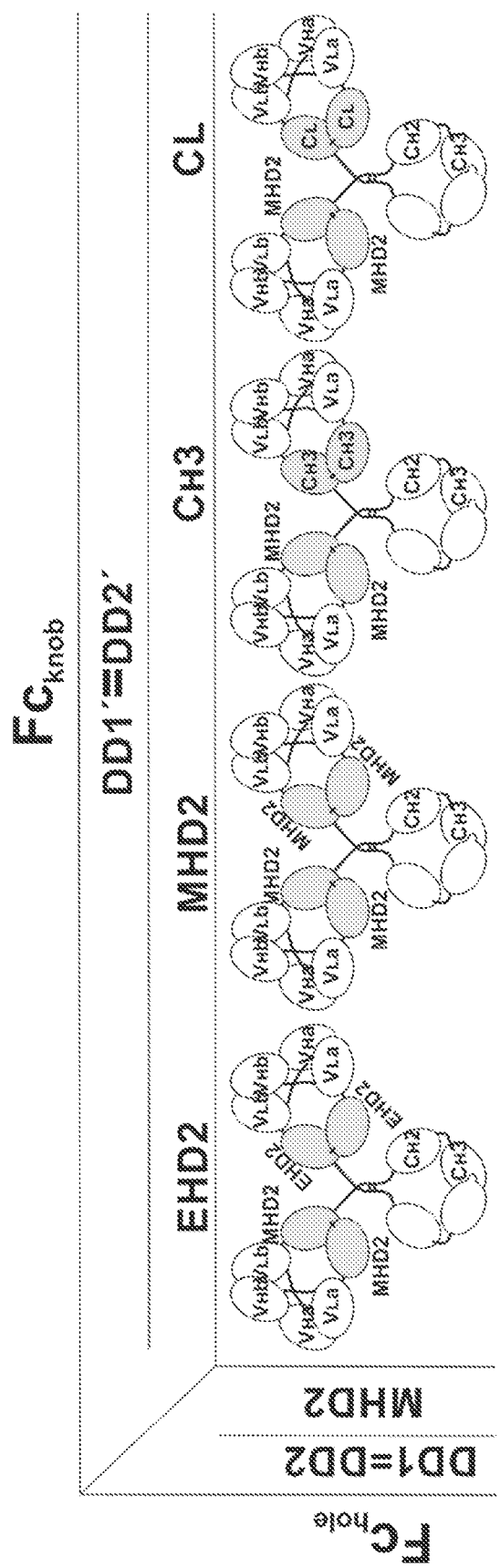
Figure 19F:
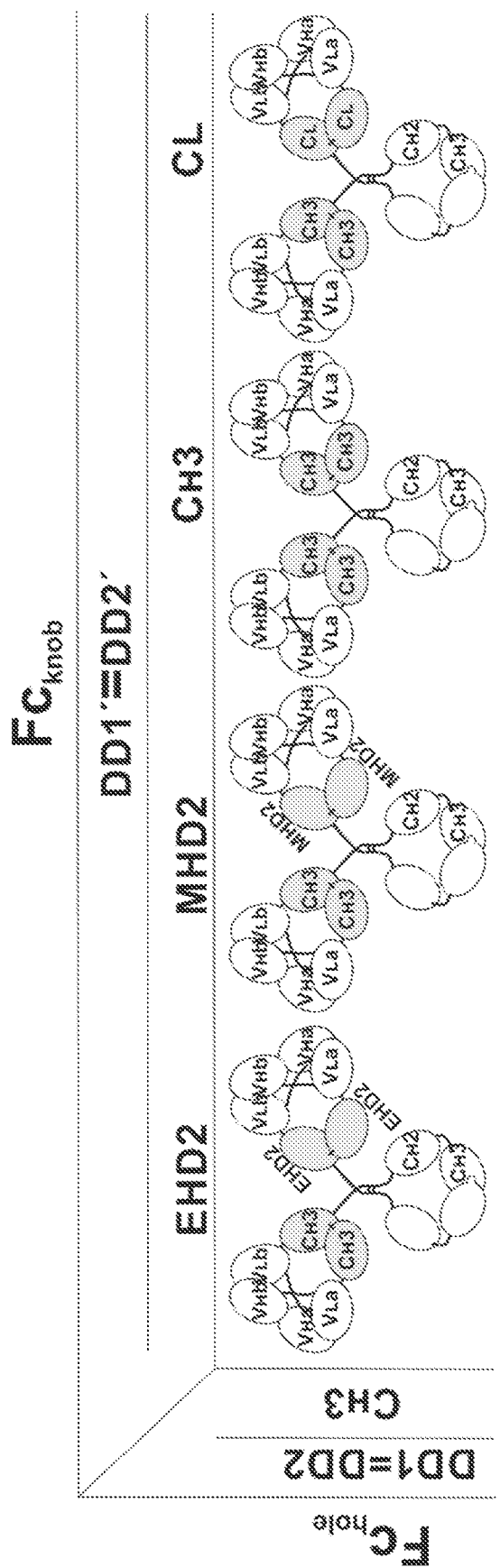
Figure 19G:
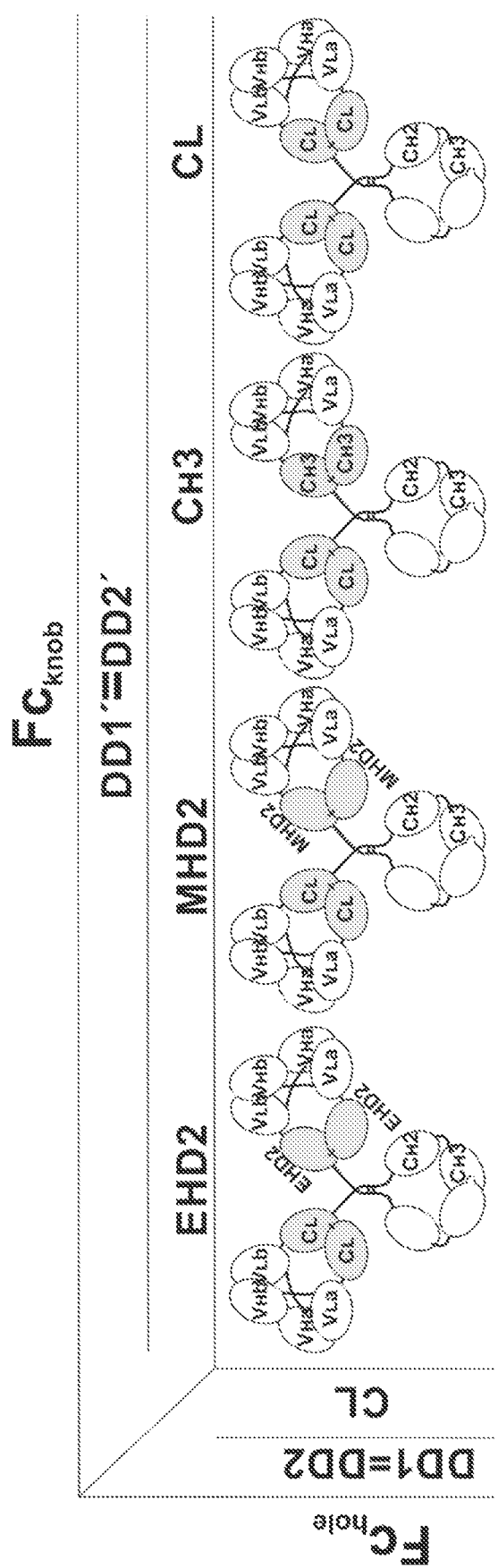
Figure 20:
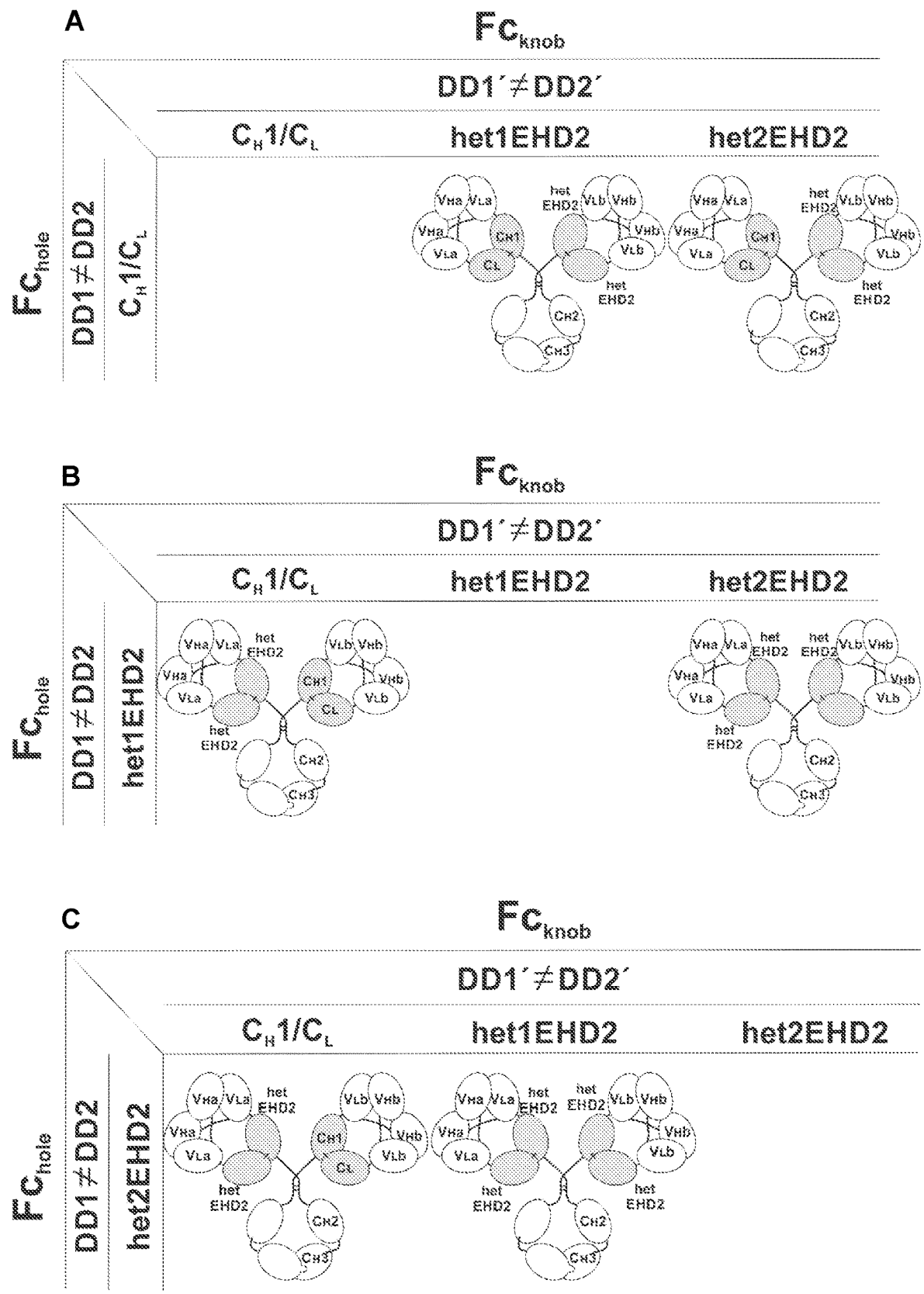
Figure 20:
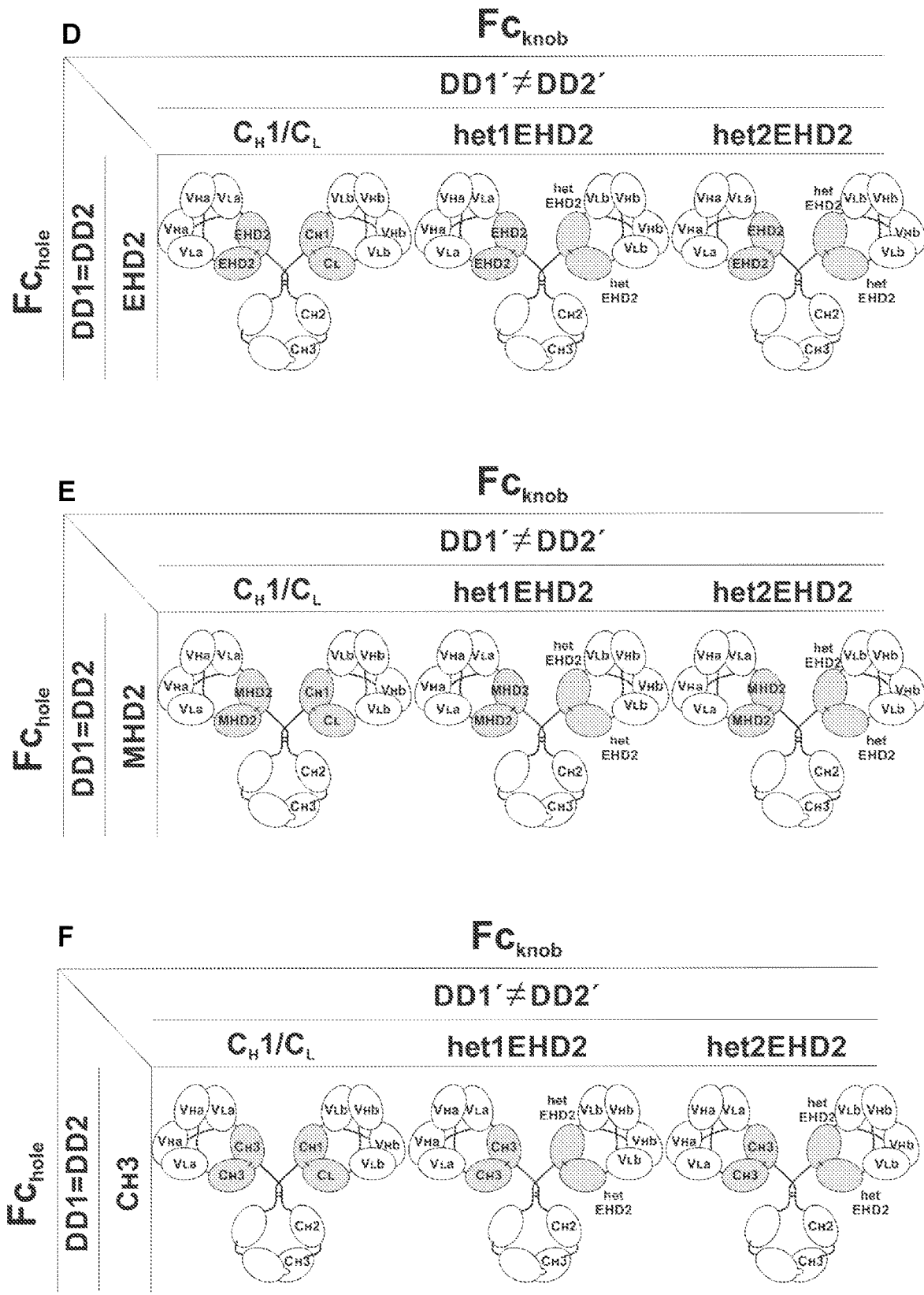
Figure 20:
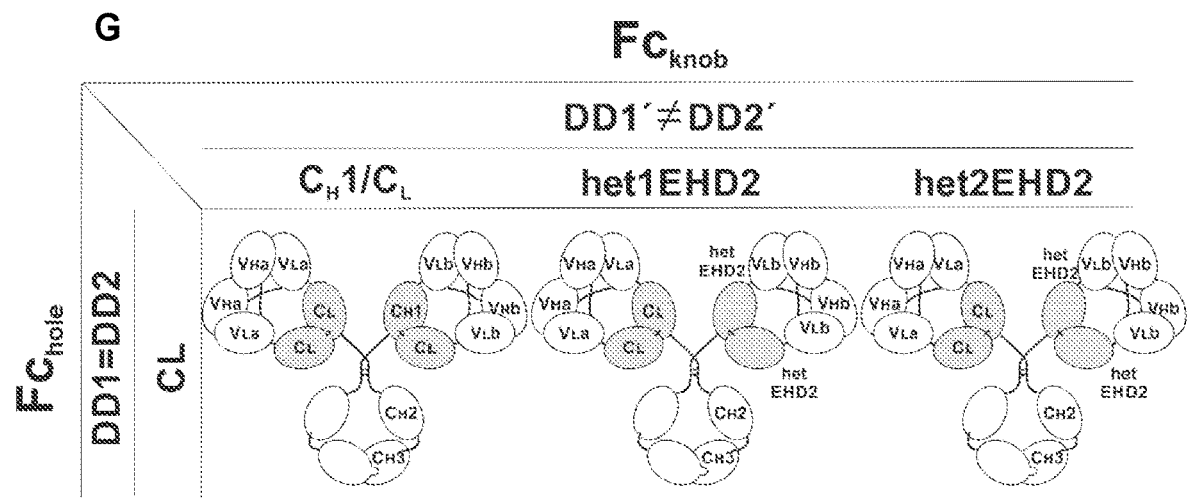
Figure 21A:
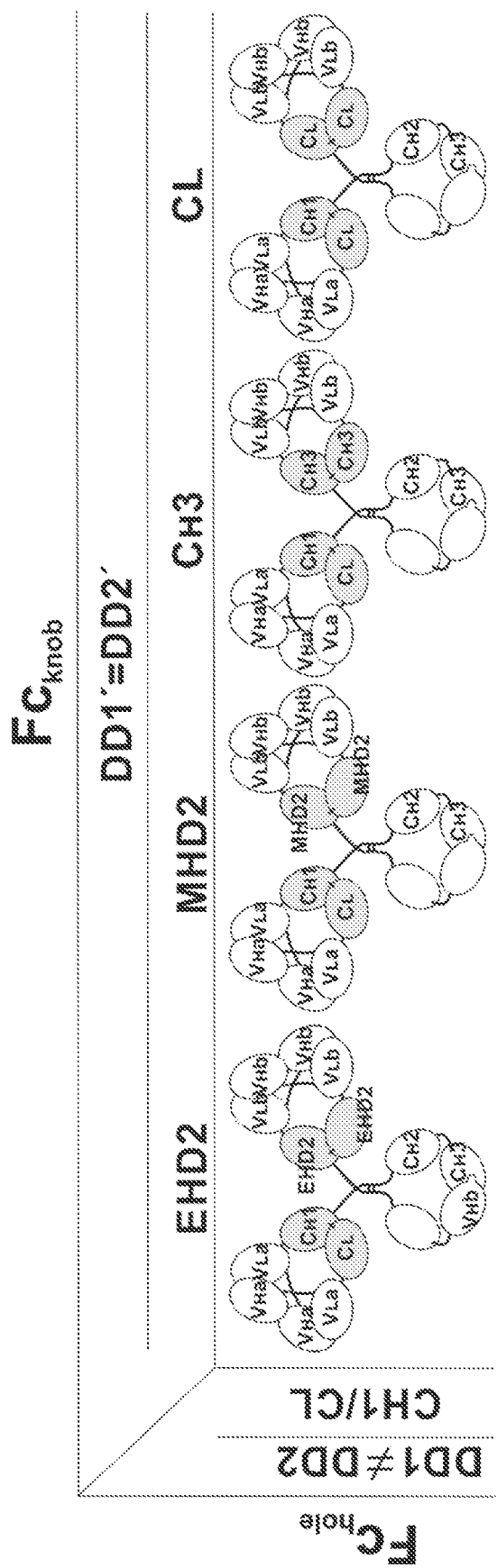
Figure 21B:
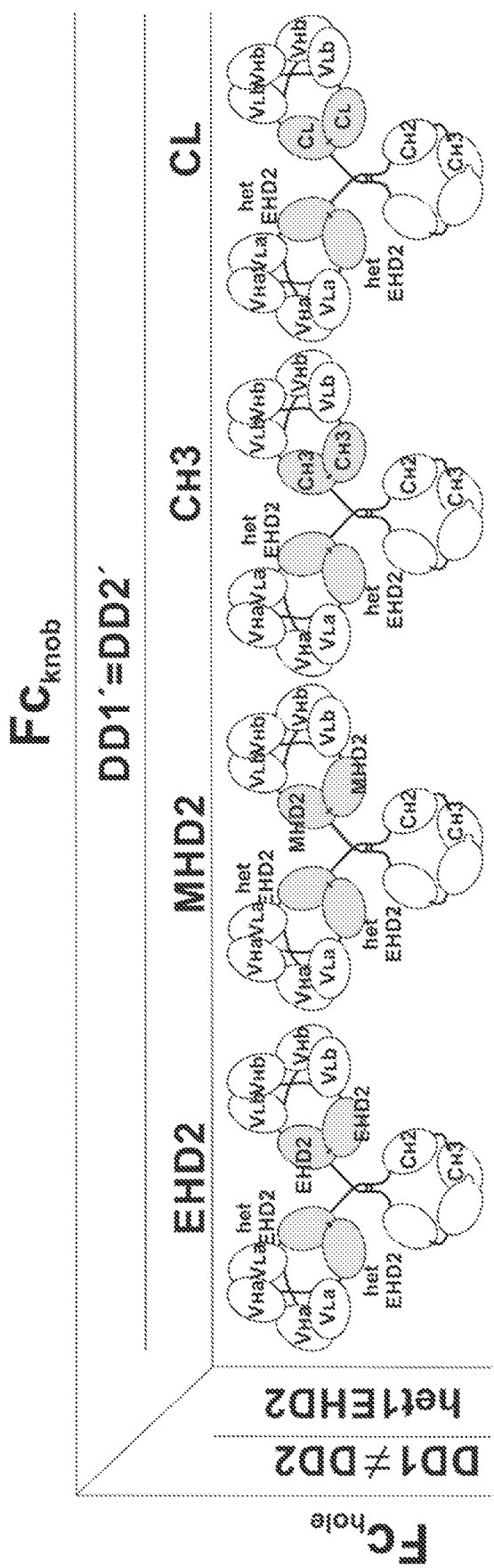
Figure 21C:
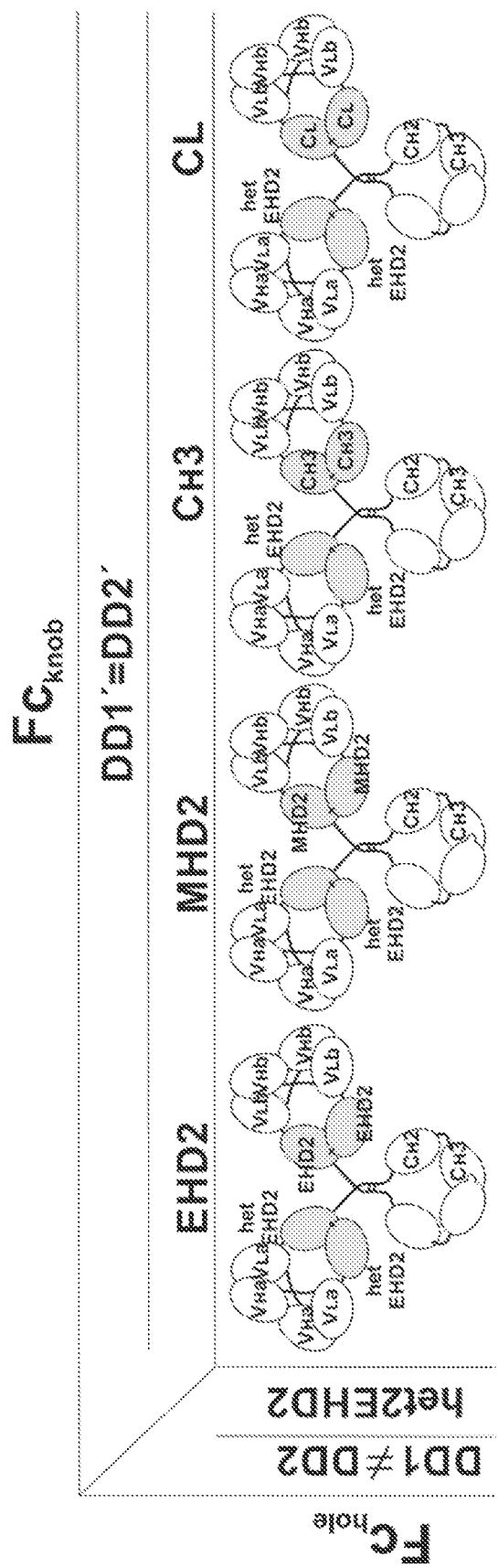
Figure 21D:
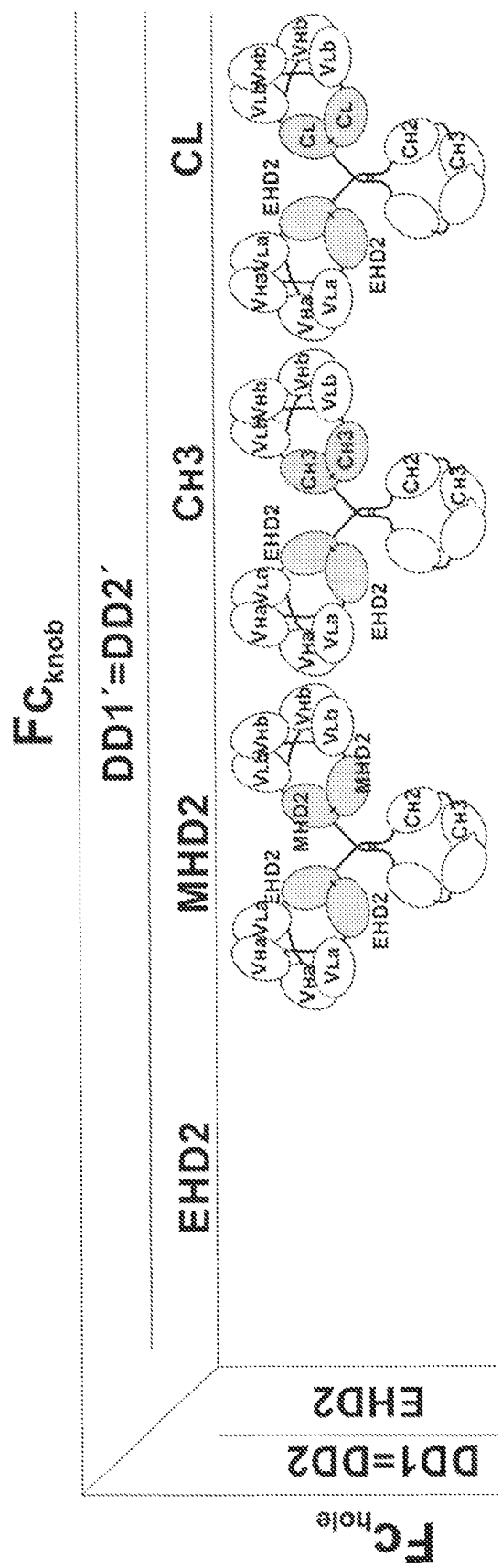
Figure 21E:
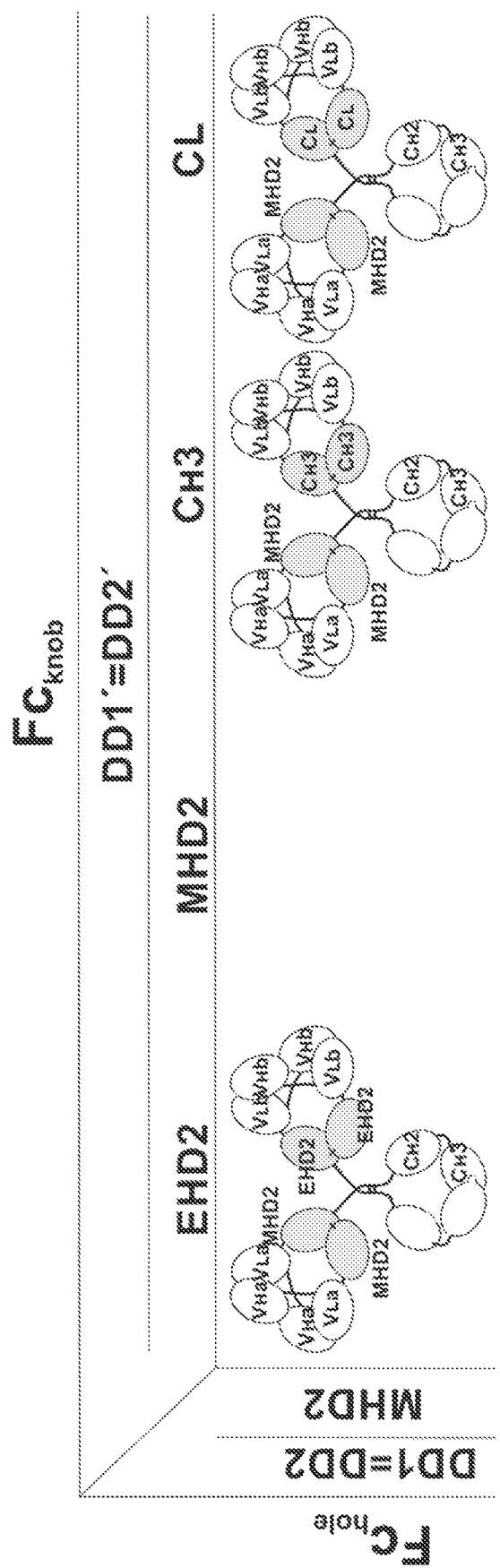
Figure 21F:
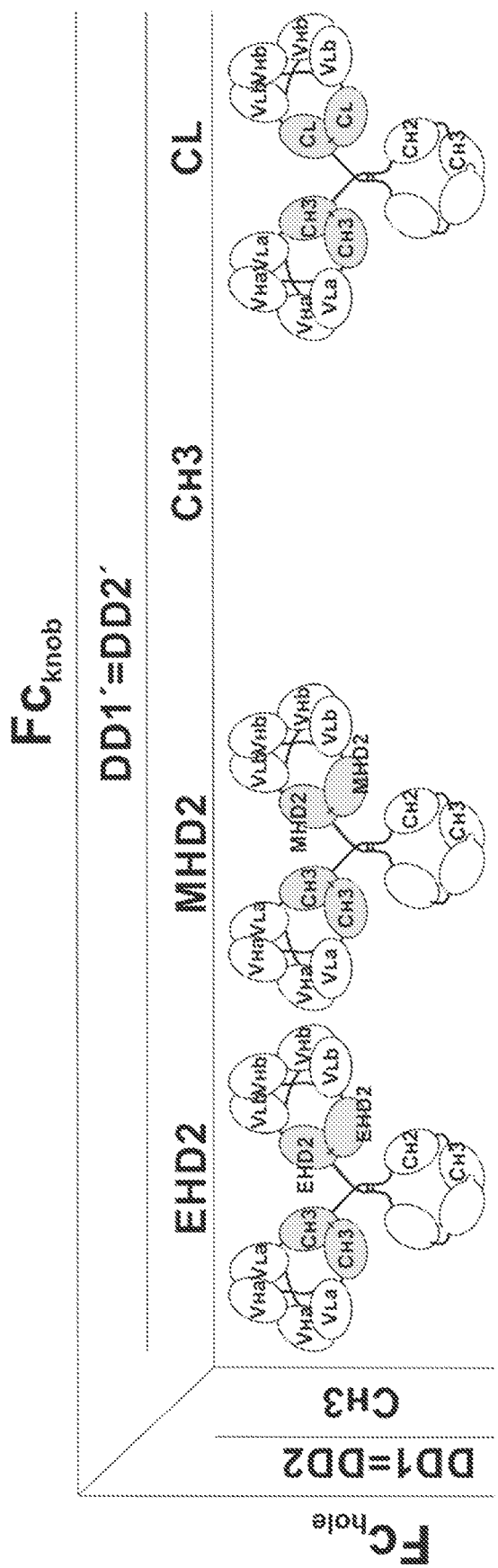
Figure 21G:
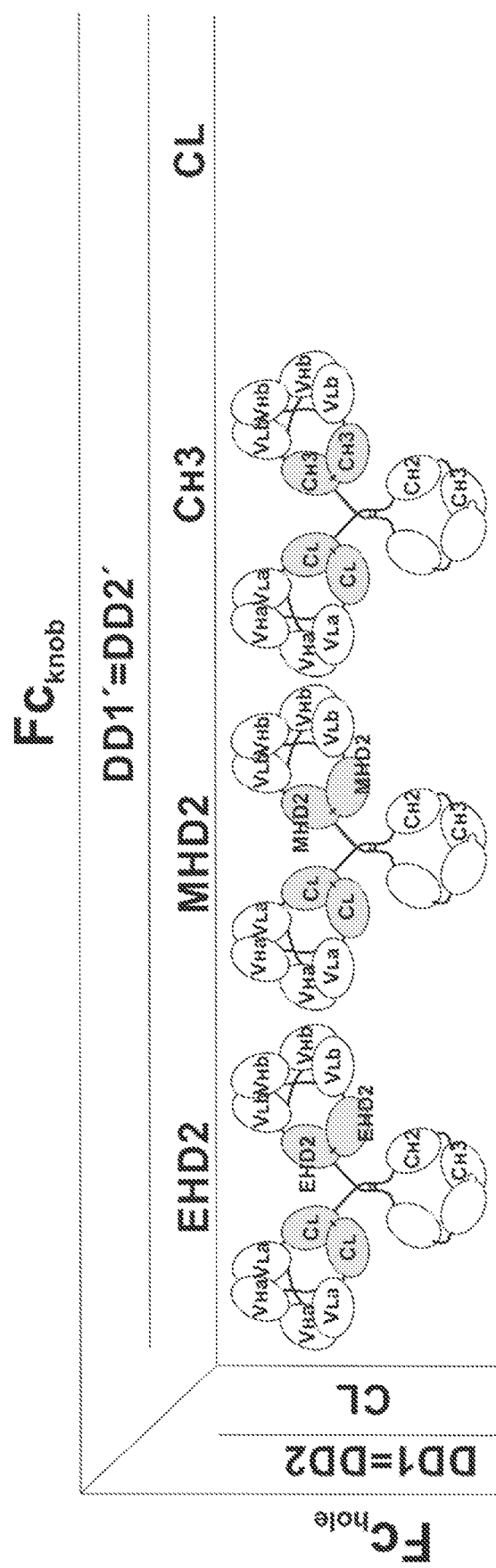
Figure 22:
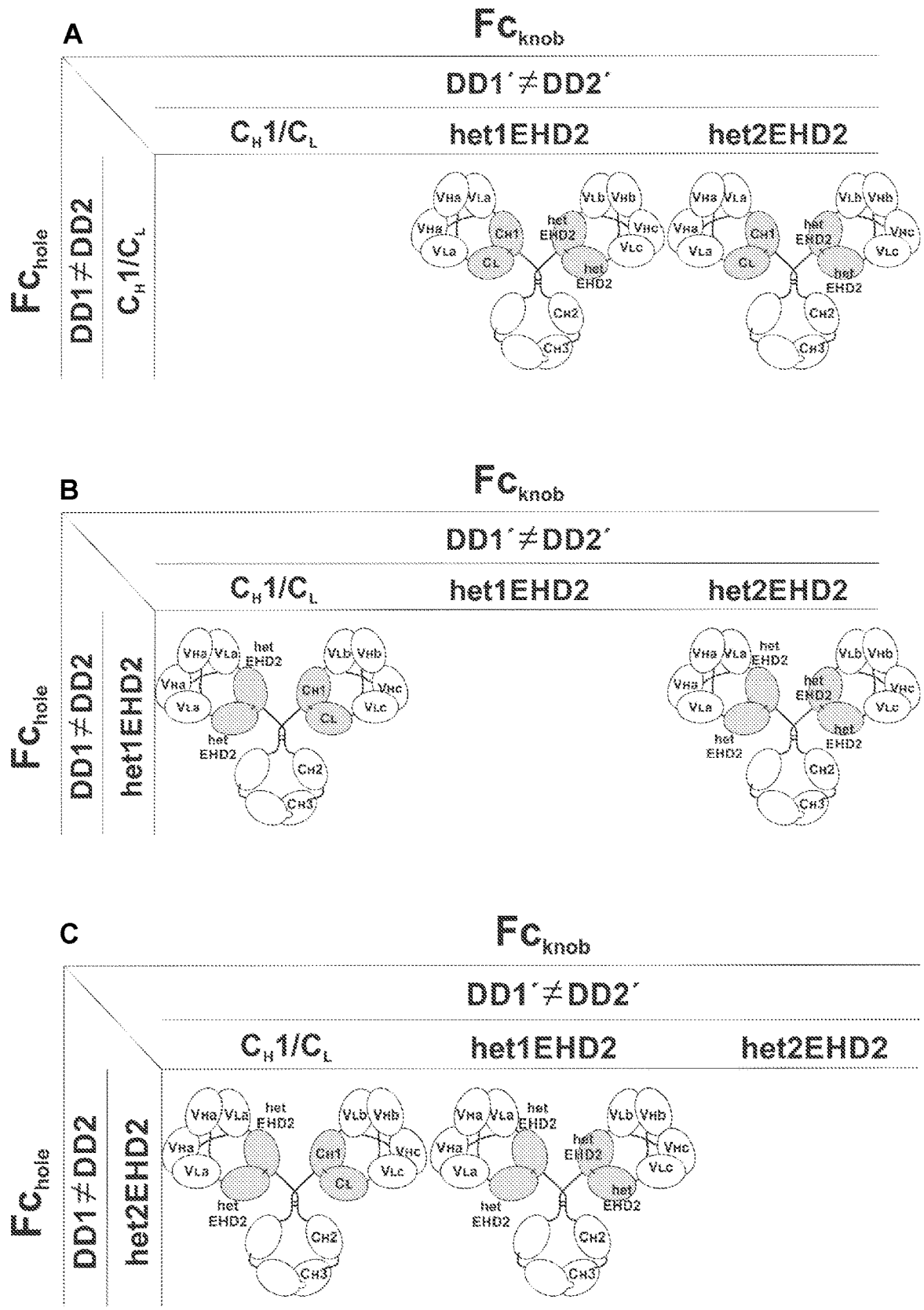
Figure 22:
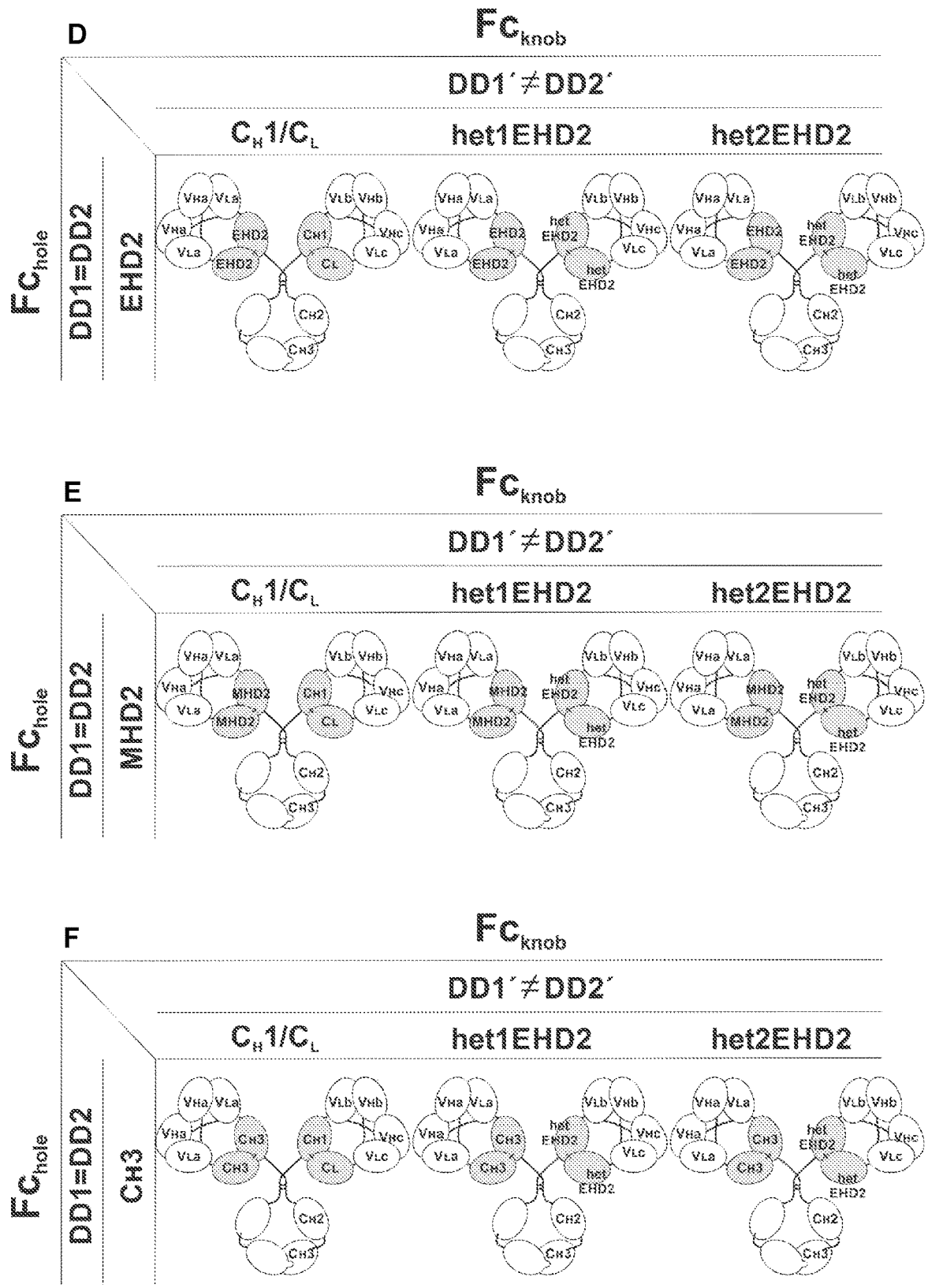
Figure 22:
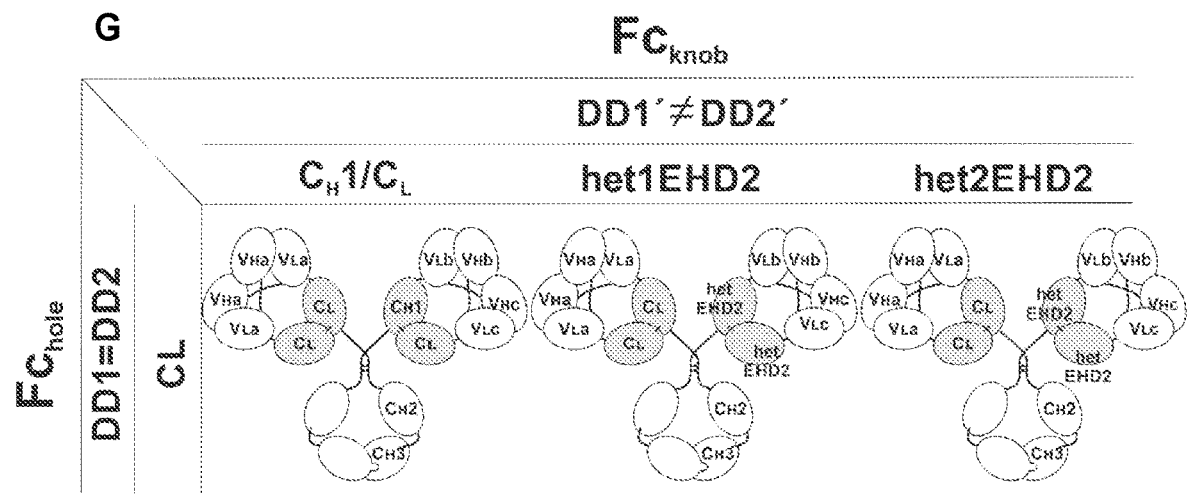
Figure 23A:
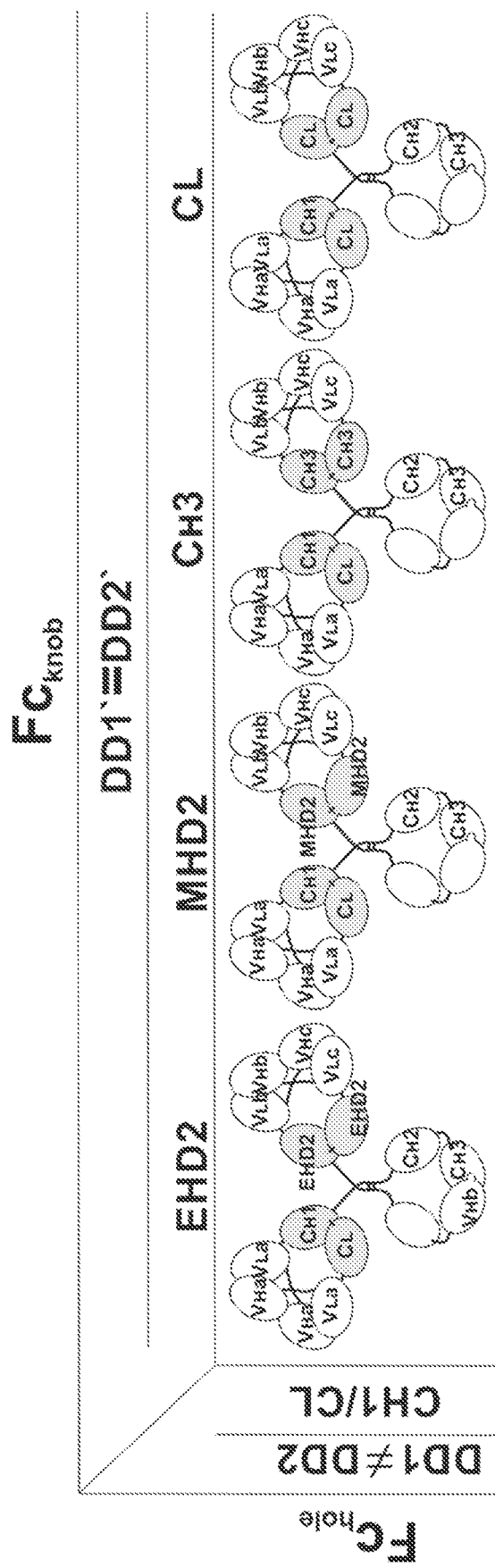
Figure 23B:
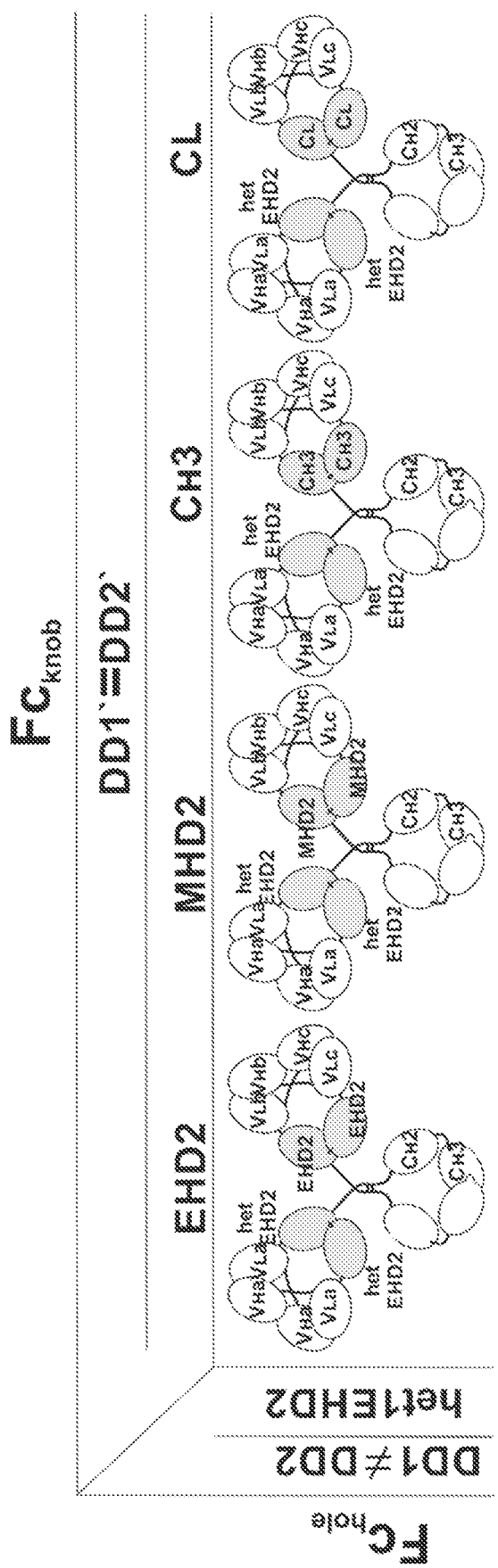
Figure 23C:
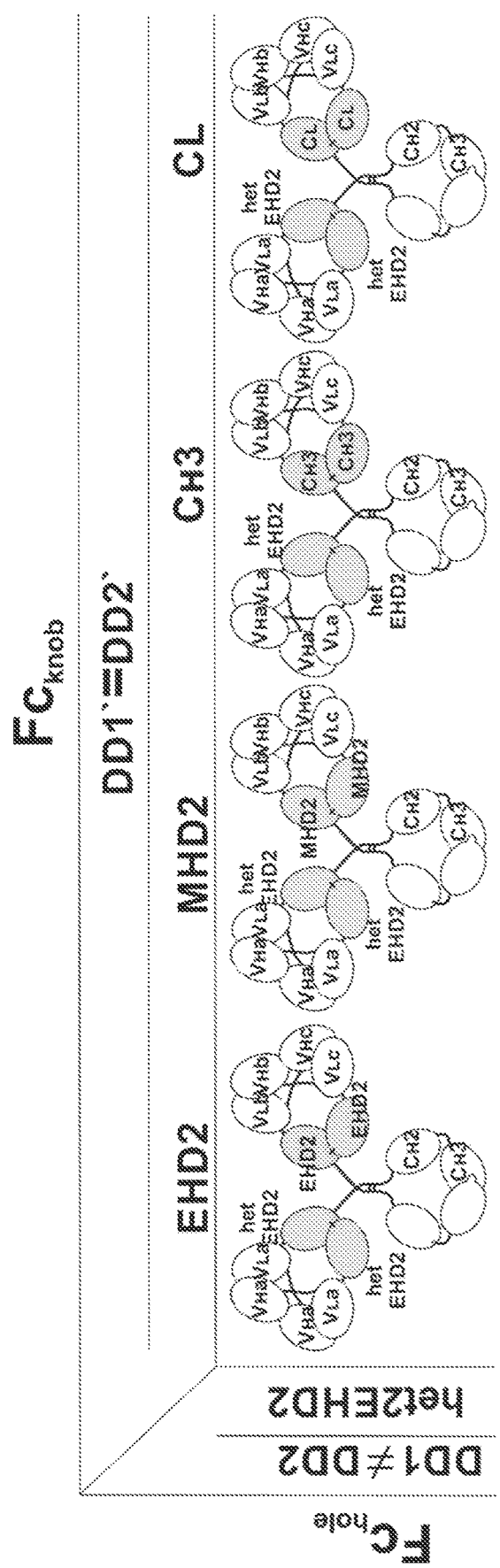
Figure 23D:
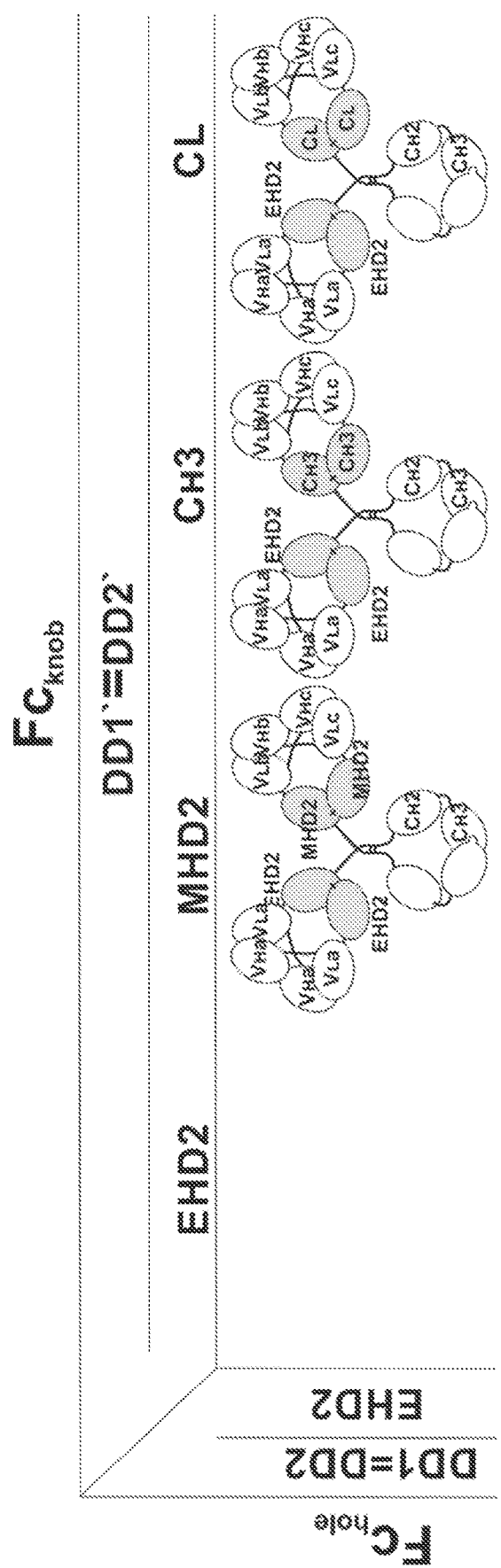
Figure 23E:
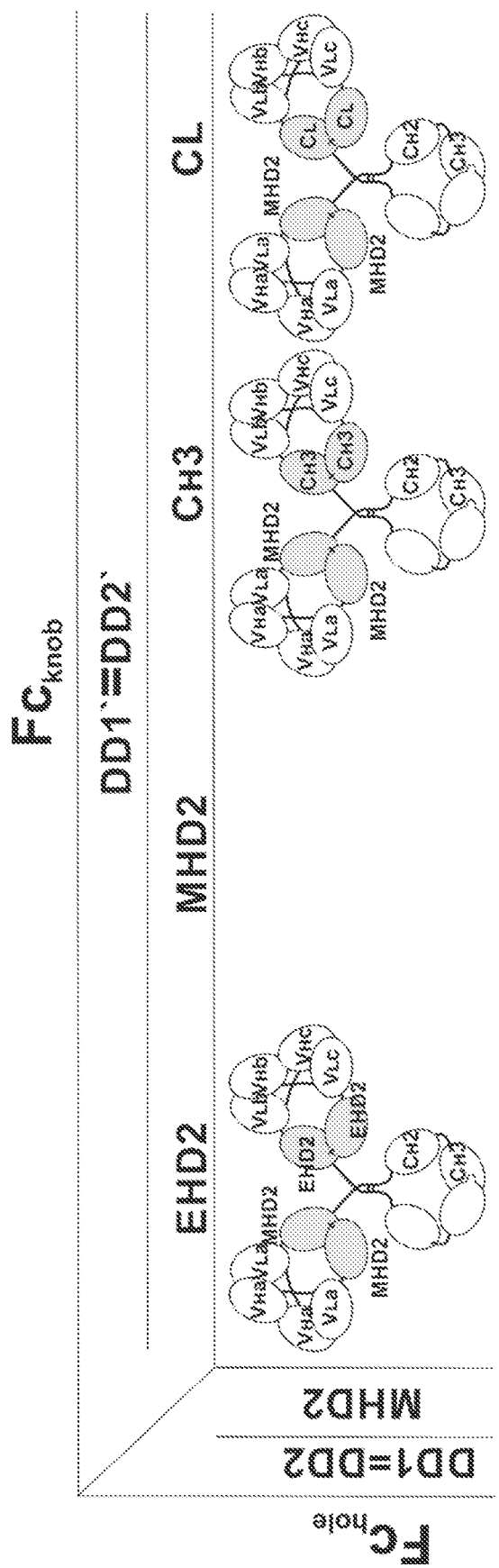
Figure 23F:
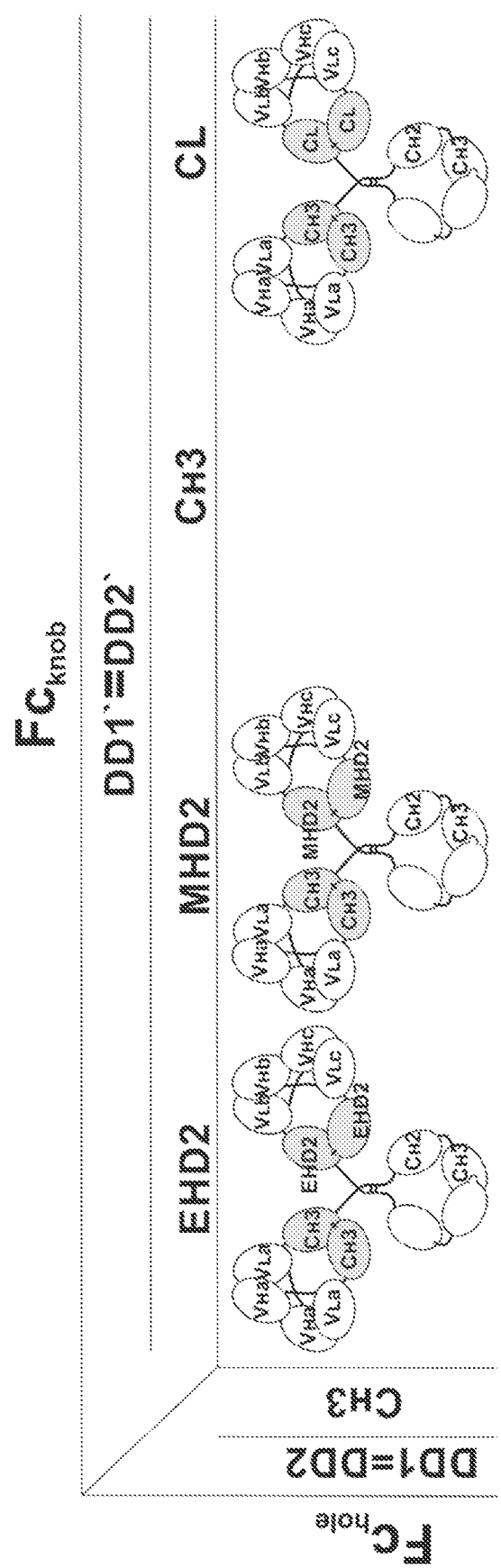
Figure 23G:
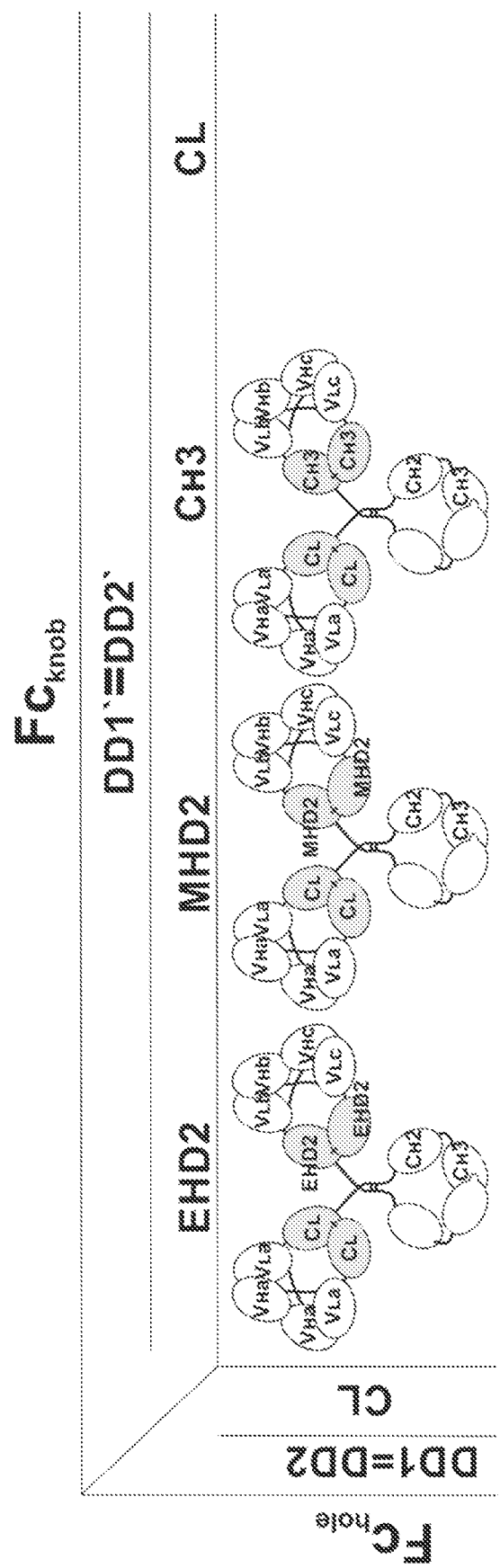
Figure 24:
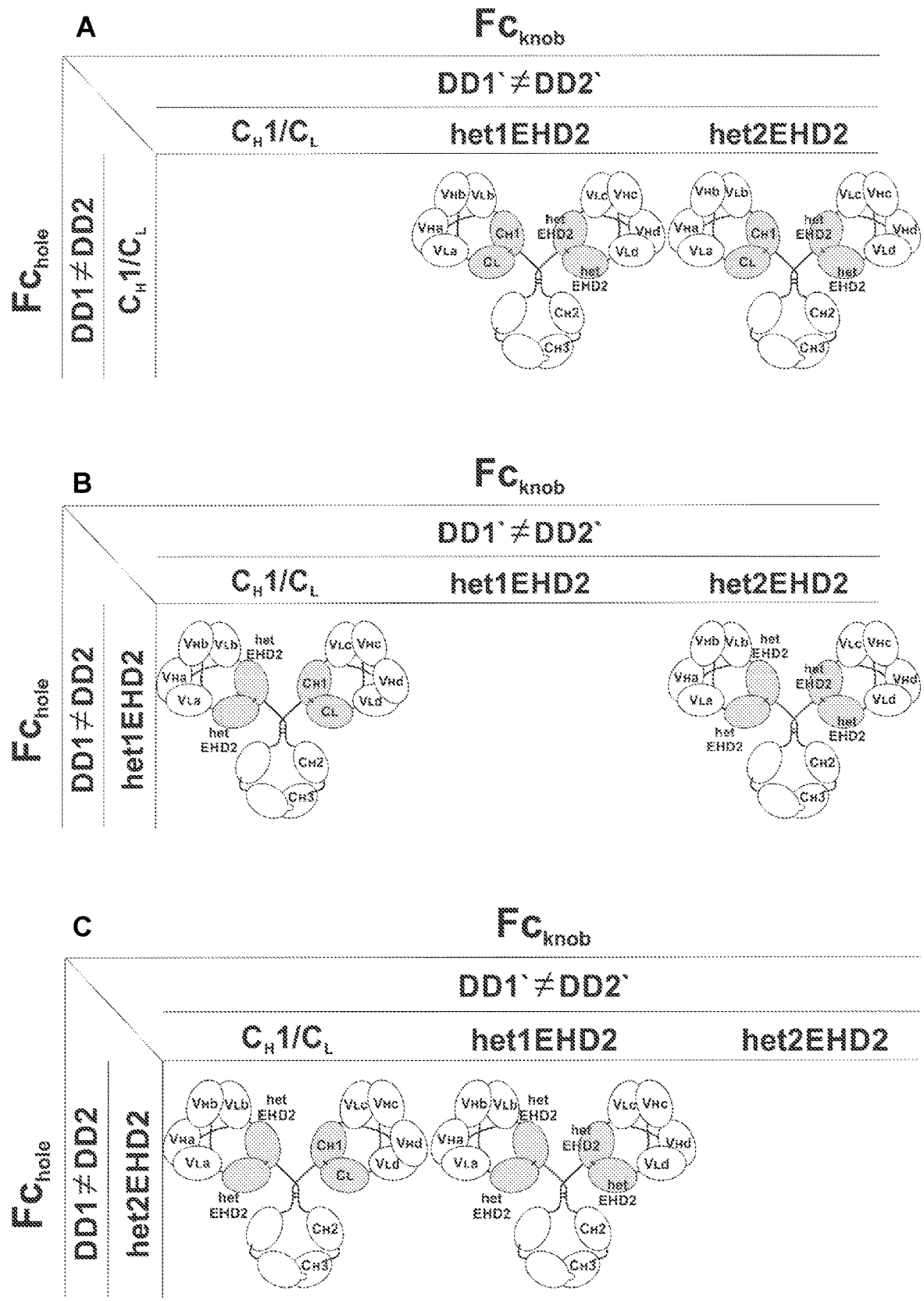
Figure 24:
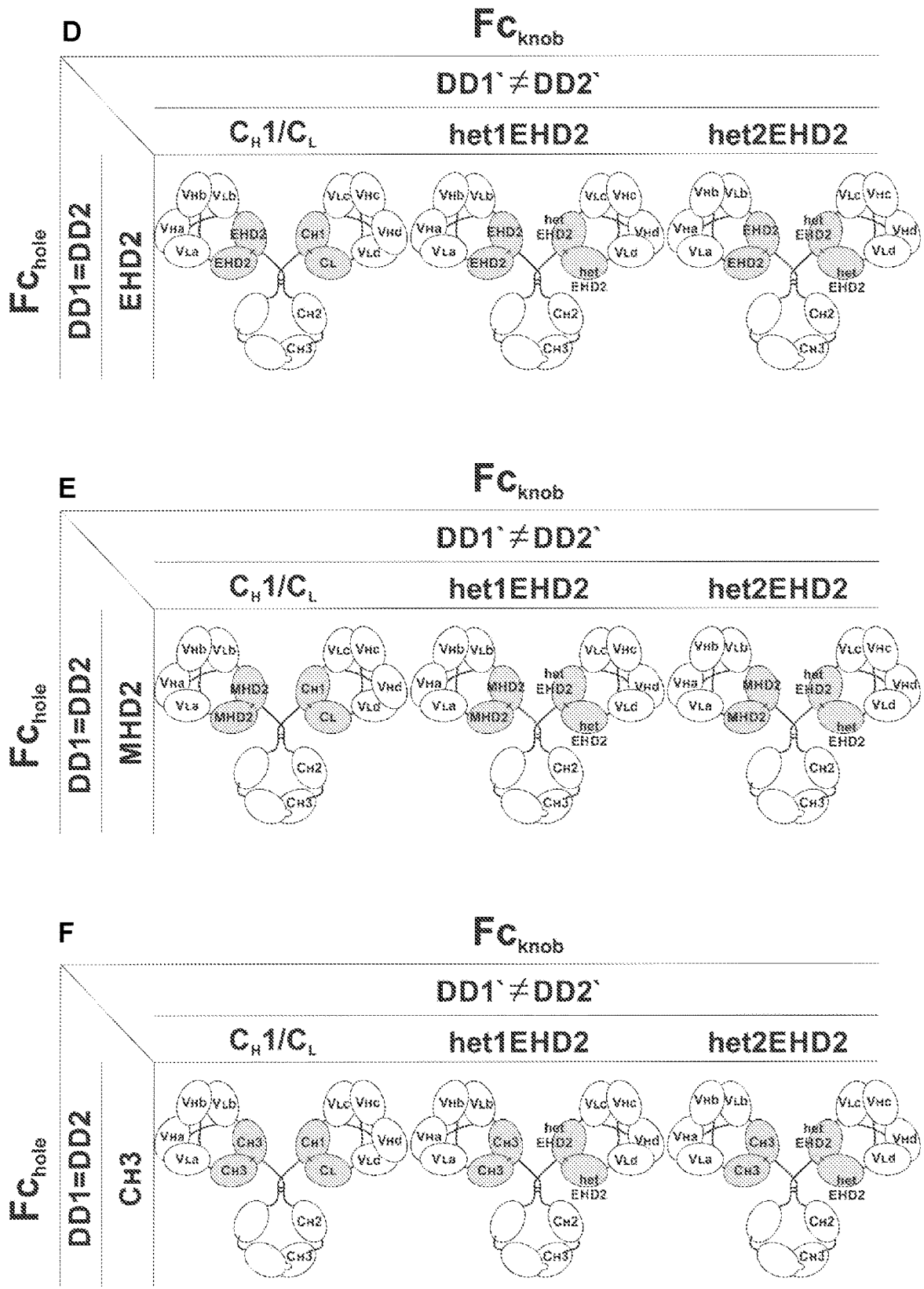
Figure 24:
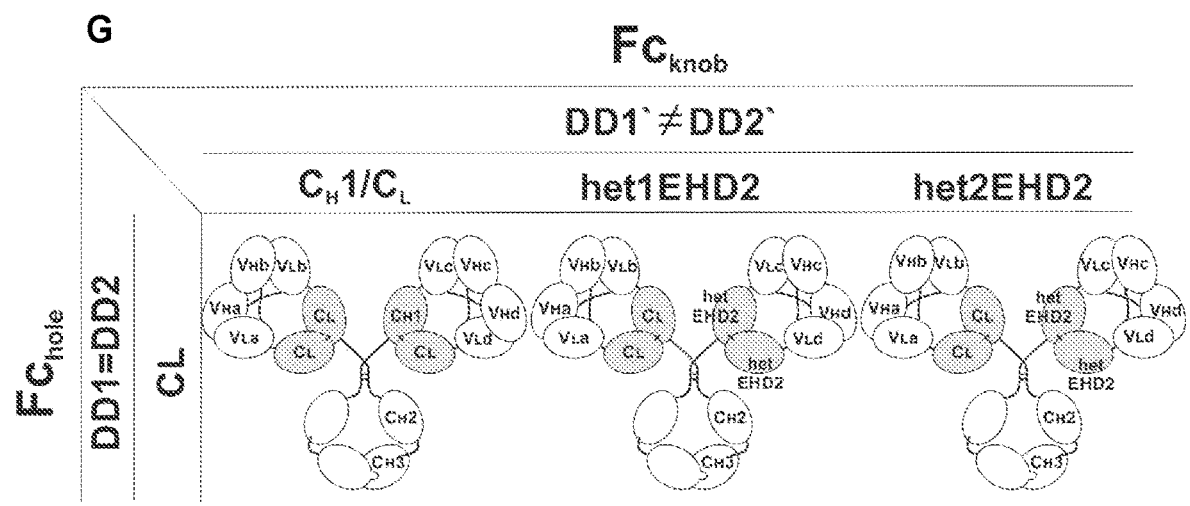
Figure 25A:
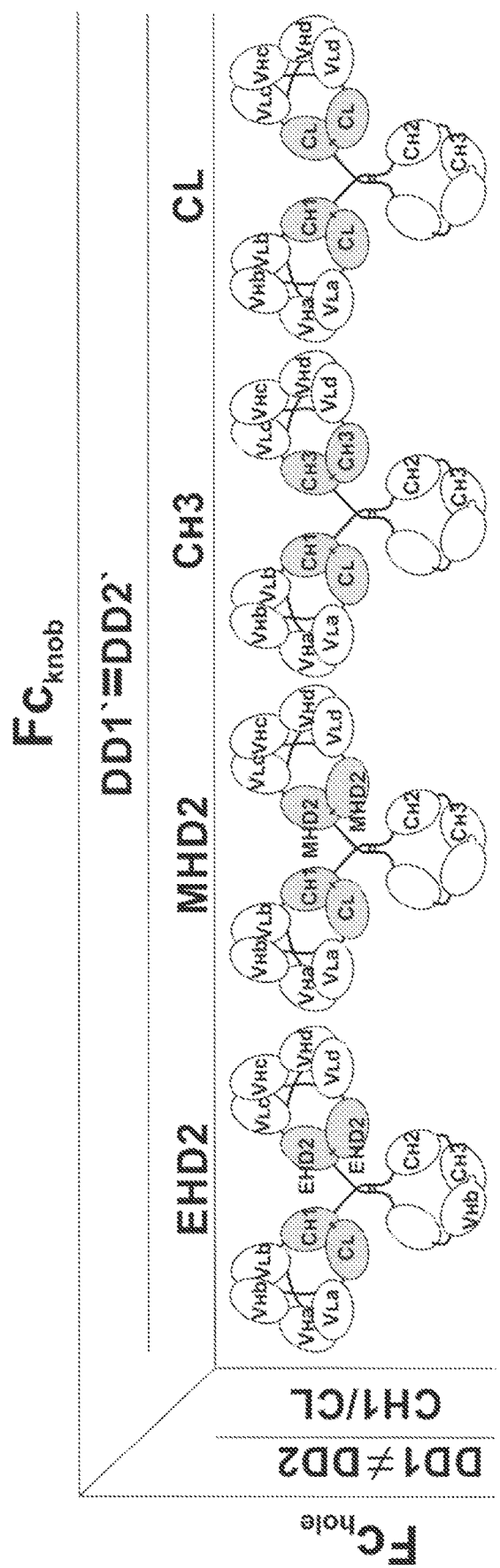
Figure 25B:
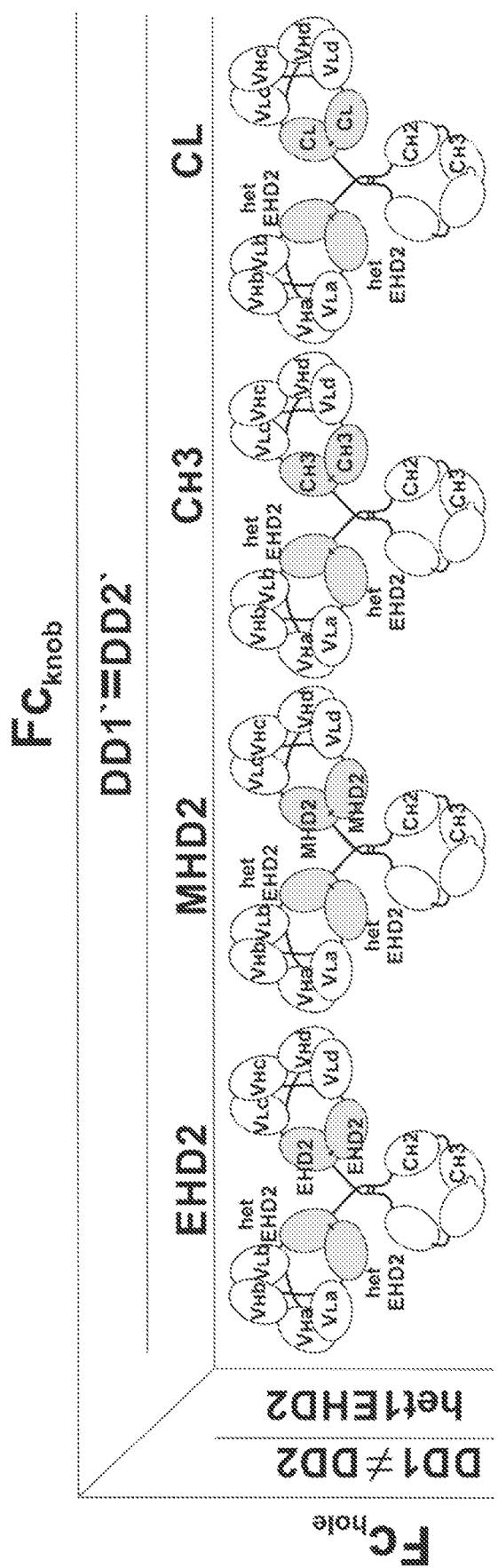
Figure 25C:
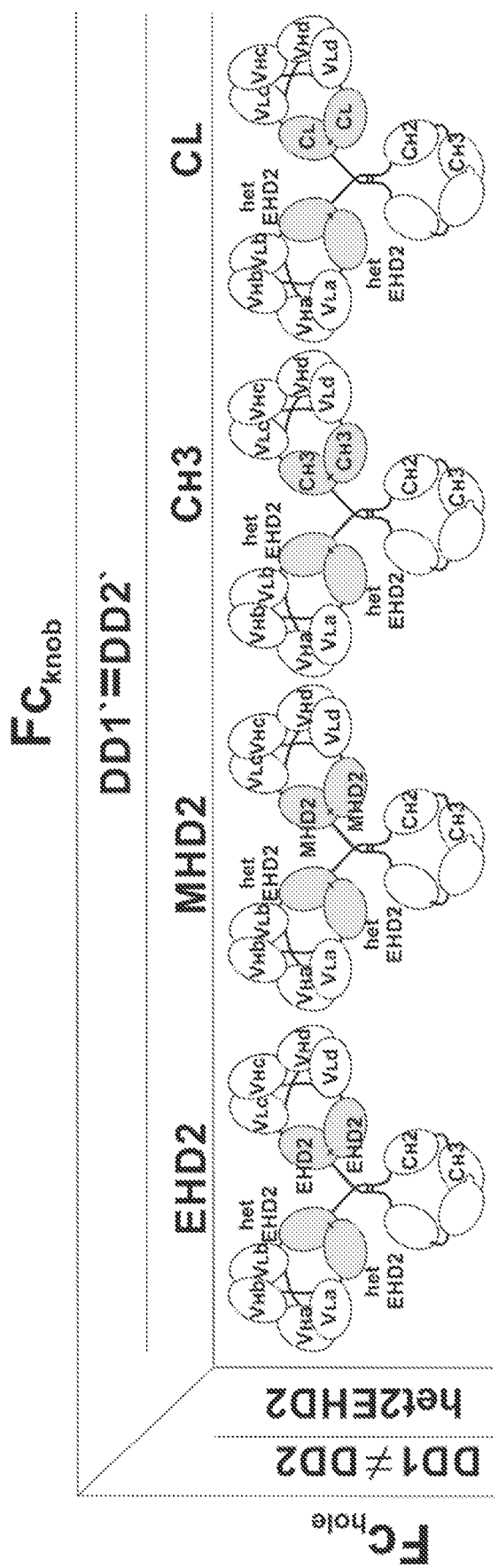
Figure 25D:
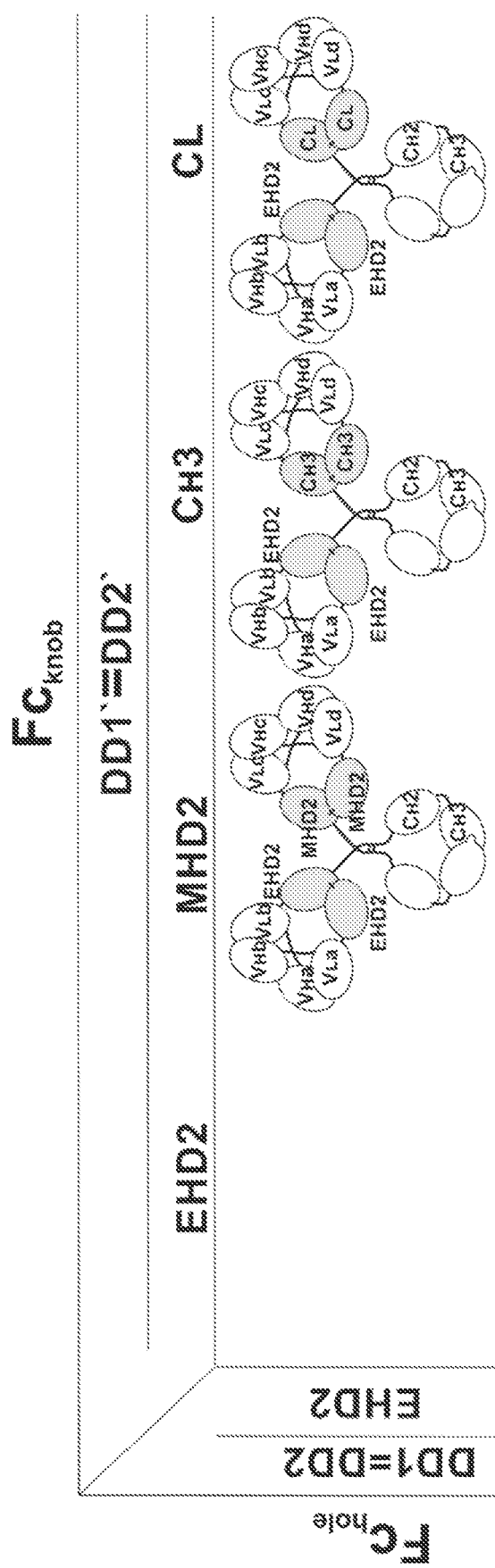
Figure 25E:
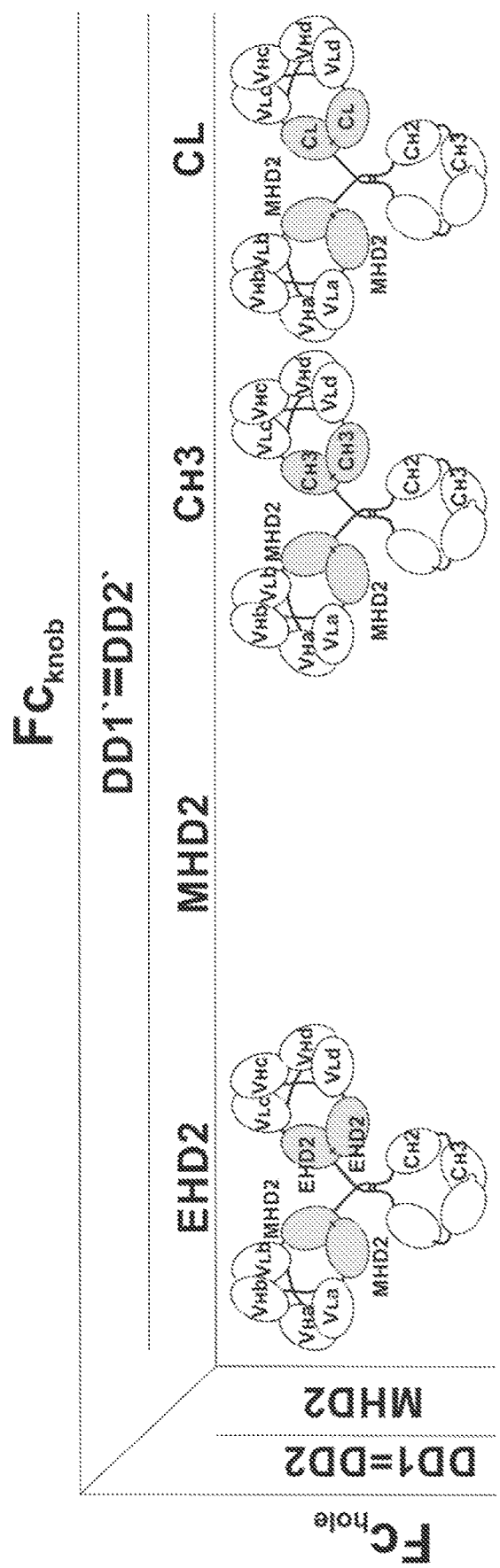
Figure 25F:
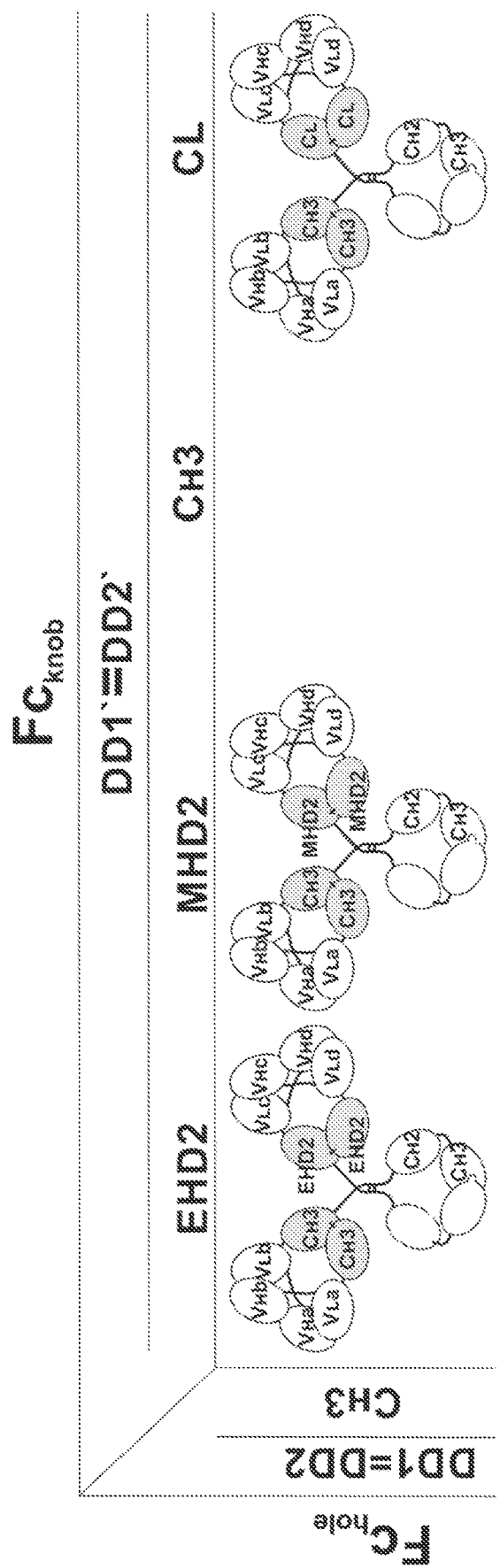
Figure 25G:
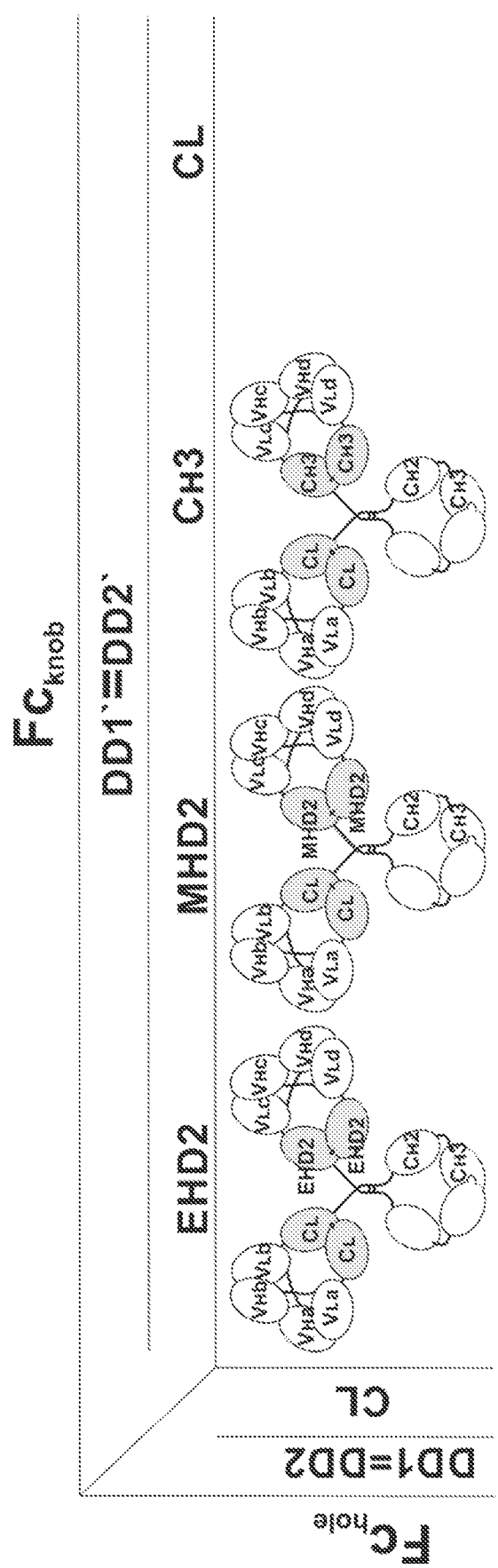

FIG. 14: Schematic overview of dimerization modules used for the generation of trivalent db-scFv molecules using heterodimeric Fc part. Dimerization modules are split into heterodimer and homodimer using the example of a trispecific db-scFv molecule. het1EHD2 contains a C247S mutation in the light chain and C337S mutation in the heavy chain, het2EHD2 contains a C337S in the light chain and C247S mutation in the heavy chain.

FIG. 15A-D: Schematic overview of the antigen-binding sites of tetravalent Db-Ig molecules using heterodimeric Fc part. Schematic illustration of the tetravalent (mono-(4+0), bi- (2+2, 3+1), tri- (2+1+1), and tetraspecific (1+1+1+1)) Db-Ig molecules combining two diabody moieties. Specificities of the antigen-binding sites are colored with white, black, dark and light grey.

FIG. 16A-G: Schematic overview of hetero-dimerization modules (Fc$_{knob}$) used for the generation of tetravalent, monospecific Db-Ig molecules using a heterodimeric Fc part. Combinatorial overview of dimerization modules used for the generation tetravalent, monospecific Db-Ig molecules. het1EHD2 contains a C247S mutation in the light chain and C337S mutation in the heavy chain, het2EHD2 contains a C337S in the light chain and C247S mutation in the heavy chain.

FIG. 17A-G: Schematic overview of homo-dimerization modules (Fc$_{knob}$) used for the generation of tetravalent, monospecific Db-Ig molecules using a heterodimeric Fc part. Combinatorial overview of dimerization modules used for the generation tetravalent, monospecific Db-Ig molecules.

FIG. 18A-G: Schematic overview of hetero-dimerization modules (Fc$_{knob}$) used for the generation of tetravalent, bispecific Db-Ig molecules with a symmetric architecture using a heterodimeric Fc part. Combinatorial overview of dimerization modules used for the generation tetravalent, bispecific Db-Ig molecules. het1EHD2 contains a C247S mutation in the light chain and C337S mutation in the heavy chain, het2EHD2 contains a C337S in the light chain and C247S mutation in the heavy chain.

FIG. 19A-G: Schematic overview of homo-dimerization modules (Fc$_{knob}$) used for the generation of tetravalent, bispecific Db-Ig molecules with a symmetric architecture using a heterodimeric Fc part. Combinatorial overview of dimerization modules used for the generation tetravalent, bispecific Db-Ig molecules.

FIG. 20A-G: Schematic overview of hetero-dimerization modules (Fc$_{knob}$) used for the generation of tetravalent, bispecific Db-Ig molecules with an asymmetric architecture using a heterodimeric Fc part. Combinatorial overview of dimerization modules used for the generation tetravalent, bispecific Db-Ig molecules. het1EHD2 contains a C247S mutation in the light chain and C337S mutation in the heavy chain, het2EHD2 contains a C337S in the light chain and C247S mutation in the heavy chain.

FIG. 21A-G: Schematic overview of homo-dimerization modules (Fc$_{knob}$) used for the generation of tetravalent, bispecific Db-Ig molecules with an asymmetric architecture using a heterodimeric Fc part. Combinatorial overview of dimerization modules used for the generation tetravalent, bispecific Db-Ig molecules.

FIG. 22A-G: Schematic overview of hetero-dimerization modules (Fc$_{knob}$) used for the generation of tetravalent, trispecific Db-Ig molecules using a heterodimeric Fc part. Combinatorial overview of dimerization modules used for the generation tetravalent. trispecific Db-Ig molecules. het1EHD2 contains a C247S mutation in the light chain and C337S mutation in the heavy chain, het2EHD2 contains a C337S in the light chain and C247S mutation in the heavy chain.

FIG. 23A-G: Schematic overview of homo-dimerization modules (Fc$_{knob}$) used for the generation of tetravalent, trispecific Db-Ig molecules using a heterodimeric Fc part. Combinatorial overview of dimerization modules used for the generation tetravalent, trispecific Db-Ig molecules.

FIG. 24A-G: Schematic overview of hetero-dimerization modules (Fc$_{knob}$) used for the generation of tetravalent, tetraspecific Db-Ig molecules using a heterodimeric Fc part. Combinatorial overview of dimerization modules used for the generation tetravalent, tetraspecific Db-Ig molecules. het1EHD2 contains a C247S mutation in the light chain, het2EHD2 contains a C337S in the heavy chain.

FIG. 25A-G: Schematic overview of homo-dimerization modules (Fc$_{knob}$) used for the generation of tetravalent, tetraspecifc Db-Ig molecules using a heterodimeric Fc part. Combinatorial overview of dimerization modules used for the generation tetravalent, tetraspecific Db-Ig molecules.

Figure 26:
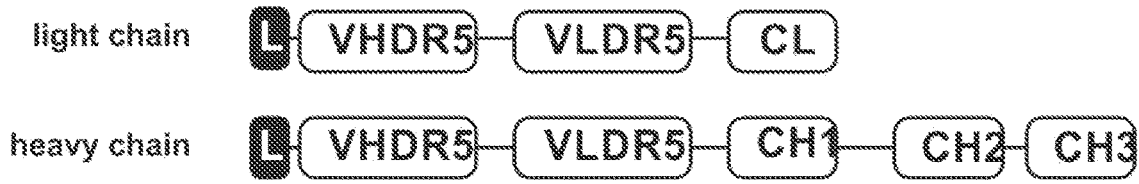
Figure 26:
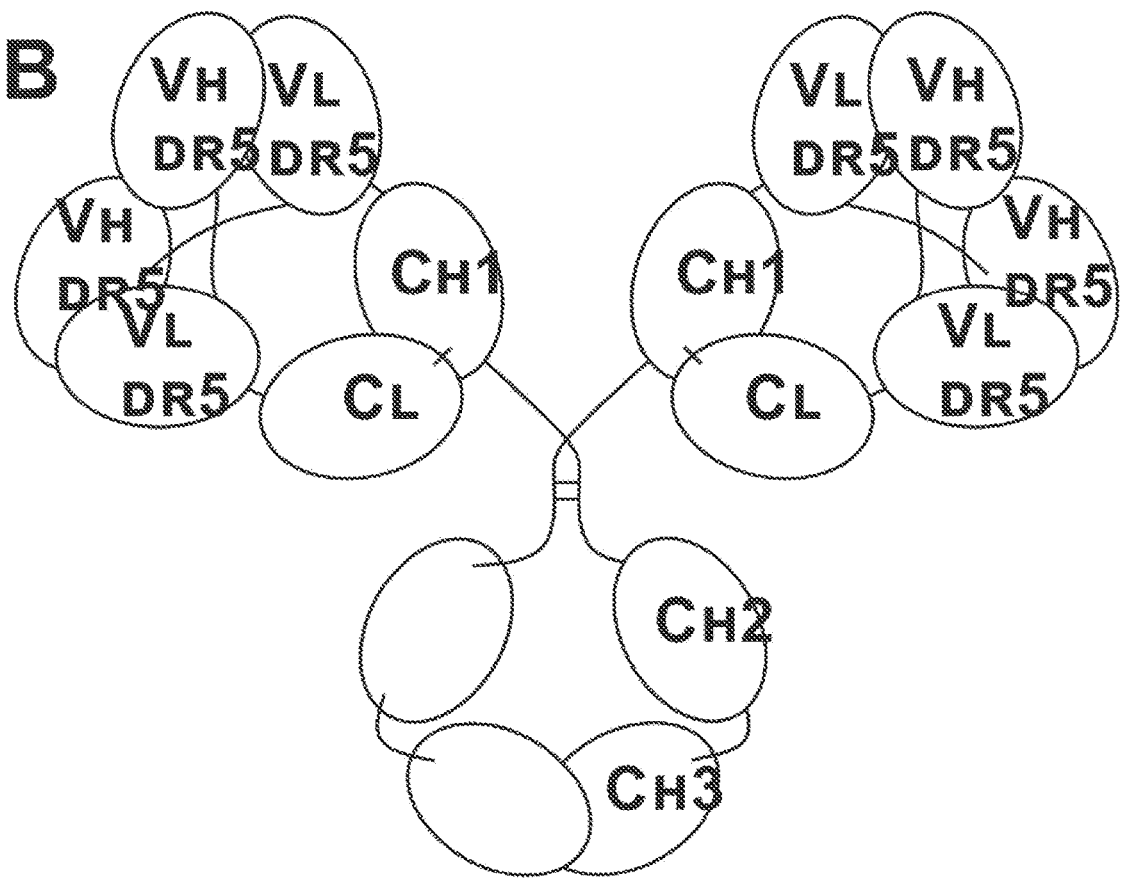
Figure 26:
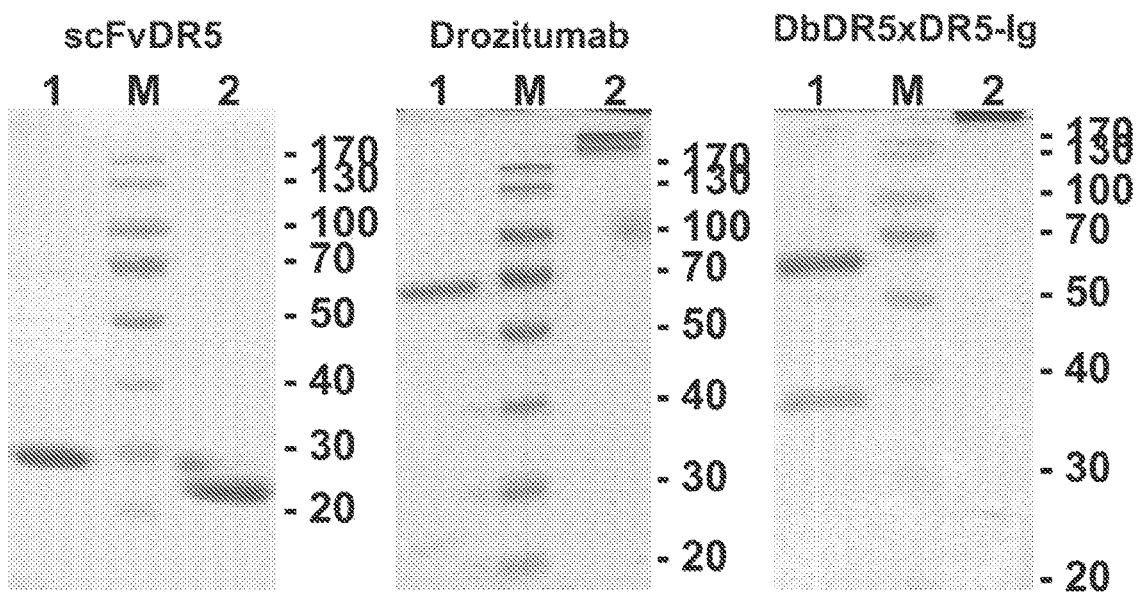
Figure 26:
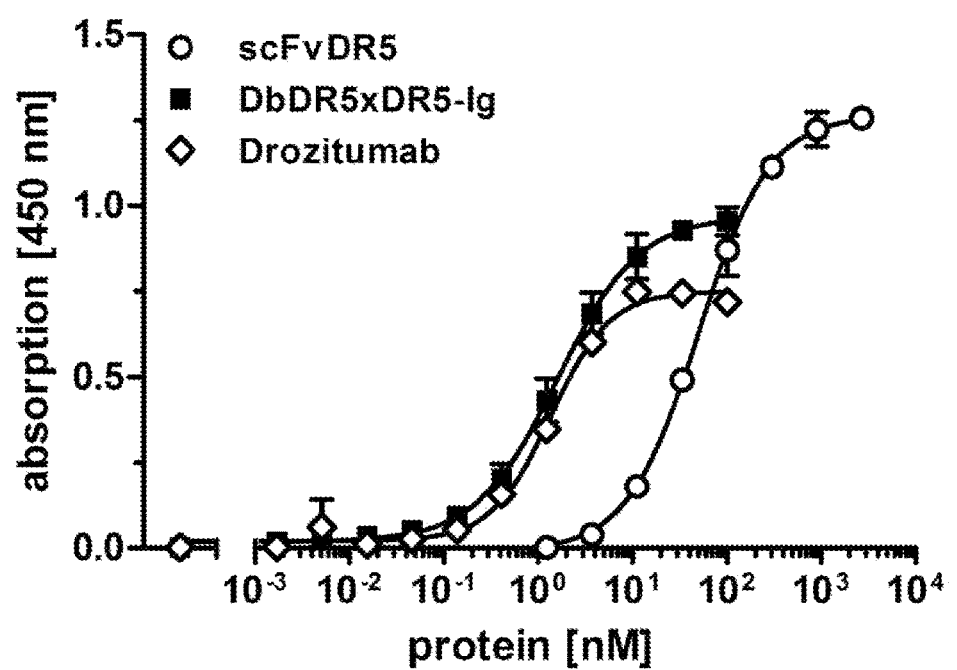

FIG. 26: Biochemical characterization and binding studies of DbDR5xDR5-Ig. A) Schematic illustration of the light and the heavy chain of the DbDR5xDR5-Ig fusion protein. B) Schematic structure of the domains in the DbDR5xDR5-Ig fusion protein. C) SDS-PAGE analysis (10 or 12% PAA; Coomassie stained) of scFvDR5, Drozitumab, and DbDR5xDR5-Ig fusion protein under reducing (1) and non-reducing (2) conditions (M: marker). D) Binding of the tetravalent DbDR5xDR5-Ig was analyzed by ELISA using a Fc fusion protein of the extracellular domain of DR5 as antigen. Bound protein was detected with an HRP-conjugated anti-human Fab antibody. Parenteral antibody (Drozitumab; detected with HRP-conjugated anti-huFab antibody) and the monovalent scFvDR5 (detected with an HRP-conjugated anti-His antibody) were used as control. Optical density was measured at 450 nm.

Figure 27:
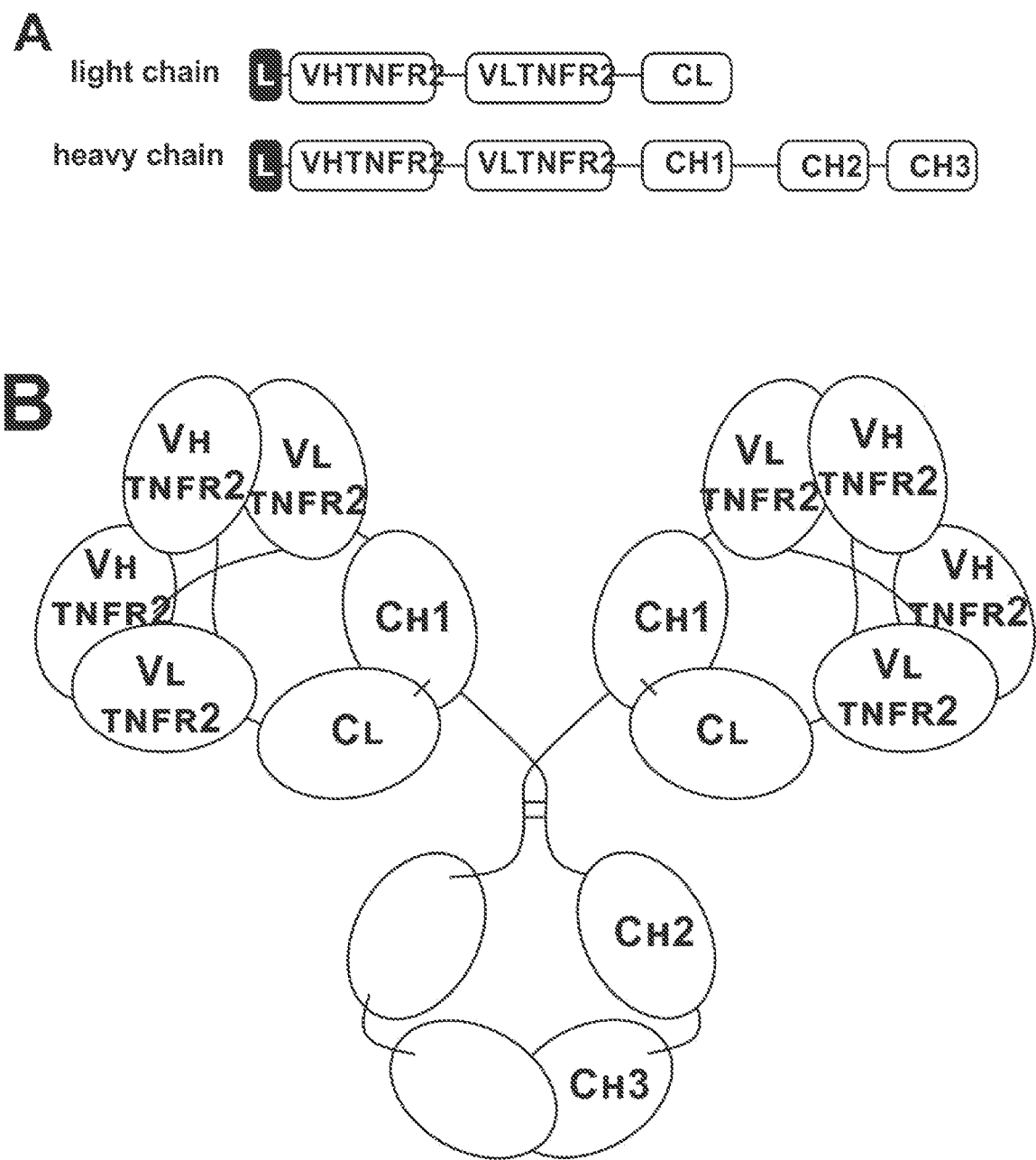
Figure 27:
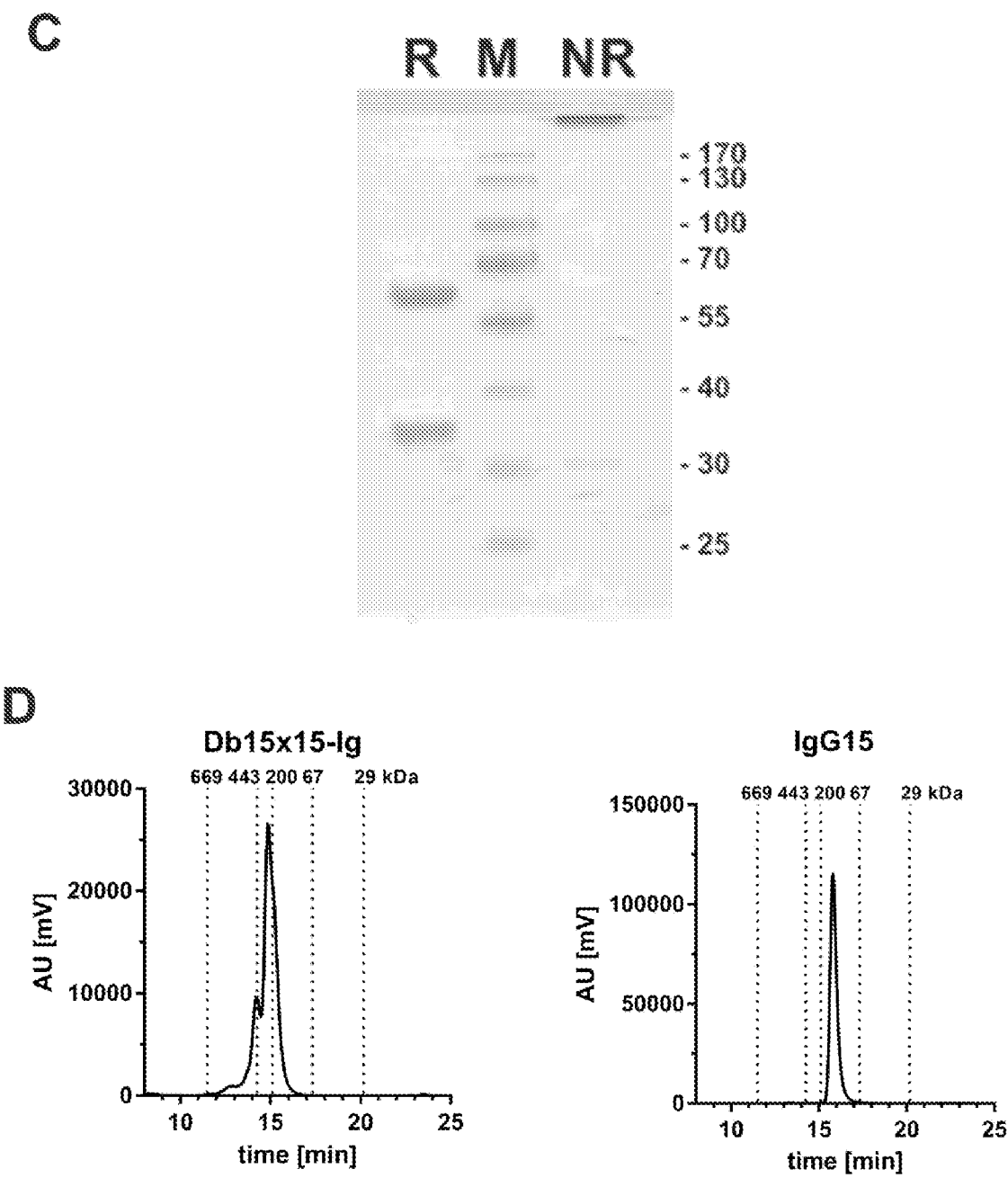
Figure 27:
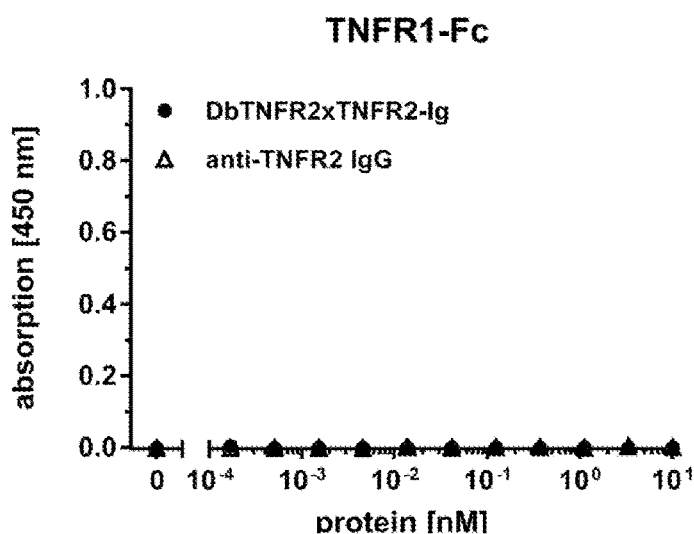
Figure 27:
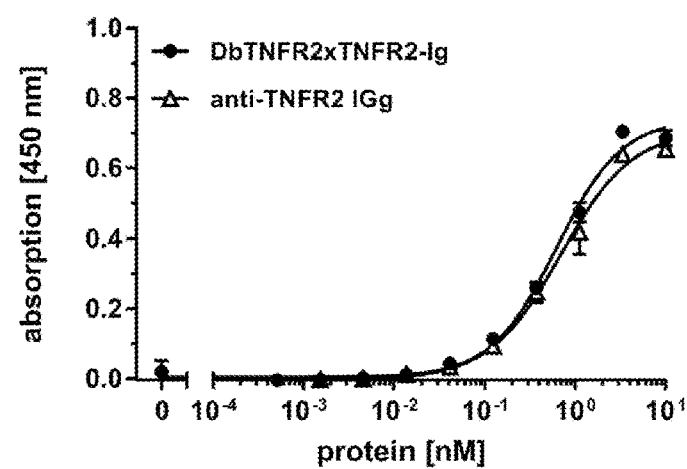
Figure 27:
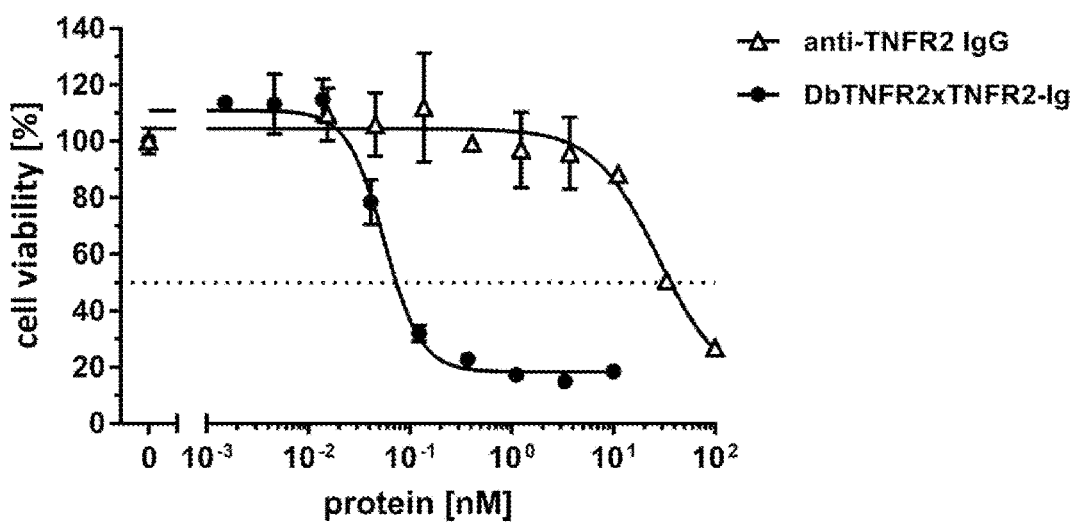

FIG. 27: Biochemical characterization, binding studies and bioactivity of DbTNFR2xTNFR2-Ig. A) Schematic illustration of the light and the heavy chain of the DbTNFR2xTNFR2-Ig fusion protein. B) Schematic structure of the domains in the DbTNFR2xTNFR2-Ig fusion protein. C) SDS-PAGE analysis (12% PAA; Coomassie stained) of DbTNFR2xTNFR2-Ig fusion protein under reducing (R) and non-reducing (NR) conditions (M: marker). D) Size exclusion chromatography of DbTNFR2xTNFR2-Ig and anti-TNFR2 IgG. E) Binding of the tetravalent DbTNFR2xTNFR2-Ig was analyzed by ELISA using a Fc fusion protein of the extracellular domain of TNFR1 and TNFR2 (Enbrel) as antigen. Bound protein was detected with an HRP-conjugated anti-human Fab antibody. Parenteral antibody (anti-TNFR2 IgG; detected with HRP-conjugated anti-huFab antibody) was included as control. Optical density was measured at 450 nm. F) Cell death induction assay using Kym-1 cells (10,000 cells/well). Titration of antibodies (anti-TNFR2 IgG and DbTNFR2xTNFR2-Ig) was incubated with cells for 24 hours. Cell viability was analyzed using MTT assay.

Figure 28:
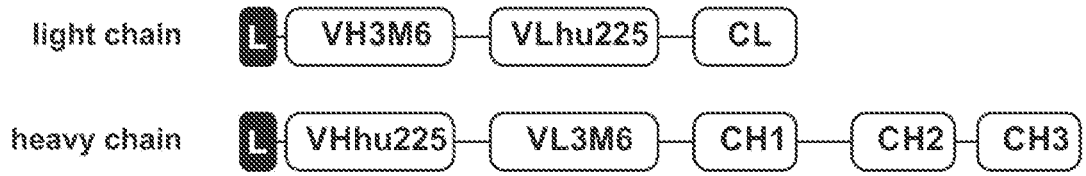
Figure 28:
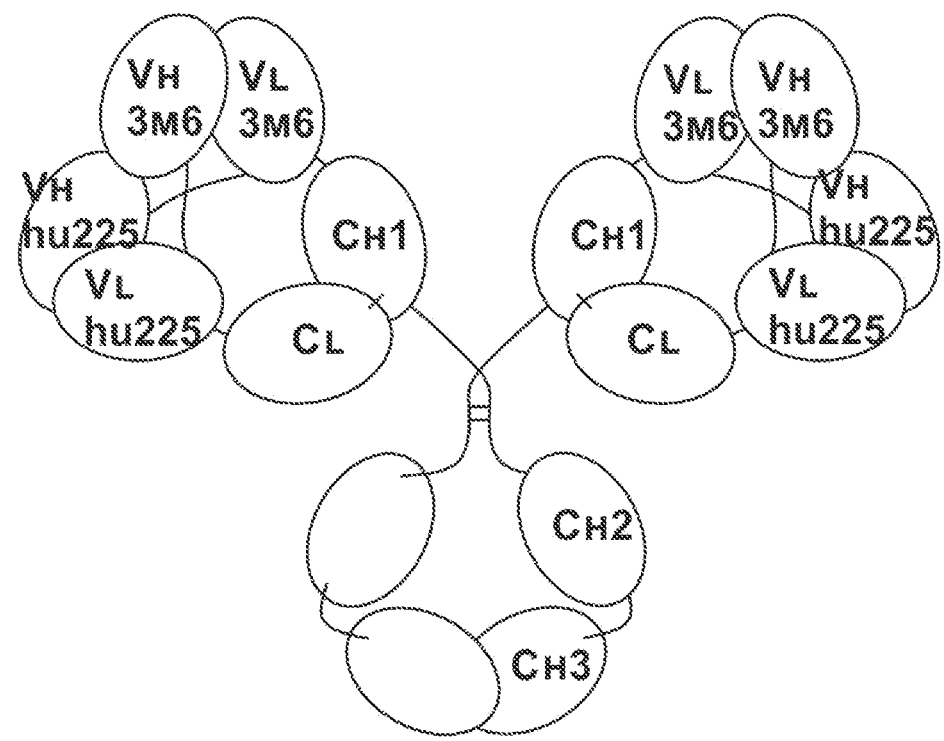
Figure 28:
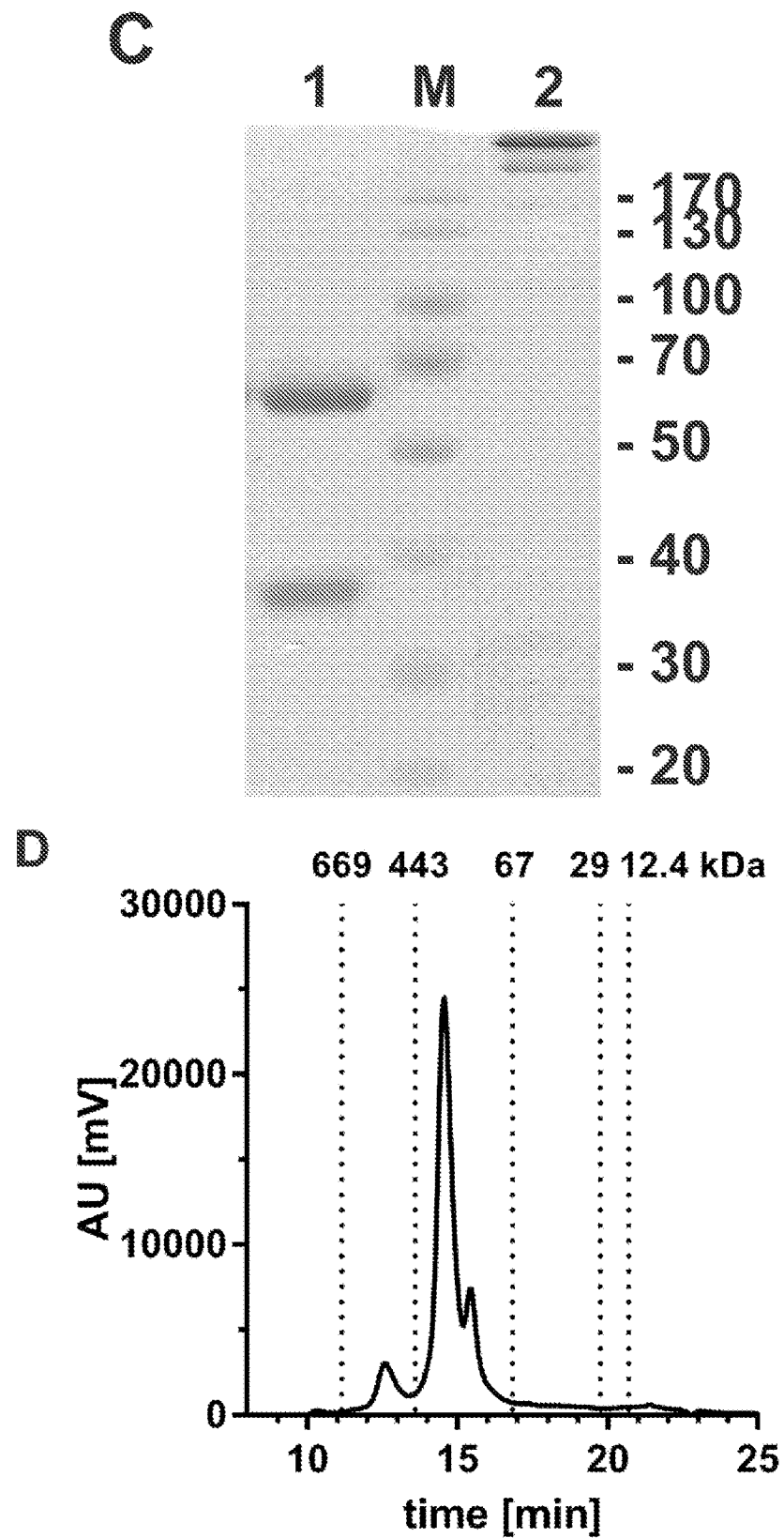
Figure 28:
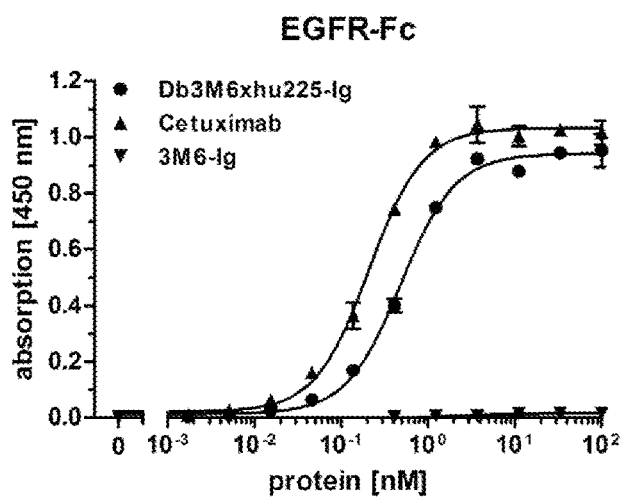
Figure 28:
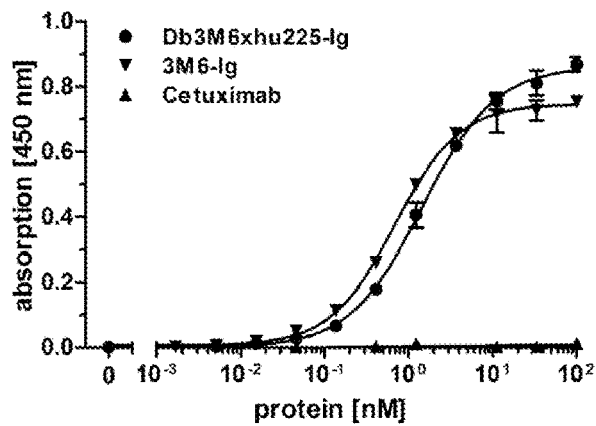
Figure 28:
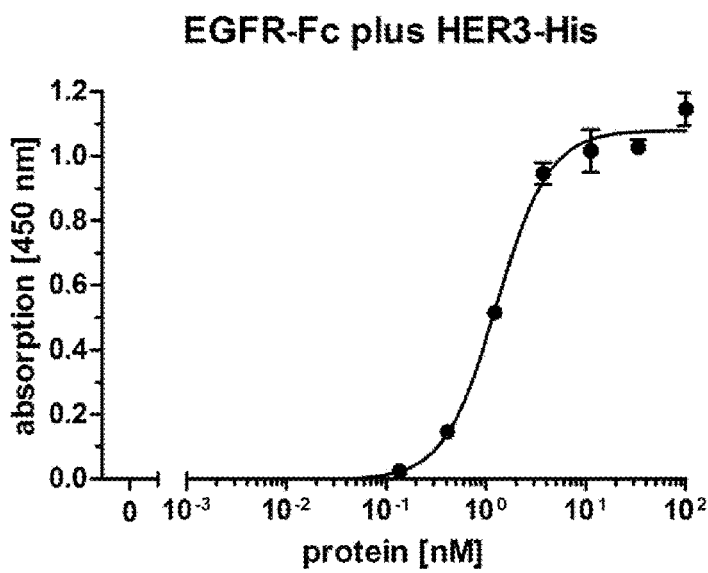

FIG. 28: Biochemical characterization and binding of Db3M6xhu225-Ig. A) Schematic illustration of the light and the heavy chain of the Db3M6xhu225-Ig fusion protein. B) Schematic structure of the domains in the Db3M6xhu225-Ig fusion protein. C) SDS-PAGE analysis (10% PAA; Coomassie stained) of the Db3M6xhu225-Ig fusion protein under reducing (1) and non-reducing (2) conditions (M: marker). D) Size exclusion chromatography of Db3M6xhu225-Ig fusion protein. E) Binding of the bispecific, tetravalent Db3M6xhu225-Ig was analyzed by ELISA using a Fc fusion protein of the extracellular domain of EGFR or HER3 as antigen. Bound protein was detected with an HRP-conjugated anti-human Fab antibody. Parenteral antibodies (Cetuximab and 3M6-IgG) were used as control. Optical density was measured at 450 nm. F) Simultaneous binding of the bispecific Db3M6xhu25-Ig fusion protein was analyzed via ELISA using a Fc fusion protein of the extracellular domain of EGFR as first antigen. Serial dilution of Db3M6xhu225-Ig was added to the wells. Finally, the second antigen, HER3-His, was added to the wells. Bound HER3-His was detected using a HRP-conjugated anti-His antibody. Optical density was measured at 450 nm.

Figure 29:
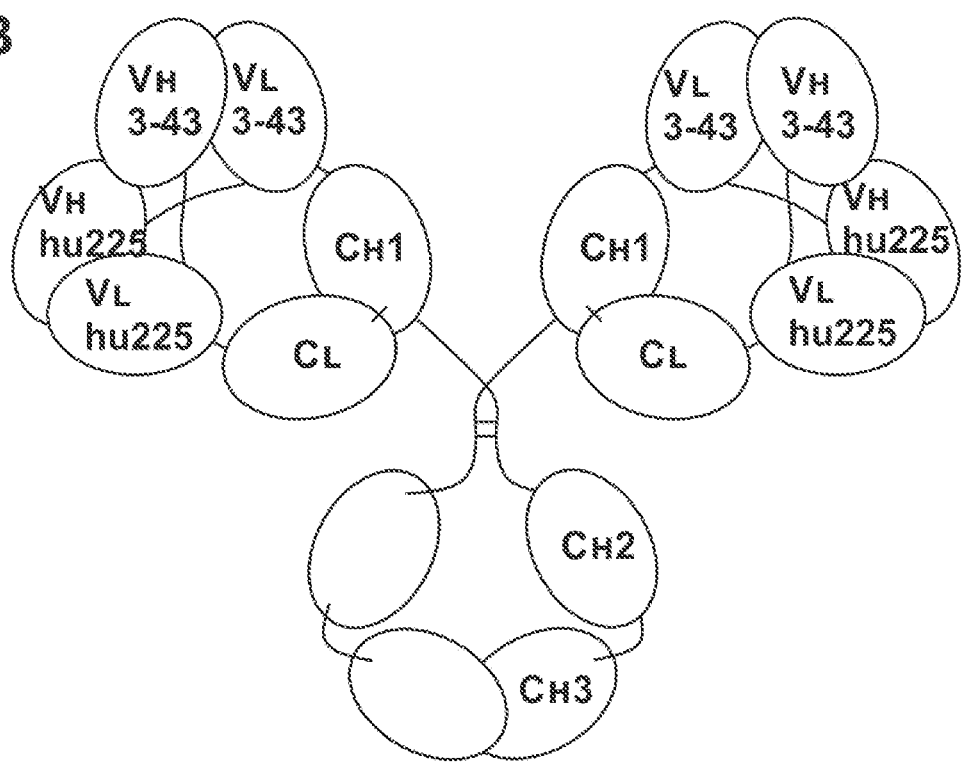
Figure 29:
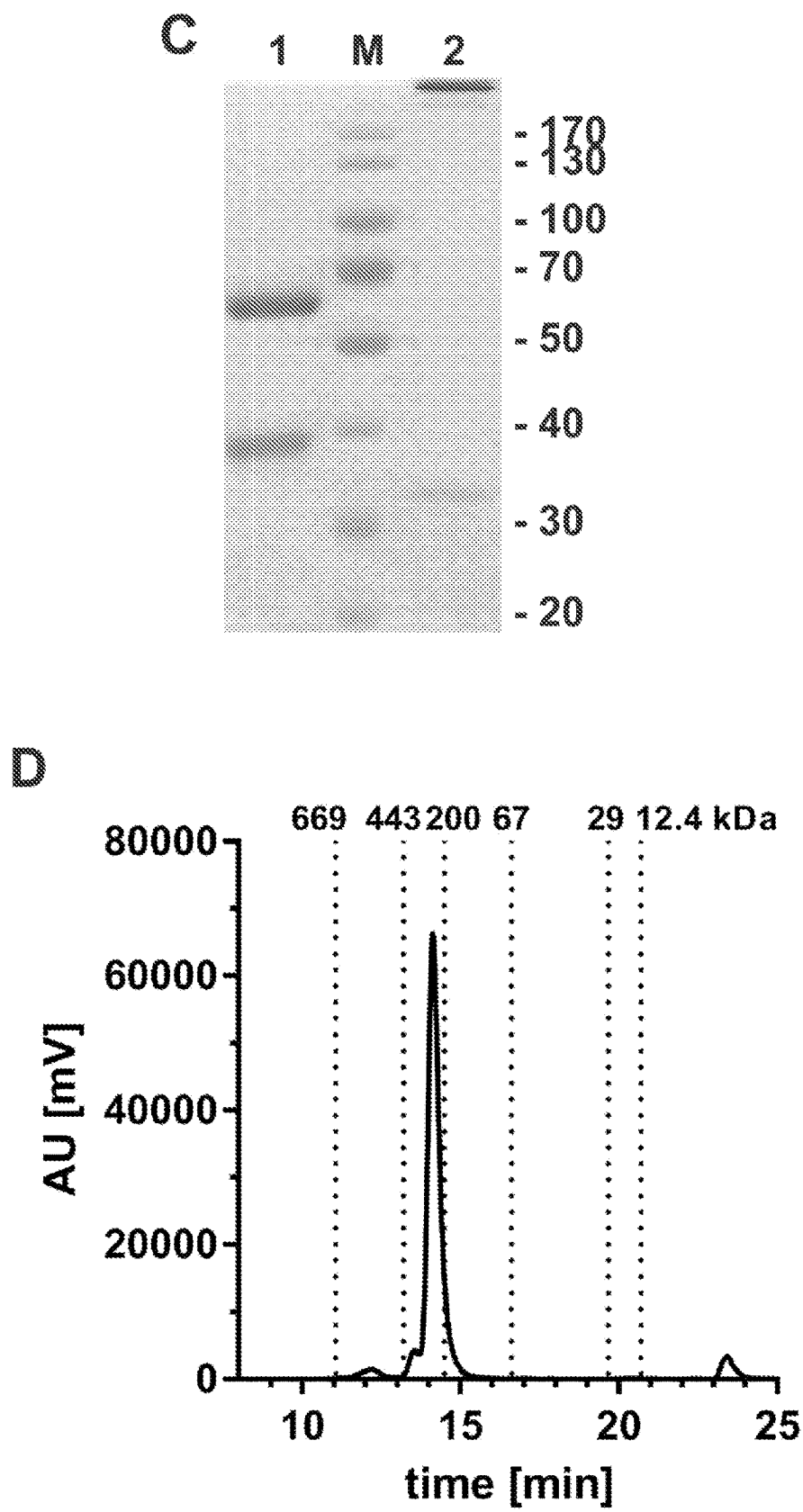
Figure 29:
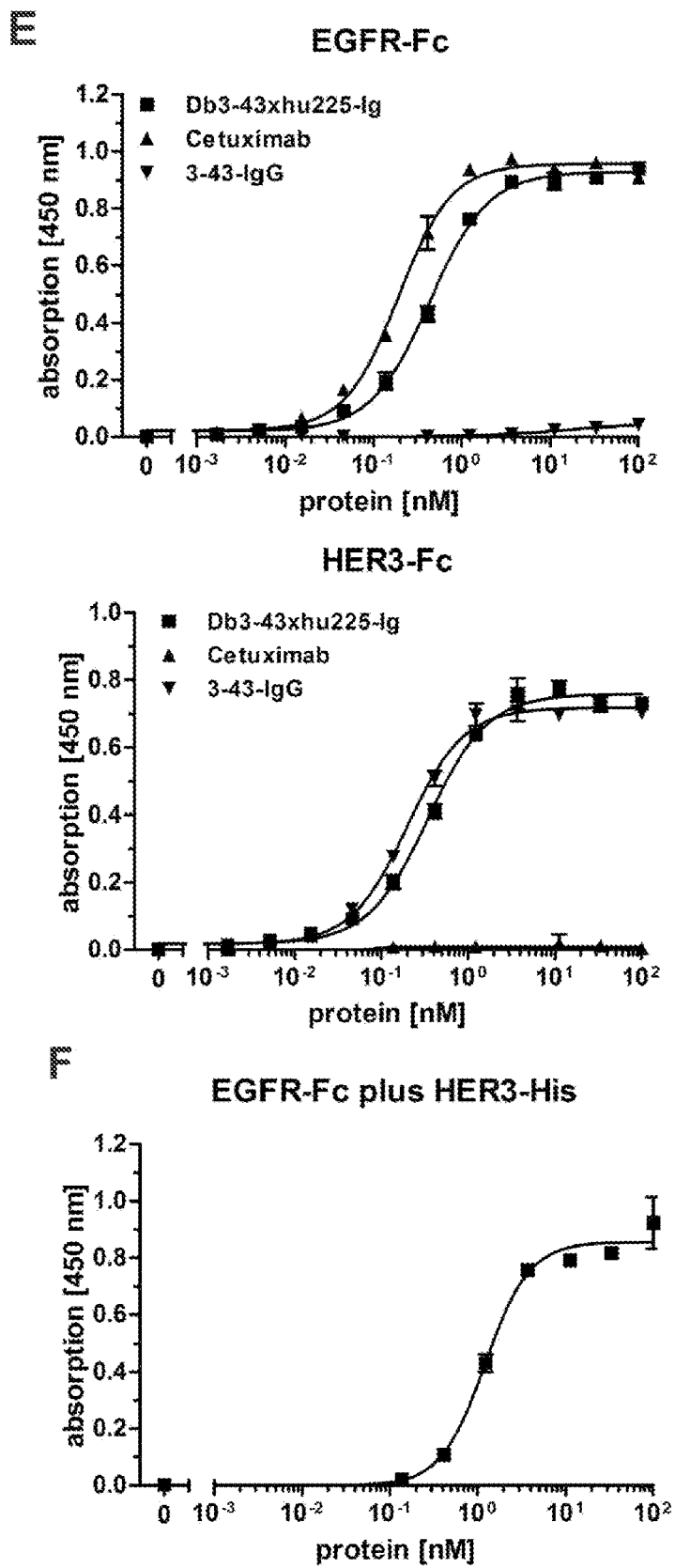

FIG. 29: Biochemical characterization and binding of Db3-43xhu225-Ig. A) Schematic illustration of the light and the heavy chain of the Db3-43xhu225-Ig fusion protein. B) Schematic structure of the domains in the Db3-43xhu225-Ig fusion protein. C) SDS-PAGE analysis (10% PAA; Coomassie stained) of the Db3-43xhu225-Ig fusion protein under reducing (1) and non-reducing (2) conditions (M: marker). D) Size exclusion chromatography of Db3-43xhu225-Ig fusion protein. E) Binding of the bispecific, tetravalent Db3-43xhu225-Ig was analyzed by ELISA using a Fc fusion protein of the extracellular domain of EGFR or HER3 as antigen. Bound protein was detected with an HRP-conjugated anti-human Fab antibody. Parenteral antibodies (Cetuximab and 3-43-IgG) were used as control. Optical density was measured at 450 nm. F) Simultaneous binding of the bispecific Db3-43xhu25-Ig fusion protein was analyzed via ELISA using a Fc fusion protein of the extracellular domain of EGFR as first antigen. Serial dilution of Db3-43xhu225-Ig was added to the wells. Finally, the second antigen, HER3-His, was added to the wells. Bound HER3-His was detected using a HRP-conjugated anti-His antibody. Optical density was measured at 450 nm.

Figure 30:
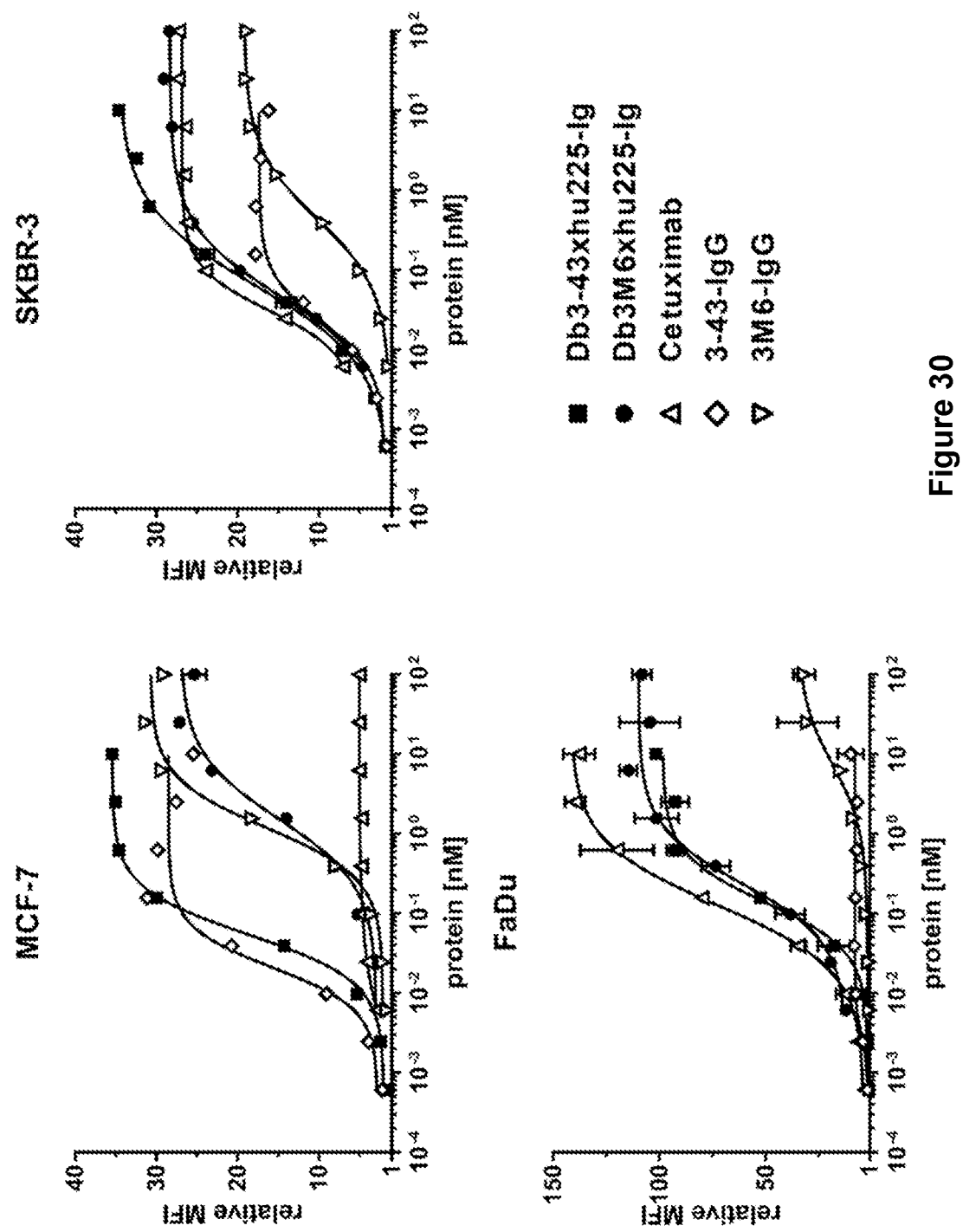

FIG. 30: Binding of bispecific DbEGFRxHER3-Ig to EGFR- and/or HER3-expressing tumor cell lines. Different tumor cell lines (MCF-7, SKBR-3, and FaDu) were incubated with a serial dilution of bispecific, tetravalent DbEGFRxHER3-Ig (db3M6xhu225-Ig and Db3-43xhu225-Ig) or the parental monoclonal antibodies (Cetuximab, 3M6-IgG, and 3-43-IgG). Bound antibody was detected via PE-labeled anti-human Fc secondary antibody. Cells were analyzed using a Miltenyi MACSquant.

Figure 31:
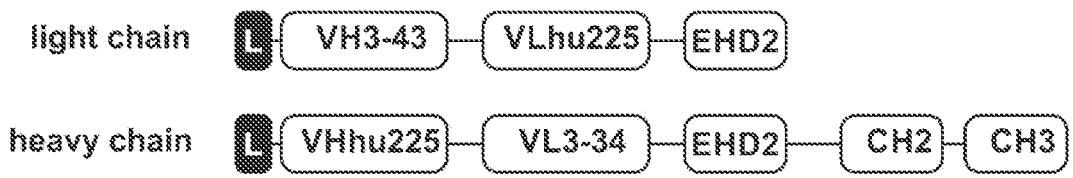
Figure 31:
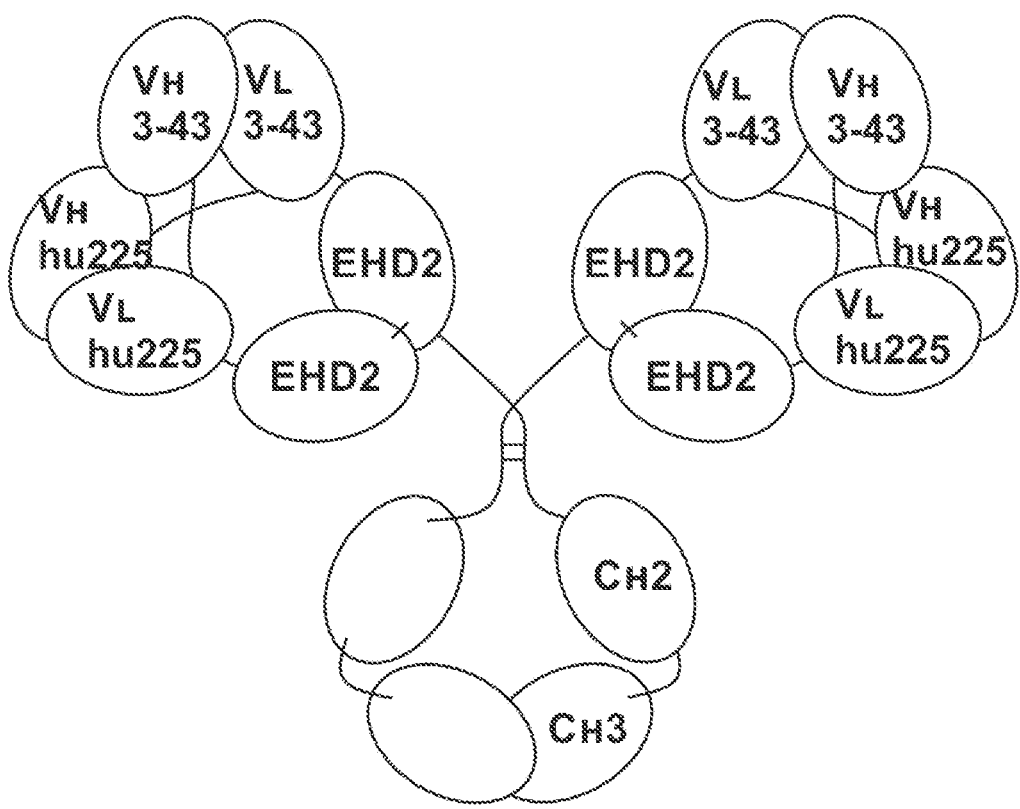
Figure 31:
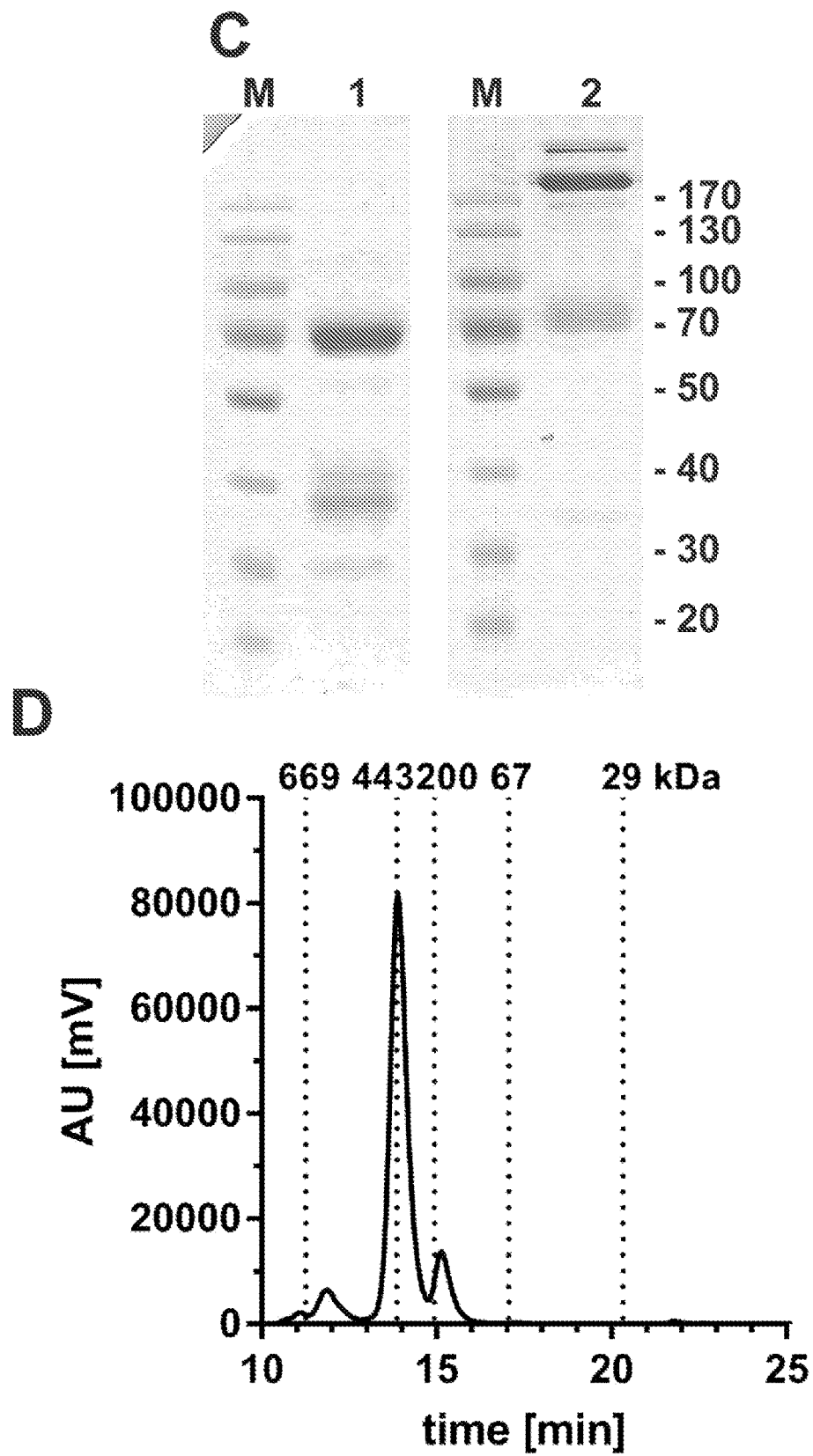
Figure 31:
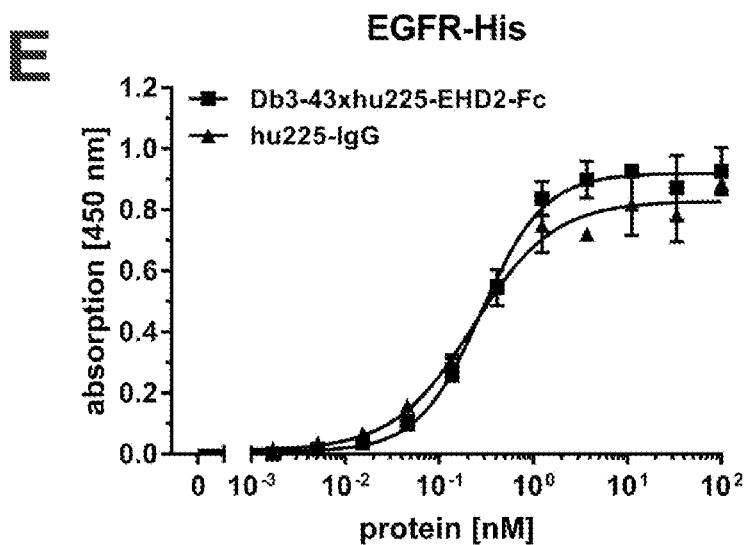
Figure 31:
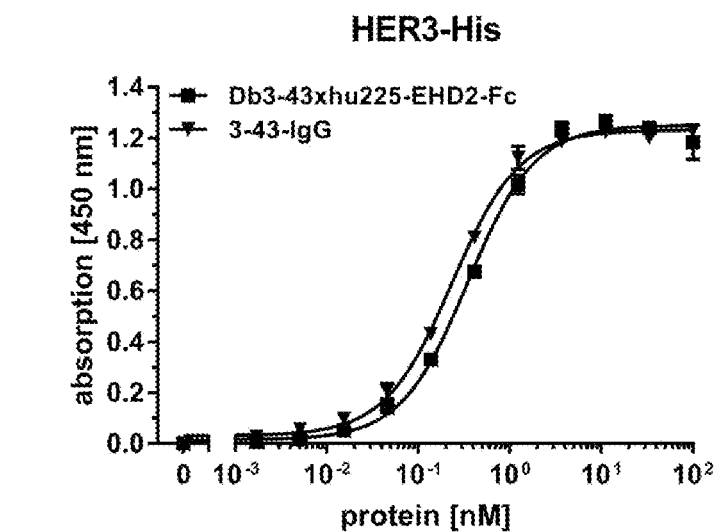
Figure 31:
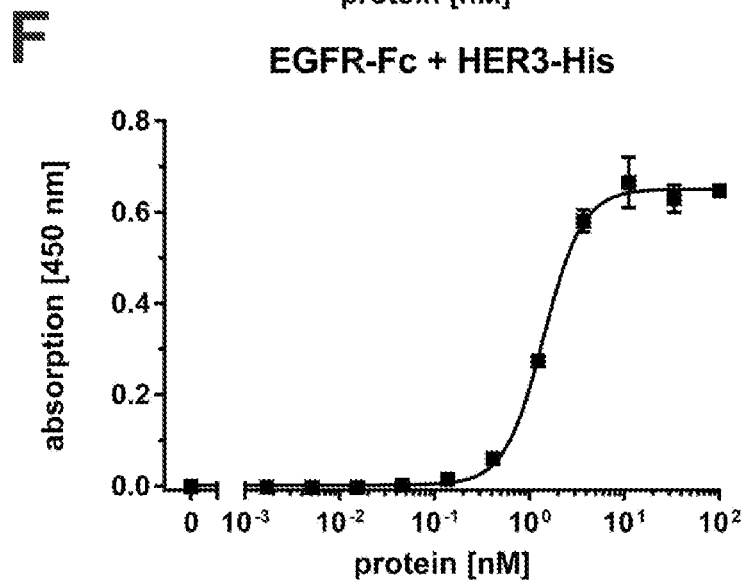

FIG. 31: Biochemical characterization and binding of Db3-43xhu225-EHD2-Fc. A) Schematic illustration of the light and the heavy chain of the Db3-43xhu225-EHD2-Fc fusion protein. B) Schematic structure of the domains in the Db3-43xhu225-EHD2-Fc fusion protein. C) SDS-PAGE analysis (10% PAA; Coomassie stained) of the Db3-43xhu225-EHD2-Fc fusion protein under reducing (1) and non-reducing (2) conditions (M: marker). D) Size exclusion chromatography of Db3-43xhu225-EHD2-Fc fusion protein. E) Binding of the bispecific, tetravalent Db3-43xhu225-EHD2-Fc was analyzed by ELISA using His-tagged protein of the extracellular domain of EGFR or HER3 as antigen. Bound protein was detected with an HRP-conjugated anti-human Fc antibody. Parenteral antibodies (hu225-IgG and 3-43-IgG) were used as control. Optical density was measured at 450 nm. F) Simultaneous binding of the bispecific Db3-43xhu25-EHD2-Fc fusion protein was analyzed via ELISA using a Fc fusion protein of the extracellular domain of EGFR as first antigen. Serial dilution of Db3-43xhu225-EHD2-Fc was added to the wells. Finally, the second antigen, HER3-His, was added to the wells. Bound HER3-His was detected using a HRP-conjugated anti-His antibody. Optical density was measured at 450 nm.

Figure 32:
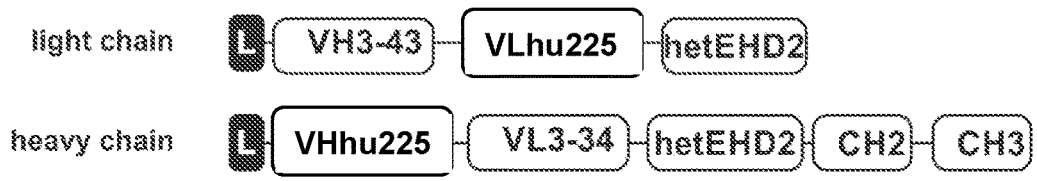
Figure 32:
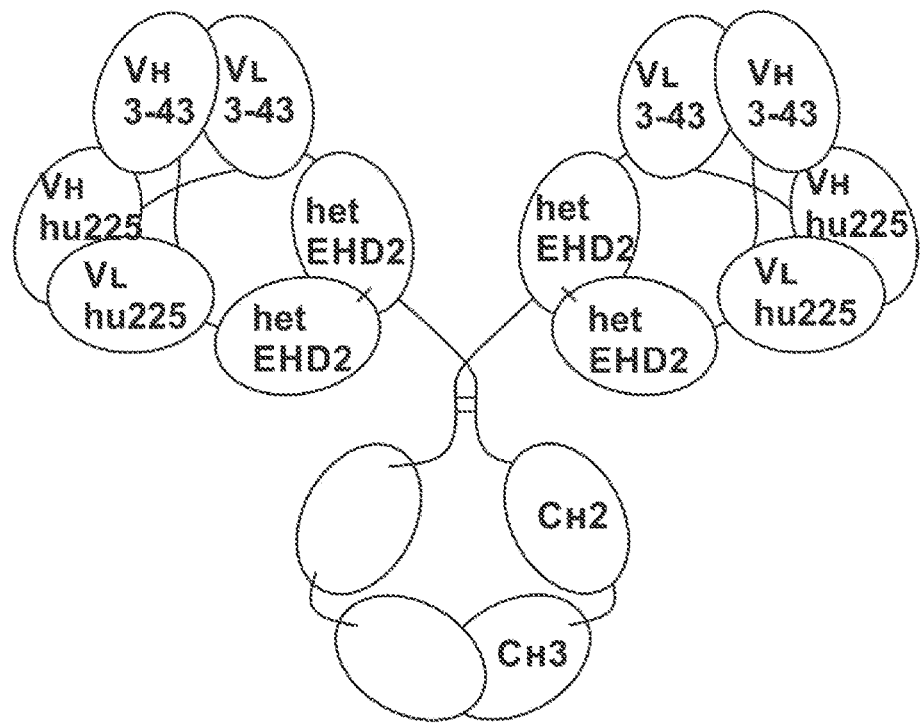
Figure 32:
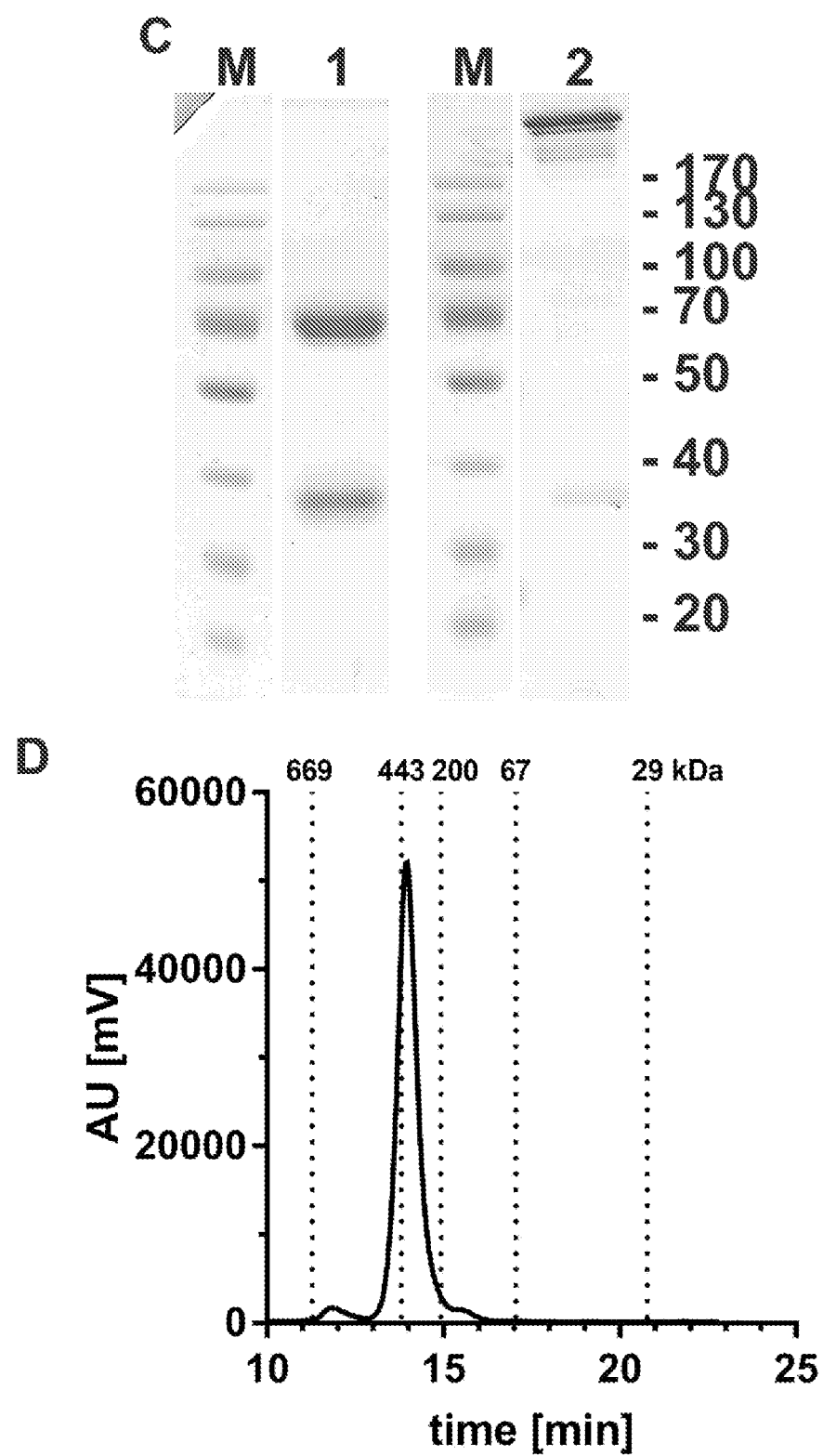
Figure 32:
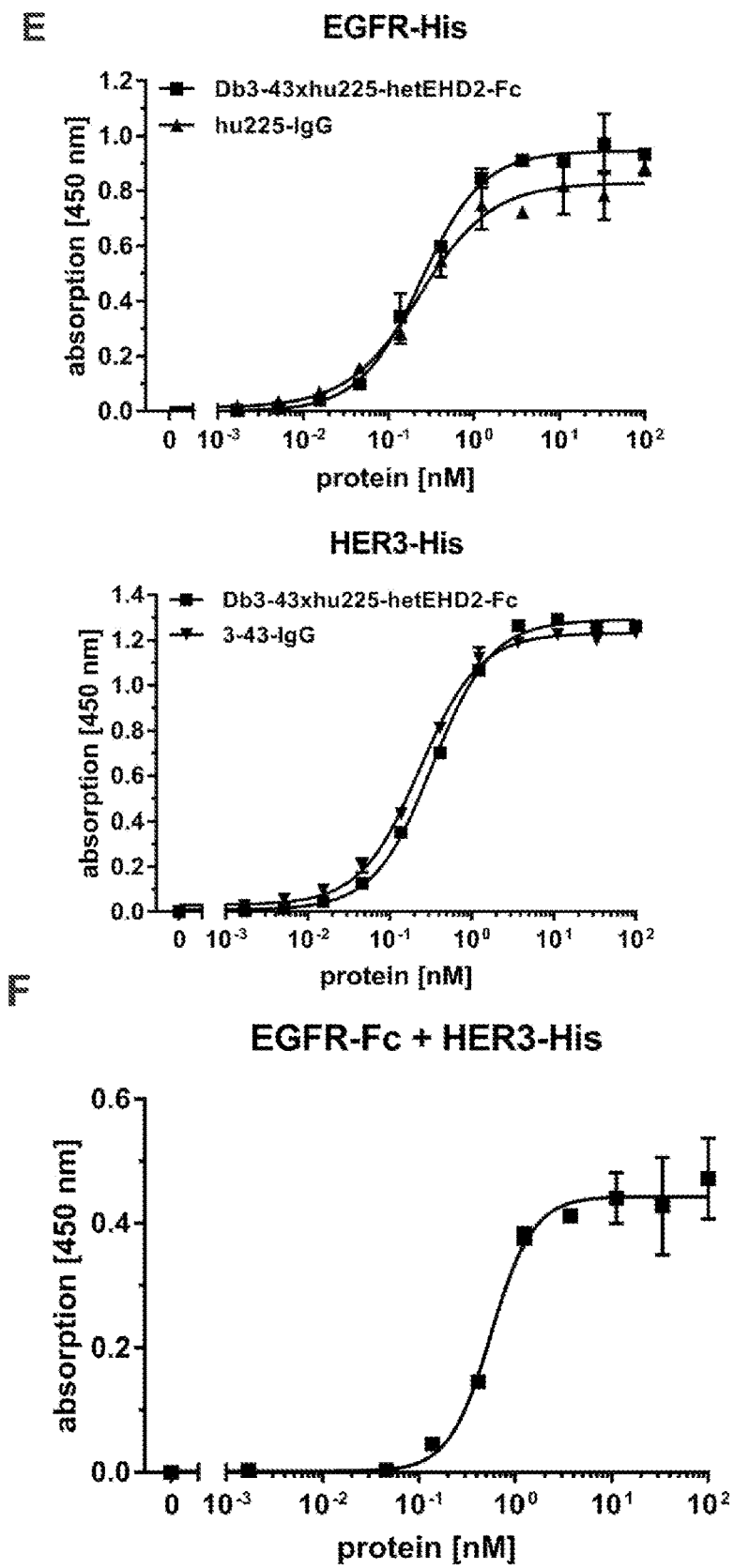

FIG. 32: Biochemical characterization and binding of Db3-43xhu225-het1EHD2-Fc. A) Schematic illustration of the light and the heavy chain of the Db3-43xhu225-het1EHD2-Fc fusion protein (C247S in first EHD2 of the light chain, C337S in second EHD2 of the heavy chain). B) Schematic structure of the domains in the Db3-43xhu225-het1EHD2-Fc fusion protein. C) SDS-PAGE analysis (10% PAA; Coomassie stained) of the Db3-43xhu225-het1EHD2-Fc fusion protein under reducing (1) and non-reducing (2) conditions (M: marker). D) Size exclusion chromatography of Db3-43xhu225-het1EHD2-Fc fusion protein. E) Binding of the bispecific, tetravalent Db3-43xhu225-het1EHD2-Fc was analyzed by ELISA using His-tagged protein of the extracellular domain of EGFR or HER3 as antigen. Bound protein was detected with an HRP-conjugated anti-human Fc antibody. Parenteral antibodies (hu225-IgG and 3-43-IgG) were used as control. Optical density was measured at 450 nm. F) Simultaneous binding of the bispecific Db3-43xhu25-hetEHD2-Fc fusion protein was analyzed via ELISA using a Fc fusion protein of the extracellular domain of EGFR as first antigen. Serial dilution of Db3-43xhu225-hetEHD2-Fc was added to the wells. Finally, the second antigen, HER3-His, was added to the wells. Bound HER3-His was detected using a HRP-conjugated anti-His antibody. Optical density was measured at 450 nm.

Figure 33:
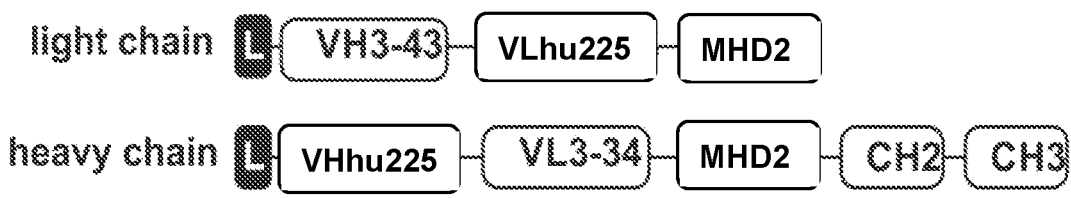
Figure 33:
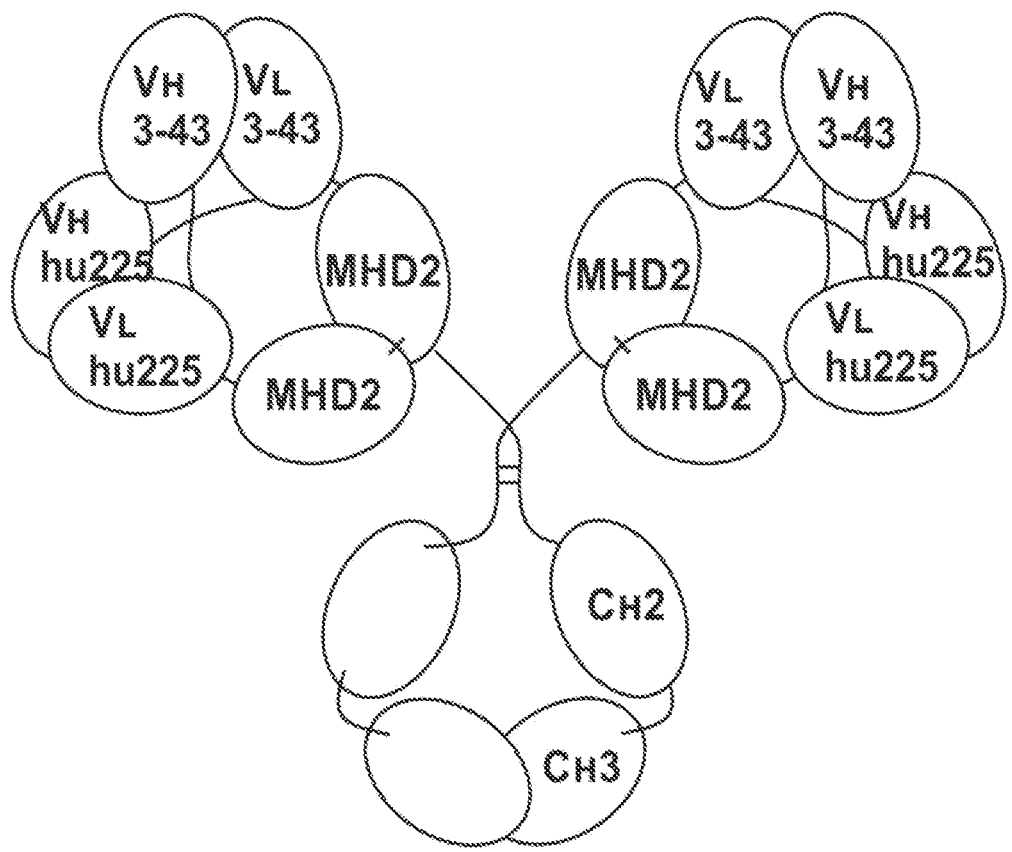
Figure 33:
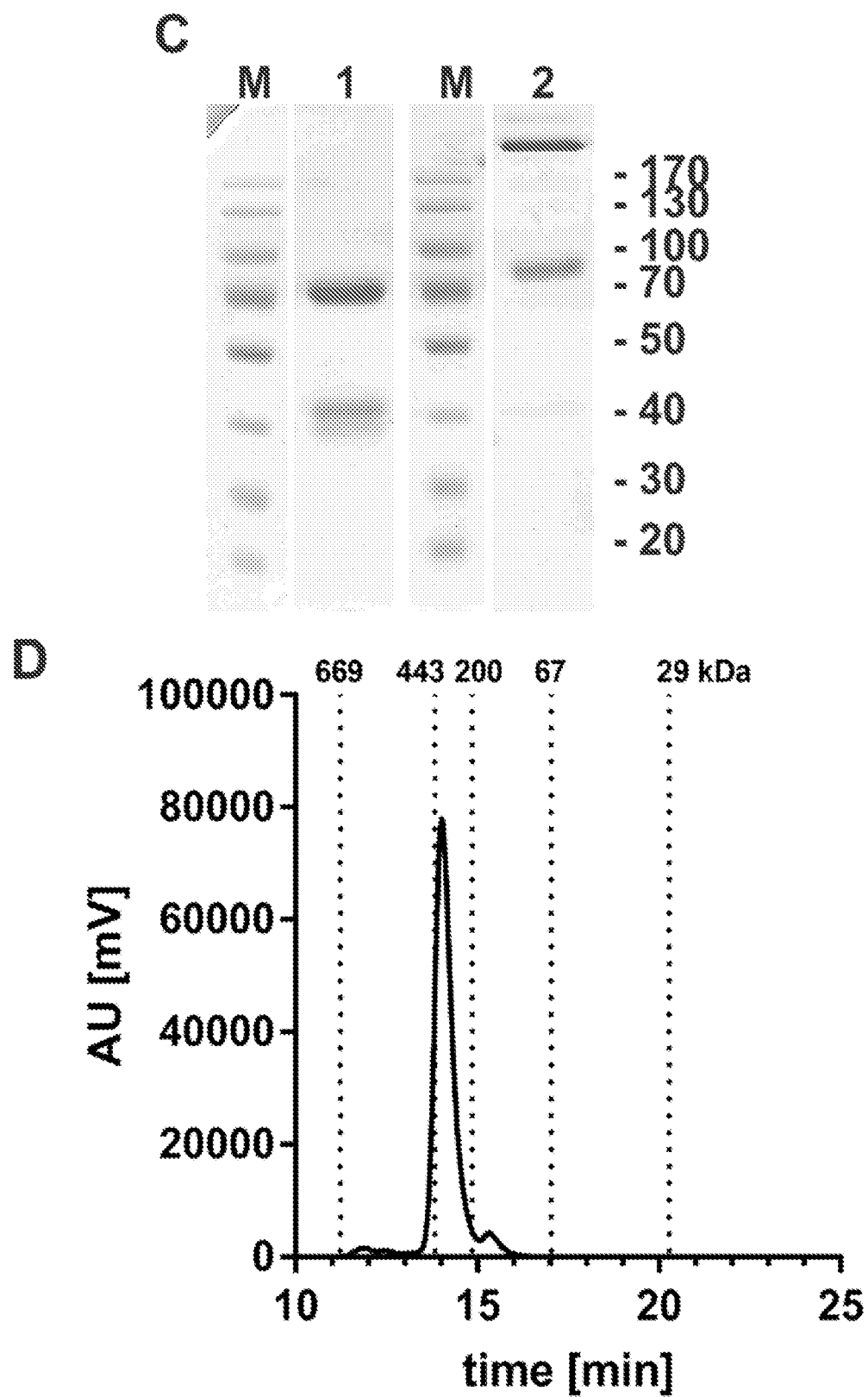
Figure 33:
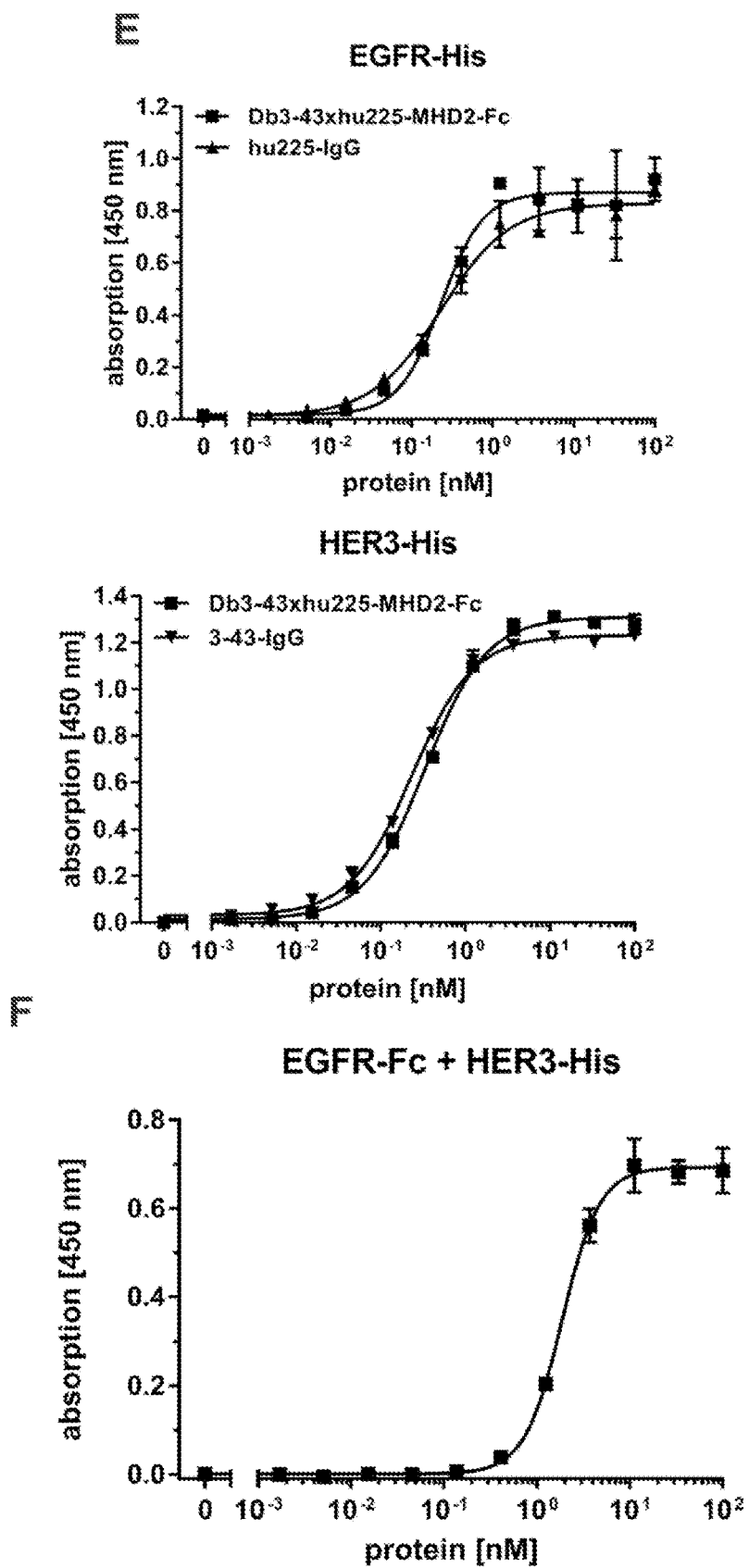

FIG. 33: Biochemical characterization and binding of Db3-43xhu225-MHD2-Fc. A) Schematic illustration of the light and the heavy chain of the Db3-43xhu225-MHD2-Fc fusion protein. B) Schematic structure of the domains in the Db3-43xhu225-MHD2-Fc fusion protein. C) SDS-PAGE analysis (10% PAA; Coomassie stained) of the Db3-43xhu225-MHD2-Fc fusion protein under reducing (1) and non-reducing (2) conditions (M: marker). D) Size exclusion chromatography of Db3-43xhu225-MHD2-Fc fusion protein. E) Binding of the bispecific, tetravalent Db3-43xhu225-MHD2-Fc was analyzed by ELISA using His-tagged protein of the extracellular domain of EGFR or HER3 as antigen. Bound protein was detected with an HRP-conjugated anti-human Fc antibody. Parenteral antibodies (hu225-IgG and 3-43-IgG) were used as control. Optical density was measured at 450 nm. F) Simultaneous binding of the bispecific Db3-43xhu25-MHD2-Fc fusion protein was analyzed via ELISA using a Fc fusion protein of the extracellular domain of EGFR as first antigen. Serial dilution of Db3-43xhu225-MHD2-Fc was added to the wells. Finally, the second antigen, HER3-His, was added to the wells. Bound HER3-His was detected using a HRP-conjugated anti-His antibody. Optical density was measured at 450 nm.

Figure 34A:
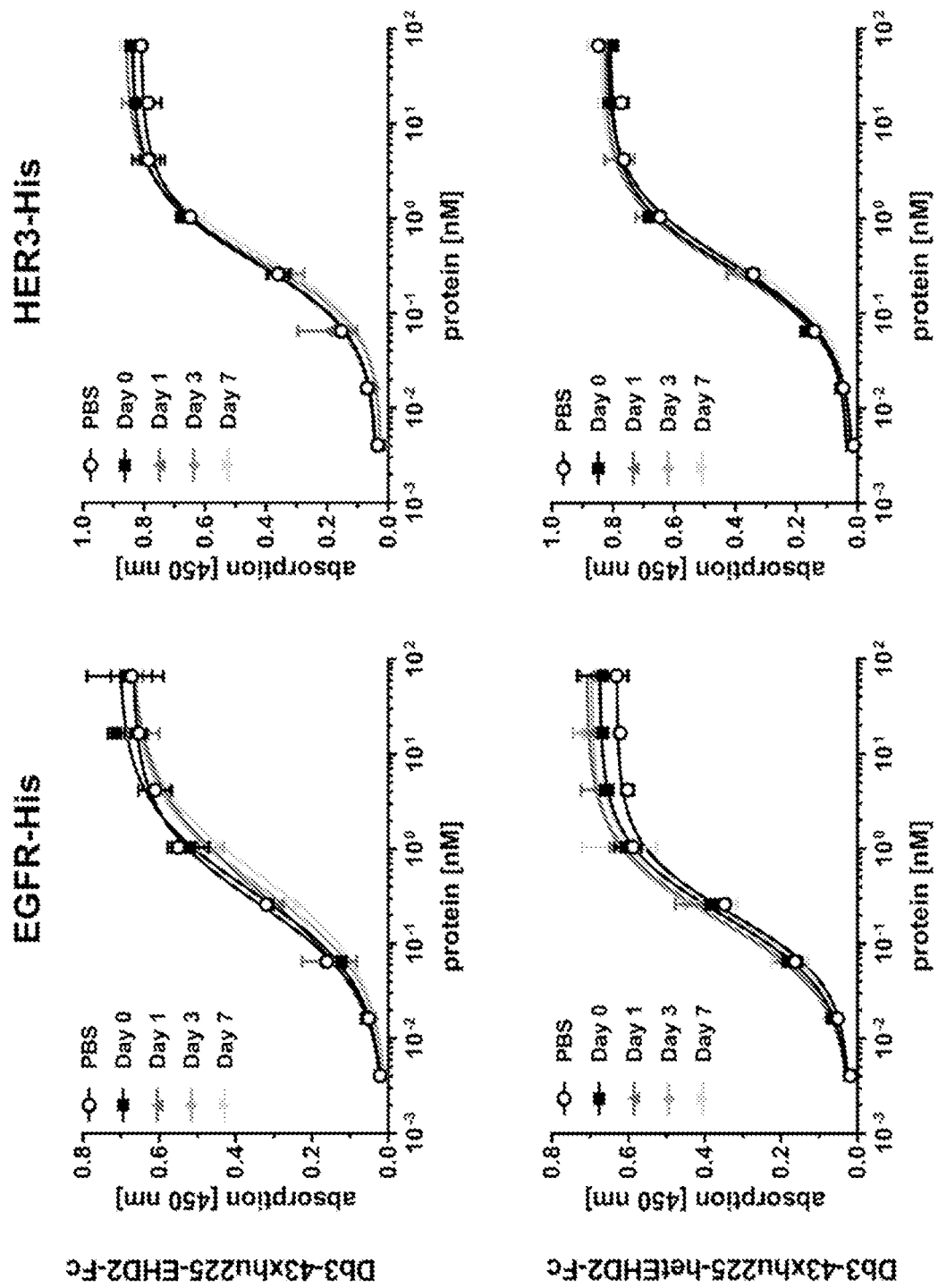
Figure 34B:
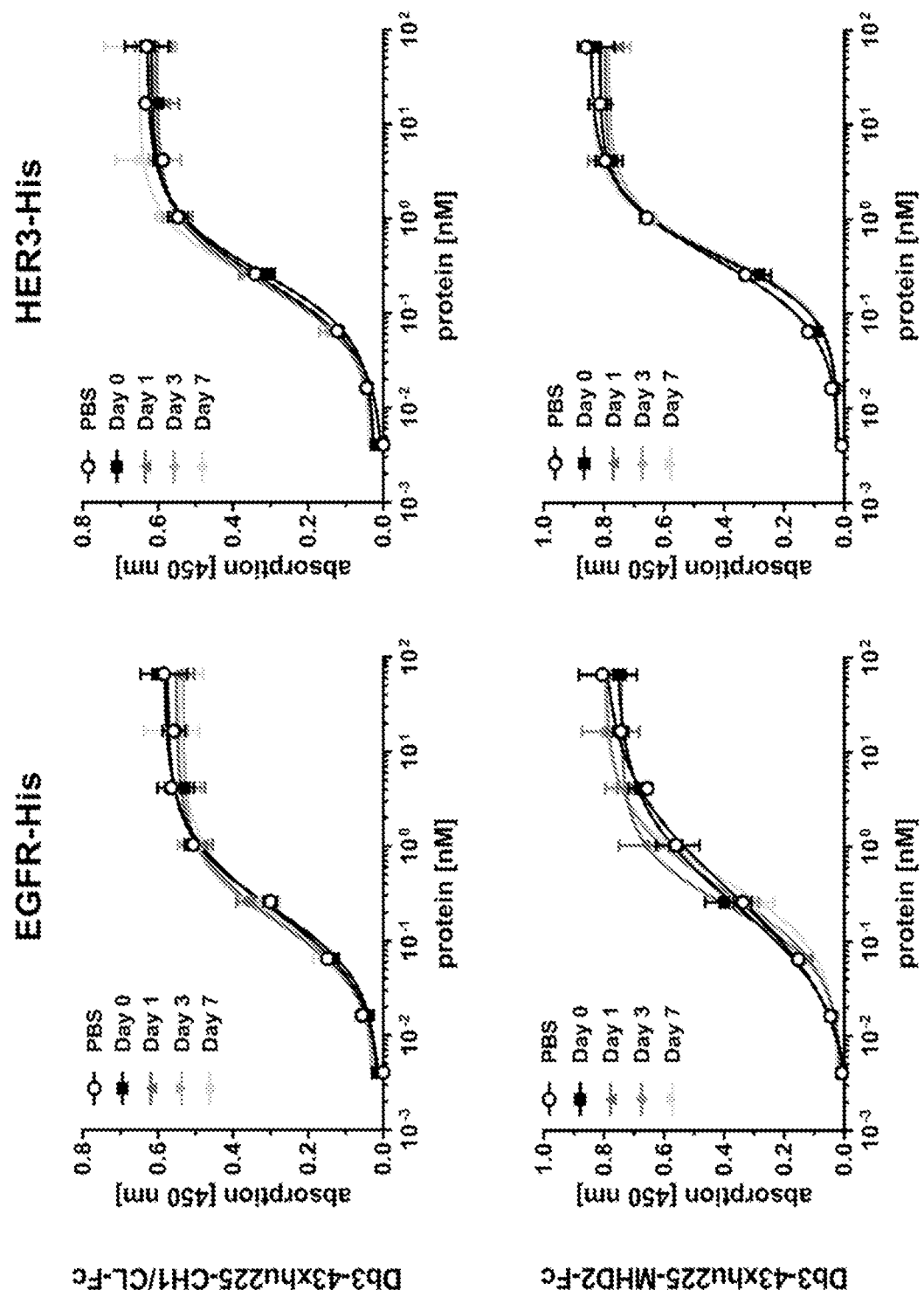

FIG. 34A-B: Stability of bispecific, tetravalent binding molecules in human plasma. The bispecific, tetravalent molecules (db3-43xhu225-Ig, Db3-43xhu225-EHD2-Fc, Db3-43xhu225-hetEHD2-Fc, and Db3-43xhu225-MHD2-Fc) were diluted in 50% human plasma and incubated at 37° C. for 1, 3, 5, or 7 days. Finally, binding of the bispecific molecules to both His-tagged antigens, EGFR-His or HER3-His, was analyzed via ELISA. Bound protein was detected with a HRP-conjugated anti-human Fc antibody. Bispecific molecules, which were diluted in PBS and stored at 4° C., were included as control. Optical density was measured at 450 nm.

Figure 35:
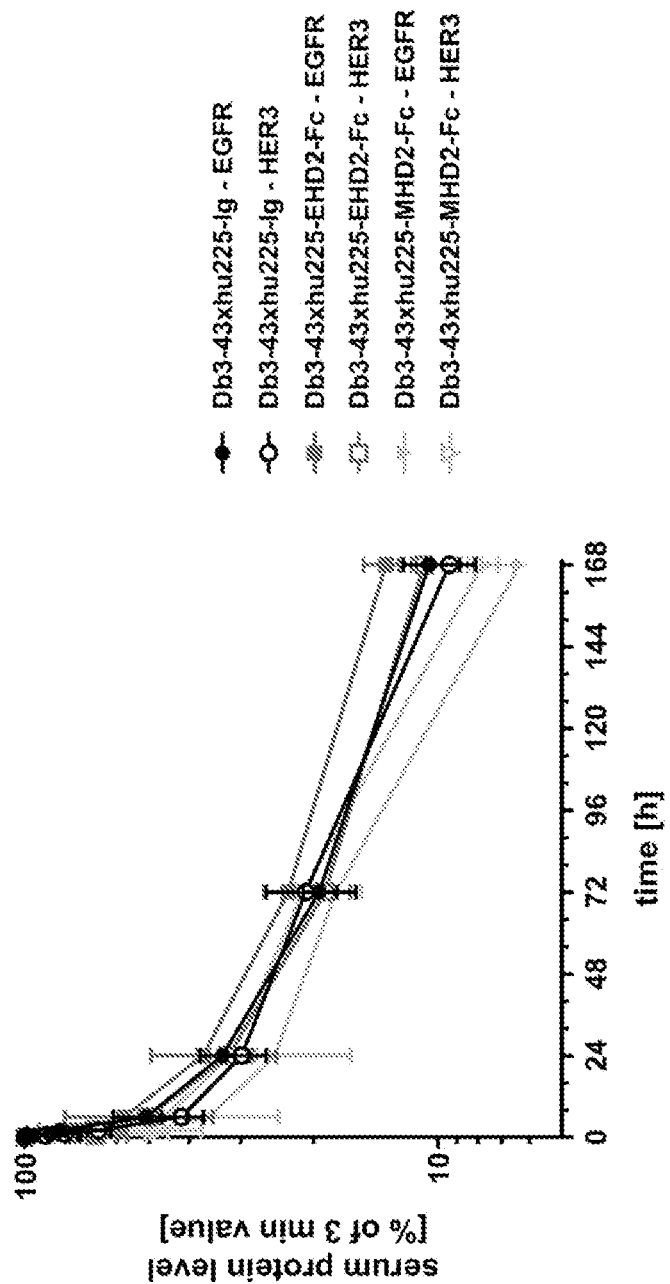

FIG. 35: Pharmacokinetic of bispecific, tetravalent binding molecules in SWISS mice. Pharmacokinetic profile of Db3-43xhu225-Ig, Db3-43xhu225-EHD2-Fc, and Db3-43xhu225-MHD2-Fc was determined in female SWISS mice (3 mice). 25 µg protein were injected intravenously into the tail vein. Concentrations of serum samples collected after indicated time intervals were determined via ELISA using either EGFR-Fc and HER3-Fc fusion protein (for detection of Db3-43xhu225-Ig) or His-tagged EGFR and HER3 (for analysis of Db3-43xhu225-EHD2-Fc and Db3-43xhu225-MHD2-Fc) as coated antigen. Bound Db3-43xhu225-Ig molecules were detected using a HRP-conjugated anti-human Fab secondary antibody, whereas bound Db3-43xhu225-EHD2-Fc, and Db3-43xhu225-MHD2-Fc was detected using a HRP-conjugated anti-human Fc secondary antibody. Serum protein levels are represented as relative (% of 3 min value) values.

Figure 36:
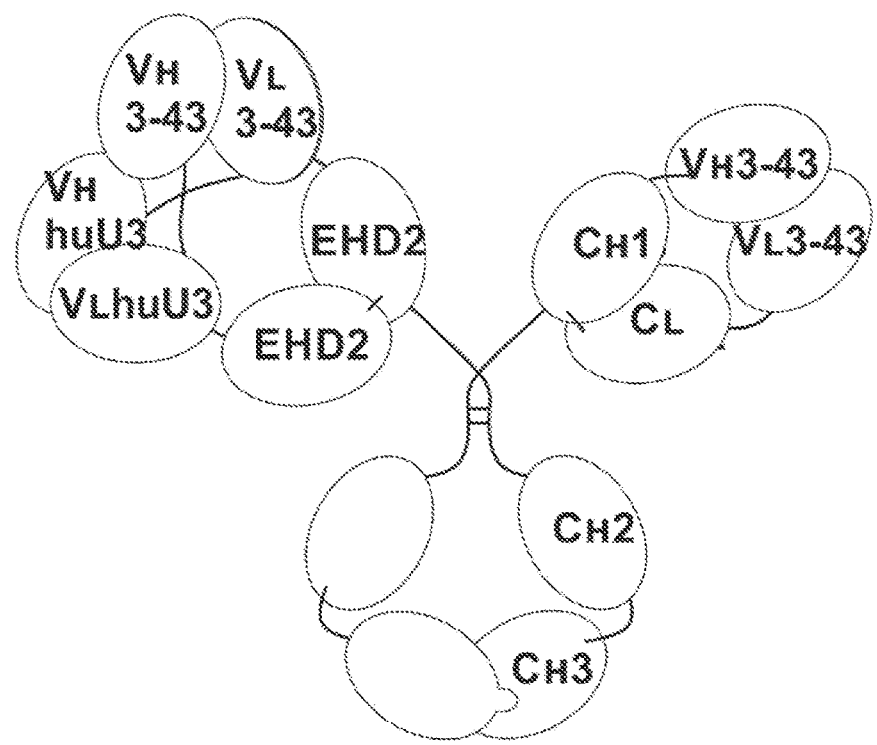
Figure 36:
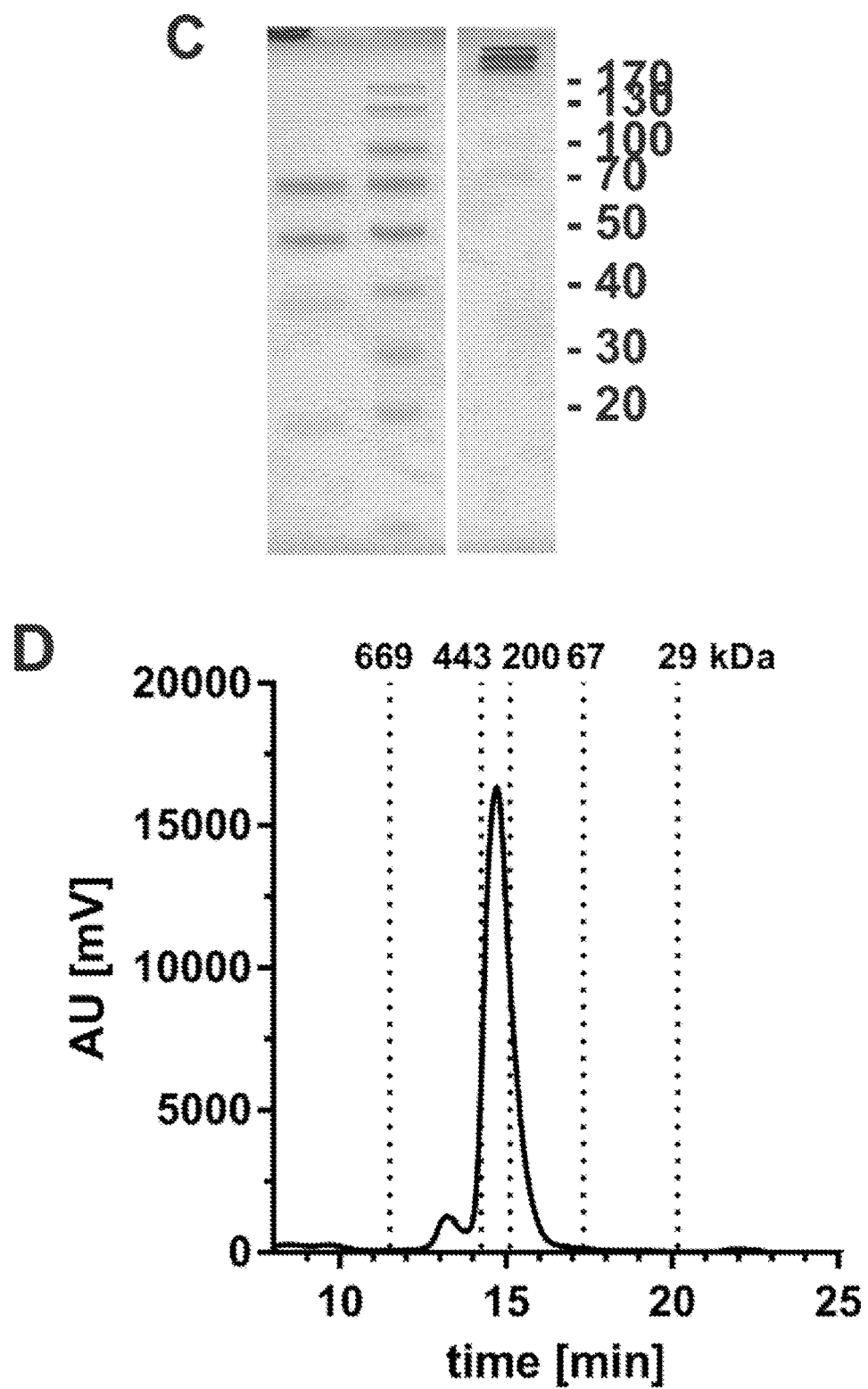
Figure 36:
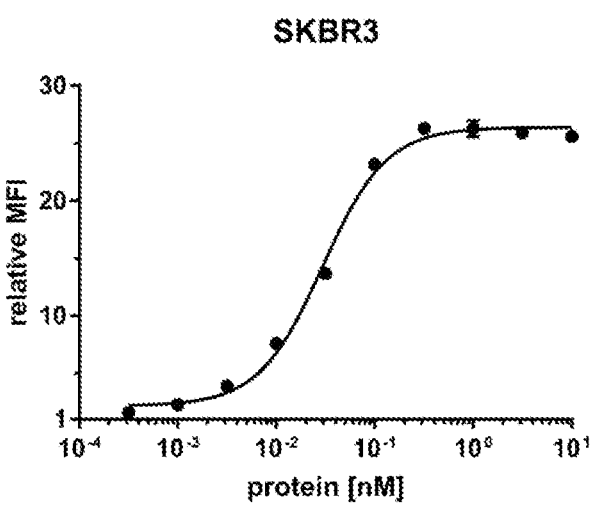
Figure 36:
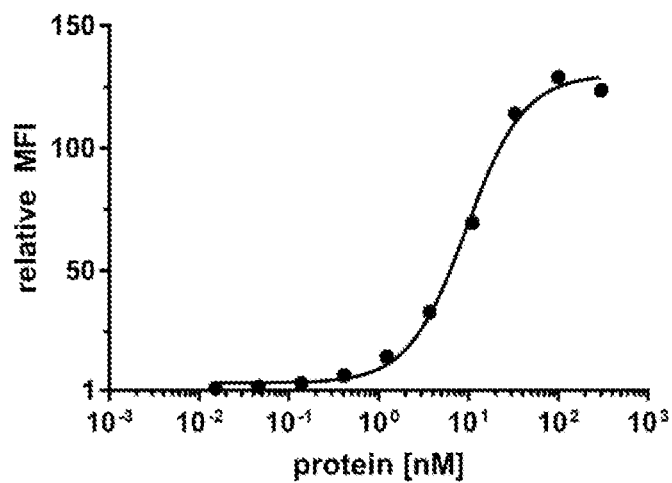
Figure 36:
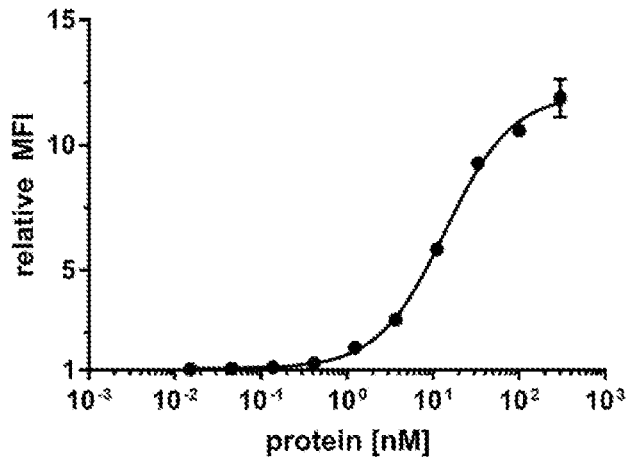

FIG. 36: Biochemical characterization and binding of Db3-43xhuU3-EHD2-Fab3-43-Feu, A) Schematic illustration of the light and the heavy chains of the diabody and Fab moiety of the Db3-43xhuU3-EHD2-Fab3-43-Fc$_{kih}$ fusion protein. B) Schematic structure of the domains in the Db3-43xhuU3-EHD2-Fab3-43-Fc$_{kih}$ fusion protein. C) SDS-PAGE analysis (12% PAA; Coomassie stained) of the Db3-43xhuU3-EHD2-Fab3-43-Fc$_{kih}$ fusion protein under reducing (1) and non-reducing (2) conditions (M: marker). D) Size exclusion chromatography of Db3-43xhuU3-EHD2-Fab3-43-Fc$_{kih}$ fusion protein. E) Binding of the bispecific, trivalent db3-43xhuU3-EHD2-Fab3-43-Fc$_{kih}$ was analyzed by flow cytometry using HER3-positive SKBR3 cells or CD3-positive Jurkat cells. Bound protein was detected with a PE-labeled anti-human Fc antibody. F) Simultaneous binding of the bispecific Db3-43xhuU3-EHD2-Fab3-43-Fc$_{kih}$ fusion protein was analyzed via flow cytometry using CD3-positive Jurkat cells and His-tagged HER3. Serial dilution of Db3-43xhuU3-EHD2-Fab3-43-Fc$_{kih}$ was incubated with the cells. Finally, the second antigen, HER3-His, was added to the cells. Bound HER3-His was detected using a PE-labeled anti-His antibody.

Figure 37:
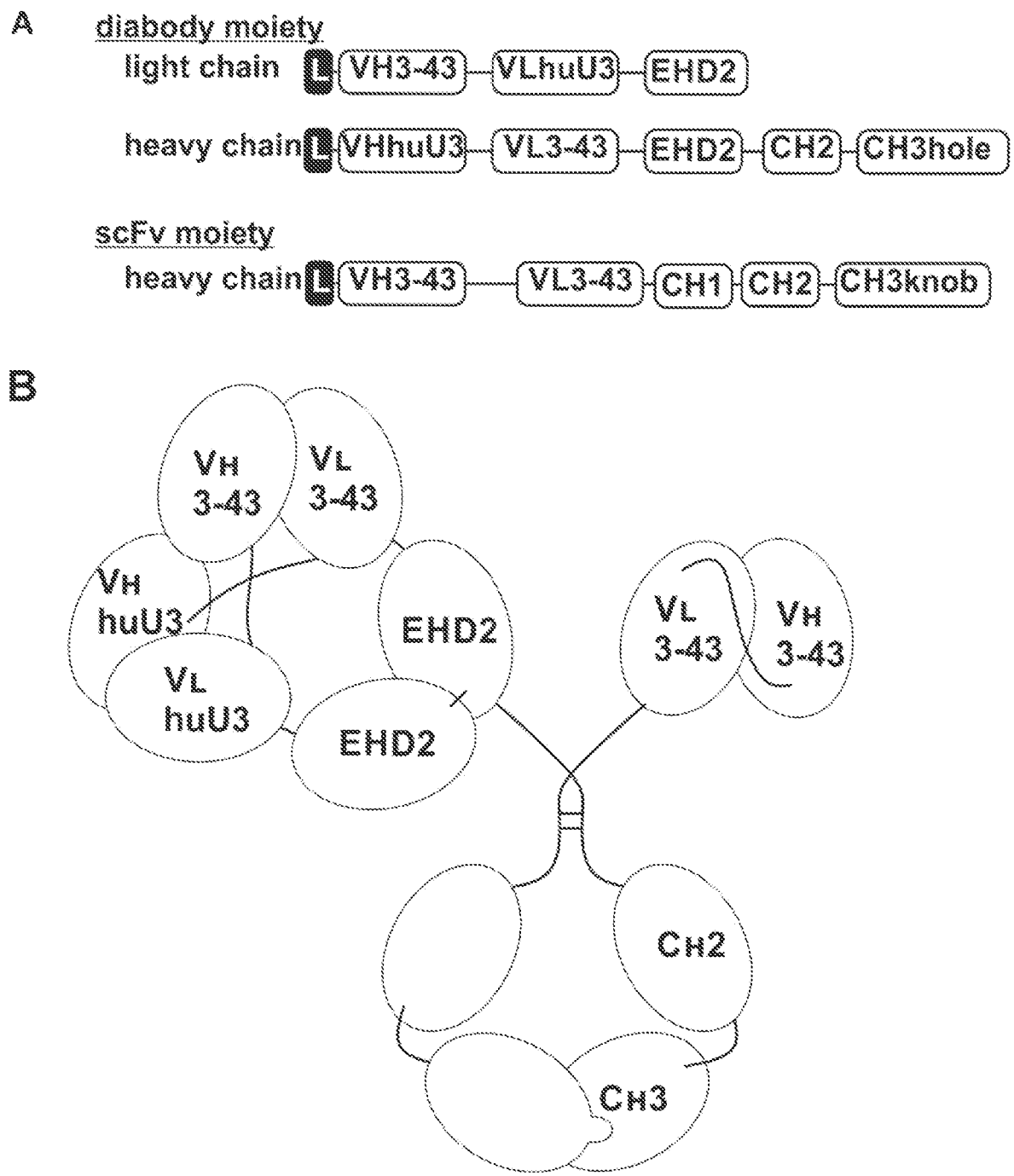
Figure 37:
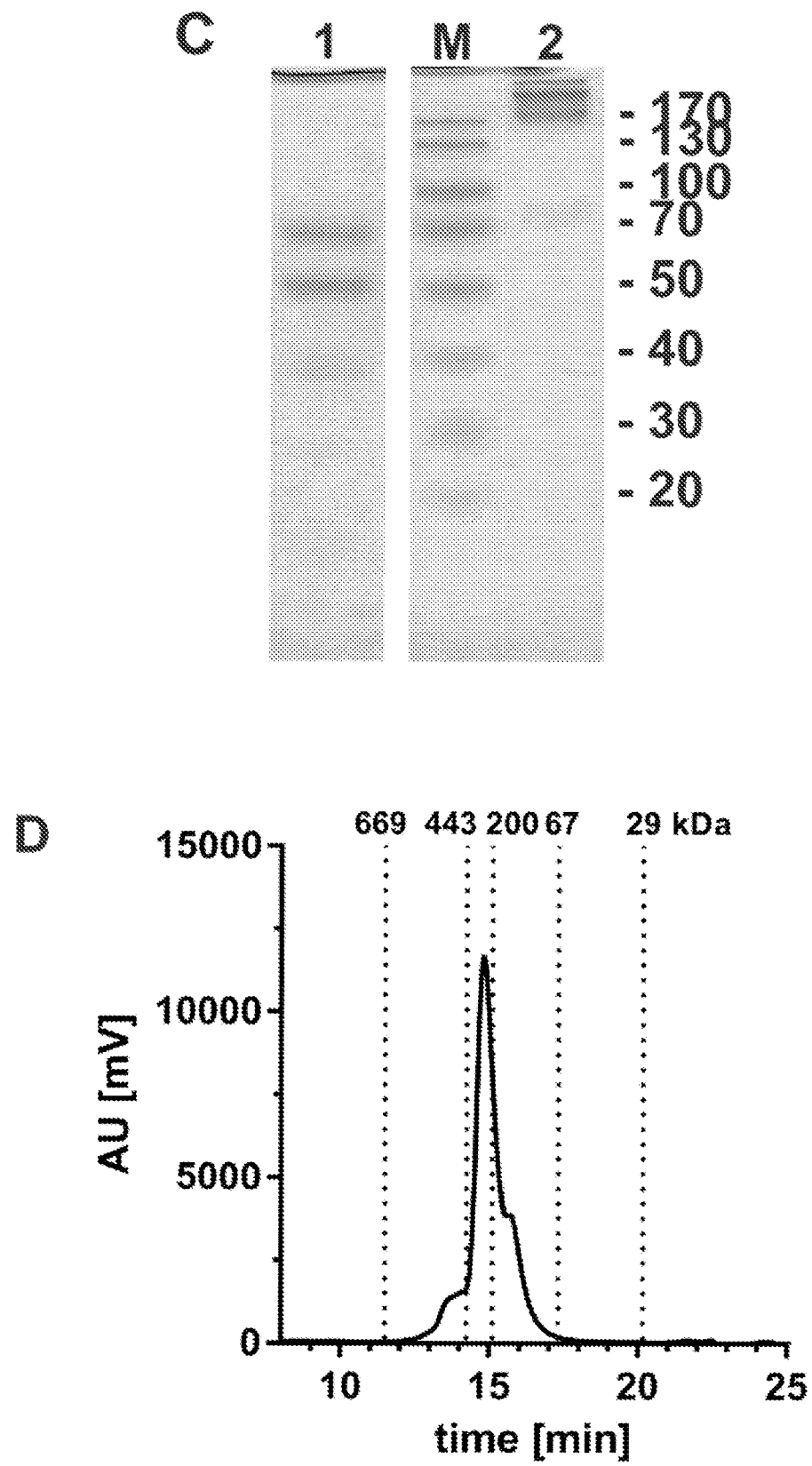
Figure 37:
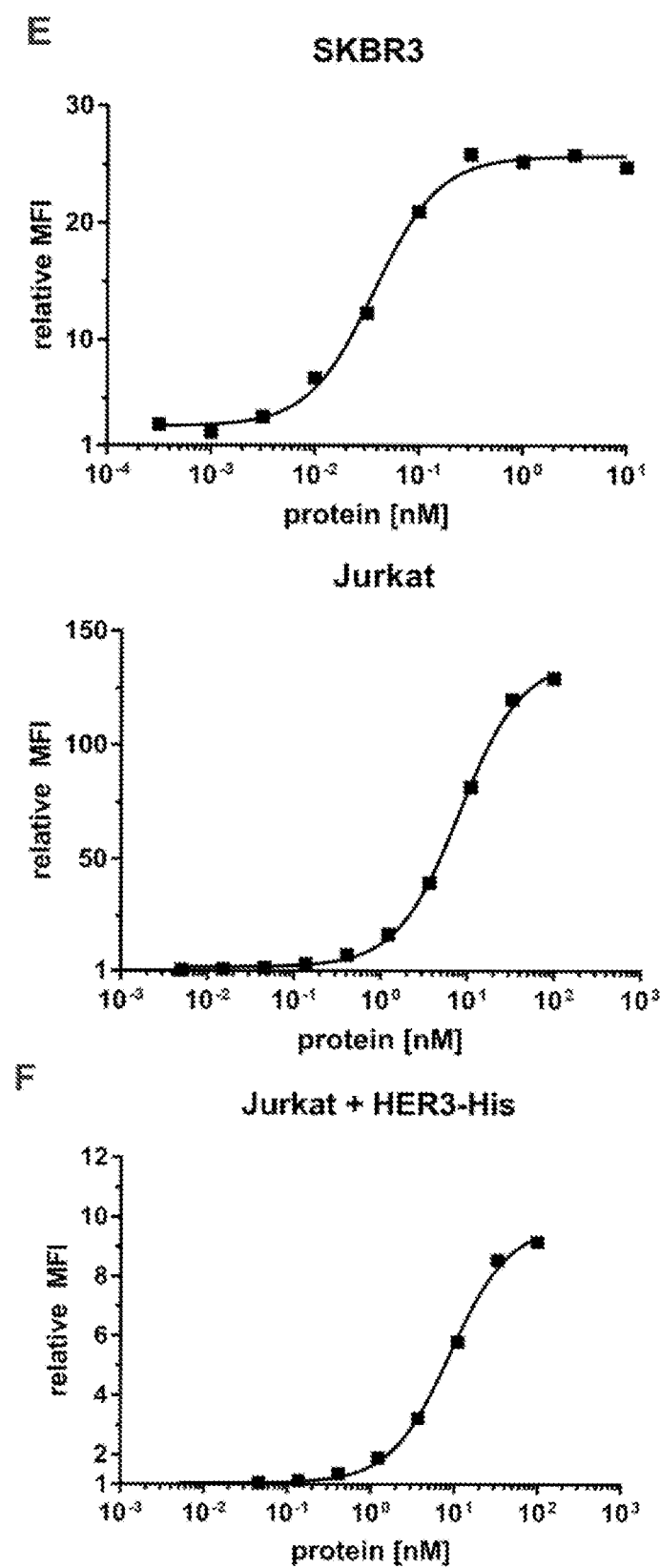

FIG. 37: Biochemical characterization and binding of Db3-43xhuU3-EHD2-scFv3-43-Fc$_{kih}$. A) Schematic illustration of the light and the heavy chain of the diabody and the scFv moiety of the Db3-43xhuU3-EHD2-scFv3-43-Fc$_{kih}$ fusion protein. B) Schematic structure of the domains in the Db3-43xhuU3-EHD2-scFv3-43-Fc$_{kih}$ fusion protein. C) SDS-PAGE analysis (12% PAA; Coomassie stained) of the Db3-43xhuU3-EHD2-scFv3-43-Fc$_{kih}$ fusion protein under reducing (1) and non-reducing (2) conditions (M: marker). D) Size exclusion chromatography of Db3-43xhuU3-EHD2-scFv3-43-Fc$_{kih}$ fusion protein. E) Binding of the bispecific, trivalent Db3-43xhuU3-EHD2-scFv3-43-Fc$_{kih}$ was analyzed by flow cytometry using HER3-positive SKBR3 cells or CD3-positive Jurkat cells. Bound protein was detected with a PE-labeled anti-human Fc antibody. F) Simultaneous binding of the bispecific Db3-43xhuU3-EHD2-scFv3-43-Fc$_{kih}$ fusion protein was analyzed via flow cytometry using CD3-positive Jurkat cells and His-tagged HER3. Serial dilution of Db3-43xhuU3-EHD2-scFv3-43-Fc$_{kih}$ was incubated with the cells. Finally, the second antigen, HER3-His, was added to the cells. Bound HER3-His was detected using a PE-labeled anti-His antibody.

Figure 38:
Figure 38:
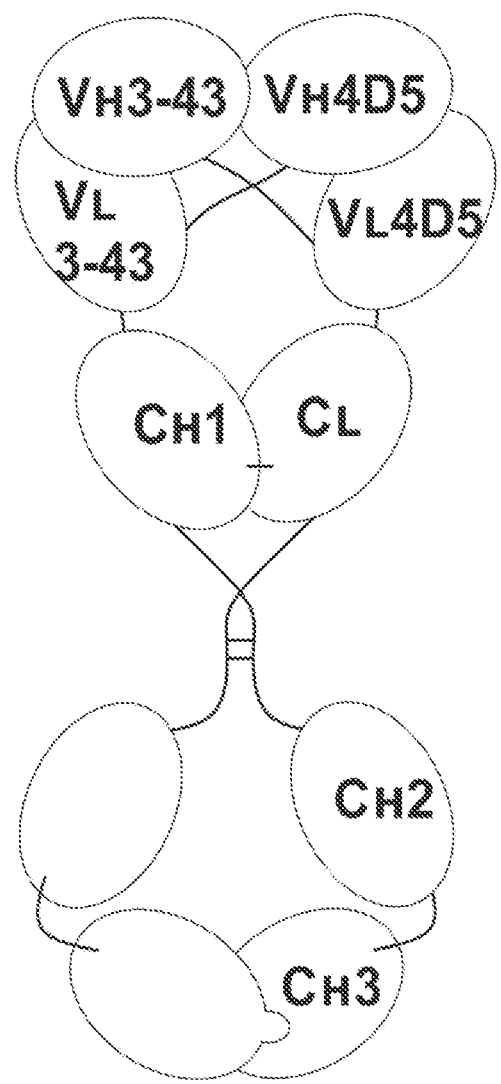
Figure 38:
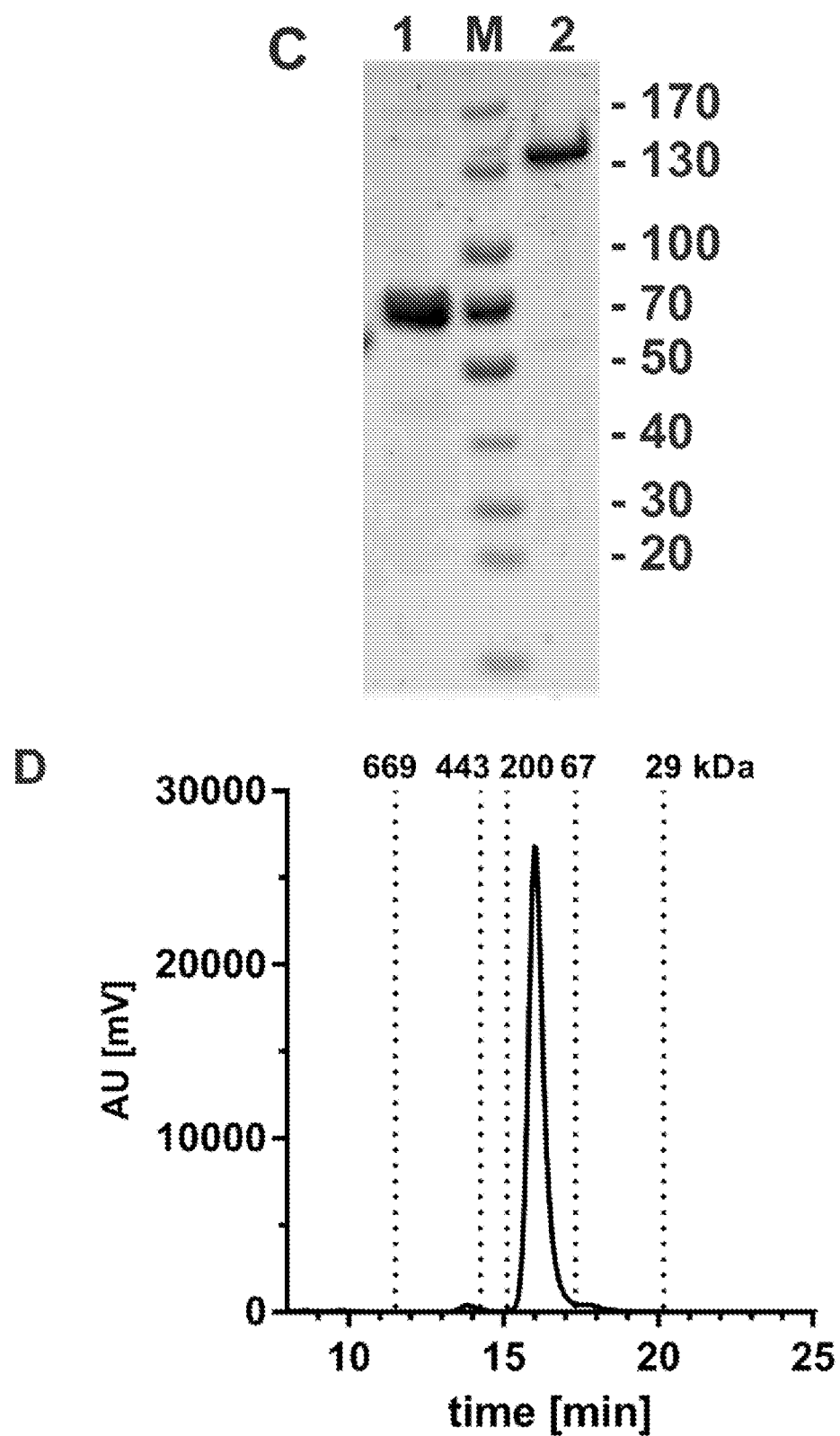
Figure 38:
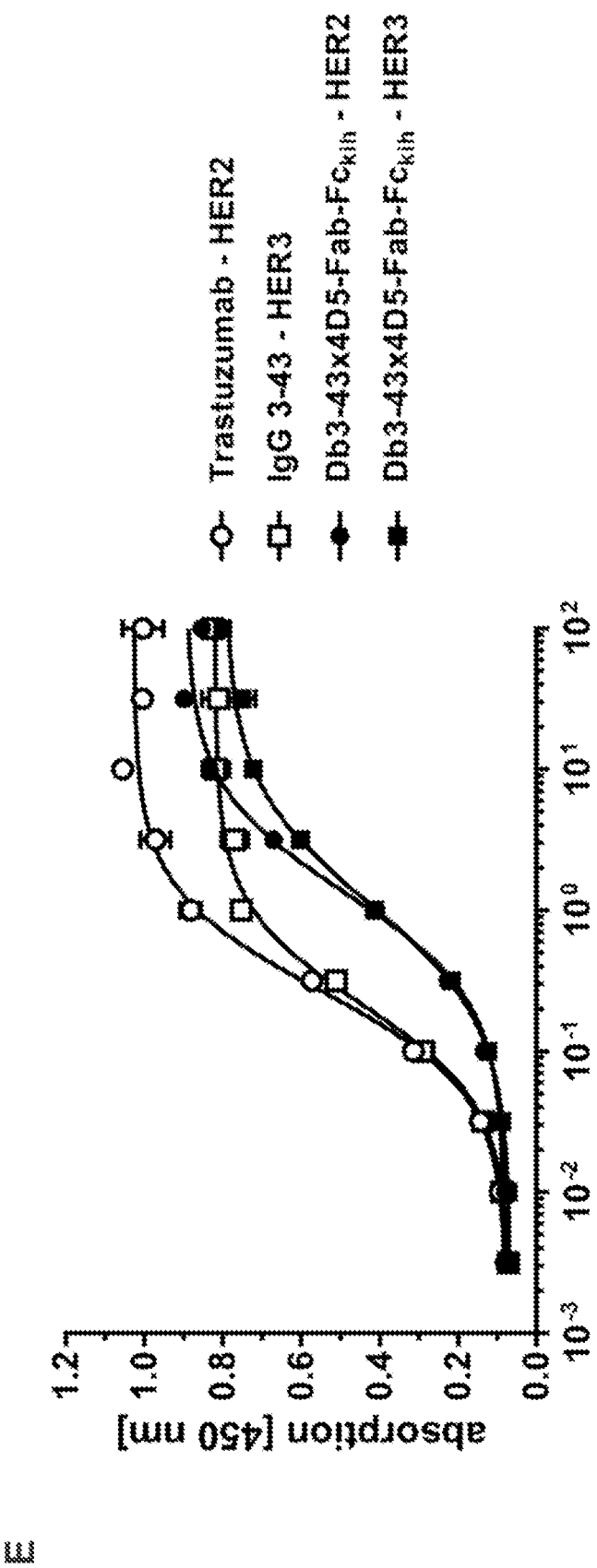

FIG. 38: Biochemical characterization and binding of Db3-43x4D5-Fab-Fc$_{kih}$. A) Schematic illustration of both heavy chains of the Db3-43x4D5-Fab-Fc$_{kih}$ fusion protein. B) Schematic structure of the domains in the Db3-43x4D5-Fab-Fc$_{kih}$ fusion protein. C) SDS-PAGE analysis (gradient PAA; Coomassie stained) of the Db3-43x4D5-Fab-Fc$_{kih}$ fusion protein under reducing (1) and non-reducing (2) conditions (M: marker). D) Size exclusion chromatography of Db3-43x4D5-Fab-Fc$_{kih}$ fusion protein. E) Binding of the bispecific, bivalent Db3-43x4D5-Fab-Fc$_{kih}$ was analyzed by ELISA using Fc fusion proteins of the extracellular domain of HER2 or HER3 as antigen. Bound protein was detected with an HRP-conjugated anti-human Fab antibody. Parenteral antibodies (Trastuzumab and IgG 3-43) were used as control. Optical density was measured at 450 nm.

LIST OF SEQUENCES

SEQ ID NO: 1 Amino acid sequence of peptide linker: GGGGS
SEQ ID NO: 2 Amino acid sequence of TCR α
SEQ ID NO: 3 Amino acid sequence of TCR β
SEQ ID NO: 4 Amino acid sequence of FcRn alpha 3
SEQ ID NO: 5 Amino acid sequence of β2 microglobulin
SEQ ID NO: 6 Amino acid sequence of HLA-A
SEQ ID NO: 7 Amino acid sequence of HLA-B α3
SEQ ID NO: 8 Amino acid sequence of HLA-D α2
SEQ ID NO: 9 Amino acid sequence of HLA-D β2
SEQ ID NO: 10 Amino acid sequence of the C-terminal end of $V_H$: TVSS
SEQ ID NO: 11 Amino acid sequence of the C-terminal end of $V_L$-λ: TVL
SEQ ID NO: 12 Amino acid sequence of the C-terminal end of $V_L$-κ: IK
SEQ ID NO: 13 Amino acid sequence of $V_H$DR5-$V_L$DR5-$C_H$1-$C_H$2-$C_H$3
SEQ ID NO: 14 Amino acid sequence of $V_H$DR5-$V_L$DR5-$C_L$
SEQ ID NO: 15 Amino acid sequence of $V_H$TNFR2-$V_L$TNFR2-$C_H$1-$C_H$2-$C_H$3
SEQ ID NO: 16 Amino acid sequence of $V_H$TNFR2-$V_L$TNFR2-$C_L$
SEQ ID NO: 17 Amino acid sequence of $V_H$hu225-$V_L$3M6-$C_H$1-$C_H$2-$C_H$3
SEQ ID NO: 18 Amino acid sequence of $V_H$3M6-$V_L$hu225-$C_L$
SEQ ID NO: 19 Amino acid sequence of $V_H$hu225-$V_L$3-43-$C_H$1-$C_H$2-$C_H$3
SEQ ID NO: 20 Amino acid sequence of $V_H$3-43-$V_L$hu225-$C_L$
SEQ ID NO: 21 Amino acid sequence of $V_H$hu225-$V_L$3-43-EHD2-$C_H$2-$C_H$3
SEQ ID NO: 22 Amino acid sequence of $V_H$3-43-$V_L$hu225-EHD2
SEQ ID NO: 23 Amino acid sequence of $V_H$hu225-$V_L$3-43-hetEHD2-$C_H$2-$C_H$3
SEQ ID NO: 24 Amino acid sequence of $V_H$3-43-$V_L$hu225-hetEHD2
SEQ ID NO: 25 Amino acid sequence of $V_H$hu225-$V_L$3-43-MHD2-$C_H$2-$C_H$3
SEQ ID NO: 26 Amino acid sequence of $V_H$3-43-$V_L$hu225-MHD2
SEQ ID NO: 27 Amino acid sequence of $V_H$huU3-$V_L$3-43-EHD2-$C_H$2-$C_H$3
SEQ ID NO: 28 Amino acid sequence of $V_H$3-43-$V_L$huU3-EHD2
SEQ ID NO: 29 Amino acid sequence of $V_H$3-43-$C_H$1-$C_H$2-$C_H$3$_{knob}$
SEQ ID NO: 30 Amino acid sequence of $V_L$3-43-$C_L$
SEQ ID NO: 31 Amino acid sequence of $V_H$3-43-$V_L$3-43-$C_H$2-$C_H$3$_{knob}$
SEQ ID NO: 32 Amino acid sequence of $V_H$4D5-$V_L$3-43-$C_H$1-$C_H$2-$C_H$3$_{hole}$
SEQ ID NO: 33 Amino acid sequence of $V_H$3-43-$V_L$4D5-$C_L$-$C_H$2-$C_H$3$_{knob}$
SEQ ID NO: 34 Amino acid sequence of Human EHD2
SEQ ID NO: 35 Amino acid sequence of Human MHD2
SEQ ID NO: 36 Amino acid sequence of Fc-Δab (incl. hinge)

DETAILED DESCRIPTIONS OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages, different aspects of the invention are defined in more detail. Each aspect so defined may be combined with any other aspect or aspects unless clearly indicated to the contrary. In particular, any feature indicated as being optional, preferred or advantageous may be combined with any other feature or features indicated as being optional, preferred or advantageous.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments; however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

In the following, some definitions of terms frequently used in this specification are provided. These terms will, in each instance of its use, in the remainder of the specification have the respectively defined meaning and preferred meanings.

As used in this specification and the appended claims, the singular forms "a", "an", and "the" include plural referents, unless the content clearly dictates otherwise.

The term "antigen binding protein", as used herein, refers to any molecule or part of a molecule that can specifically bind to a target molecule or target epitope. Preferred binding proteins in the context of the present application are (a) antibodies or antigen-binding fragments thereof; (b) oligonucleotides; (c) antibody-like proteins; or (d) peptidomimetics.

The term "binding" according to the invention preferably relates to a specific binding. "Specific binding" means that a binding protein (e.g. an antibody) binds stronger to a target such as an epitope for which it is specific compared to the binding to another target. A binding protein binds stronger to a first target compared to a second target if it binds to the first target with a dissociation constant ($K_d$) which is lower than the dissociation constant for the second target. Preferably the dissociation constant ($K_d$) for the target to which the binding protein binds specifically is more than 10-fold, preferably more than 20-fold, more preferably more than 50-fold, even more preferably more than 100-fold, 200-fold, 500-fold or 1000-fold lower than the dissociation constant ($K_d$) for the target to which the binding protein does not bind specifically.

As used herein, the term "$K_d$" (measured in "mol/L", sometimes abbreviated as "M") is intended to refer to the dissociation equilibrium constant of the particular interaction between a binding protein (e.g. an antibody or fragment thereof) and a target molecule (e.g. an antigen or epitope thereof). Methods for determining binding affinities of compounds, i.e. for determining the dissociation constant $K_D$, are known to a person of ordinary skill in the art and can be selected for instance from the following methods known in the art: Surface Plasmon Resonance (SPR) based technology, Bio-layer interferometry (BLI), quartz crystal microbalance (QCM), enzyme-linked immunosorbent assay (ELISA), flow cytometry, isothermal titration calorimetry (ITC), analytical ultracentrifugation, radioimmunoassay (RIA or IRMA) and enhanced chemiluminescence (ECL). In the context of the present application, the "$K_d$" value is determined by surface plasmon resonance spectroscopy (Biacore™) or by quartz crystal microbalance (QCM) at room temperature (25° C.).

The term "antigen-binding fragment" of an antibody (or simply "binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain or a VL domain, a VHH, a Nanobody, or a variable domain of an IgNAR; (vi) isolated complementarity determining regions (CDR), and (vii) combinations of two or more isolated CDRs which may optionally be joined by a synthetic peptide linker. Furthermore, although the two domains of the Fv fragment, VL and VH, are coded for by separate genes, they can be joined, using recombinant methods, by a synthetic peptide linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is a binding-domain immunoglobulin fusion protein comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies. Further examples of "antigen-binding fragments" are so-called microantibodies, which are derived from single CDRs. For example, Heap et al., 2005, describe a 17 amino acid residue microantibody derived from the heavy chain CDR3 of an antibody directed against the gp120 envelope glycoprotein of HIV-1. Other examples include small antibody mimetics comprising two or more CDR regions that are fused to each other, preferably by cognate framework regions. Such a small antibody mimetic comprising $V_H$ CDR1 and $V_L$ CDR3 linked by the cognate $V_H$ FR2 has been described by Qiu et al., 2007.

The dimerization domains of the invention that are based immunoglobulins can be of any class (e.g., IgG, IgE, IgM, IgD, IgA and IgY), or subclass of immunoglobulin molecule (e.g., IgG1, IgG2, IgG3, IgG4, IgA1 and IgA2). Similarly, antibodies that may be non-covalently or covalently attached to the antigen-binding protein complex of the present invention, may be of any of the above indicated immunoglobulin type.

Antibodies and antigen-binding fragments thereof usable in the invention may be from any animal origin including birds and mammals. Preferably, the antibodies or fragments are from human, chimpanzee, rodent (e.g. mouse, rat, guinea pig, or rabbit), chicken, turkey, pig, sheep, goat, camel, cow, horse, donkey, cat, or dog origin. It is particularly preferred that the antibodies are of human or murine origin. Antibodies of the invention also include chimeric molecules in which an antibody constant region derived from one species, preferably human, is combined with the antigen binding site derived from another species, e.g. mouse. Moreover antibodies of the invention include humanized molecules in which the antigen binding sites of an antibody derived from a non-human species (e.g. from mouse) are combined with constant and framework regions of human origin.

As exemplified herein, antibodies of the invention can be obtained directly from hybridomas which express the antibody, or can be cloned and recombinantly expressed in a host cell (e.g., a CHO cell, or a lymphocytic cell). Further examples of host cells are microorganisms, such as *E. coli*, and fungi, such as yeast. Alternatively, they can be produced recombinantly in a transgenic non-human animal or plant.

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g. mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g. from a transfectoma, (c) antibodies isolated from a recombinant, combinatorial antibody library, and (d) antibodies prepared, expressed, created or isolated by any other means that involve splicing of immunoglobulin gene sequences to other DNA sequences.

Thus, "antibodies and antigen-binding fragments thereof" suitable for use in the present invention include, but are not limited to, polyclonal, monoclonal, monovalent, bispecific, heteroconjugate, multispecific, recombinant, heterologous, heterohybrid, chimeric, humanized (in particular CDR-grafted), deimmunized, or human antibodies, Fab fragments, Fab' fragments, F(ab')$_2$ fragments, fragments produced by a Fab expression library, Fd, Fv, disulfide-linked Fvs (dsFv), single chain antibodies (e.g. scFv), diabodies or tetrabodies (Holliger P. et al. (1993) Proc. Natl. Acad. Sci. U.S.A. 90(14), 6444-6448), nanobodies (also known as single domain antibodies), anti-idiotypic (anti-Id) antibodies (including, e.g., anti-Id antibodies to antibodies of the invention), and epitope-binding fragments of any of the above.

The term "naturally occurring", as used herein, as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

As used herein, the term "nucleic acid aptamer" refers to a nucleic acid molecule that has been engineered through repeated rounds of in vitro selection or SELEX (systematic evolution of ligands by exponential enrichment) to bind to a target molecule (for a review see: Brody E. N. and Gold L. (2000), Aptamers as therapeutic and diagnostic agents. J. Biotechnol. 74(1):5-13). The nucleic acid aptamer may be a DNA or RNA molecule. The aptamers may contain modifications, e.g. modified nucleotides such as 2'-fluorine-substituted pyrimidines.

As used herein, the term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affibodies, anticalins, and designed ankyrin repeat proteins (for review see: Binz H. K. et al. (2005) Engineering novel binding proteins from nonimmunoglobulin domains. Nat. Biotechnol. 23(10):1257-1268). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins. Antibody-like proteins are sometimes referred to as "peptide aptamers".

As used herein, a "peptidomimetic" is a small protein-like chain designed to mimic a peptide. Peptidomimetics typically arise from modification of an existing peptide in order to alter the molecule's properties. For example, they may arise from modifications to change the molecule's stability or biological activity. This can have a role in the development of drug-like compounds from existing peptides. These modifications involve changes to the peptide that will not occur naturally (such as altered backbones and the incorporation of nonnatural amino acids).

The "percentage of sequences identity" is determined by comparing two optimally aligned sequences over a comparison window, wherein the portion of the sequence in the comparison window can comprise additions or deletions (i.e. gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" is used herein in the context of two or more nucleic acids or polypeptide sequences, to refer to two or more sequences or subsequences that are the same, i.e. comprise the same sequence of nucleotides or amino acids. Sequences are "substantially identical" to each other if they have a specified percentage of nucleotides or amino acid residues that are the same (e.g., at least 70%, at least 75%, at least 80, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity over a specified region), when compared and aligned for maximum correspondence over a comparison window, or designated region as measured using one of the following sequence comparison algorithms or by manual alignment and visual inspection. These definitions also refer to the complement of a test sequence. Accordingly, the term "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

The term "sequence comparison" is used herein to refer to the process wherein one sequence acts as a reference sequence, to which test sequences are compared. When using a sequence comparison algorithm, test and reference sequences are entered into a computer, if necessary subsequence coordinates are designated, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise.

In a sequence alignment, the term "comparison window" refers to those stretches of contiguous positions of a sequence which are compared to a reference stretch of contiguous positions of a sequence having the same number of positions. The number of contiguous positions selected may range from 4 to 1000, i.e. may comprise 4, 5, 10, 20, 30, 40, 50, 60, 70, 80, 90, 100, 150, 200, 250, 300, 350, 400, 450, 500, 550, 600, 650, 700, 750, 800, 850, 900, 950, or 1000 contiguous positions. Typically, the number of contiguous positions ranges from about 20 to 800 contiguous positions, from about 20 to 600 contiguous positions, from about 50 to 400 contiguous positions, from about 50 to about 200 contiguous positions, from about 100 to about 150 contiguous positions.

Methods of alignment of sequences for comparison are well known in the art. Optimal alignment of sequences for comparison can be conducted, for example, by the local homology algorithm of Smith and Waterman (Adv. Appl. Math. 2:482, 1970), by the homology alignment algorithm of Needleman and Wunsch (J. Mol. Biol. 48:443, 1970), by the search for similarity method of Pearson and Lipman (Proc. Natl. Acad. Sci. USA 85:2444, 1988), by computerized implementations of these algorithms (e.g., GAP, BEST-FIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)). Algorithms suitable for determining percent sequence identity and sequence similarity are the BLAST and BLAST 2.0 algorithms, which are described in Altschul et al. (Nuc. Acids Res. 25:3389-402, 1977), and Altschul et al. (J. Mol. Biol. 215:403-10, 1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands. The BLAST algorithm also performs a statistical analysis of the similarity between two sequences (see, e.g., Karlin and Altschul, Proc. Natl. Acad. Sci. USA 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

"Conservative substitutions" may be made, for instance, on the basis of similarity in polarity, charge, size, solubility, hydrophobicity, hydrophilicity, and/or the amphipathic nature of the amino acid residues involved. Amino acids can be grouped into the following six standard amino acid groups:

(1) hydrophobic: Met, Ala, Val, Leu, Be;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. Some preferred conservative substitutions within the above six groups are exchanges within the following sub-groups: (i) Ala, Val, Leu and Ile; (ii) Ser and Thr; (ii) Asn and Gln; (iv) Lys and Arg; and (v) Tyr and Phe. Given the known genetic code, and recombinant and synthetic DNA techniques, the skilled scientist readily can construct DNAs encoding the conservative amino acid variants.

As used herein, "non-conservative substitutions" or "non-conservative amino acid exchanges" are defined as exchanges of an amino acid by another amino acid listed in a different group of the six standard amino acid groups (1) to (6) shown above.

The term "nucleic acid" and "nucleic acid molecule" are used synonymously herein and are understood as single or double-stranded oligo- or polymers of deoxyribonucleotide or ribonucleotide bases or both. Nucleotide monomers are composed of a nucleobase, a five-carbon sugar (such as but not limited to ribose or 2'-deoxyribose), and one to three phosphate groups. Typically, a nucleic acid is formed through phosphodiester bonds between the individual nucleotide monomers, In the context of the present invention, the term nucleic acid includes but is not limited to ribonucleic acid (RNA) and deoxyribonucleic acid (DNA) molecules but also includes synthetic forms of nucleic acids comprising other linkages (e.g., peptide nucleic acids as described in Nielsen et al. (Science 254:1497-1500, 1991). Typically, nucleic acids are single- or double-stranded molecules and are composed of naturally occurring nucleotides. The depiction of a single strand of a nucleic acid also defines (at least partially) the sequence of the complementary strand. The nucleic acid may be single or double stranded, or may contain portions of both double and single stranded sequences. Exemplified, double-stranded nucleic acid molecules can have 3' or 5' overhangs and as such are not required or assumed to be completely double-stranded over their entire length. The nucleic acid may be obtained by biological, biochemical or chemical synthesis methods or any of the methods known in the art, including but not limited to methods of amplification, and reverse transcription of RNA. The term nucleic acid comprises chromosomes or chromosomal segments, vectors (e.g., expression vectors), expression cassettes, naked DNA or RNA polymer, primers, probes, cDNA, genomic DNA, recombinant DNA, cRNA, mRNA, tRNA, microRNA (miRNA) or small interfering RNA (siRNA). A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

Nucleic acids may be degraded by endonucleases or exonucleases, in particular by DNases and RNases which can be found in the cell. It may, therefore, be advantageous to modify the nucleic acids of the invention in order to stabilize them against degradation, thereby ensuring that a high concentration of the nucleic acid is maintained in the cell over a long period of time. Typically, such stabilization can be obtained by introducing one or more internucleotide phosphorus groups or by introducing one or more non-phosphorus internucleotides. Accordingly, nucleic acids can be composed of non-naturally occurring nucleotides and/or modifications to naturally occurring nucleotides, and/or changes to the backbone of the molecule. Modified internucleotide phosphate radicals and/or non-phosphorus bridges in a nucleic acid include but are not limited to methyl phosphonate, phosphorothioate, phosphoramidate, phosphorodithioate and/or phosphate esters, whereas non-phosphorus internucleotide analogues include but are not limited to, siloxane bridges, carbonate bridges, carboxymethyl esters, acetamidate bridges and/or thioether bridges. Further examples of nucleotide modifications include but are not limited to: phosphorylation of 5' or 3' nucleotides to allow for ligation or prevention of exonuclease degradation/polymerase extension, respectively; amino, thiol, alkyne, or biotinyl modifications for covalent and near covalent attachments; fluorphores and quenchers; and modified bases such as deoxyInosine (dI), 5-Bromo-deoxyuridine (5-Bromo-dU), deoxyUridine, 2-Aminopurine, 2,6-Diaminopurine, inverted dT, inverted Dideoxy-T, dideoxyCytidine (ddC 5-Methyl deoxyCytidine (5-Methyl dC), locked nucleic acids (LNA's), 5-Nitroindole, Iso-dC and -dG bases, 2'-O-Methyl RNA bases, Hydroxmethyl dC, 5-hydroxybutynl-2'-deoxyuridine, 8-aza-7-deazaguanosine and Fluorine Modified Bases. Thus, the nucleic acid can also be an artificial nucleic acid which includes but is not limited to polyamide or peptide nucleic acid (PNA), morpholino and locked nucleic acid (LNA), as well as glycol nucleic acid (GNA) and threose nucleic acid (TNA).

The term "C-terminus" (also known as the carboxyl-terminus, carboxy-terminus, C-terminal tail, C-terminal end, or COOH-terminus) as referred to within the context of the present invention is the end of an amino acid chain (protein or polypeptide), terminated by a free carboxyl group (—COOH). When the protein is translated from messenger RNA, it is created from N-terminus to C-terminus. The term "N-terminus" (also known as the amino-terminus, $NH_2$-terminus, N-terminal end or amine-terminus) refers to the start of a protein or polypeptide terminated by an amino acid with a free amine group (—$NH_2$). The convention for writing peptide sequences is to put the N-terminus on the left and write the sequence from N- to C-terminus.

A "peptide linker" in the context of the present invention refers to an amino acid sequence, i.e. polypeptide, which sterically separates two parts within the engineered polypeptides of the present invention. Typically such peptide linker consists of between 1 and 100, preferably 3 to 50 more preferably 5 to 20 amino acids. Thus, such peptide linkers have a minimum length of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids, and a maximum length of at least 100, 95, 90, 85, 80, 75, 70, 65, 60, 55, 50, 45, 40, 35, 34, 33, 32, 31, 30, 29, 28, 27, 26, 25, 24, 23, 22, 21, 20, 19, 18, 17, 16, or 15 amino acids or less. Peptide linkers may also provide flexibility among the two parts that are linked together. Such flexibility is generally increased, if the amino acids are small. Accordingly, flexible peptide linkers comprise an increased content of small amino acids, in particular of glycins and/or alanines, and/or hydrophilic amino acids such as serines, threonines, asparagines and glutamines. Preferably, more than 20%, 30%, 40%, 50%, 60% or more of the amino acids of the peptide linker are small amino acids.

The term "Fc part with increased or reduced effector function" refers to a Fc part, which can form a homodimer or heterodimer, and binds to the respective effector molecules either with increased or reduced affinity, thus altering the effector function, e.g. ADCC, CMC, or FcRn-mediated recycling. There are different IgG variants with altered interaction for human FcγRIIIa (CD16) described in literature (Presta et al., 2008), e.g. IgG1-DE (S239D, I332E) resulting in 10-fold increased ADCC, or IgG1-DEL (S239D, I332E, A330L) resulting in 100-fold increased ADCC. Besides increasing the effector function, there also Fc parts with reduced effector function described in the literature. For the IgG1-P329G LALA variant (L234S, L235A, P329G) almost complete abolished interaction with the whole Fcγ receptor family was reported, resulting in effector silent molecules (Schlothauer et al., 2016). In addition, reduced binding to FcγRI, which was described for the IgG-Δab variant (E233P, L234V, L235A, 4236G, A327G, A330S, P331S) also resulted in reduced effector function (Armour et al., 1999) (also described in Strohl et al., 2009). Besides altering binding to receptors of immune cells (e.g. human FcγRIIIa), also binding to FcRn can be altered by introducing substitutions in the Fc part. Due to increased (or reduced) binding to the FcRn molecule, half-life of the Fc-containing molecule is affected, e.g. IgG1-YTE (M252Y, S254T, T256E) resulting in 3-4 fold increased terminal half-life of the protein, or IgG1-QL (T250Q, M428L) resulting in 2.5-fold increased terminal half-life (Presto et al., 2008; Strohl et al., 2009).

The term "heterodimerizing Fc" part relates to variants of a Fc part, which are able to form heterodimers. Besides the knob-into-hole technology (chain 1: T366S, L368A, Y407V; chain 2: T366W) there are other variants of the Fc part described in literature for the generation of heterodimeric Fc parts (Krah et al., 2007; Ha et al., 2016; Mimoto et al., 2016; Brinkmann & Kontermann, 2017).

Embodiments

In the following different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a first aspect, the present invention provides an antigen-binding protein complex comprising at least one dual binding module (DBM), and one homo- or hetero-dimerization module (HDM) and optionally a binding or effector module (BEM), wherein a. a first DBM module (DBM1) comprises two polypeptides, wherein the first polypeptide (P1) comprises a first dimerization domain (DD1) and a first variable heavy chain ($V_H1$) and a first variable light chain ($V_L1$), wherein said $V_H1$ and $V_L1$ are connected by a peptide linker (L1), with a length preventing binding of $V_H1$ and $V_L1$ to each other, and the second polypeptide (P2) comprises a second dimerization domain (DD2) and a second variable heavy chain ($V_H2$) and a second variable light chain ($V_L2$), wherein said $V_H2$ and $V_L2$ are connected by a peptide linker (L2), with a length preventing binding of $V_H2$ and $V_L2$, to each other and wherein $V_H1$ binds to $V_L2$ and $V_L1$ binds to $V_H2$ and each variable domain pair forms a binding site, and wherein DD1 specifically binds to DD2;

b. a second DBM module (DBM2), when present comprises two polypeptides, wherein the first polypeptide (P1') comprises a first dimerization domain (DD1') and a first variable heavy chain ($V_H1'$) and a first variable light chain ($V_L1'$), wherein said $V_H1'$ and $V_L1'$ are connected by a peptide linker (L1'), with a length preventing binding of $V_H1'$ and $V_L1'$ to each other, and the second polypeptide (P2') comprises a second dimerization domain (DD2') and a second variable heavy chain ($V_H2'$) and a second variable light chain ($V_L2'$), wherein said $V_H2'$ and $V_L2'$ are connected by a peptide linker (L2'), with a length preventing binding of $V_H2'$ and $V_L2'$ to each other, and wherein $V_H1'$ binds to $V_L2'$ and $V_L1'$ binds to $V_H2'$ and each variable domain pair forms a binding site, wherein DD1' specifically binds to DD2';

c. the BEM module, when present, comprises two polypeptides, wherein the third polypeptide (P3) comprises a third dimerization domain (DD3) and a third variable heavy chain domain ($V_H3$) and the fourth polypeptide (P4) comprises a fourth dimerization domain (DD4) and a third variable light chain ($V_L3$) domain, wherein $V_H3$ binds $V_L3$ and forms a binding site, wherein DD3 specifically binds to DD4;

d. at least one HDM module comprises two polypeptides, wherein:
  (i) in case no DBM2 or BEM are present:
    (a) the fifth polypeptide (P5) is covalently linked to P1 of DBM1 and comprises a fifth dimerization domain (DD5) and the sixth polypeptide (P6) comprises a sixth dimerization domain (DD6), which specifically binds to DD5; or
    (b) fifth polypeptide (P5) is covalently linked to P1 of DBM1 and comprises a fifth dimerization domain (DD5) and the sixth polypeptide (P6) is covalently linked to P2 of DBM1 and comprises a sixth dimerization domain (DD6), which specifically binds to DD5; or
  (ii) in case DBM2 or BEM are present the fifth polypeptide (P5) is covalently linked to P1 or P2 of DBM1 and comprises a fifth dimerization domain (DD5) and the sixth polypeptide (P6) is covalently linked to either P1' or P2' of DBM2 or either to P3 or P4 of the BEM and comprises a sixth dimerization domain (DD6), which specifically binds to DD5.

It is preferred that in each case the various polypeptides which are indicated to be linked to each other are linked by a peptide bond, i.e. form one polypeptide chain.

In a preferred embodiment, P5 essentially consists or consists of DD5.

In a preferred embodiment, P6 essentially consists or consists of DD6.

Given the various arrangements of the polypeptide outlined above it is preferred that from N- to C-terminus the polypeptide chain comprising the elements of the antigen binding protein complex are linked as follows:

(i) P1-P5, and P2 and P6 are not linked to each other;
(ii) P5-P1, and P2 and P6 are not linked to each other;
(iii) P1-P5, and P2-P6;
(iv) P5-P1, and P6-P2;
(v) P1-P5, and P3-P6;
(vi) P2-P5, and P3-P6:
(vii) P1-P5, and P4-P6;
(viii) P2-P5, and P4-P6;
(ix) P5-P1, and P6-P3;
(x) P5-P2, and P6-P3;
(xi) P5-P1, and P6-P4;
(xii) P5-P2, and P6-P4;
(xiii) P1-P5; and P1'-P6, and P2 and P2' are not linked to P5 or P6;
(xiv) P2-P5; and P1'-P6, and P1 and P2' are not linked to P5 or P6;
(xv) P1-P5; and P2'-P6, and P2 and P1' are not linked to P5 or P6;
(xvi) P2-P5; and P2'-P6, and P1 and P1' are not linked to P5 or P6;
(xvii) P5-P1; and P6-P1', and P2 and P2' are not linked to P5 or P6;
(xviii) P5-P2; and P6-P1', and P1 and P2' are not linked to P5 or P6;
(xix) P5-P1; and P6-P2', and P2 and P1' are not linked to P5 or P6;
(xx) P5-P1; and P6-P2', and P1 and P1' are not linked to P5 or P6;
(xxi) P1-P5, and P6-P2;
(xxii) P5-P1, and P2-P6;
(xxiii) P1-P5, and P6-P3;
(xxiv) P2-P5, and P6-P3;
(xxv) P1-P5, and P6-P4;
(xxvi) P2-P5, and P6-P4;
(xxvii) P5-P1, and P3-P6;
(xxviii) P5-P2, and P3-P6;
(xxix) P5-P1, and P4-P6;
(xxx) P5-P2, and P4-P6;
(xxxi) P1-P5; and P6-P1', and P2 and P2' are not linked to P5 or P6;
(xxxii) P2-P5; and P6-P1', and P1 and P2' are not linked to P5 or P6;
(xxxiii) P1-P5; and P6-P2', and P2 and P1' are not linked to P5 or P6;
(xxxiv) P2-P5; and P6-P2', and P1 and P1' are not linked to P5 or P6;
(xxxv) P5-P1; and P1'-P6, and P2 and P2' are not linked to P5 or P6;
(xxxvi) P5-P2; and P1'-P6, and P1 and P2' are not linked to P5 or P6;
(xxxvii) P5-P1; and P2'-P6, and P2 and P1' are not linked to P5 or P6; or (xxxviii) P5-P1; and P2'-P6, and P2 and P1' are not linked to P5 or P6.

In a particular embodiment of the first aspect of the invention it is preferred that P1 and P2 and if present also P1', P2', P3 or P4 are located at the N-terminus of the linked polypeptide chains.

Thus in a particular embodiment of the first aspect of the invention, the antigen-binding protein complex comprises only one DBM, i.e. DBM1, and one HDM. In this embodiment P5 is covalently linked to P1 of DBM1 and comprises DD5 and P6 comprises, essentially consists of or consists of DD6, which specifically binds to DD5. P2 may be non-covalently associated with P1 through the interaction of DD1 and DD2 or additionally stabilized by Cys-Cys bonds, e.g. are in the arrangement as outlined above under (i) and (ii). It is preferred that further functional groups, in particular a pharmaceutical active moiety and/or an imaging molecule is coupled to the N- and/or C-terminus of DD6.

In another particular embodiment of the first aspect of the invention, the antigen-binding protein complex comprises only one DBM, i.e. DBM1, and one HDM. In this embodiment P5 is covalently linked to P1 of DBM1 and P6 is covalently linked to P2 of DBM1. If P1 and P2 are located N-terminally, e.g. are in the arrangement as outlined above under (iii), it is preferred that further functional groups, in particular to a pharmaceutical active moiety and/or an imaging molecule are coupled to the C-terminus of DD5 and/or DD6. This is the preferred arrangement. If P1 and P2 are located C-terminally, e.g. are in the arrangement as outlined above under (iv), it is preferred that further functional groups, in particular to a pharmaceutical active moiety and/or an imaging molecule are coupled to the N-terminus of DD5 and DD6.

In another particular embodiment of the first aspect of the invention, the antigen-binding protein complex comprises only one DBM, i.e. DBM1, one BEM and one HDM. In this embodiment polypeptides P1, P2, P3, P4, P5 and P6 can be positioned with the polypeptide chains as indicated in alternatives (v) to (xii). As noted above, it is preferred that P1, or P2 (depending on whether P1 or P2 is covalently linked to P5) and P3 or P4 (depending on whether P3 or P4 is covalently linked to P6) are all located at the N-terminus of the polypeptide chain. The respective polypeptide not mentioned above in alternatives (v) to (xii) may bind to the antigen-binding protein complex through its respective dimerization domain solely by non-covalent bonds linked or may additionally be stabilized by Cys-Cys bonds. If P1 or P2 and P3 or P4 are located N-terminally, e.g. are in the arrangement as outlined above under (v) to (viii), it is preferred that further functional groups, in particular to a pharmaceutical active moiety and/or an imaging molecule are coupled to the C-terminus of DD5 and DD6. This is the preferred arrangement. If P1 or P2 and P3 or P4 are located C-terminally, e.g. are in the arrangement as outlined above under (ix) to (xii), it is preferred that further functional groups, in particular to a pharmaceutical active moiety and/or an imaging molecule are coupled to the N-terminus of DD5 and DD6.

In another particular embodiment of the first aspect of the invention, the antigen-binding protein complex comprises two DBM, i.e. DBM1 and DBM2 and one HDM. In this embodiment polypeptides P1, P2, P1', P2', P5 and P6 can be positioned with the polypeptide chains as indicated in alternatives (xiii) to (xx). As noted above, it is preferred that P1, or P2 (depending on whether P1 or P2 is covalently linked to P5) and P1' or P2' (depending on whether P1' or P2' is covalently linked to P6) are all located at the N-terminus of the polypeptide chain. The respective polypeptide not mentioned above in alternatives (xiii) to (xvi) is non-covalently linked to the antigen-binding protein complex through its respective dimerization domain. If P1 or P2 and P1' or P2' are located N-terminally, e.g. are in the arrangement as outlined above under (xiii) to (xvi), it is preferred that further functional groups, in particular to a pharmaceutical active moiety and/or an imaging molecule are coupled to the N-terminus of DD5 and DD6. This is the preferred arrangement. If P1 or P2 and P1' or P2' are located C-terminally, e.g. are in the arrangement as outlined above under (xvii) to (xx), it is preferred that further functional groups, in particular to a pharmaceutical active moiety and/or an imaging molecule are coupled to the N-terminus of DD5 and DD6.

It should be understood that in any of above outlined basic arrangements of the antigen-binding protein complex there are free N-terminal and/or C-terminal ends of the polypeptide chains which are available for the attachment of further functional groups. Alternatively, or additionally functional groups, in particular pharmaceutical active moieties and/or an imaging molecules may be coupled to side chains of amino acids within the polypeptide chains such as Lys, Arg, Glu or Asp. Such functional groups include, for example DBMs and BEMs. Thus, even if it is indicated above that the antigen-binding protein complex comprises one or two DBMs this does not exclude that it comprises one or more further DBMs and/or BEMs coupled to the N- and/or C-terminal and/or the side chain of an internal amino acid.

Each DBM comprises two variable light and variable heavy chains, wherein the $V_H$ chain of P1, and if present P1' interacts with a $V_L$ chain of P2, and if present P2' and a $V_L$ chain of P1, and if present P1' interacts with a $V_H$ chain of P2, and if present P2' to form a bivalent binding complex. Thus, the respective $V_L$ and $V_H$ chains are arranged in P1, and if present in P1' to interact with the respective $V_H$ and $V_L$ in P2, and if present in P2'. To ascertain that the $V_L$ and $V_H$ within one polypeptide, e.g. the $V_L$ and $V_H$ chains of P1 do not fold to interact with each other the $V_L$ and $V_H$ chains are connected by a peptide linker "L" that has a length that disfavor or prevents the intrachain interaction of $V_L$ and $V_H$ and, thus favors the interchain interaction between $V_L$ and $V_H$ chains on, e.g. P1 and P2 or P1' and P2'. The skilled person can easily determine suitable lengths of L that disfavors or prevents intrachain interaction of $V_L$ and $V_H$ within one polypeptide chain.

In a preferred embodiment of the first aspect of the invention, L1, L2 and optionally L1', and/or L2' has a length of between 4 to 12 amino acids, i.e. 4, 5, 6, 7, 8, 9, 10, 11, or 12, preferably of 4 to 10, more preferably 4 to 8, most preferably 5. It is preferred that the length of L1 and L2 and/or L1' and L2' are identical. In a particular embodiment L1, L1', L2 and/or L2' are GGGGS (SEQ ID NO: 1).

The C-terminal end of each $V_H$ specified herein, is in each case defined by the C-terminal sequence TVSS (SEQ ID NO: 10). The C-terminal end of each $V_L$-λ specified herein, is in each case defined by the C-terminal sequence TVL (SEQ ID NO: 11). The C-terminal end of each $V_L$-κ specified herein, is in each case defined by the C-terminal sequence IK (SEQ ID NO: 12). Preferably, the N-terminus of each $V_H$, $V_L$-λ and $V_L$-κ is EVQ, QVQ, SEL, SQS, DIQ or QAG. On the basis of the above defined C-terminal and N-terminal sequences of the various $V_H$, $V_L$-λ and $V_L$-κ the skilled person can determine the exact length of a peptide linker connecting $V_H$, $V_L$-λ and $V_L$-κ, respectively.

In a preferred embodiment of the first aspect of the invention, the variable domains of P1 and P2 of DBM1 (referred to as $V_H1$, $V_L1$ for P1 and $V_L2$, $V_H2$ for P2) and optionally the variable domains of DBM2 are arranged as follows from N- to C-terminus:
(i) $V_H1$-L1-$V_L1$ and $V_L2$-L2-$V_H2$; or
(ii) $V_L1$-L1-$V_H1$ and $V_H2$-L2-$V_L2$; or
(iii) $V_H1$-L1-$V_L1$ and $V_H2$-L2-$V_L2$; or
(iv) $V_L1$-L1-$V_H1$ and $V_L2$-L2-$V_H2$
and optionally, if present
(v) $V_H1'$-L1'-$V_L1'$ and $V_L2'$-L2'-$V_H2'$; or
(vi) $V_L1'$-L1'-$V_H1'$ and $V_H2'$-L2'-$V_L2'$; or
(vii) $V_H1'$-L1'-$V_L1'$ and $V_H2'$-L2'-$V_L2'$; or
(ix) $V_L1'$-L1'-$V_H1'$ and $V_L2'$-L2'-$V_H2'$.

In another preferred embodiment of the first aspect of the invention, the variable domains of DBM1 are arranged as follows from N- to C-terminus: $V_H1$-L1-$V_L1$ and $V_H2$-L2-$V_L2$.

In another preferred embodiment of the first aspect of the invention, the variable domains of DBM1 and DBM2 are arranged as follows from N- to C-terminus: $V_H1$-L1-$V_L1$ and $V_H2$-L2-$V_L$ and $V_H1'$-L1'-$V_L1'$ and $V_H2'$-L2'-$V_L2'$. Within P1 and P2, and if present P1' and P2', respectively, it is preferred if the variable domains are located at the N-terminus and DD1, DD2, and if present DD1' and DD2' at the C-terminus.

In any of above outlined arrangements it is possible that DD1 and DD2, and if present DD1', DD2' are located at the C-terminus of the two variable domains or at the N-terminus of the two variable domains. The former is preferred, when P5 and P6 are located at the C-terminus of P1, P2, P1' and/or P2' as the case may be (see, e.g. above arrangements (i), (iii), (v) to (viii) and (xiii) to (xvi)). If DD1 and DD2 are located at the N-terminus of the two variable domains, it is preferred that P5 and P6 are located at the N-terminus of P1, P2, P1' and/or P2' as the case may be (see, e.g. above arrangements (ii), (iv), (ix) to (xii) and (xvii) to (xx)). Out of those two the arrangements (i), (iii), (v) to (viii) and (xiii) to (xvi) are particularly preferred in which DD1 and DD2 are located at the C-terminus of the two variable domains.

It is particularly preferred, that in any of above outlined arrangements (i) to (iv), (xiii) to (xxii) and (xxxi) to (xxxviii), DD1 and DD2 are located at the C-terminus of the two variable domains irrespective of whether P5 and P6 are located at the N-terminus of P1, P2, P1' or P2' or whether P5 and P6 are located at the C-terminus of P1, P2, P1' and/or P2'.

If the antigen-binding complex of the present invention comprises BEM and, thus P3 and P4, it is possible that DD3 and DD4 are located at the C-terminus of the variable domain or at the N-terminus of the variable domain. The former is preferred, when P6 is located at the C-terminus of P3 or P4 as the case may be (see, e.g. above arrangements (v) to (viii)). If DD3 and DD4 are located at the N-terminus of the variable domain, it is preferred that P6 is located at the N-terminus of P3 or P4 as the case may be (see, e.g. above arrangements (ix) to (xii)). Out of those two the arrangements (v) to (viii) are particularly in which DD3 and DD4 are located at the C-terminus of the respective variable domain.

It is particularly preferred, that in any of above outlined arrangements (v) to (xii) and (xxiii) to (xxx), DD3 and DD4 are located at the C-terminus of the variable domain irrespective of whether P6 is located at the N-terminus of P3 or P4 or whether P6 is located at the C-terminus of P3 or P4.

In one embodiment, within P1 and P2, and if present P1' and P2' an additional peptide linker connects the variable domain to the DD1 and DD2, and if present DD1' and DD2'. If present such a peptide linker can have a length between 1 to 15 amino acids, preferably between 1 to 10 amino acids, more preferably 1 to 5 amino acids, most preferably such a peptide linker has a length of 1, 2 or 3 amino acids.

However, the present inventors have found that within P1 and P2, and if present P1' and P2' no additional peptide linker is required to connect the variable domains, which each comprise a linker between the light and heavy chain, to the DD1 and DD2, and if present DD1' and DD2'. This is advantageous because any peptide linker or peptide linker junction with a variable domain or dimerization domain may create a new epitope that can create a detrimental immune response. Additionally, the omission of a peptide linker between the dimerization domain and the variable domains facilitates the rapid exchange of the variable domains in different constructs without the need for optimization of peptide linker length. To determine whether P1 comprises no peptide linker between DD1 and the variable domain ($V_H1$ or $V_L1$ depending on the orientation of $V_H1$ and $V_L1$ within P1) it is necessary to determine the respective N- and C-terminal sequence. Of the variable domain and the dimerization domain. The N- and C-terminal end of $V_H$ and $V_L$ are well known in the art and have been outlined above. Depending on the respective dimerization domain the C-terminus and N-terminus of the dimerization domain may vary. If the dimerization domain is derived from a naturally occurring protein, e.g. an immunoglobulin, the dimerization domain is, preferably, directly linked to the variable domain in the sense of the present invention, i.e. linked without a peptide linker, if there are no non-naturally occurring amino acids at its C- or N-terminus.

Accordingly, in a particular embodiment of the first aspect of the invention, $V_H1$ or $V_L1$ is linked to DD1 and optionally $V_H1'$ and $V_L1'$ is directly linked to DD1' and/or $V_H2$ or $V_L2$ is directly linked to DD2 and optionally $V_H2'$ and $V_L2'$ is linked to DD2'. Preferably, $V_H1$ or $V_L1$ is linked to DD1 and $V_H1'$ and $V_L1'$ is directly linked to DD1' and/or $V_H2$ or $V_L2$ is directly linked to DD2 and optionally $V_H2'$ and $V_L2'$ is linked to DD2'. Preferably, $V_H1$ or $V_L1$ is linked to DD1 and optionally $V_H1'$ and $V_L1'$ is directly linked to DD1' and/or $V_H2$ or $V_L2$ is directly linked to DD2 and $V_H2'$ and $V_L2'$ is linked to DD2'. Preferably, $V_H1$ or $V_L1$ is linked to DD1 and optionally $V_H1'$ and $V_L1'$ is directly linked to DD1' and $V_H2$ or $V_L2$ is directly linked to DD2 and optionally $V_H2'$ and $V_L2'$ is linked to DD2'. Preferably, $V_H1$ or $V_L1$ is linked to DD1 and optionally $V_H1'$ and $V_L1'$ is directly linked to DD1' or $V_H2$ or $V_L2$ is directly linked to DD2 and optionally $V_H2'$ and $V_L2'$ is linked to DD2'. Preferably, $V_H1$ or $V_L1$ is linked to DD1 and $V_H1'$ and $V_L1'$ is directly linked to DD1' and $V_H2$ or $V_L2$ is directly linked to DD2 and optionally $V_H2'$ and $V_L2'$ is linked to DD2'. Preferably, $V_H1$ or $V_L1$ is linked to DD1 and $V_H1'$ and $V_L1'$ is directly linked to DD1' or $V_H2$ or $V_L2$ is directly linked to DD2 and optionally $V_H2'$ and $V_L2'$ is linked to DD2'. Preferably, $V_H1$ or $V_L1$ is linked to DD1 and optionally $V_H1'$ and $V_L1'$ is directly linked to DD1' and $V_H2$ or $V_L2$ is directly linked to DD2 and $V_H2'$ and $V_L2'$ is linked to DD2'. Preferably, $V_H1$ or $V_L1$ is linked to DD1 and optionally $V_H1'$ and $V_L1'$ is directly linked to DD1' or $V_H2$ or $V_L2$ is directly linked to DD2 and $V_H2'$ and $V_L2'$ is linked to DD2'. Preferably, $V_H1$ or $V_L1$ is linked to DD1 and $V_H1'$ and $V_L1'$ is directly linked to DD1' and $V_H2$ or $V_L2$ is directly linked to DD2 and $V_H2'$ and $V_L2'$ is linked to DD2'. Preferably, $V_H1$ or $V_L1$ is linked to DD1 and $V_H1'$ and $V_L1'$ is directly linked to DD1' or $V_H2$ or $V_L2$ is directly linked to DD2 and $V_H2'$ and $V_L2'$ is linked to DD2'.

The omission of a peptide linker is particularly preferred, if the dimerization domains DD1 and DD2, and if present DD1' and DD2' are CH1/CL, EHD2, hetEHD2, MHD. It is noted that in the example section when EHD2, hetEHD2, or MHD is used as DD1 and DD2, and if present DD1' and DD2' there is 2 amino acid long peptide linker between VL and DD, which is a cloning artifact.

In a preferred embodiment of the first aspect of the invention, the pair of DD1 and DD2 of DBM1 and optionally the pair of DD1' and DD2' of DBM2 or DD3 and DD4 of BEM are homodimers or heterodimers. Preferably, the homodimers or heterodimers are in each case independently selected from:
a. CH2 domains of IgE (EHD2);
b. CH2 domains of IgM (MHD2);
c. CH3 domains of IgG, IgA or IgD;
d. CH4 domains of IgE or IgM;
e. CL and CH1;
f. heterodimerizing variants of EHD2 or MHD2, in particular het1EHD2(EHD2(C247S)/EHD2(C337S)) or het2EHD2(EHD2(C337S)/EHD2(C247S));
g. heterodimerizing variants of $C_H3$ grafted with $C_H1/C_L$, FcRnα3 (SEQ ID NO: 4)/β2-microglobulin (SEQ ID NO: 5), HLA-A (SEQ ID NO: 6)/β2-microglobulin (SEQ ID NO: 5), HLA-Bα3 (SEQ ID NO: 7)/β2-microglobulin (SEQ ID NO: 5), or HLA-Dα2 (SEQ ID NO: 8)/HLA-Dβ2 (SEQ ID NO: 9);
h. heterodimerizing variants of $C_H1/C_L$ grafted with TCRα (SEQ ID NO: 2)/TCRβ (SEQ ID NO: 3);
i. T-cell receptor α (TCRα) and T-cell receptor β (TCRβ); or
j. heterodimerizing variants of $C_H1/C_L$, in particular CR3 ($C_H1$ substituted with T192E; $C_L$ substituted with N137K), MUT4 ($C_H1$ substituted with L143Q and S188V; $C_L$ substituted with V133T and S176V), or DuetMab ($C_H1$ substituted with F126C; $C_L$ substituted with S121C).

In another preferred embodiment of the first aspect of the invention, the pair of DD1 and DD2 of DBM1 and optionally the pair of DD1' and DD2' of DBM2 or DD3 and DD4 of BEM are homodimers. Preferably, the homodimers are in each case independently selected from:
a. $C_H2$ domains of IgE (EHD2);
b. $C_H2$ domains of IgM (MHD2);
c. $C_H3$ domains of IgG, IgA or IgD; or
d. $C_H4$ domains of IgE or IgM.

In another preferred embodiment of the first aspect of the invention, the pair of DD1 and DD2 of DBM1 and the pair of DD1' and DD2' of DBM2 are homodimers. Preferably, the homodimers are in each case independently selected from:
a. $C_H2$ domains of IgE (EHD2);
b. $C_H2$ domains of IgM (MHD2);
c. $C_H3$ domains of IgG, IgA or IgD; or
d. $C_H4$ domains of IgE or IgM.

In another preferred embodiment of the first aspect of the invention, the pair of DD1 and DD2 of DBM1 and the pair of DD3 and DD4 of BEM are homodimers. Preferably, the homodimers are in each case independently selected from:
a. $C_H2$ domains of IgE (EHD2);
b. $C_H2$ domains of IgM (MHD2);
c. $C_H3$ domains of IgG, IgA or IgD; or
d. $C_H4$ domains of IgE or IgM.

In another preferred embodiment of the first aspect of the invention, the pair of DD1 and DD2 of DBM1 and optionally the pair of DD1' and DD2' of DBM2 or DD3 and DD4 of BEM are heterodimers. Preferably, the heterodimers are in each case independently selected from:
a. $C_L$ and $C_H1$;
b. heterodimerizing variants of EHD2 or MHD2, in particular het1EHD2(EHD2(C247S)/EHD2(C337S)) or het2EHD2(EHD2(C337S)/EHD2(C247S));
c. heterodimerizing variants of $C_H3$ grafted with $C_H1/C_L$, FcRnα3 (SEQ ID NO: 4)/β2-microglobulin (SEQ ID NO: 5), HLA-A (SEQ ID NO: 6)/β2-microglobulin (SEQ ID NO: 5), HLA-Bα3 (SEQ ID NO: 7)/β2-microglobulin (SEQ ID NO: 5), or HLA-Dα2 (SEQ ID NO: 8)/HLA-Dβ2 (SEQ ID NO: 9);
d. heterodimerizing variants of $C_H1/C_L$ grafted with TCRα (SEQ ID NO: 2)/TCRβ (SEQ ID NO: 3);
e. T-cell receptor α (TCRα) and T-cell receptor β (TCRβ); or
f. heterodimerizing variants of $C_H1/C_L$, in particular CR3 ($C_H1$ substituted with T192E; $C_L$ substituted with N137K), MUT4 ($C_H1$ substituted with L143Q and S188V; $C_L$ substituted with V133T and S176V), or DuetMab ($C_H1$ substituted with F126C; $C_L$ substituted with S121C).

In another preferred embodiment of the first aspect of the invention, the pair of DD1 and DD2 of DBM1 and the pair of DD1' and DD2' of DBM2 are heterodimers. Preferably, the heterodimers are in each case independently selected from:
a. CL and CH1;
b. heterodimerizing variants of EHD2 or MHD2, in particular het1EHD2(EHD2(C247S)/EHD2(C337S)) or het2EHD2(EHD2(C337S)/EHD2(C247S));
c. heterodimerizing variants of $C_H3$ grafted with $C_H1/C_L$, FcRnα3 (SEQ ID NO: 4)/β2-microglobulin (SEQ ID NO: 5), HLA-A (SEQ ID NO: 6)/β2-microglobulin (SEQ ID NO: 5), HLA-Bα3 (SEQ ID NO: 7)/β2-microglobulin (SEQ ID NO: 5), or HLA-Dα2 (SEQ ID NO: 8)/HLA-Dβ2 (SEQ ID NO: 9);
d. heterodimerizing variants of $C_H1/C_L$ grafted with TCRα (SEQ ID NO: 2)/TCRβ (SEQ ID NO: 3);
e. T-cell receptor α (TCRα) and T-cell receptor β (TCRβ); or
f. heterodimerizing variants of $C_H1/C_L$, in particular CR3 ($C_H1$ substituted with T192E; $C_L$ substituted with N137K), MUT4 ($C_H1$ substituted with L143Q and S188V; $C_L$ substituted with V133T and S176V), or DuetMab ($C_H1$ substituted with F126C; $C_L$ substituted with S121C).

In another preferred embodiment of the first aspect of the invention, the pair of DD1 and DD2 of DBM1 and the pair of DD3 and DD4 of BEM are heterodimers. Preferably, the heterodimers are in each case independently selected from:
a. $C_L$ and $C_H1$;
b. heterodimerizing variants of EHD2 or MHD2, in particular het1EHD2(EHD2(C247S)/EHD2(C337S)) or het2EHD2(EHD2(C337S)/EHD2(C247S));
c. heterodimerizing variants of $C_H3$ grafted with $C_H1/C_L$, FcRnα3 (SEQ ID NO: 4)/β2-microglobulin (SEQ ID NO: 5), HLA-A (SEQ ID NO: 6)/β2-microglobulin (SEQ ID NO: 5), HLA-Bα3 (SEQ ID NO: 7)/β2-microglobulin (SEQ ID NO: 5), or HLA-Dα2 (SEQ ID NO: 8)/HLA-Dβ2 (SEQ ID NO: 9);
d. heterodimerizing variants of $C_H1/C_L$ grafted with TCRα (SEQ ID NO: 2)/TCRβ (SEQ ID NO: 3);
e. T-cell receptor α (TCRα) and T-cell receptor β (TCRβ); or
f. heterodimerizing variants of $C_H1/C_L$, in particular CR3 ($C_H1$ substituted with T192E; $C_L$ substituted with N137K), MUT4 ($C_H1$ substituted with L143Q and S188V; $C_L$ substituted with V133T and S176V), or DuetMab ($C_H1$ substituted with F126C; $C_L$ substituted with S121C).

In a preferred embodiment of the first aspect of the invention, the pair of DD5 and DD6 are homodimers. More preferably, the homodimers are in each case independently selected from:
a. Fc-part and effector-modified variants thereof (increased or reduced effector function), in particular G1Δab variant (E233P, L234V, L235A, ΔG236, A327G, A330S, P331S) of an antibody;
b. CH2 domains of IgE (EHD2);
c. CH2 domains of IgM (MHD2);
d. CH3 domains of IgG, IgA or IgD; or
e. CH4 domains of IgE or IgM.

In another preferred embodiment of the first aspect of the invention, the pair of DD5 and DD6 are heterodimers. More preferably, the heterodimers are in each case independently selected from:
a. a heterodimerizing Fc-part of an antibody, in particular a knob-in-hole variant of a Fc-part; preferably variants with modified, i.e. increased or decreased effector function;
b. heterodimerizing variants of EHD2 or MHD2, in particular het1EHD2(EHD2(C247S)/EHD2(C337S)) or het2EHD2(EHD2(C337S)/EHD2(C247S));
c. heterodimerizing variants of $C_H3$ grafted with $C_H1/C_L$, FcRnα3 (SEQ ID NO: 4)/β2-microglobulin (SEQ ID NO: 5), HLA-A (SEQ ID NO: 6)/β2-microglobulin (SEQ ID NO: 5), HLA-Bα3 (SEQ ID NO: 7)/β2-microglobulin (SEQ ID NO: 5), or HLA-Dα2 (SEQ ID NO: 8)/HLA-Dβ2 (SEQ ID NO: 9);
d. heterodimerizing variants of $C_H1/C_L$ grafted with TCRα (SEQ ID NO: 2)/TCRβ (SEQ ID NO: 3);
e. T-cell receptor α (TCRα) and T-cell receptor β (TCRβ); or
f. heterodimerizing variants of $C_H1/C_L$, in particular CR3 ($C_H1$ substituted with T192E; $C_L$ substituted with N137K), MUT4 ($C_H1$ substituted with L143Q and S188V; $C_L$ substituted with V133T and S176V), or Duet-Mab ($C_H1$ substituted with F126C; $C_L$ substituted with S121C). More preferably, the homodimers or heterodimers are Fc-part and effector-modified variants thereof (increased or reduced effector function), in particular G1 Δab variant (E233P, L234V, L235A, ΔG236, A327G, A330S, P331S) of an antibody.

In a preferred embodiment of the first aspect of the invention:
a. DD1/DD2≠DD5/DD6;
b. DD1/DD2=DD1'/DD2'≠DD5/DD6;
c. DD1/DD2≠DD1'/DD2'≠DD5/DD6;
d. DD1/DD2=DD3/DD4≠DD5/DD6; or
e. DD1/DD2≠DD3/DD4≠DD5/DD6.

In a preferred embodiment, DD1/DD2≠DD5/DD6. In another preferred embodiment, DD1/DD2=DD1'/DD2'≠DD5/DD6. In another preferred embodiment, DD1/DD2≠DD1'/DD2'≠DD5/DD6. In another preferred embodiment, DD1/DD2=DD3/DD4≠DD5/DD6. In another preferred embodiment, DD1/DD2≠DD3/DD4≠DD5/DD6.

In a preferred embodiment of the first aspect of the invention, the antigen-binding protein complex is:
a. bivalent and mono- or bi-specific;
b. trivalent and mono, bi or tri-specific; or
c. tetravalent and mono-, bi-, tri- or tetra-specific.

Preferably, the antigen-binding protein complex of the invention is bivalent and monospecific. Preferably, the antigen-binding protein complex of the invention is bivalent and bispecific. The bivalent formats can be generated as monospecific and bispecific molecules using either a monospecific or a bispecific diabody moiety (FIG. 9). For the generation of these different bivalent molecules, different dimerization modules can be used (FIG. 10).

Figure 12:
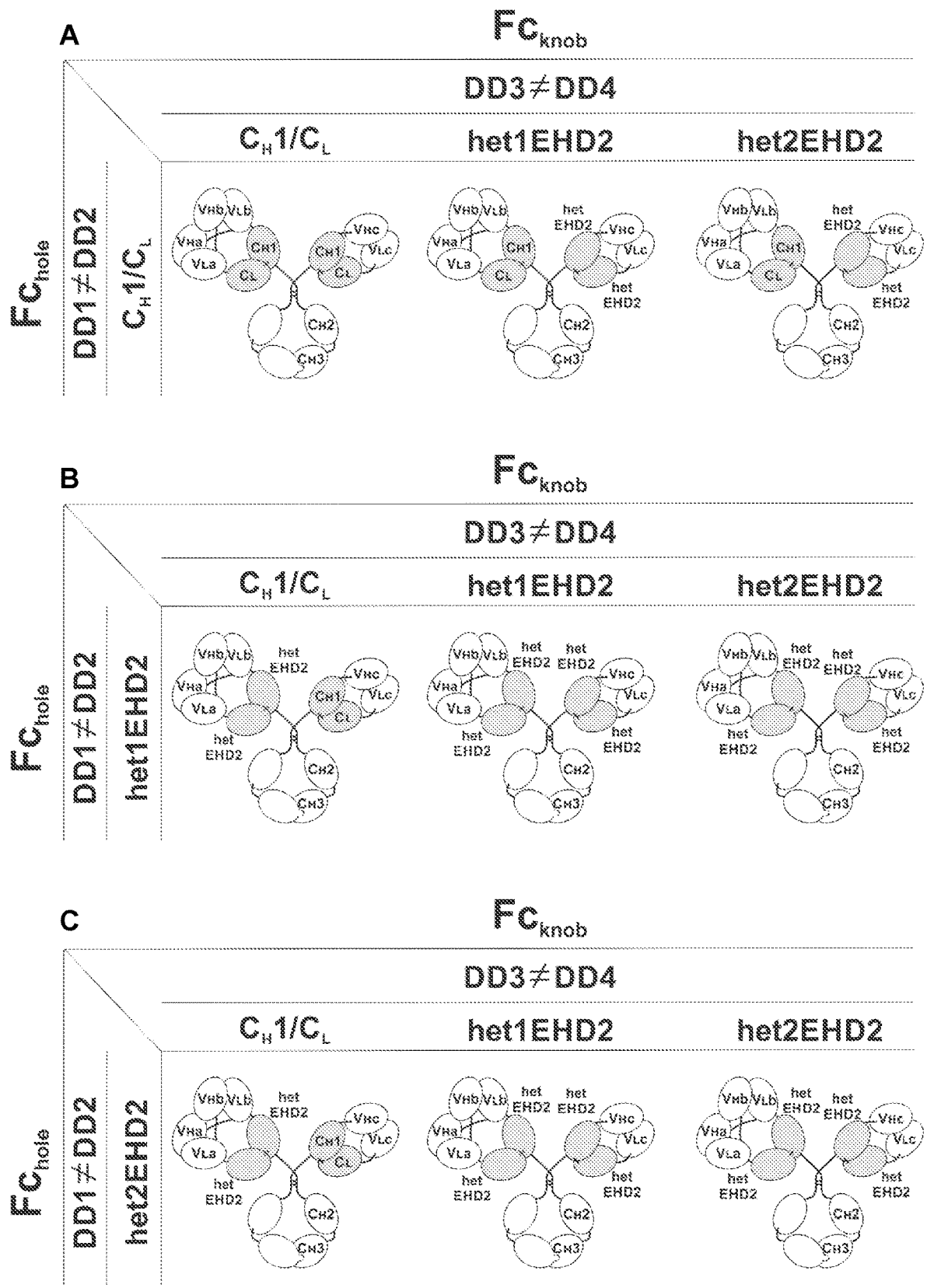
Figure 12:
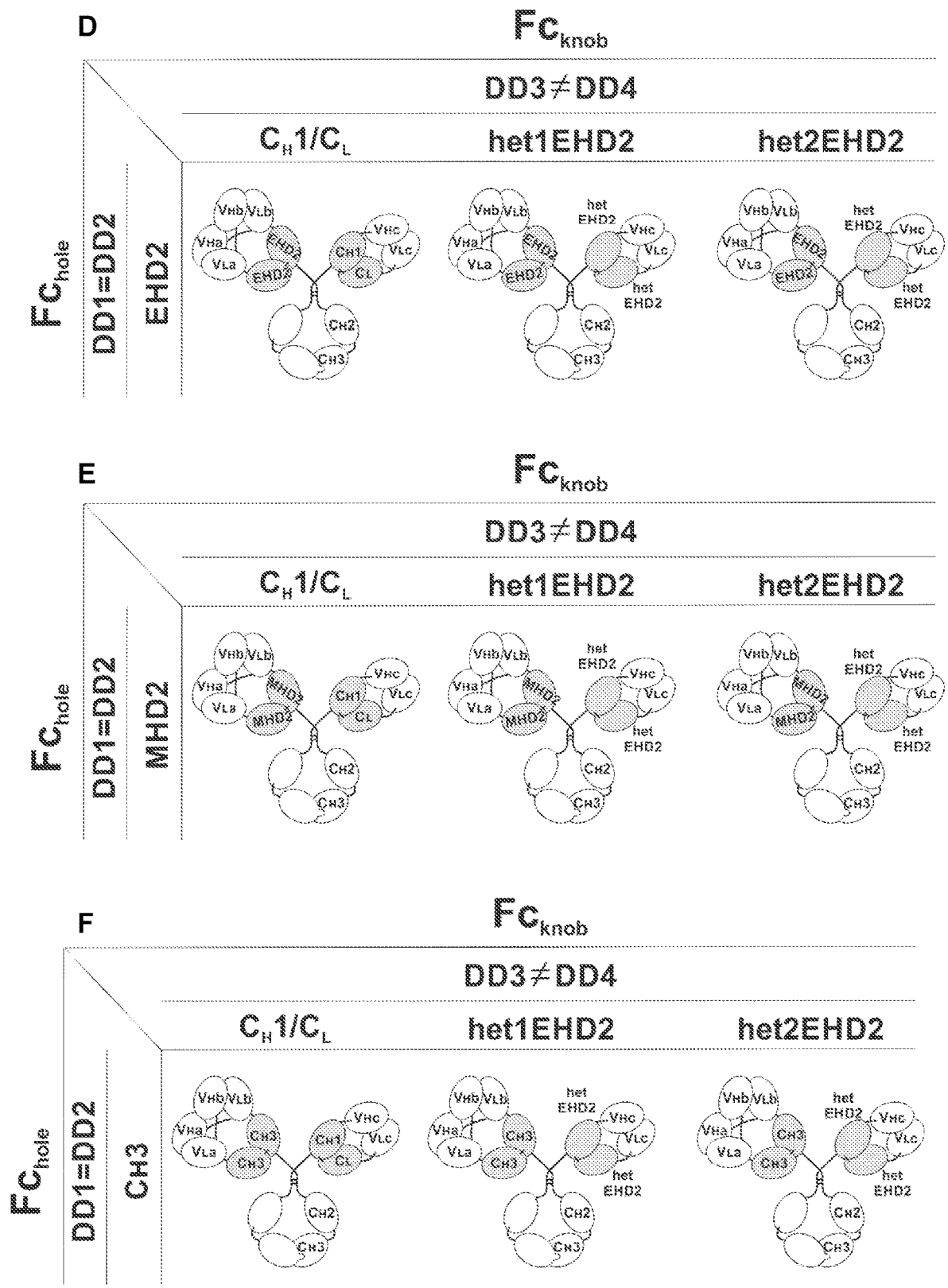
Figure 12:
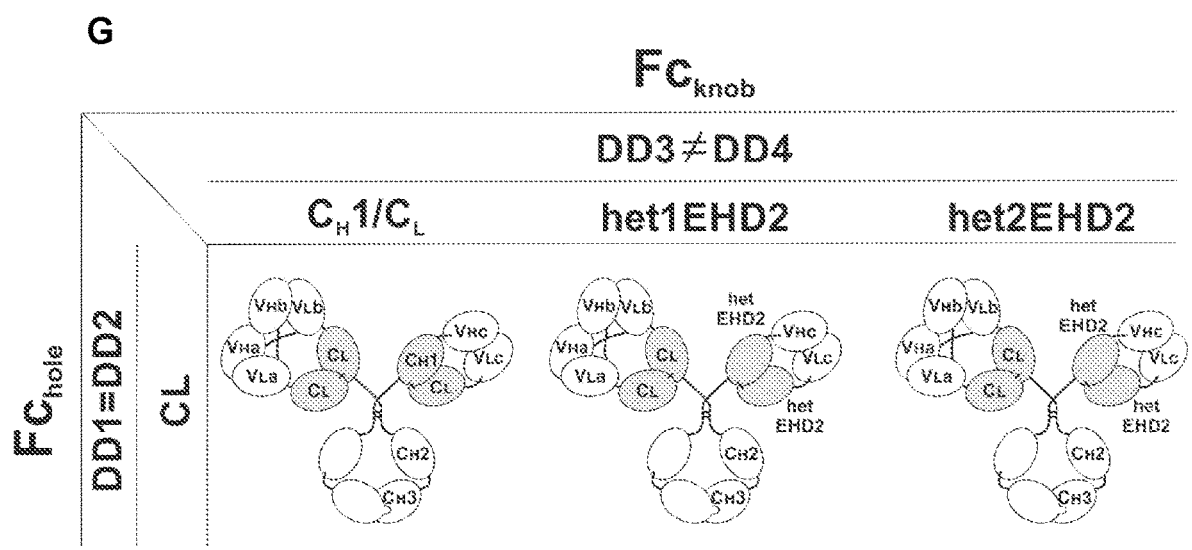
Figure 13A:
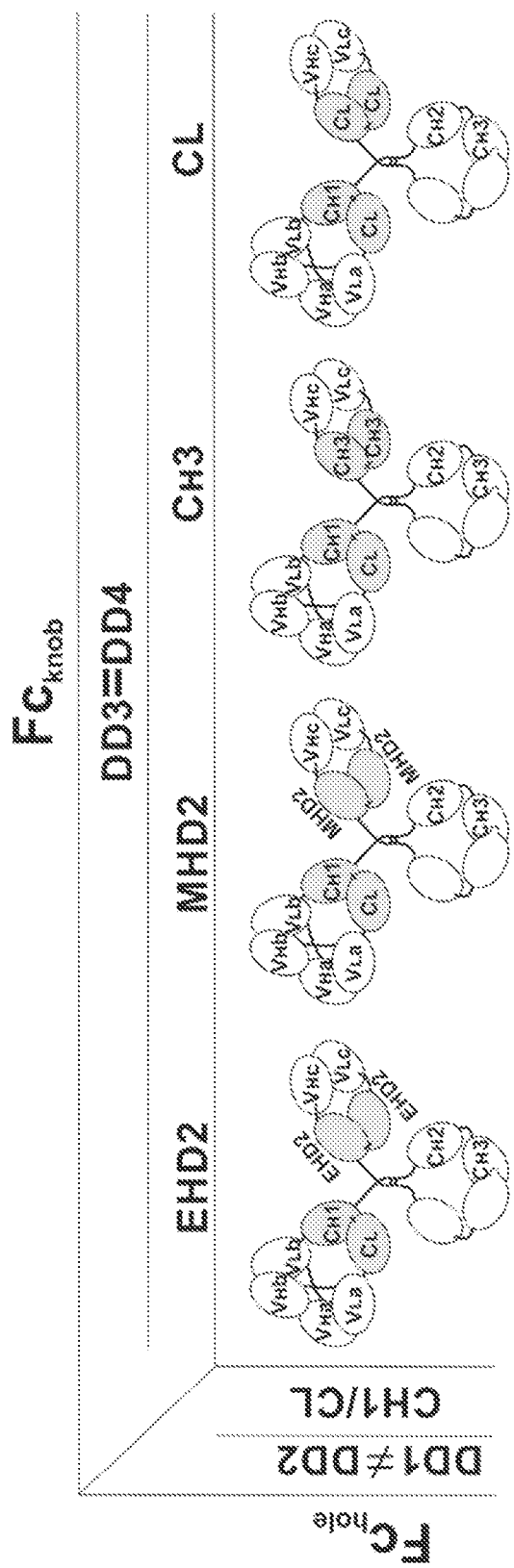
Figure 13B:
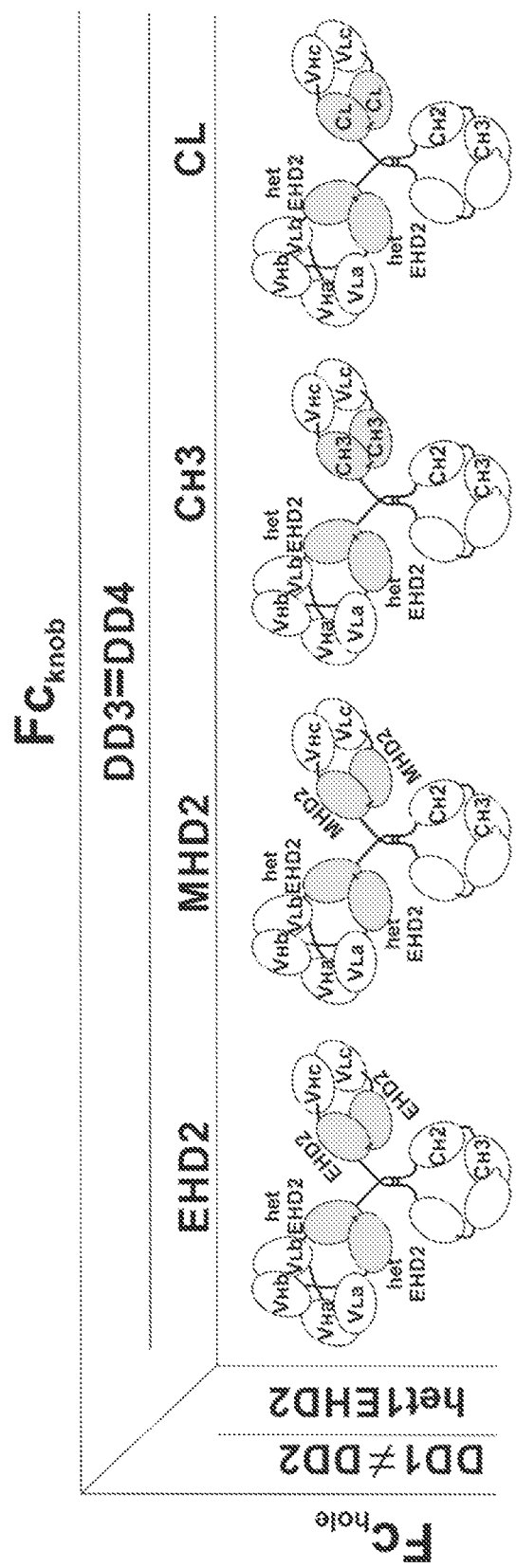
Figure 13C:
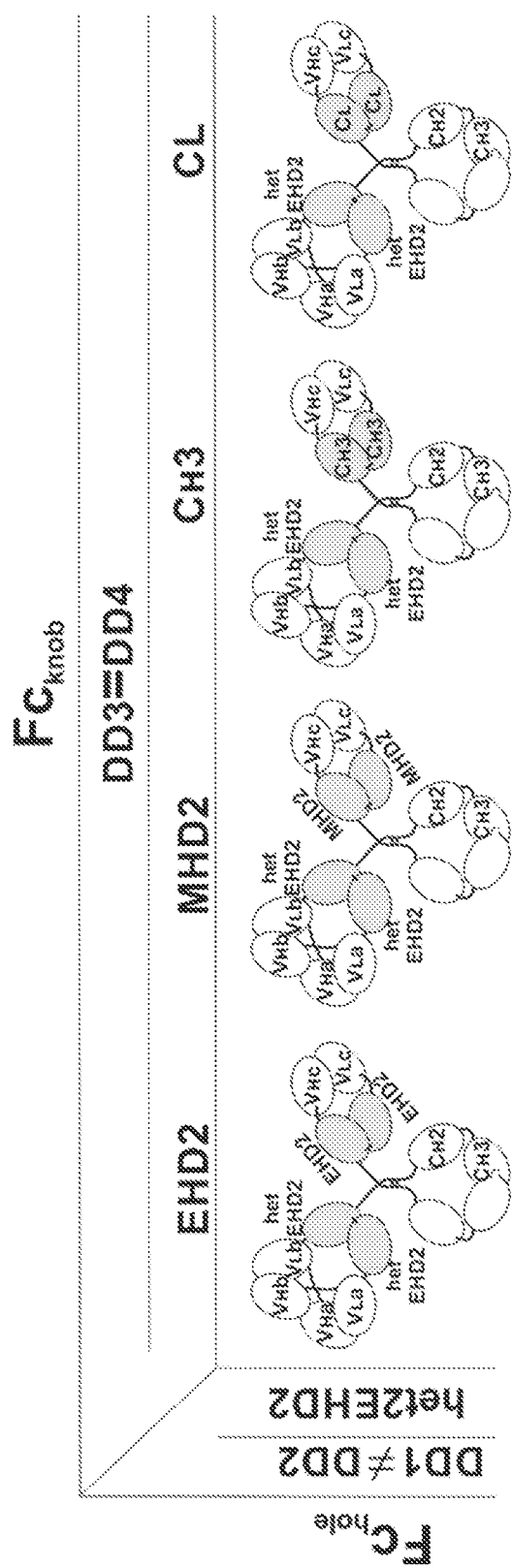
Figure 13D:
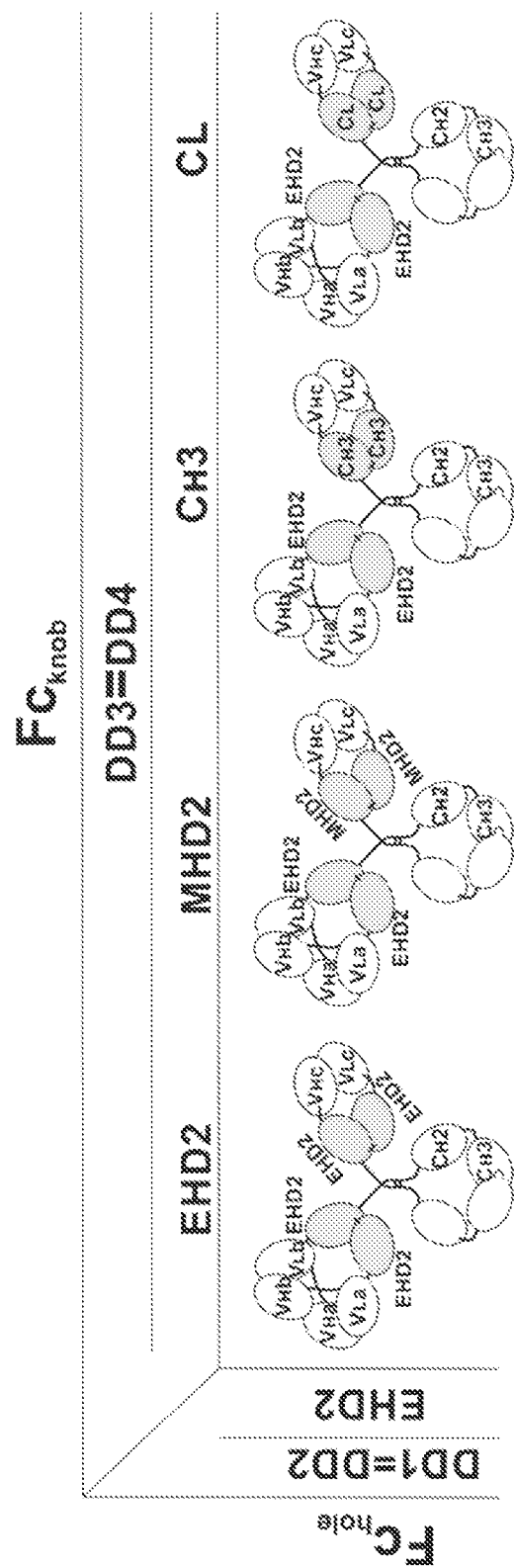
Figure 13E:
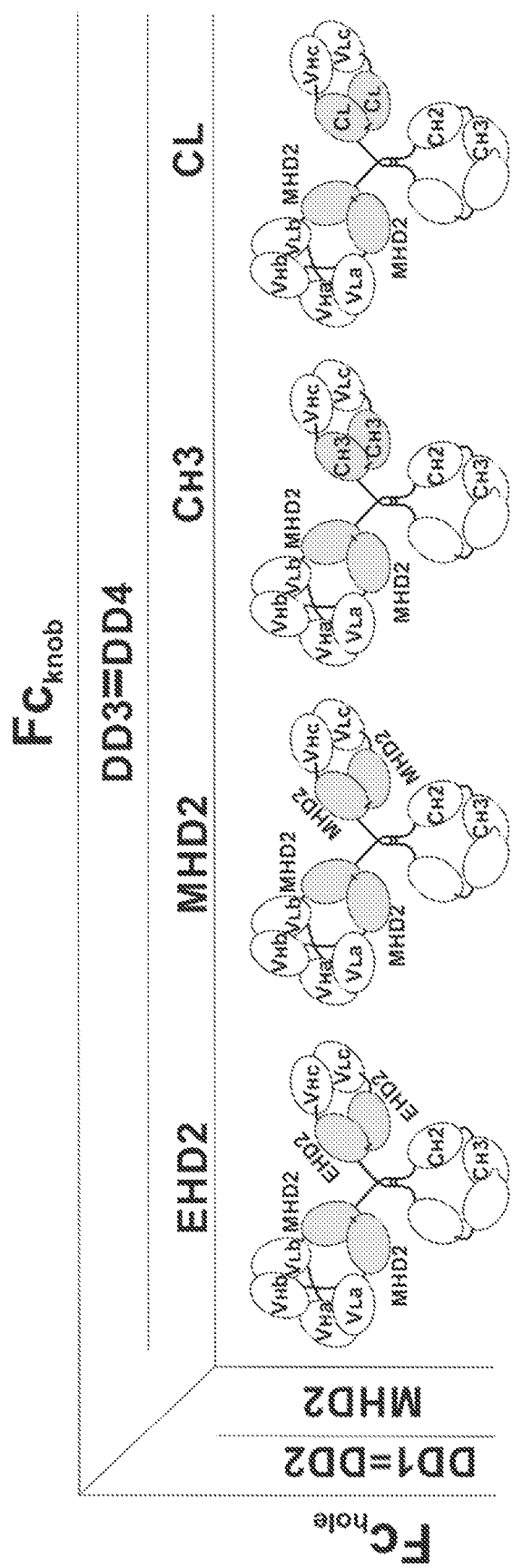
Figure 13F:
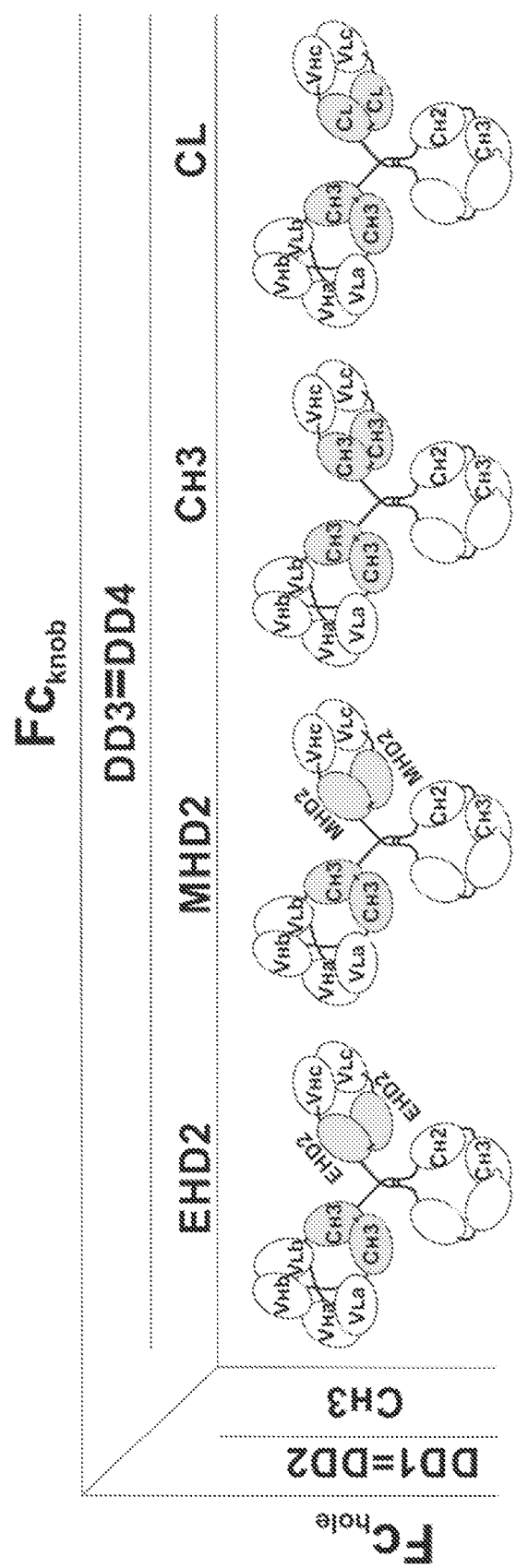
Figure 13G:
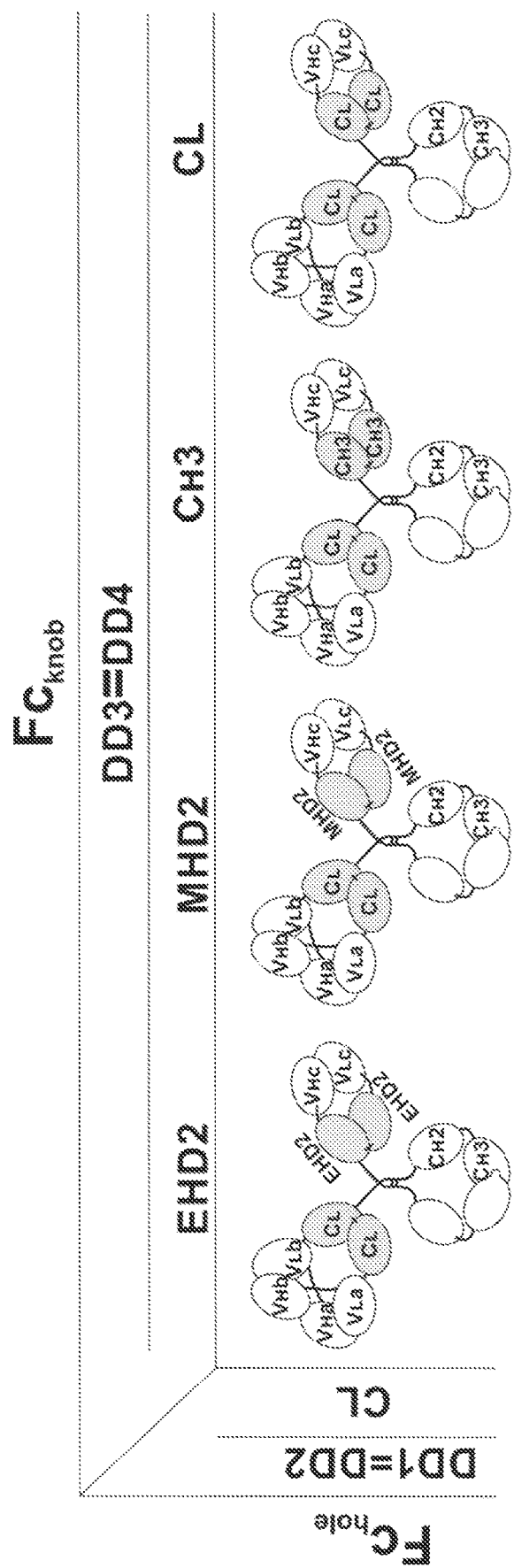

Preferably, the antigen-binding protein complex of the invention is trivalent and monospecific. Preferably, the antigen-binding protein complex of the invention is trivalent and bispecific. Preferably, the antigen-binding protein complex of the invention is trivalent and trispecific. The trivalent molecules can be generated by using all three described modules (DBM+HDM and BEM+HDM). Alternatively, in the absence of a BEM the diabody moiety of DBM can be combined with a monovalent antigen-binding molecule (pharmaceutical moiety: e.g. Fab or scFv) (FIG. 11) attached to P6 to create a trivalent molecule. In case of the combination of diabody and Fab, different possibilities of the dimerization domains for DBM P6 can be used. A combinatorial overview of the dimerization domains of mono-, bi- and trispecific molecules is shown in FIG. 12 (using heterodimerization domain in BEM) and FIG. 13 (using homo-dimerization modules in BEM). As the combination of a diabody with a scFv results in only one dimerization domain (DBM) in the molecules, the diversity of these molecules is reduced compared to the Db-Fab molecules (FIG. 14).

Preferably, the antigen-binding protein complex of the invention is tetravalent and monospecific. Preferably, the antigen-binding protein complex of the invention is tetravalent and bispecific. Preferably, the antigen-binding protein complex of the invention is tetravalent and trispecific. Preferably, the antigen-binding protein complex of the invention is tetravalent and tetraspecific. Tetravalent molecules can be generated by using two diabody moieties, each located in the DBM1 and DBM2 module. Using a heterodimeric Fc part, mono-, bi-, tri-, and tetraspecific molecules can be generated (FIG. 15). Two dimerization modules, located in DBM1 and DBM2, are used for the generation of tetravalent molecules. The monospecific tetravalent molecules obtain a symmetric architecture, for which reason all combinations of the different dimerization domains (for DBM1 and DBM2), including the usage of the same dimerization domain in both modules, result in the correct assembly of the molecules (FIG. 16; using hetero-dimerization modules in DBM2) (FIG. 17; using homo-dimerization domains in DBM2). In addition, same possibilities of the dimerization domains can be used for the generation of symmetric tetravalent, bispecific molecules (FIG. 18; using hetero-dimerization domains in DBM2) (FIG. 19; using homo-dimerization domains in DBM2). Different dimerization domains (for DBM1 and DBM2) can be used to generate asymmetric tetravalent, bispecific molecules. The tetravalent, trispecific (FIG. 20; using hetero-dimerization domains in DBM2+FIG. 21; using homo-dimerization domains in DBM2) and tetraspecific (FIG. 22; using hetero-dimerization domains in DBM2+FIG. 23; using homo-dimerization domains in DBM2) molecules also obtain an asymmetric architecture. Thus, different dimerization modules (for DBM1 and DBM2) have to be used for the generation of correct assembled molecules.

The antigen-binding protein complex of the invention may be used to target pharmaceuticals or imaging molecules to particular tissues or cells within the body of a patient. Accordingly, in a preferred embodiment of the first aspect of the invention, the antigen-binding protein complex further comprises at least one pharmaceutical active moiety and imaging molecule. In another preferred embodiment of the first aspect of the invention, the antigen-binding protein complex further comprises at least one pharmaceutical active moiety or imaging molecule. The pharmaceutical active moiety and imaging molecule may be covalently or non-covalently coupled to the antigen-binding protein complex. Preferably, the pharmaceutically active moiety is coupled covalently to one of the polypeptide chains of the antigen binding protein complex. Preferably, it may be coupled to an amino acid side chain, e.g. of an amino acid with a free carboxy or amino group or to a free N- or C-terminus of one of the polypeptide chains of the antigen-binding protein complex.

In a preferred embodiment of the first aspect of the invention, the pharmaceutical active moiety is selected from the group consisting of ligands, and effector molecules.

In a preferred embodiment of the first aspect of the invention, the pharmaceutical active moiety is a ligand and the ligand is selected from the group consisting of antigen-binding molecules, scaffold proteins, natural ligands, ligand-binding receptor fragments, and aptamers, preferably, preferably the antigen-binding molecule is selected from the group consisting of an antibody fragment, a Fab fragment, a Fab' fragment, a heavy chain antibody, a single-domain antibody (sdAb), variable domain of a heavy chain antibody, VHH, Nanobodies, a single-chain variable fragment (scFv), a tandem scFv, a bispecific T-cell engager (BiTEs), a single-chain diabody, a DART, a triple body, a nanoantibody, an alternative scaffold protein and a fusion protein thereof. More preferably, the ligand is a scFv.

In a preferred embodiment of the first aspect of the invention, the pharmaceutical active moiety is an effector molecule and the effector molecules, i.e. small molecules, peptides or polypeptides that bind to a protein and thereby alter the activity of that protein, include but are not limited to cytokines, chemokines, immuno(co)-stimulatory molecules, immunosuppressive molecules, death ligands, apoptosis-inducing proteins, enzymes (e.g. kinases) prodrug-converting enzymes, RNases, agonistic antibody or antibody fragment, antagonistic antibody or antibody fragment, toxins, growth factors, hormone, coagulation factor, fibrinolytic protein, peptides mimicking these, and fragments, fusion proteins or derivatives thereof.

In preferred embodiments, cytokines are interleukins and/or interferons. Interleukins (IL) include but are not limited to Interleukin-1, Interleukin-2, Interleukin-3, Interleukin-4, Interleukin-5, Interleukin-6, Interleukin-7, Interleukin-8, Interleukin-9, Interleukin-10, Interleukin-11, Interleukin 12, Interleukin-13, Interleukin-14, Interleukin-15, Interleukin-16, Interleukin-17, Interleukin-18, Interleukin-19, Interleukin-20, Interleukin-21, Interleukin-22, Interleukin-23, Interleukin-24, Interleukin-25, Interleukin-26 Interleukin-27, Interleukin-28, Interleukin-29, Interleukin-30, Interleukin-31, Interleukin-32, Interleukin-33, Interleukin-34 and Interleukin-35. Interferons (IFN) include but are not limited to interferon type I (e.g. IFN-$\alpha$, IFN-$\beta$ and IFN-$\omega$), interferon type II (e.g. IFN-$\gamma$), and interferon type III. In particular included are interferon $\alpha$1, interferon $\alpha$2, interferon $\alpha$4, interferon $\alpha$5, interferon $\alpha$6, interferon $\alpha$7, interferon $\alpha$8, interferon $\alpha$10, interferon $\alpha$13, interferon $\alpha$14, interferon $\alpha$16, interferon $\alpha$17, interferon $\alpha$21, interferon $\beta$1, TNF, TRAIL, and FasL In preferred embodiments chemokines include but are not limited to CC chemokines, CXC chemokines, C chemokines, and CX3C chemokines. In particular chemokine include but are not limited to CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, XCL1, XCL2, and CX3CL1.

In preferred embodiments, immuno-(co)stimulatory proteins include but are not limited to B7.1, B7.2, 4-1BBL, LIGHT, ICOSL, GITRL, CD27L, CD40L, OX40L, PD-L1, PD-L2 and CD70, and derivatives thereof.

Immuno-suppressive proteins preferably include but are not limited to IL1-Ra, IL-10, CTLA-4, PD-1, PD-L1, and PD-L2 and toxins preferably include but are not limited to *Pseudomonas* exotoxin A, Diphtheria toxin and ricin. Preferably, the toxin is not diphtheria toxin.

In preferred embodiments apoptosis-inducing proteins include but are not limited to Bid, Bik, Puma, and Bim, and proapoptotic cytokines (death ligands) such as but not limited to TNF, scTNF, TRAIL, scTRAIL, and FasL and derivatives thereof.

In preferred embodiments enzymes include but are not limited to oxidoreductases, transferases, hydrolases, lyases, isomerases, ligases. Kinases include but are not limited to AGC kinases such as PKA, PKC and PKG, CaM kinases such as calcium/calmodulin-dependent protein kinases and serine/threonine protein kinases (e.g. DAPK2), CK1 such as the casein kinase 1 group, CMGC such as CDK, MAPK, GSK3 and CLK kinases, STE such as homologs of yeast Sterile 7, Sterile 11, and Sterile 20 kinases, tyrosine kinases (TK), the tyrosine-kinase like group of kinases (TKL), receptor-associated tyrosine kinases, MAP kinases, and histidine kinases.

Pro-drug-converting enzymes include but are not limited to esterases such as but not limited to acetylesterase, thiolester hydrolases, phosphoric monoester hydrolases, phosphoric diester hydrolases, triphosphoric monoester hydrolases, sulfuric ester hydrolases (sulfatases), diphosphoric monoester hydrolases, and phosphoric triester hydrolases; phosphatases such as but not limited to tyrosine-specific phosphatases, serine/threonine specific phosphatases, dual specificity phosphatases, histidine phosphatase, and lipid phosphatase; and reductases such as but not limited to 5-alpha reductase, dihydrofolate reductase, HMG-CoA reductase, methemoglobin reductase, ribonucleotide reductase, thioredoxin reductase, *E. coli* nitroreductase, methylenetetrahydrofolate reductase, and carboxypeptidase G2, cytosine deaminase, nitroreductase, thymidine kinase and derivatives thereof.

RNAses include endoribonucleases such as but are not limited to RNase A, RNase H, RNase I, RNase III, RNase L, RNase P, RNase PhyM, RNase T1, RNase T2, RNase U2, RNase V1, and RNase V, and exoribonucleases such as but not limited to Polynucleotide Phosphorylase (PNPase), RNase PH, RNase II, RNase R, RNase D, RNase T, Oligoribonuclease Exoribonuclease I, and Exoribonuclease II and derivatives thereof.

In preferred embodiments growth factors include but are not limited to Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor Myostatin (GDF-8), Nerve growth factor (NGF) and other neurotrophins, Platelet-derived growth factor (PDGF), Thrombopoietin (TPO), Transforming growth factor alpha (TGF-$\alpha$), Transforming growth factor beta (TGF-β), Vascular endothelial growth factor (VEGF), Wnt Signaling Pathway, and placental growth factor (P1GF).

In preferred embodiments, coagulation factors include but are not limited to Thrombin, Factor V, Factor VII, Factor VIII, Factor IX, Factor X, Factor XI, Factor XII and Factor XIII, and active fragments or derivatives thereof.

In preferred embodiments fibrinolytic proteins include but are not limited to plasmin, urokinase, plasminogen, α2-antiplasmin, tissue-plasminogen activator (t-PA), and plasminogen activator inhibitor-1 (PAI-1) and derivatives thereof.

In a preferred embodiment of the first aspect of the invention, targets of the antigen binding site of the binding molecule are targets that are overexpressed on tumor cells and include receptor-tyrosine-kinases, such as EGFR, HER2, HER3, HER4, ROR1, ROR2, cMET, AXL, RET, ALK, FGFR2 and IGF-1R, members of the TNF receptor-superfamily, such as DR4, DR5, Fas, TNFR1 and TNFR2, or are overexpressed on cells of the tumor-microenvironment, such as FAP and CD105.

In another preferred embodiment of the first aspect of the invention, targets of the antigen binding site of the binding molecule are targets that are expressed by cells of the immune system to regulate their activity, such as CD3, CD16, 4-1BB, OX40, CD40, CD27, RANK, BCMA, GITR, TROY, RELT, HVEM, TNFR2, PD-1, CTLA-4, ICOS, B7-1 and B7-2.

In one embodiment, at least one target of the antigen binding site of the binding molecule is selected from the group consisting of ABCF1; ACVR1; ACVR1B; ACVR2; ACVR2B; ACVRL1; ADORA2A; Aggrecan; AGR2; AICDA; AIF1; AIG1; AKAP1; AKAP2; ALK; AMH; AMHR2; ANGPT1; ANGPT2; ANGPTL3; ANGPTL4; ANPEP; APC; APOC1; AR; AXL; AZGP1(zinc-a-glycoprotein); B7.1; B7.2; BAD; BAFF; BAFF-R; BAG1; BAI1; BCL2; BCL6; BCMA; BDNF; BLNK; BLR1 (MDR15); BlyS; BMP1; BMP2; BMP3B (GDF10); BMP4; BMP6; BMP8; BMPR1A; BMPR1BBMPR2; BPAG1 (plectin); BRCA1; B7-H3; C19orf10(IL27w); C1s; C3; C4A; C5; C5R1; CA-125; CANT1; CASP1; CASP4; CAV1; CCBP2 (D6/JAB61); CCL1 (1-309); CCL11 (eotaxin); CCL13 (MCP-4); CCL15 (MIP-1d); CCL16 (HCC-4); CCL17 (TARC); CCL18 (PARC); CCL19 (MIP-3b); CCL2 (MCP-1); MCAF; CCL20 CMJP-3a); CCL21 (MIP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MIP-1a); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-1RB/RA); CCR3 (CKR3 CMKBR3); CCR4; CCR5 (CMKBRS/ChemR13); CCR6 (CMKBR6/CKR-L3 STRL22/DRY6); CCR7 (CKR7 EB11); CCR8 (CMKBR81/TER1/CKR-L1); CCR9 (GPR-9-6); CCRL1 (VSHK1); CCRL2 (L-CCR); CD164; CD2; CD5; CD7; CD15; CD19; CD1G; CD11a; CD20; CD200; CD22; CD23; CD24; CD25; CD27; CD28; CD3; CD30; CD33; CD37; CD38; CD3E; CD3G; CD3Z; CD4; CD40; CD40L; CD41; CD44; CD44 v6; CD4SRB; CD51; CD52; CD56; CD6; CD62L; CD69; CD70; CD72; CD73; CD74; CD79A; CD79B; CDB; CD80; CD81; CD83; CD86; CD105; CD117; CD123; CD125; CD137L; CD137; CD147; CD152; CD154; CD221; CD276; CD279; CD319; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21Wap1/Cip1); CDKNIB (p27Kipl); CDKN1C; CDKN2A (p16INK4a); CDKN2B; CDKN2C; CDKN3; CEA; CEACAM5; CEBPB; CER1; CFD; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLDN18.2; CLN3; CLU (clusterin); cMET; CMKLR1; CMKOR1 (RDC1); CNR1; COL18A1; COL1A1; COL4A3; COL6A1; CR2; CRP; CSF1 (M-CSF); CSFR1; CSF2 (GM-CSF); CSF3 (GCSF); CTLA4; CTNNB1 (b-catenin); CTSB (cathepsin B); $CX3C_L1$ (SCYD1); CX3CR1 (V28); CXCL1 (GRO1); CXCL10 (IP-10); CXCL11 (I-TAC/IP-9); CXCL12 (SDF1); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYC1; CYSLTR1; DAB2IP; DES; DKFZp451J0118; DNCL1; DLL3; DPP4; DR3; DR4; DR5; DR6; E2F1; ECGF1; EDA1; EDA2; EDAR; EDA2R; EDG1; EpCAMEFNA1; EFNA3; EFNB2; EGF; EGFL7; EGFR; ELAC2; ENG; ENO1; ENO2; ENO3; EPHA3; EPHB4; EPO; ERBB2 (Her-2); EREG; ERK8; ESR1; ESR2; F3 (TF); FADD; FAP; FasL; FASN; FCER1A; FCER2; FCGR3A; FGF; FGF1 (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR1; FGFR2; FGFR3; FGFR4; FIGF (VEGFD); FIL1 (EPSILON); FIL1 (ZETA); F1112584; FLJ25530; FLRT1 (fibronectin); FLT1; folate receptor 1; FOS; FOSL1 (FRA-1); FY (DARC); GABRP (GABAa); GAGEB1; GAGEC1; GALNAC4S-GST; GATA3; gelatinase B; GD2; GD3; GDF5; GDF8; GFI1; GGT1; GITR; GITRL; GM-CSF; GNAS1; GNRH1; GPNMB; GPR2 (CCR10); GPR31; GPR44; GPR81 (FKSG80); GRCC10 (C10); GRP; GSN (Gelsolin); GSTP1; HAVCR2; HDAC4; HDAC5; HDAC7A; HDAC9; HER2; HER3; HER4; HGF; H1F1A; HIP1; histamine and histamine receptors; HLA-A; HLA-DRA; HM74; HMOX1; HMW-MAA Hsp-90; HVEM; TNF-RHUMCYT2A; ICAM-1; ICEBERG; ICOSL; ID2; IFN-α; IFNA1; IFNA2; IFNA4; IFNA5; IFNA6; IFNA7; IFNB1; IFNgamma; IFNW1; IGBP1; IGF1; IGF1R; IGP1R; IGF2; IGFBP2; IGFBP3; IGFBP6; IGHE; IL-1; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; IL1F10; IL1F5; IL1F6; IL1F7; IL1F8; TL1F9; IL1HY1; IL1R1; IL1R2; IL1RAP; IL1RAPL1; IL1RAPL2; IL1RL1; IL1RL2 IL1RN; IL2; IL24; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); IL7; IL7R; IL8; IL8RA; IL8RB; IL8RB; IL9; IL9R; ILK; INHA; INHBA; INSL3; INSL4; integrin $α_vβ_3$; integrin $β_7$; IRAK1; IRAK2; TGA1; ITGA2; ITGA3; ITGA6 (a6 integrin); ITGAV; JTGB3; ITGB4 (b 4 integrin); JAG1; JAK1; JAK3; JUN; K6HF; KAI1; KDR; KIR2D; KITLG; KLFS (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); LAMAS; LEP (leptin); LEY; LIGHT; Lingo-p75; Lingo-Troy; LIV-1; LPS; LTA (TNF-b); LTB; LTB4R (GPR16); LTB4R2; LTBR; MACMARCKS; MAG or Omgp; MAP2K7 (c-Jun); MCAM; MCSP; MDK; MET; MER; MIB1; midkine; MIF; MIP-2; MKI67 (Ki-67); MMP2; MMP9; MSLN; MS4A1; MSMB; MT3 (metallothionectin-III); MTSS1; MUC1(mucin); MUC2; MYC; MYD88; myostatin; NCA-2; NCK2; nectin-4; neurocan; NFKB1; NFKB2; NGFB (NGF); NGFR; NgR-Lingo;

NOGO-A; NgR-Nogo66 (Nogo); NgR-p75; NgR-Troy; NME1 (NM23A); NOTCH-1; NOX5; NPPB; NR0B1; NR0B2; NR1D1; NR1D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT3; NT4; NT5E; NTN4; ODZ1; OPRD1; OX40; OX40L; P2RX7; PAP; PART1; PATE; PAWR; PCA3; PCDC1; PCNA; PCSK9; PD1; PD-L1; PDGFA; PDGFB; PDGR; igfPECAM1; PF4 (CXCL4); PGF; PGR; phosphacan; PIAS2; PIK3CG; PLAU (uPA); uPAR; PLG; PLXDC1; PPBP (CXCL7); PPID; PR1; PRKCQ; PRKD1; PRL; PROC; PROK2; PSAP; PSCA; PSMA; PTAFR; PTEN; PTGS2 (COX-2); PTN; PTK7; VEGFR1; VEGFR2; VEGFR3; RAC2 (p21Rac2); RANK; RANKL; RARB; RELT; RET; RGS1; RGS13; RGS3; RNF110 (ZNF144); ROBO2; RON; ROR1; ROR2; RYK; S100A2; SCGB1D2 (lipophilin B); SCGB2A1 (mammaglobin 2); SCGB2A2 (mammaglobin 1); SCYE1 (endothelial Monocyte-activating cytokine); SDF2; SERPINA1; SERPINA3; SERPINB5 (maspin); SERPINE1 (PAI-1); SERPINF1; SHBG; SLA2; SLC2A2; SLC33A1; SLC43A1; SLIT2; SPAK; SPP1; SPRR1B (Sprl); SOST; ST6GAL1; STAB1; STATE; STEAP; STEAP2; TAC1; TAG-72; tau protein; TB4R2; TBX21; TCP10; TDGF1; TEK; TGFA; TGFB1; TGPB1I1; TGFB2; TGFB3; TGFBI; TGFBR1; TGFBR2; TGFBR3; TH1L; THBS1(throrttbospondin-1); THBS2; THBS4; THPO; TIE (Tie-1); TIE-1; TIE-2; TIMP3; tissue factor; TLR10; TLR2; TLR3; TLR4; TLR5; TLR6; TLR7; TLR8; TLR9; TNF; TNF-a; TNF-b; TNFAIP2 (B94); TNFAIP3; TNFRSF11A; TNFRSF1A; TNFRSF1B; TNFRSP21; TNFRSF5; TNFRSF6 (Fas); TNFRSF7; TNFRSF8; TNFRSF9; TNFSF10 (TRAIL); TNFSF11 (TRANCE); TNFSF12 (APO3L); TNFSF13 (April); TNPSF13B; TNFSF14 (HVEM-L); TNFSFi5 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TNF-R1; TNF-R2; TOLLIP; Toll-like receptors; TOP2A (topoisomerase Iia); TP53; TPM1; TPM2; TRADD; TRAF1; TRAF2; TRAF3; TRAF4; TRAF5; TRAF6; TRAIL-R1; TRAIL-R2; TRAIL-R3; TRAIL-R4; TREM1; TREM2; TRPC6; TROY; TSLP; TWEAK; TYRO3; TYRP1; VAP-1; VEGF; VEGFB; VEGFC; versican; VHL C5; vimentin; VLA-4; VWF; XCL1 (lymphotactin); XCL2 (SCM-1b); XCR1 (GPR5/CCXCR1); YY1; and ZFPM2.

Preferred embodiments of the first aspect of the invention include dual targeting strategies wherein DBM1 alone, DBM1 and DBM2, DBM1 and BEM or DBM1 and a ligand binding effector, e.g. a scFv, which is coupled to P6 bind to two different targets.

In embodiments in which the bispecific antigen-binding molecule is used for cell-cell recruitment, e.g. an immune effector cell like a T cell or macrophage is recruited to a tumor cell, it is preferred that both valences of DBM1 bind to the tumor cell, and the BEM or ligand binding effector, e.g. a scFv coupled to P6 bind to the immune effector cell. This approach provides high avidity binding to the tumor cell on one hand and prevents immune effector cell activation which may result from bivalent binding of a target on the immune effector cell.

In other embodiments of bispecific targeting, e.g. in which the specificities are directed at to two targets expressed on the surface of the same cell, DBM1 and DBM2 may be bispecific, i.e. each binds two targets. This arrangement also has the advantage that DD5 and DD6 can be homodimerizing since DBM1 and DBM2 are identical.

In preferred examples of bispecific targeting the antigen-binding complex may bind two receptors expressed by tumor cells, or cells of the tumor microenvironment by antagonistic antibodies, especially targeting combinations of EGFRxHER2, EGFRxHER3, HER2xHER3, EGFRxHER4, HER3xAXL, HER3xcMET, multivalent binding to and activation of apoptosis-inducing members of the TNF receptor superfamily, especially DR5 (TRAILR2), TNFR2, or immunostimulatory members of the TNF receptor superfamily, especially 4-1BB, CD40, OX40, CD27, and GITR, dual targeting of a TNF receptor superfamily member and a tumor-associated antigen, and effector cell retargeting to tumor cells, especially by binding to a trigger molecule on T cells (CD3) or NK cells (CD16) and a tumor-associated antigen (EGFR, HER2, HER3, HER4, FAP).

In a preferred embodiment of the first aspect of the invention, the imaging molecule is selected from the group consisting of bioluminescent reagents, chemiluminescent reagents, fluorescent imaging reagents, photosensitizers, chelating reagents, and radioactive moieties. More preferably, the imaging molecule is a bioluminescent, chemiluminescent and fluorescent imaging reagent such as but not limited to luciferase from *Renilla reniformis* and/or *Metridia Longa*, peroxalate, polymethines (e.g. cyanine dyes such as Cy3, Cy5, Cy5.5, Cy7) squaraine derivatives, phthalocyanine, porphhyrin derivatives, and BODIPY analogous (BODIPY FL, BODIPY R6G, BODIPY TR, BODIPY TMR, BODIPY 581/591, BODIPY 630/650, BODIPY 650/665), as well as fluorescent proteins such as but not limited to GFP, EGPF, CFP, BFP, YFP, DsRED (Chudakov et al. (2010) Physiol. Rev. 90:1103-1163).

Chelating reagents are capable of binding at least one metal ion, such as but not limited to calcium, magnesium, iron, aluminium, zinc, copper, arsenic, lead, thallium, and mercury ions, by chelation. Such chelating reagents may comprise ethylenediamine tetraacetic acid (EDTA), ethylenediamine tetraacetic acid (calcium disodium versante) (CaNa2-EDTA), dimercaprol (BAL), dimercaptosuccinic acid (DMSA), dimercapto-propane sulfonate (DMPS), ferritin, deferoxamine and deferasirox, deferiprone (1,2-dimethyl-3-hydroxyl-4-pyridinone), DOTA, DTPA, DADT, DADS, DO3A, N2S2MAMA, Triamidethiol, phosphonates, organic gadolinium complexes, penicillamine, and antibiotic drugs of the tetracycline family.

In one embodiment of the first aspect of the invention, the antigen-binding protein complex of the invention does not comprise $V_H$hu225-$V_L$3-43-$C_H$1-$C_H$2-$C_H$3 and $V_H$3-43-$V_L$hu225-$C_L$, in particular, if $V_H$hu225-$V_L$3-43-$C_H$1-$C_H$2-$C_H$3 has the amino acid sequence according to SEQ ID NO: 19 and $V_H$3-43-$V_L$hu225-$C_L$ has the amino acid sequence according to SEQ ID NO: 20.

Thus, in one embodiment of the first aspect of the invention, the antigen-binding protein complex does not comprise amino acid sequences SEQ ID NO: 19 and SEQ ID NO: 20.

In a second aspect, the present invention relates to the antigen-binding protein complex of the first aspect for use in medicine.

In a third aspect, the present invention relates to the antigen-binding protein complex of the first aspect for use in the prophylaxis, treatment or diagnosis of a disorder or disease such as but not limited to autoimmune diseases, allergic diseases, cancer type diseases, cutaneous conditions, endocrine diseases, eye diseases and disorders, genetic disorders, infectious diseases, intestinal diseases, neurological disorders, and mental illness. Exemplified, autoimmune diseases include but are not limited to Diabetes mellitus type 1, rheumatoid arthritis, psoriasis, Crohns Disease, autoimmune cardiomyopathy, autoimmune hepatitis, Hashimoto's thyroiditis, and Sjogern's syndrome. Exemplified, allergic diseases include but are not limited to allergic rhinitis, asthma, atopic eczema, anaphylaxis, insect venom allergies, drug allergies, and food allergies. Exemplified, cancer type diseases include but are not limited to Basal cell carcinoma, Bladder cancer, Bone cancer, Brain tumor, Breast cancer, Burkitt lymphoma, Cervical cancer, Colon Cancer, Cutaneous T-cell lymphoma, Esophageal cancer, Retinoblastoma, Gastric (Stomach) cancer, Gastrointestinal stromal tumor, Glioma, Hodgkin lymphoma, Kaposi sarcoma, Leukemias, Lymphomas, Melanoma, Oropharyngeal cancer, Ovarian cancer, Pancreatic cancer, Pleuropulmonary blastoma, Prostate cancer, Throat cancer, Thyroid cancer, and Urethral cancer. Exemplified, cutaneous conditions include but are not limited to Acne, Dermatitis, Eczema, conditions of the skin appendages, conditions of the subcutaneous fat, disturbances of pigmentation, epidermal nevi, epidermal neoplasms, epidermal cysts, erythemas, frostbites genodermatoses, mucinoses, neurocutaneous conditions (e.g. Wiskott-Aldrich syndrome), and psoriasis. Exemplified, endocrine diseases include but are not limited to Diabetes mellitus type 1 and type 2, Osteoporosis, and Cushing's disease. Exemplified, genetic disorders include but are not limited to color blindness, cystic fibrosis, Down syndrome, Sickle-cell disease, and Turner syndrome. Exemplified, infectious diseases include but are not limited to infections diseases caused by viruses, bacteria, worms, prions or other pathogens or parasites such as African sleeping sickness, AIDS, HIV infection, Anthrax, Borreliosis, Calicivirus infection (Norovirus and Sapovirus), Chickenpox, *Chlamydia* infection, Cholera, *Clostridium* infection, Colorado tick fever (CTF), common cold, Creutzfeldt-Jakob disease, Dengue fever (DEN-1, DEN-2, DEN-3 and DEN-4), Ebola, Enterovirus infection, infections with Human herpesvirus 6 (HHV-6) and Human herpesvirus 7 (HHV-7), Gonorrhea, Streptoccocal infections (group A and B), Hand, foot and mouth disease (HFMD), *Helicobacter pylori* infection, Hepatitis (A, B, C, and D), Herpes infection, Papillomavirus infection, Parainfluenza virus infection, Influenza, Lassa fever, Marburg fever, Measles, Meningitis, Mumps, Pasteurellosis, *Pediculus* infection, Plague, Pneumococcal infection, Respiratory syncytial virus infection, Rotavirus infection, Rubella virus infection, *Salmonella* food poisoning and infection, SARS, Scabies infections, Schistosomiasis, Smallpox, Staphylococcal food poisoning and infection, Syphilis, Tetanus, *Trichophyton* infection, Tuberculosis, Typhus, Venezuelan equine encephalitis, and Yellow fever. Exemplified, intestinal diseases include but are not limited to Gastroenteritis, Ileus, Ileitis, Colitis, Appendicitis, Coeliac disease, Irritable bowel syndrome, Diverticular disease, Diarrhea, Polyp, and Ulcerative colitis. Exemplified, neurological disorders include but are not limited to Amyotrophic Lateral Sclerosis (ALS), Alzheimer's disease, Brain damage, Creutzfeldt-Jakob disease, Cushing's syndrome, Dyslexia, Encephalitis, Epilepsy, Headache, Huntington's disease, Migraine, Multiple sclerosis, Parkinson's disease, Polio, Rabies, Schizophrenia, and Stroke. Exemplified, mental illness include but are not limited to Acute stress disorder, attention-deficit hyperactivity disorder (ADHD), Autistic disorder, Borderline personality disorder, Bulimia nervosa, Burn Out, Schizophrenia, Depression, Cognitive disorder, Communication disorder, Eating disorder, Kleptomania, Learning disorders, Male erectile disorder, Melancholia, Obsessive-compulsive disorder (OCD), Paranoia Pathological gambling, Posttraumatic stress disorder (PTSD), Psychotic disorder, Hypersomnia, Insomnia, and Tourette's syndrome.

In a preferred embodiment of the third aspect, the present invention relates to the antigen-binding protein complex of the first aspect for use in the prophylaxis, treatment or diagnosis of cancer. Preferably, the cancer is selected from the group consisting of Basal cell carcinoma, Bladder cancer, Bone cancer, Brain tumor, Breast cancer, Burkitt lymphoma, Cervical cancer, Colon Cancer, Cutaneous T-cell lymphoma, Esophageal cancer, Retinoblastoma, Gastric (Stomach) cancer, Gastrointestinal stromal tumor, Glioma, Hodgkin lymphoma, Kaposi sarcoma, Leukemias, Lymphomas, Melanoma, Oropharyngeal cancer, Ovarian cancer, Pancreatic cancer, Pleuropulmonary blastoma, Prostate cancer, Throat cancer, Thyroid cancer and Urethral cancer.

EXAMPLES

Example 1: A Monospecific and Tetravalent Diabody-Ig (Db-Ig) Targeting Death Receptor 5 (DR5)

A monospecific, tetravalent DbDR5xDR5-Ig molecule was generated by combining a db molecule, specific for DR5 (variable domains originate from Drozitumab), with the constant domains of an IgG antibody. Thus, the DbDR5xDR5-Ig molecule consists of two different polypeptides, $V_H DR5xVLDR5-C_L$ (light chain) and $V_H DR5xVLDR5-C_H 1-C_H 2-C_H 3$ (heavy chain) (FIG. 26A). The monospecific, tetravalent agonistic DbDR5xDR5-Ig exhibits four antigen binding sites for DR5 (FIG. 26B).

The binding molecule was expressed in transiently transfected HEK293-6E cells after co-administration of two plasmids, using polyethylenimine (PEI) as transfection reagent. The plasmids for transfection are based on pSec-TagA (Invitorgen). One day before transfection, $1·10^6$ cells per ml were seeded in FreeStyle F17 Expression Medium supplemented with 4 mM GlutaMAX (Thermo Fisher Scientific) and 0.1% kolliphor P188, overnight shaking with 115 rpm in humidified atmosphere at 37° C. and 5% $CO_2$. For 100 ml of cells to transfect, 5 ml F15 Expression Medium was either mixed with 200 μl PEI (Polyscience, Inc.) (sample A) or with 100 μg of plasmids (50 μg plasmid of heavy chain and 50 μg plasmid of light chain) (sample B). Sample A and sample B were separately prepared and incubated for 5 minutes at RT. After combining sample A with sample B, mixture was incubated for additional 15 minutes at RT and finally added to the cells. After cultivation of cells for 24 hours, protein secretion was induced by adding 2.5 ml Tryptone N1 (0.5% (w/v); TN1; Organo Technie) per 100 ml of cell suspension. After 96 hours of cultivation, cells were removed from medium by centrifugation (1,500×g; 10 minutes) and secreted protein was purified using $C_H 1$-CaptureSelect affinity chromatography (Thermo Fisher Scientific) using PBS as washing buffer and glycine buffer (100 mM; pH 3.5) as elution buffer. SDS-PAGE analysis revealed two bands under reducing conditions at approximately 65 kDa and 35 kDa corresponding to the heavy and light chain, and one major band under non-reducing conditions at approximately 220 kDa corresponding to the monospecific, tetravalent Db-Ig molecule (FIG. 26C). In addition, the monovalent scFvDR5 and the bivalent antibody Drozitumab were also analyzed via SDS-PAGE analysis. For the scFvDR5 molecule, one single band at approximately 27 kDa were observed under reducing and non-reducing conditions. The antibody Drozitumab showed two bands at approximately 25 kDa and 60 kDa under reducing conditions corresponding to the light and heavy chain of the protein. Under non-reducing conditions, one major band at approximately 200 kDa was observed. Binding of the tetravalent DbDR5xDR5-Ig, the parental bivalent antibody (Drozitumab), and the monovalent scFvDR5 to the extracellular domain (ECD) of DR5 (aa 48-212) was determined by ELISA. The DR5-Fc fusion protein was coated onto polystyrene microtiter plates at a concentration of 2 μg/ml diluted in PBS. Remaining binding sites were blocked with PBS, 2% skimmed milk (MPBS). Plates were then incubated with serial dilutions of the tetravalent DbDR5xDR5-Ig, the bivalent antibody Drozitumab, or the monovalent scFvDR5. After washing, bound antibodies were detected with an HRP-conjugated anti-human Fab antibody (DbDR5xDR5-Ig and Drozitumab) or an HRP-conjugated anti-His antibody (scFvDR5) and TMB, $H_2O_2$ as substrate. ELISA analysis revealed that binding activity of the parental antibody Drozitumab to the extracellular domain (ECD) of DR5 is retained in the Db-Ig format. The tetravalent DbDR5-Ig showed concentration-dependent binding to DR5 with an $EC_{50}$ value in the low nanomolar range (1.6 nM) (FIG. 26D). The parental antibody Drozitumab-IgG bound with a similar $EC_{50}$ values to DR5 (1.4 nM), whereas the monovalent scFv showed an $EC_{50}$ value of approximately 50 nM (Table 1).

TABLE 1

Binding properties of anti-DR5 antibodies.

| construct | DR5 |
| --- | --- |
| DbDR5xDR5-Ig | 1.6 |
| Drozitumab | 1.2 |
| scFvDR5 | 50 |

$EC_{50}$ values [nM] of binding to the extracellular domain (ECD) of DR5-Fc fusion proteins were determined by ELISA.

Example 2: A Monospecific and Tetravalent Diabody-Ig (Db-Ig) Activating TNF-Receptor 2 (TNFR-2)

A monospecific, tetravalent DbTNFR2xTNFR2-Ig molecule was generated by combining a db molecule, specific for TNFR2 (variable domains originate from IgG15), with the constant domains of an IgG antibody. Thus, the DbTNFR2xTNFR2-Ig molecule consists of two different polypeptides, $V_H$TNFR2x$V_L$TNFR2-$C_L$ (light chain) and $V_H$TNFR2x$V_L$TNFR2-$C_H$1-$C_H$2-$C_H$3 (heavy chain) (FIG. 27A). The monospecific, tetravalent agonistic DbTNFR2xTNFR2-Ig exhibits four antigen binding sites for TNFR2 (FIG. 27B). DbTNFR2xTNFR2-Ig was expressed in transiently transfected HEK293-6E cells after co-administration of two plasmids encoding for the light chain and the heavy chain, using polyethylenimine as transfection reagent. Protein secreted into cell culture supernatant was purified using $C_H$1-CaptureSelect affinity chromatography. SDS-PAGE analysis revealed two bands under reducing conditions at approximately 65 kDa and 35 kDa corresponding to the heavy and light chain, and one major band under non-reducing conditions at approximately 220 kDa corresponding to the intact monospecific, tetravalent Db-Ig molecule (FIG. 27C). After additional FPLC-SEC purification, HPLC-SEC confirmed purity and integrity of the DbTNFR2xTNFR2-Ig molecule. In addition, parental anti-TNFR2 IgG was also analyzed via HPLC-SEC and purity and integrity of this molecule was confirmed. Binding of the tetravalent DbTNFR2xTNFR2-Ig and the parental bivalent antibody (anti-TNFR2 IgG to the extracellular domain (ECD) of TNFR1 (aa 29-197) as well as to TNFR2 (Enbrel) was determined by ELISA. The TNFR1-Fc and TNFR2-Fc (Enbrel) fusion protein was coated onto polystyrene microtiter plates at a concentration of 2 μg/ml diluted in PBS. Remaining binding sites were blocked with PBS, 2% skimmed milk (MPBS). Plates were then incubated with serial dilutions of the tetravalent DbTNFR2xTNFR2-Ig or the bivalent anti-TNFR2 IgG. After washing, bound molecules were detected with an HRP-conjugated anti-human Fab antibody and TMB, $H_2O_2$ as substrate. ELISA analysis revealed that binding activity of the parental antibody anti-TNFR2 IgG to the extracellular domain (ECD) of TNFR2 is retained in the mono specific, tetravalent DbTNFR2xTNFR2-Ig format. The monospecific, tetravalent DbTNFR2xTNFR2-Ig showed a concentration-dependent binding to TNFR2-Fc with an $EC_{50}$ value in the low sub-nanomolar range (0.7 nM), similar as the bivalent anti-TNFR2 IgG (0.7 nM) (FIG. 27D). Binding of the TNFR2-specific molecules to TNFR1-Fc was not detected (Table 2).

TABLE 2

Binding properties and bioactivity of anti-TNFR2 antibodies.

| | ELISA | | Bioactivity |
| --- | --- | --- | --- |
| construct | TNFR1 | TNFR2 | Kym-1 |
| DbDR5xDR5-Ig | — | 0.7 | 28 nM |
| Anti-TNFR2 IgG | — | 0.7 | 56 pM |

$EC_{50}$ values [nM] of binding to the extracellular domain (ECD) of TNFR1-Fc and TNFR2-Fc (Enbrel) fusion proteins were determined by ELISA. $EC_{50}$ values of bioactivity were determined in cell-death induction assay using Kym-1 cells
—: no binding detected Bioactivity of the different TNFR2-specific antibodies was tested in a cell-death induction assay using Kym-1 cells. The day before the experiment, 10,000 cells per well were seeded in a 96 well plate and incubated over night at 37° C. Titration of the different anti-TNFR2 antibodies was diluted in medium and added to the cells. After 24 hours of incubation at 37° C., cell viability was analyzed via MTT assay. Cell death was induced by both constructs in a concentration-dependent manner. The tetravalent DbTNFR2xTNFR2-Ig molecule revealed an $EC_{50}$ value of approximately 56 pM, strongly increased by the factor of approximately 50 compared to the bivalent anti-TNFR2 antibody with an $EC_{50}$ value of approximately 30 nM. Although binding to TNFR2 via ELISA revealed similar $EC_{50}$ values, for the tetravalent and bivalent TNFR2-specific molecules, bioactivity of DbTNFR2xTNFR2-Ig was increased approximately 500-fold compared to the bivalent antibody (FIG. 27F; Table 2).

Example 3: A Bispecific and Tetravalent Diabody-Ig Fusion Protein (Db-Ig) Targeting EGFR (Hu225) and HER3 (3M6)

A bispecific, tetravalent Db3M6xhu225-Ig molecule was generated by combining a db molecule, specific for EGFR (hu225; humanized version of C225 (Cetuximab, Erbitux)) and HER3 (3M6; modified variable domain of MM-121 (Merrimack)), with the constant domains of an IgG antibody. Thus, the Db3M6xhu225-Ig molecule consists of two different polypeptides, $V_H$3M6xVLhu225-$C_L$ (light chain) and $V_H$hu225xVLhu3M6-$C_H$1-$C_H$2-$C_H$3 (heavy chain)

(FIG. 28A). The bispecific Db3M6xhu225-Ig exhibits two antigen binding sites for EGFR and two antigen binding sites for HER3 (FIG. 28B).

Db3M6xhu225-Ig was expressed in transiently transfected HEK293-6E cells after co-administration of two plasmids encoding for the light and the heavy chain, using polyethylenimine as transfection reagent. Protein secreted into cell culture supernatant was purified using Protein G affinity chromatography. SDS-PAGE analysis revealed two bands under reducing conditions at approximately 65 kDa and 35 kDa corresponding to the heavy and light chain, and one major band under non-reducing conditions at approximately 220 kDa corresponding to the bispecific, tetravalent Db-Ig molecule (FIG. 28C). Purity, integrity and homogeneity of the Db3M6xhu225-Ig molecule were confirmed by size exclusion chromatography (FIG. 28D). Binding of the tetravalent Db3M6xhu225-Ig and the monospecific parental antibodies (Cetuximab (anti-EGFR) and 3M6-IgG (anti-HER3)) to the extracellular domain (ECD) of EGFR (aa 25-645) and HER3 (aa 21-643) was determined by ELISA. The EGFR-Fc or the HER3-Fc fusion protein was coated onto polystyrene microtiter plates at a concentration of 2 µg/ml diluted in PBS. Remaining binding sites were blocked with PBS, 2% skimmed milk (MPBS). Plates were then incubated with serial dilution of the bispecific, tetravalent Db3M6xhu225-Ig or the monospecific parental antibodies. After washing, bound antibodies were detected with an HRP-conjugated anti-human Fab antibody and TMB, $H_2O_2$ as substrate. ELISA analysis revealed that binding activity of the parental antibodies to the extracellular domain (ECD) of EGFR and HER3 is retained in the Db-Ig format. The bispecific, tetravalent Db3M6xhu225-Ig showed a concentration-dependent binding to EGFR with an $EC_{50}$ value in the sub-nanomolar range (0.5 nM) and to HER3 in the nanomolar range (1.4 nM) (FIG. 28E). The parental antibodies bound with similar $EC_{50}$ values to their corresponding antigens (Cetuximab to EGFR with 0.21 nM; IgG 3-43 with 0.7 nM; Table 3). Simultaneous binding to both antigens, EGFR and HER3, was confirmed by a second binding ELISA analysis. As first antigen, EGFR-Fc fusion protein, was coated onto polystyrene microtiter plates at 2 µg/ml in PBS. Remaining binding sites were blocked with PBS, 2% skimmed milk (MPBS). Plates were then incubated with serial dilution of the bispecific Db3M6xhu225-Ig in MPBS. After washing, the second antigen, HER3-His (300 nM diluted in MPBS), was added to the plates. After washing, bound HER3-His (second antigen) was detected with an HRP-conjugated anti-His antibody and TMB, $H_2O_2$ as substrate. The second antigen was bound to the bispecific Db3M6xhu225-Ig in a concentration-dependent manner with an $EC_{50}$ value in the nanomolar range (1.3 nM) (FIG. 28F) similar as binding of db3M6xhu225-Ig to coated HER3-Fc. Thus, this result demonstrates the unrestricted accessibility of both antigen binding sites within the Db-Ig molecule.

TABLE 3

Binding properties of Db3M6xhu225-Ig.

| construct | ELISA | | | Flow cytometry | | |
|---|---|---|---|---|---|---|
| | EGFR | HER3 | EGFR + HER3 | MCF-7 | SKBR-3 | FaDu |
| Db3M6xhu225-Ig | 0.48 | 1.4 | 1.3 | 1.54 | 0.065 | 0.24 |
| Cetuximab | 0.21 | — | n.p. | — | 0.031 | 0.13 |
| 3M6-IgG | — | 0.7 | n.p. | 1.18 | 0.44 | 7.5 |

$EC_{50}$ values [nM] of binding to the extracellular domain (ECD) of EGFR and HER3 fusion proteins were determined by ELISA. The $EC_{50}$ values [nM] of binding to MCF-7, SKBR-3, and FaDu cells were assessed by flow cytometry.
—: no binding detected;
n.p.: not performed Example 4: A Bispecific and Tetravalent Diabody-Ig Fusion Protein (Db-Ig) Targeting EGFR (hu225) and HER3 (3-43) using $C_H1$ and $C_L$ A bispecific, tetravalent Db3-43xhu225-Ig molecule was generated by combining a db molecule, specific for EGFR (hu225; humanized version of C225 (Cetuximab, Erbitux)) and HER3 (3-43), with the constant domains of an IgG antibody. Thus, the Db3-43xhu225-Ig molecule consists of two different polypeptides, $V_H3$-43x$VL$hu225-$C_L$ (light chain) and $V_H$hu225x$VL$hu3-43-$C_H1$-$C_H2$-$C_H3$ (heavy chain) (FIG. 29A). The bispecific Db3-43xhu225-Ig exhibits two antigen binding sites for EGFR and two antigen binding sites for HER3 (FIG. 29B).

Db3-43xhu225-Ig was expressed in transiently transfected HEK293-6E cells after co-administration of two plasmids encoding for the light chain and the heavy chain, using polyethylenimine as transfection reagent. Protein secreted into cell culture supernatant was purified using $C_H1$-CaptureSelect affinity chromatography. SDS-PAGE analysis revealed two bands under reducing conditions at approximately 65 kDa and 35 kDa corresponding to the heavy and light chain, and one major band under non-reducing conditions at approximately 220 kDa corresponding to the bispecific, tetravalent Db3-43xhu225-Ig molecule (FIG. 29C). Purity, integrity and homogeneity of the Db3-43xhu225-Ig molecule were confirmed by size exclusion chromatography (FIG. 29D). Binding of the Db3-43xhu225-Ig and the monospecific parental antibodies (Cetuximab (anti-EGFR) and 3-43-IgG (anti-HER3)) to the extracellular domain (ECD) of EGFR (aa 25-645) and HER3 (aa 21-643) was determined by ELISA. The EGFR-Fc or the HER3-Fc fusion protein was coated onto polystyrene microtiter plates at a concentration of 2 µg/ml diluted in PBS. Remaining binding sites were blocked with PBS, 2% skimmed milk (MPBS). Plates were then incubated with serial dilution of the bispecific, tetravalent Db3-43xhu225-Ig or the monospecific, bivalent parental antibodies. After washing, bound antibodies were detected with an HRP-conjugated anti-human Fab antibody and TMB, $H_2O_2$ as substrate. ELISA analysis revealed that binding activity of the parental antibodies to the extracellular domain (ECD) of EGFR and HER3 is retained in the Db-Ig format. The bispecific, tetravalent Db3-43xhu225-Ig showed concentration-dependent binding to EGFR and HER3 with $EC_{50}$ values in the sub-nanomolar range (0.43 nM for EGFR; 0.34 nM for HER3) (FIG. 29E). The parental antibodies bound with similar $EC_{50}$ values to their corresponding antigens (Table 4). Simultaneous binding to both antigens, EGFR and HER3, was confirmed by a second ELISA binding analysis. As first antigen, EGFR-Fc fusion protein was coated onto polystyrene microtiter plates at 2 μg/ml in PBS. Remaining binding sites were blocked with PBS, 2% skimmed milk (MPBS). Plates were then incubated with serial dilution of the bispecific, tetravalent Db3-43xhu225-Ig in MPBS. After washing, the second antigen, HER3-His (300 nM diluted in MPBS), was added to the plates. After washing, bound HER3-His (second antigen) was detected with an HRP-conjugated anti-His antibody and TMB, $H_2O_2$ as substrate. The second antigen was bound to the bispecific, tetravalent Db3-43xhu225-Ig in a concentration-dependent manner with an $EC_{50}$ value in the sub-nanomolar range (0.85 nM) FIG. 29F) similar as binding of Db3-43xhu225-Ig to coated HER3-Fc. Thus, this result demonstrates the unrestricted accessibility of both antigen binding sites within the Db3-43xhu225-Ig molecule.

Regarding the cell line SKBR-3, which expresses EGFR and HER3 in similar ranges, the bispecific, tetravalent Db3-43xhu225-Ig molecule bound with an $EC_{50}$ value of 0.047 nM, similar to the binding of both parental antibodies Cetuximab (0.031 nM) and 3-43-IgG (0.022 nM). The Db3M6xhu225-Ig molecule bound to SKBR-3 cells with an $EC_{50}$ value of approximately 0.065 nM, whereas the parental antibody 3M6-IgG showed reduced binding with an $EC_{50}$ value of 0.44 nM. This result underlines the advantage of a bispecific, tetravalent antibody, as its binding to cells benefits from the parental antibody with the strongest binding. Concerning binding to FaDu cells, Db3-43xhu225-Ig bound with an $EC_{50}$ value of 0.14 nM. As FaDu cells express very high amount of EGFR and comparative low amount of HER3, Db3-43xhu225-Ig bound most likely preferential with the anti-EGFR (hu225) moieties to the cells. Indeed, the parental anti-EGFR antibody Cetuximab bound to the cells with a similar $EC_{50}$ value (0.13 nM). As expected, the parental anti-HER3 3-43-IgG also bound with comparative low fluorescence signal to the cells with an $EC_{50}$ value of

TABLE 4

Binding properties of Db3-43xhu225-Ig.

| construct | ELISA | | | Flow cytometry | | |
|---|---|---|---|---|---|---|
| | EGFR | HER3 | EGFR + HER3 | MCF-7 | SKBR-3 | FaDu |
| Db3-43xhu225-Ig | 0.43 | 0.34 | 0.85 | 0.054 | 0.047 | 0.14 |
| Cetuximab | 0.19 | — | n.p. | — | 0.031 | 0.13 |
| 3-43-IgG | — | 0.20 | n.p. | 0.021 | 0.022 | 0.003 |

$EC_{50}$ values [nM] of binding to the extracellular domain (ECD) of EGFR and HER3 fusion proteins were determined by ELISA. The $EC_{50}$ values [nM] of binding to MCF-7, SKBR-3, and FaDu cells were assessed by flow cytometry.
—: no binding detected;
n.p.: not performed

Example 5: Flow Cytometry of Bispecific, Tetravalent Db-Ig Molecules Targeting EGFR (hu225) and HER3 (3M6 or 3-43)

Binding studies of Db3M6xhu225-Ig (Example 3), Db3-43xhu225-Ig (Example 4) and parental monoclonal antibodies (Cetuximab, 3-43-IgG, and 3M6-IgG) to EGFR- and/or HER3-expressing cells (MCF-7, SKBR-3, and FaDu) (Table 5) were analyzed via flow cytometry. Adherent cells were washed with PBS and shortly trypsinized at 37° C. Trypsin was quenched with FCS containing medium and removed by centrifugation (500×g, 5 minutes). 100,000 cells per well were seeded and incubated with a serial dilution of Db3-43xhu225-Ig, Db3M6xhu225-Ig, or parental monoclonal antibodies diluted in PBA (PBS containing 2% (v/v) FCS, 0.02% (w/v) $NaN_3$) for one hour at 4° C. Cells were washed twice using PBA. Bound antibodies were detected using PE-labeled anti-human Fc secondary antibody, which was incubated for another hour at 4° C. After washing, median fluorescence intensity (MFI) was measured with a Milltenyi MACSQuant® Analyzer 10. Relative MFI (to unstained cells) were calculated by MACSQuant® software and Excel. For the HER3-positive MCF-7 cell line, binding of the bispecific, tetravalent Db3-43xhu225-Ig bound in the sub-nanomolar range with an $EC_{50}$ value of 0.054 nM. The parental anti-HER3 3-43-IgG bound with similar $EC_{50}$ values (0.021 nM) to the cells. Similar results, however with reduced $EC_{50}$ values was observed for the bispecific, tetravalent Db3M6xhu225-Ig (1.54 nM) and 3M6-IgG (1.18 nM). No binding to MCF-7 cells was observed for the anti-EGFR antibody Cetuximab.

0.003 nM. The $EC_{50}$ value of db3M6xhu225-Ig was determined with a concentration of 0.24 nM, which is in the same range as obtained for Db3-43xhu225-Ig and Cetuximab. The parental antibody 3M6-IgG showed reduced binding with an $EC_{50}$ value of 7.5 nM. In general, flow cytometry binding analysis confirmed the retained binding activity of the bispecific, tetravalent antibodies (db3-43xhu225-Ig and Db3M6xhu225-Ig) compared to the monoclonal monospecific parental antibodies (Cetuximab, 3-43-IgG, and 3M6-IgG) (FIG. 30; Table 3 and Table 4).

TABLE 5

Receptor expression of the tumor cell line MCF-7, SKBR-3, and FaDu.

| cell line | EGFR | HER3 |
|---|---|---|
| MCF-7 | 1,000 | 17,000 |
| SKBR-3 | 30,000 | 14,000 |
| FaDu | 143,000 | 3,000 |

Receptor expression of the different cell lines was quantified using QFIT kit.

Example 6: A Bispecific and Tetravalent Diabody Fusion Protein Targeting EGFR (Hu225) and HER3 (3-43) Using EHD2 as Dimerization Domain A bispecific, tetravalent Db3-43xhu225-EHD2-Fc molecule was generated by combining a db molecule, specific for EGFR (hu225; humanized version of C225 (Cetuximab, Erbitux)) and HER3 (3-43), with the $C_H2$ domain of IgE (EHD2) and a homodimeric Fc part. Thus, the Db3-

43xhu225-EHD2-Fc molecule consists of two different polypeptides, $V_H3$-43x$V_L$hu225-EHD2 (light chain) and $V_H$hu225xVLhu3-43-EHD2-$C_H2$-$C_H3$ (heavy chain) (FIG. 31A). The bispecific Db3-43xhu225-EHD2-Fc exhibits two antigen binding sites for EGFR and two antigen binding sites for HER3 (FIG. 31B).

Db3-43xhu225-EHD2-Fc was expressed in transiently transfected HEK293-6E cells after co-administration of two plasmids encoding for the light and the heavy chain, using polyethylenimine as transfection reagent. Protein secreted into cell culture supernatant was purified using FcXL-CaptureSelect affinity chromatography. SDS-PAGE analysis revealed two bands under reducing conditions at approximately 70 kDa and 35 kDa corresponding to the heavy and light chain. Under non-reducing conditions, one major band was detected at approximately 200 kDa and two minor band at approximately 220 kDa and 75 kDa (FIG. 31C). Purity, integrity and homogeneity of the Db3-43xhu225-EHD2-Fc molecule were confirmed by size exclusion chromatography (FIG. 31D). Binding of the bispecific, tetravalent Db3-43xhu225-EHD2-Fc and the monospecific parental antibodies (hu225-IgG (anti-EGFR) and 3-43-IgG (anti-HER3)) to the extracellular domain (ECD) of EGFR (aa 25-645) and HER3 (aa 21-643) was determined by ELISA. The His-tagged EGFR or HER3 proteins were used as antigens and coated onto polystyrene microtiter plates at a concentration of 2 μg/ml diluted in PBS. Remaining binding sites were blocked with PBS, 2% skimmed milk (MPBS). Plates were then incubated with serial dilution of the bispecific, tetravalent Db3-43xhu225-EHD2-Fc or the monospecific parental antibodies. After washing, bound antibodies were detected with an HRP-conjugated anti-human Fc antibody and TMB, $H_2O_2$ as substrate. ELISA analysis revealed that binding activity of the parental antibodies to the extracellular domain (ECD) of EGFR and HER3 is retained in the Db3-43xhu225-EHD2-Fc molecule. The bispecific, tetravalent Db3-43xhu225-EHD2-Fc showed concentration-dependent binding to EGFR and HER3 with $EC_{50}$ values in the sub-nanomolar range (0.28 nM for EGFR; 0.35 nM for HER3) (FIG. 31E). The parental antibodies bound with similar $EC_{50}$ values to their corresponding antigens (Table 6). Simultaneous binding to both antigens, EGFR and HER3, was confirmed by a second binding ELISA analysis. As first antigen, EGFR-Fc fusion protein was coated onto polystyrene microtiter plates at 2 μg/ml in PBS. Remaining binding sites were blocked with PBS, 2% skimmed milk (MPBS). Plates were then incubated with serial dilution of the bispecific Db3-43xhu225-EHD2-Fc in MPBS. After washing, the second antigen, HER3-His (300 nM diluted in MPBS), was added to the plates. After washing, bound HER3-His (second antigen) was detected with an HRP-conjugated anti-His antibody and TMB, $H_2O_2$ as substrate. The second antigen was bound to the bispecific Db3-43xhu225-EHD2-Fc in a concentration-dependent manner with an $EC_{50}$ value in the sub-nanomolar range (1.4 nM) (FIG. 31F) similar as binding of Db3-43xhu225-EHD2-Fc to coated HER3-His. Thus, this result demonstrates the simultaneous binding of both antigen binding sites within the Db3-43xhu225-EHD2-Fc molecule.

TABLE 6

Binding properties of Db3-43xhu225-EHD2-Fc, Db3-43xhu225-hetEHD2-Fc, and Db3-34xhu225-MHD2-Fc.

| construct | ELISA | | |
|---|---|---|---|
| | EGFR | HER3 | EGFR + HER3 |
| Db3-43xhu225-EHD2-Fc | 0.28 | 0.35 | 1.4 |
| Db3-43xhu225-hetEHD2-Fc | 0.24 | 0.34 | 0.56 |
| Db3-43xhu225-MHD2-Fc | 0.23 | 0.34 | 1.8 |
| hu225-IgG | 0.23 | n.p. | n.p. |
| 3-43-IgG | n.p. | 0.23 | n.p. |

$EC_{50}$ values [nM] of binding to the extracellular domain (ECD) of EGFR and HER3 fusion proteins were determined by ELISA.
—: no binding detected;
n.p.: not performed Example 7: A Bispecific and Tetravalent Diabody Fusion Protein Targeting EGFR (Hu225) and HER3 (3-43) Using het1EHD2 as Dimerization Module A bispecific, tetravalent Db3-43xhu225-het1EHD2-Fc molecule was generated by combining a db molecule, specific for EGFR (hu225; humanized version of C225 (Cetuximab, Erbitux)) and HER3 (3-43), with a mutated version of $C_H2$ domain of IgE (hetEHD2), which forms heterodimers of EHD2(C247S, N275Q) (light chain) and EHD2(C337S) (heavy chain), and a homodimeric Fc part. Thus, the Db3-43xhu225-het1EHD2-Fc molecule consists of two different polypeptides, $V_H3$-43xVLhu225-EHD2(C247S, N275Q) (light chain) and $V_H$hu225xVLhu3-43-EHD2(C337S)-$C_H2$-$C_H3$ (heavy chain) (FIG. 32A). The bispecific, tetravalent Db3-43xhu225-het1EHD2-Fc exhibits two antigen binding sites for EGFR and two antigen binding sites for HER3 (FIG. 32B).

Db3-43xhu225-het1EHD2-Fc was expressed in transiently transfected HEK293-6E cells after co-administration of two plasmids encoding for the light and the heavy chain, using polyethylenimine as transfection reagent. Protein secreted into cell culture supernatant was purified using FcXL-CaptureSelect affinity chromatography. SDS-PAGE analysis revealed two bands under reducing conditions at approximately 70 kDa and 35 kDa corresponding to the heavy and light chain, and one major band under non-reducing conditions at approximately 220 kDa (FIG. 32C). Purity, integrity and homogeneity of the Db3-43xhu225-het1EHD2-Fc molecule were confirmed by size exclusion chromatography (FIG. 32D). Binding of the bispecific Db3-43xhu225-het1EHD2-Fc and the monospecific parental antibodies (hu225-IgG (anti-EGFR) and 3-43-IgG (anti-HER3)) to the extracellular domain (ECD) of EGFR (aa 25-645) and HER3 (aa 21-643) was determined by ELISA. The His-tagged EGFR or HER3 proteins were coated onto polystyrene microtiter plates at a concentration of 2 μg/ml diluted in PBS. Remaining binding sites were blocked with PBS, 2% skimmed milk (MPBS). Plates were then incubated with serial dilution of the bispecific Db3-43xhu225-het1EHD2-Fc or the monospecific parental antibodies. After washing, bound antibodies were detected with an HRP-conjugated anti-human Fc antibody and TMB, $H_2O_2$ as substrate. ELISA analysis revealed that binding activity of the parental antibodies to the extracellular domain (ECD) of EGFR and HER3 is retained in the Db3-43xhu225-het1EHD2-Fc molecule. The bispecific, tetravalent db3-43xhu225-het1EHD2-Fc showed concentration-dependent binding to EGFR and HER3 with an $EC_{50}$ value in the sub-nanomolar range (0.24 nM for EGFR; 0.34 nM for HER3) (FIG. 32E). The parental antibodies bound with similar $EC_{50}$ values to their corresponding antigens (Table 6). Simultaneous binding to both antigens, EGFR and HER3, was confirmed by a second binding ELISA analysis. As first antigen, EGFR-Fc fusion protein was coated onto polystyrene microtiter plates at 2 µg/ml in PBS. Remaining binding sites were blocked with PBS, 2% skimmed milk (MPBS). Plates were then incubated with serial dilution of the bispecific Db3-43xhu225-het1EHD2-Fc in MPBS. After washing, the second antigen, HER3-His (300 nM diluted in MPBS), was added to the plates for one additional hours at RT. After washing, bound HER3-His (second antigen) was detected with an HRP-conjugated anti-His antibody and TMB, $H_2O_2$ as substrate. The second antigen was bound to the bispecific Db3-43xhu225-het1EHD2-Fc in a concentration-dependent manner with an $EC_{50}$ value in the sub-nanomolar range (0.56 nM) (FIG. 32F) similar as binding of Db3-43xhu225-het1EHD2-Fc to coated HER3-His. Thus, this result demonstrates the unrestricted accessibility of both antigen binding sites within the Db3-43xhu225-het1EHD2-Fc molecule.

Example 8: A Bispecific and Tetravalent Diabody Fusion Protein Targeting EGFR (Hu225) and HER3 (3-43) Using MHD2 as Dimerization Domain A bispecific, tetravalent Db3-43xhu225-MHD2-Fc molecule was generated by combining a db molecule, specific for EGFR (hu225; humanized version of C225 (Cetuximab, Erbitux)) and HER3 (3-43), with the $C_H2$ domain of IgM (MHD2) and a homodimeric Fc part. Thus, the Db3-43xhu225-MHD2-Fc molecule consists of two different polypeptides, $V_H3-xV_Lhu225-MHD2$ (light chain) and $V_Hhu225xV_Lhu3-43-MHD2-C_H2-C_H3$ (heavy chain) (FIG. 33A). The bispecific Db3-43xhu225-MHD2-Fc exhibits two antigen binding sites for EGFR and two antigen binding sites for HER3 (FIG. 33B).

Db3-43xhu225-MHD2-Fc was expressed in transiently transfected HEK293-6E cells after co-administration of two plasmids encoding for the light and the heavy chain, using polyethylenimine as transfection reagent. Protein secreted into cell culture supernatant was purified using FcXL-CaptureSelect affinity chromatography. SDS-PAGE analysis revealed two bands under reducing conditions at approximately 70 kDa and 35 kDa corresponding to the heavy and light chain, and two bands under non-reducing conditions at approximately 200 kDa and 80 kDa corresponding most likely to the dimer of the heavy and the light chain (FIG. 33C). Purity, integrity and homogeneity of the Db3-43xhu225-MHD2-Fc molecule were confirmed by size exclusion chromatography (FIG. 33D). Binding of the Db3-43xhu225-MHD2-Fc and the monospecific parental antibodies (hu225-IgG (anti-EGFR) and 3-43-IgG (anti-HER3)) to the extracellular domain (ECD) of EGFR (aa 25-645) and HER3 (aa 21-643) was determined by ELISA. The His-tagged EGFR or HER3 proteins were coated onto polystyrene microtiter plates at a concentration of 2 µg/ml diluted in PBS. Remaining binding sites were blocked with PBS, 2% skimmed milk (MPBS). Plates were then incubated with serial dilution of the bispecific Db3-43xhu225-MHD2-Fc or the monospecific parental antibodies. After washing, bound antibodies were detected with an HRP-conjugated anti-human Fc antibody and TMB, $H_2O_2$ as substrate. ELISA analysis revealed that binding activity of the parental antibodies to the extracellular domain (ECD) of EGFR and HER3 is retained in the db3-43xhu225-MHD2-Fc molecule. The bispecific, tetravalent Db3-43xhu225-MHD2-Fc showed concentration-dependent binding to EGFR and HER3 with $EC_{50}$ values in the sub-nanomolar range (0.23 nM for EGFR; 0.34 nM for HER3) (FIG. 33E). The parental antibodies bound with similar $EC_{50}$ values to their corresponding antigens (Table 6). Simultaneous binding to both antigens, EGFR and HER3, was confirmed by a second binding ELISA analysis. As first antigen, EGFR-Fc fusion protein was coated onto polystyrene microtiter plates at 2 µg/ml in PBS. Remaining binding sites were blocked with PBS, 2% skimmed milk (MPBS). Plates were then incubated with serial dilution of the bispecific Db3-43xhu225-EHD2-Fc in MPBS. After washing, the second antigen, HER3-His (300 nM diluted in MPBS), was added to the plates. After washing, bound HER3-His (second antigen) was detected with an HRP-conjugated anti-His antibody and TMB, $H_2O_2$ as substrate. The second antigen was bound to the bispecific db3-43xhu225-MHD2-Fc in a concentration-dependent manner with an $EC_{50}$ value in the nanomolar range (1.9 nM) (FIG. 33F). This result demonstrated the simultaneous binding of both antigen binding sites within the Db3-43xhu225-MHD2-Fc molecule.

Example 9: Serum Stability of Bispecific, Tetravalent Binding Molecules Targeting EGFR (Hu225) and HER3 (3-43)

Stability of the bispecific, tetravalent molecules (db3-43xhu225-Ig (Example 4), Db3-43xhu225-EHD2-Fc (Example 6), Db3-43xhu225-het1EHD2-Fc (Example 7), Db3-43xhu225-MHD2-Fc (Example 8)) was analyzed in human plasma. 200 nM of the bispecific molecules diluted in 50% human plasma were incubated at 37° C. for 1, 3, or 7 days. Stability of the proteins was analyzed via ELISA binding studies. The bispecific molecules, which were diluted in PBS and stored at 4° C., were included as control. The His-tagged EGFR or HER3 antigens were coated onto polystyrene microtiter plates at a concentration of 2 µg/ml diluted in PBS. Remaining binding sites were blocked with PBS, 2% skimmed milk (MPBS). Plates were then incubated with serial dilution of the bispecific molecules (plasma mixture) diluted 1 to 3 in MPBS (starting concentration: 66.66 nM; dilution: 1 to 4). After washing, bound antibodies were detected with a HRP-conjugated anti-human Fc antibody. Compared with the control molecules, ELISA analysis revealed that incubation of all bispecific antibodies in human plasma at 37° C. up to 7 days did only marginal or even not change the binding activity of the bispecific molecules to the extracellular domain of EGFR and HER3. $EC_{50}$ values were determined in the range of 154 to 538 pM for EGFR-His and 198 to 458 pM for HER3-His. In addition, the maximal absorption of the bispecific antibodies, which were incubated for the different time points, was measured in the same range. Thus, the here described bispecific, tetravalent binding molecules obtained high stability under physiological like properties (FIG. 34).

Example 10: In Vivo Half-Life of Bispecific and Tetravalent Diabody-Ig Fusion Protein (Db-Ig) Targeting EGFR (Hu225) and HER3 (3-43)

The pharmacokinetic profile of the bispecific, tetravalent binding molecules (db3-43xhu225-Ig (Example 4), Db3-43xhu225-EHD2-Fc (Example 6), Db3-43xhu225-MHD2-Fc (Example 8)) was analyzed in SWISS mice. 25 µg of the protein was diluted in 100 µl sterile PBS and injected intravenously into the tail. After certain time points (3 minutes, 30 minutes, 1 hour, 2 hours, 6 hours, 1 day, 3 days, and 6 days) blood samples were taken from the tail and incubated on ice for 10 minutes. Clotted blood was centrifuged (16,000×g, 20 minutes, 4° C.) and serum samples were stored at −20° C. Protein serum concentration was determined via ELISA. For the db3-43xhu225-Ig molecule, EGFR-Fc or HER3-Fc fusion proteins were coated onto polystyrene microtiter plates at a concentration of 2 μg/ml diluted in PBS. For Db3-43xhu225-EHD2-Fc and Db3-43xhu225-MHD2-Fc, EGFR-His and HER3-His molecules were used as coated antigens (same conditions). Remaining binding sites were blocked with PBS, 2% skimmed milk (MPBS). Plates were then incubated with serum diluted in MPBS. After washing, bound antibodies were detected either with an HRP-conjugated anti-human Fab antibody for Db3-43xhu225-Ig, or with an HRP-conjugated anti-human Fc antibody for Db3-43xhu225-EHD2-Fc and Db3-43xhu225-MHD2-Fc. TMB and $H_2O_2$ was used as substrate. Serum concentration of the Db3-43xhu225-Ig molecule was interpolated from a standard curve of purified fusion protein and normalized to the 3 minute value (FIG. 35). In general, the pharmacokinetic profiles of the tested bispecific, tetravalent antibodies were similar with terminal half-lives in the range of 3 to 4 days (Table 7). In addition, only marginal differences were observed for the different antibodies using the different coated antigens (EGFR and HER3) in ELISA analysis. Thus, binding of the bispecific, tetravalent molecule to both antigens was still ensured after intravenous application in circulation in the blood for up to seven days.

TABLE 7

Pharmacokinetic profile of bispecific, tetravalent antibodies.

| construct | coated antigen | initial half-life [h] | terminal half-life [h] |
|---|---|---|---|
| Db3-43xhu225-Ig | EGFR | 2.7 ± 0.4 | 89.4 ± 2.2 |
|  | HER3 | 3.1 ± 1.0 | 86.0 ± 2.7 |
| Db3-43xhu225-EHD2-Fc | EGFR | 3.4 ± 1.8 | 105.0 ± 17.1 |
|  | HER3 | 2.6 ± 0.5 | 94.8 ± 5.0 |
| Db3-43xhu225-MHD2-Fc | EGFR | 0.9 ± 0.1 | 73.6 ± 8.0 |
|  | HER3 | 1.8 ± 0.5 | 70.8 ± 2.2 |

Protein concentration of serum samples were measured via ELISA using either EGFR or HER3 as coated antigen. Initial and terminal half-lives of bispecific, tetravalent antibodies were determined by Excel.

Example 11: A Bispecific, Trivalent Diabody-Fab Fusion Protein Targeting HER3 (3-43) and CD3 (huU3) Using $C_H1/C_L$ and EHD2 as Dimerization Domains A bispecific, trivalent Db3-43xhuU3-EHD2-Fab3-43-$Fc_{kih}$ molecule was generated by combining a db molecule, specific for HER3 (3-43) and CD3 (huU3; humanized version of UCHT1), with the $C_H2$ domain of IgE (EHD2), together with a HER3-specific Fab molecule by using a heterodimeric Fc part (knob-into-hole technology). Thus, the Db3-43xhuU3-EHD2-Fab3-43-$Fc_{kih}$ molecule consists of four different polypeptides, i) $V_H3$-43x$V_L$huU3-EHD2 (light chain of diabody moiety), ii) $V_H$huU3x$V_L$3-43-EHD2-$C_H2$-$C_H3_{hole}$ (heavy chain of diabody moiety), iii) $V_H3$-43-$C_H1$-$C_H2$-$C_H3_{knob}$ (heavy chain of Fab moiety), and iv) $V_L3$-43-CLX (light chain of Fab moiety) (FIG. 36A). The bispecific Db3-43xhuU3-EHD2-Fab3-43-$Fc_{kih}$ exhibits two antigen binding sites for HER3 and one antigen binding site for CD3 (FIG. 36B).

Db3-43xhuU3-EHD2-Fab3-43-$Fc_{kih}$ was expressed in transiently transfected HEK293-6E cells after co-administration of four plasmids encoding for the light and heavy chain of the diabody moiety and of the Fab moiety, using polyethylenimine as transfection reagent. Protein secreted into cell culture supernatant was purified using $C_H1$-CaptureSelect affinity chromatography and size exclusion chromatography using FPLC. SDS-PAGE analysis revealed four bands under reducing conditions at approximately 70 kDa (heavy chain of diabody moiety), 50 kDa (heavy chain of Fab moiety), 35 kDa (light chain of diabody moiety), and 20 kDa (light chain of Fab moiety). Under non-reducing conditions, one major band at approximately 200 kDa and two minor bands (above and below the major band) were observed (FIG. 36C). Purity, integrity and homogeneity of the Db3-43xhuU3-EHD2-Fab3-43-$Fc_{kih}$ molecule were confirmed by size exclusion chromatography (FIG. 36D).

Binding studies of Db3-43xhuU3-EHD2-Fab3-43-$Fc_{kih}$ to HER3-expressing (SKBR3; Table 5) and CD3-expressing cells (Jurkat) were analyzed via flow cytometry. Adherent SKBR3 cells were washed with PBS and shortly trypsinized at 37° C. Trypsin was quenched with FCS containing medium and removed by centrifugation (500×g, 5 minutes). Jurkat cells, which are suspension cells, were directly used without trypsin treatment. 100,000 cells per well were seeded and incubated with a serial dilution of Db3-43xhuU3-EHD2-Fab3-43-$Fc_{kih}$ diluted in PBA (PBS containing 2% (v/v) FCS, 0.02% (w/v) $NaN_3$) for one hour at 4° C. Cells were washed twice using PBA. Bound antibodies were detected using PE-labeled anti-human Fc secondary antibody, which was incubated for another hour at 4° C. After washing, median fluorescence intensity (MFI) was measured with a Milltenyi MACSQuant® Analyzer 10. Relative MFI (to unstained cells) were calculated by MACSQuant® software and Excel. In general, a concentration-dependent binding of the bispecific Db3-43xhuU3-EHD2-Fab3-43-$Fc_{kih}$ to the cells was observed with $EC_{50}$ values of 30 pM for SKBR3 and 9.5 nM for Jurkat cells (FIG. 36E; Table 8). Simultaneous binding of both antigens was tested via flow cytometry using CD3-expressing Jurkat cells. A titration of bispecific Db3-43xhuU3-EHD2-Fab3-43-$Fc_{kih}$ was incubated with the cells for one hour at RT. After washing cells twice with PBA, the second antigen, HER3-His, was added to the cells (300 nM) and incubated for one additional hour at RT. Cells were washed twice using PBA. Bound HER3-His was detected using a PE-labeled anti-His antibody. After washing, median fluorescence intensity (MFI) was measured with a Milltenyi MACSQuant® Analyzer 10. Relative MFI (to unstained cells) were calculated by MACSQuant® software and Excel. Again, bound HER3-His could be detected in a concentration-dependent manner with an $EC_{50}$ value of 13.8 nM, which is similar to the $EC_{50}$ value obtained for binding of Db3-43xhuU3-EHD2-Fab3-43-$Fc_{kih}$ to Jurkat cells in the absence of the second antigen (Table 8). Thus, these binding experiments confirmed the simultaneous binding and the unrestricted accessibility of both antigens (HER3 and CD3) of the Db3-43xhuU3-EHD2-Fab3-43-$Fc_{kih}$ molecule.

TABLE 8

Binding properties of bispecific, trivalent fusion proteins.

| construct | SKBR-3 | Jurkat | Jurkat + HER3-His |
|---|---|---|---|
| Db3-43xhuU3-EHD2-Fab3-43-$Fc_{kih}$ | 0.030 | 9.5 | 13.8 |
| Db3-43xhuU3-EHD2-scFv3-43-$Fc_{kih}$ | 0.037 | 8.1 | 9.0 |

$EC_{50}$ values [nM] of binding to SKBR-3, Jurkat cells as well as simultaneous binding to CD3 (Jurkat cells) and HER3-His were assessed by flow cytometry.

Example 12: A Bispecific, Trivalent Diabody-scFv Fusion Protein Targeting HER3 (3-43) and CD3 (huU3) Using EHD2 as Dimerization Domains A bispecific, trivalent Db3-43xhuU3-EHD2-scFv3-43-Fc$_{kih}$ molecule was generated by combining a db molecule, specific for HER3 (3-43) and CD3 (huU3; humanized version of UCHT1), with the $C_H2$ domain of IgE (EHD2), together with a HER3-specific scFv molecule by using a heterodimeric Fc part (knob-into-hole technology). Thus, the Db3-43xhuU3-EHD2-scFv3-43-Fc$_{kih}$ molecule consists of three different polypeptides, i) $V_H3$-43x$V_L$huU3-EHD2 (light chain of diabody moiety), ii) $V_H$huU3x$V_L3$-43-EHD2-$C_H2$-$C_H3_{hole}$ (heavy chain of diabody moiety), and iii) $V_H3$-43-$V_L3$-43-$C_H1$-$C_H2$-$C_H3_{knob}$ (FIG. 37A). The bispecific Db3-43xhuU3-EHD2-scFv3-43-Fc$_{kih}$ exhibits two antigen binding sites for HER3 and one antigen binding site for CD3 (FIG. 37B).

Db3-43xhuU3-EHD2-scFv3-43-Fc$_{kih}$ was expressed in transiently transfected HEK293-6E cells after co-administration of three plasmids encoding for the light chain and the heavy chain of the diabody moiety and for the scFv moiety, using polyethylenimine as transfection reagent. Protein secreted into cell culture supernatant was purified using FcXL-CaptureSelect affinity chromatography and size exclusion chromatography using FPLC. SDS-PAGE analysis revealed three bands under reducing conditions at approximately 70 kDa (heavy chain of diabody moiety), 50 kDa (scFv moiety), and 35 kDa (light chain of diabody moiety). Under non-reducing conditions, one major band at approximately 200 kDa and two minor bands (above and below the major band) were observed (FIG. 37C). Purity, integrity and homogeneity of the Db3-43xhuU3-EHD2-scFv3-43-Fc$_{kih}$ molecule were confirmed by size exclusion chromatography (FIG. 37D).

Binding studies of Db3-43xhuU3-EHD2-scFv3-43-Fc$_{kih}$ to HER3-expressing (SKBR; Table 5) and CD3-expressing cells (Jurkat) were analyzed via flow cytometry. Adherent SKBR3 cells were washed with PBS and shortly trypsinized at 37° C. Trypsin was quenched with FCS containing medium and removed by centrifugation (500×g, 5 minutes). Jurkat cells, which are suspension cells, were directly used without trypsin treatment. 100,000 cells per well were seeded and incubated with a serial dilution of Db3-43xhuU3-EHD2-scFv3-43-Fc$_{kih}$ diluted in PBA (PBS containing 2% (v/v) FCS, 0.02% (w/v) NaN$_3$) for one hour at 4° C. Cells were washed twice using PBA. Bound antibodies were detected using PE-labeled anti-human Fc secondary antibody, which was incubated for another hour at 4° C. After washing, median fluorescence intensity (MFI) was measured with a Milltenyi MACSQuant® Analyzer 10. Relative MFI (to unstained cells) were calculated by MACSQuant® software and Excel. In general, a concentration-dependent binding of the bispecific Db3-43xhuU3-EHD2-scFv3-43-Fc$_{kih}$ to the cells was observed with EC$_{50}$ values of 37 pM for SKBR3 and 8.1 nM for Jurkat cells (FIG. 37E; Table 8). Simultaneous binding of both antigens was tested via flow cytometry using CD3-expressing Jurkat cells. A titration of bispecific Db3-43xhuU3-EHD2-scFv3-43-Fc$_{kih}$ was incubated with the cells for one hour at RT. After washing cells twice with PBA, the second antigen, HER3-His, was added to the cells (300 nM) and incubated for additional hour at RT. Cells were washed twice using PBA. Bound HER3-His was detected using a PE-labeled anti-His antibody. After washing, median fluorescence intensity (MFI) was measured with a Milltenyi MACSQuant® Analyzer 10. Relative MFI (to unstained cells) were calculated by MACSQuant® software and Excel (FIG. 37F). Again, bound HER3-His could be detected in a concentration-dependent manner with an EC$_{50}$ value of 9.0 nM, which is similar to the EC$_{50}$ value obtained for binding of Db3-43xhuU3-EHD2-scFv3-43-Fc$_{kih}$ to Jurkat cells in the absence of the second antigen (Table 8). Thus, these binding experiments confirmed the simultaneous binding and the unrestricted accessibility of both antigens (HER3 and CD3) of the Db3-43xhuU3-EHD2-scFv3-43-Fc$_{kih}$ molecule.

Example 13: A Bispecific, Bivalent Diabody Fusion Protein Targeting HER2 (4D5) and HER3 (3-43) Using $C_H1/C_L$ A bispecific, bivalent Db3-43x4D5-Fab-Fc$_{kih}$ molecule was generated by combining a db molecule, specific for HER2 (4D5; variable domains of Trastuzumab (Herceptin)) and HER3 (3-43), with the $C_H1/C_L$ as heterodimeric domain and a heterodimeric Fc part (knob-into-hole technology). Thus, the Db3-43x4D5-Fab-Fc$_{kih}$ molecule consists of two different polypeptides, $V_H4D5xV_L3$-43-$C_H1$-$C_H2$-$C_H3_{hole}$ (heavy chain 1) and $V_H3$-43x$V_L4D5$-$C_L$-$C_H2$-$C_H3_{kih}$ (heavy chain 2) (FIG. 38A). The bispecific, bivalent Db3-43x4D5-Fab-Fc$_{kih}$ exhibits one antigen binding site for HER2 and one antigen binding site for HER3 (FIG. 38B).

Db3-43x4D5-Fab-Fc$_{kih}$ was expressed in transiently transfected HEK293-6E cells after co-administration of two plasmids encoding for both heavy chains, using polyethylenimine as transfection reagent. Protein secreted into cell culture supernatant was purified using $C_H1$-CaptureSelect affinity chromatography and size exclusion chromatography via FPLC. SDS-PAGE analysis revealed one major bands under reducing conditions at approximately 70 kDa corresponding most likely to both heavy chains of the molecules (same molecular weight). Under non-reducing conditions, one band at approximately 140 kDa was observed corresponding most likely to the intact dimer of the two heavy chains (FIG. 38C). Purity, integrity and homogeneity of the Db3-43x4D5-Fab-Fc$_{kih}$ molecule were confirmed by size exclusion chromatography (FIG. 38D). Binding of the Db3-43x4D5-Fab-Fc$_{kih}$ and the monospecific parental antibodies (Trastuzumab (anti-HER2) and IgG 3-43 (anti-HER3)) to the extracellular domain (ECD) of HER2 (aa 23-652) and HER3 (aa 21-643) was determined by ELISA. The Fc fusion proteins of HER2 or HER3 proteins were coated onto polystyrene microtiter plates at a concentration of 2 µg/ml diluted in PBS. Remaining binding sites were blocked with PBS, 2% skimmed milk (MPBS). Plates were then incubated with serial dilution of the bispecific Db3-43x4D5-Fab-Fc$_{kih}$ or the monospecific parental antibodies. After washing, bound antibodies were detected with an HRP-conjugated anti-human Fab antibody and TMB, H$_2$O$_2$ as substrate. The bispecific, bivalent Db3-43x4D5-Fab-Fc$_{kih}$ showed concentration-dependent binding to HER2 and HER3 with EC$_{50}$ values in the nanomolar range (1.3 nM for HER2; 1.1 nM for HER3) (FIG. 38E; Table 9). The parental antibodies bound with lower EC$_{50}$ values (0.27 nM for Trastuzumab to HER2; 0.21 nM for IgG 3-43 to HER3) to their corresponding antigens (Table 9). As the parental antibodies bind bivalent their respective antigen, this increased binding of the parental antibodies resulted most likely from the avidity effect. These experiments confirmed binding of Db3-43x4D5-Fab-Fc$_{kih}$ to both antigens, HER2 and HER3, in the expected range (Schmitt et al., 2017).

TABLE 9

| Binding properties of Db3-43x4D5-Fab-Fc$_{kih}$. | | |
|---|---|---|
| construct | HER2 | HER3 |
| Db3-43x4D5-FabFc$_{kih}$ | 1.3 | 1.1 |
| Trastuzumab | 0.27 | n.p. |
| IgG 3-43 | n.p. | 0.21 |

EC$_{50}$ values [nM] of binding to the extracellular domain (ECD) of HER2 and HER3 fusion proteins were determined by ELISA.
n.p.: not performed

The invention claimed is:

1. A bispecific and tetravalent antigen-binding protein complex comprising:
    a. a first dual binding module (DBM1) comprising a variable heavy chain ($V_H$) polypeptide and a variable light chain ($V_L$) polypeptide;
    b. a second dual binding module (DBM2) comprising a variable heavy chain polypeptide and a variable light chain polypeptide; and
    c. a homo- or hetero-dimerization domain (HDM) module comprising two polypeptides, wherein
    the first HDM polypeptide is covalently linked to the variable heavy or light chain of DBM1 and comprises a first HDM dimerization domain, and the second HDM polypeptide is covalently linked to the variable heavy or light chain of DBM1 and comprises a second HDM dimerization domain, which specifically binds to the first HDM dimerization domain, wherein:
    (i) the variable heavy chain polypeptide comprises the amino acid sequence of SEQ ID NO: 17 and the variable light chain polypeptide comprises the amino acid sequence of SEQ ID NO: 18;
    (ii) the variable heavy chain polypeptide comprises the amino acid sequence of SEQ ID NO: 19 and the variable light chain polypeptide comprises the amino acid sequence of SEQ ID NO: 20;
    (iii) the variable heavy chain polypeptide comprises the amino acid sequence of SEQ ID NO: 21 and the variable light chain polypeptide comprises the amino acid sequence of SEQ ID NO: 22;
    (iv) the variable heavy chain polypeptide comprises the amino acid sequence of SEQ ID NO: 23 and the variable light chain polypeptide comprises the amino acid sequence of SEQ ID NO: 24;
    (v) the variable heavy chain polypeptide comprises the amino acid sequence of SEQ ID NO: 25 and the variable light chain polypeptide comprises the amino acid sequence of SEQ ID NO: 26;
    (vi) the variable heavy chain polypeptide comprises the amino acid sequence of SEQ ID NO: 27 and the variable light chain polypeptide comprises the amino acid sequence of SEQ ID NO: 28; or
    (vii) the variable heavy chain polypeptide comprises the amino acid sequence of SEQ ID NO: 32 and the variable light chain polypeptide comprises the amino acid sequence of SEQ ID NO: 33.

2. The antigen-binding protein complex of claim 1, further comprising at least one pharmaceutically active moiety and/or imaging molecule.

3. The antigen-binding protein complex of claim 2, wherein the pharmaceutically active moiety is selected from the group consisting of a ligand and an effector molecule.

4. The antigen-binding protein complex of claim 3, wherein
    a. the ligand is selected from the group consisting of an antigen-binding molecule, scaffold protein, natural ligand, ligand-binding receptor fragment, and aptamer, wherein the antigen-binding molecule is selected from the group consisting of a Fab fragment, a Fab' fragment, a heavy chain antibody, a single-domain antibody (sdAb), variable domain of a heavy chain antibody, a single-chain variable fragment (scFv), a tandem scFv, a bispecific T-cell engager, a single-chain diabody, a triple body, a nanoantibody, and a fusion protein thereof; or
    b. the effector molecule is selected from the group consisting of cytokine, chemokine, immune (co)-stimulatory molecule, immunosuppressive molecule, death ligand, apoptosis-inducing protein, kinase, prodrug-converting enzyme, RNase, agonistic antibody or an antigen binding antibody fragment thereof, antagonistic antibody or an antigen binding fragment thereof, toxins growth factor, hormone, coagulation factor, fibrinolytic protein, and a fusion proteins.

5. The antigen-binding protein complex of claim 2, wherein the imaging molecule is selected from the group consisting of bioluminescent reagent, chemiluminescent reagent, fluorescent imaging reagent, photosensitizer, chelating reagent, and a radioactive moiety.

6. A method for treatment of EGFR and HER3, CD3 and HER3 or HER2 and HER3 expressing comprising administering to a subject in need thereof an amount effective of the antigen-binding protein complex of claim 1.

7. A bispecific tetravalent diabody-Ig, wherein the diabody-Ig molecule comprises:
   a. a first dual binding module (DMB1) comprising:
      i. a first heavy chain polypeptide comprising a diabody in a VHA-VLB orientation, wherein said VHA and VLB are connected by a peptide linker (L1) of five amino acids in length to prevent binding of VHA and VLA to each other, fused to a dimerization domain, and an Fc comprising a CH2 and a CH3 domain, and
      ii. a first light chain polypeptide comprising a VHB-VLA orientation fused to a dimerization domain; and
   b. a second DMB module (DBM2) comprising:
      i. a second heavy chain polypeptide comprising a diabody in a VHA'-VLB' orientation, wherein said VHA' and VLB' are connected by a peptide linker (L1) of five amino acids in length to prevent binding of VHA' and VLA' to each other, fused to a dimerization domain, and an Fc comprising a CH2 and a CH3 domain, and
      ii. a second light chain polypeptide comprising a VHB'-VLA' fused to a dimerization domain;
   wherein the dimerization domain is selected from the group consisting of CH1 and CL heterodimerization domain, a human IgE CH2 homodimerization domain (EHD2), a human IgM CH2 domain (MHD2), a EHD2 having C247S/C337S substitutions, and EHD2 having C337S/C247S substitutions, wherein:
   a. the variable heavy chain polypeptide comprises the amino acid sequence of SEQ ID NO: 17 and the variable light chain polypeptide comprises the amino acid sequence of SEQ ID NO: 18;
   b. the variable heavy chain polypeptide comprises the amino acid sequence of SEQ ID NO: 19 and the variable light chain polypeptide comprises the amino acid sequence of SEQ ID NO: 20;
   c. the variable heavy chain polypeptide comprises the amino acid sequence of SEQ ID NO: 21 and the variable light chain polypeptide comprises the amino acid sequence of SEQ ID NO: 22;
   d. the variable heavy chain polypeptide comprises the amino acid sequence of SEQ ID NO: 23 and the variable light chain polypeptide comprises the amino acid sequence of SEQ ID NO: 24;
   e. the variable heavy chain polypeptide comprises the amino acid sequence of SEQ ID NO: 25 and the variable light chain polypeptide comprises the amino acid sequence of SEQ ID NO: 26;
   f. the variable heavy chain polypeptide comprises the amino acid sequence of SEQ ID NO: 27 and the variable light chain polypeptide comprises the amino acid sequence of SEQ ID NO: 28; or
   g. the variable heavy chain polypeptide comprises the amino acid sequence of SEQ ID NO: 32 and the variable light chain polypeptide comprises the amino acid sequence of SEQ ID NO: 33.

8. The bispecific tetravalent diabody-Ig of claim 7, wherein the heavy chain polypeptide comprises the amino acid sequence of SEQ ID NO: 23 and the light chain polypeptide comprises the amino acid sequence of SEQ ID NO: 24; and wherein the heterodimerization domain comprises EHD2 having C247S/C337S substitutions (het-EHD2).

* * * * *

SEQUENCE LISTING

<160> NUMBER OF SEQ ID NOS: 36

<210> SEQ ID NO 1
<211> LENGTH: 5
<212> TYPE: PRT
<213> ORGANISM: Homo sapiens

<400> SEQUENCE: 1

Gly Gly Gly Gly Ser
1               5

<210> SEQ ID NO 2
<211> LENGTH: 97
<212> TYPE: PRT
<213> ORGANISM: Homo sapiens

<400> SEQUENCE: 2

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
                20                  25                  30

Thr Asn Val Ser Gln Ser Lys Asp Ser Asp Val Tyr Ile Thr Asp Lys
            35                  40                  45

Thr Val Leu Asp Met Arg Ser Met Asp Phe Lys Ser Asn Ser Ala Val
        50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp

<210> SEQ ID NO 3
<211> LENGTH: 130
<212> TYPE: PRT
<213> ORGANISM: Homo sapiens

<400> SEQUENCE: 3

Asp Leu Lys Asn Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
                20                  25                  30

Thr Gly Phe Tyr Pro Asp His Val Glu Leu Ser Trp Trp Val Asn Gly
            35                  40                  45

Lys Glu Val His Ser Gly Val Ser Thr Asp Pro Gln Pro Leu Lys Glu
        50                  55                  60

Gln Pro Ala Leu Asn Asp Ser Arg Tyr Cys Leu Ser Ser Arg Leu Arg
65                  70                  75                  80

```
Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys
    130

<210> SEQ ID NO 4
<211> LENGTH: 98
<212> TYPE: PRT
<213> ORGANISM: Homo sapiens

<400> SEQUENCE: 4

Gly Lys Gly Asn Leu Glu Trp Lys Glu Pro Ser Met Arg Leu Lys
1               5                   10                  15

Ala Arg Pro Ser Ser Pro Gly Phe Ser Val Leu Thr Cys Ser Ala Phe
            20                  25                  30

Ser Phe Tyr Pro Pro Glu Leu Gln Leu Arg Phe Leu Arg Asn Gly Leu
        35                  40                  45

Ala Ala Gly Thr Gly Gln Gly Asp Phe Gly Pro Asn Ser Asp Gly Ser
    50                  55                  60

Phe His Ala Ser Ser Ser Leu Thr Val Lys Ser Gly Asp Glu His His
65                  70                  75                  80

Tyr Cys Cys Ile Val Gln His Ala Gly Leu Ala Gln Pro Leu Arg Val
                85                  90                  95

Glu Leu

<210> SEQ ID NO 5
<211> LENGTH: 99
<212> TYPE: PRT
<213> ORGANISM: Homo sapiens

<400> SEQUENCE: 5

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met

<210> SEQ ID NO 6
<211> LENGTH: 101
<212> TYPE: PRT
<213> ORGANISM: Homo sapiens

<400> SEQUENCE: 6

Gly Lys Glu Thr Leu Gln Arg Thr Asp Ala Pro Lys Thr His Met Thr
1               5                   10                  15
```

His His Ala Val Ser Asp His Glu Ala Thr Leu Arg Cys Trp Ala Leu
            20                  25                  30

Ser Phe Tyr Pro Ala Glu Ile Thr Leu Thr Trp Gln Arg Asp Gly Glu
        35                  40                  45

Asp Gln Thr Gln Asp Thr Glu Leu Val Glu Thr Arg Pro Ala Gly Asp
    50                  55                  60

Gly Thr Phe Gln Lys Trp Ala Ala Val Val Val Pro Ser Gly Gln Glu
65                  70                  75                  80

Gln Arg Tyr Thr Cys His Val Gln His Glu Gly Leu Pro Lys Pro Leu
                85                  90                  95

Thr Leu Arg Trp Glu
            100

<210> SEQ ID NO 7
<211> LENGTH: 102
<212> TYPE: PRT
<213> ORGANISM: Homo sapiens

<400> SEQUENCE: 7

Asp Ile Glu Thr Leu Gln Arg Ala Asp Pro Pro Lys Thr His Val Thr
1               5                   10                  15

His His Pro Ile Ser Asp His Glu Ala Thr Leu Arg Cys Trp Ala Leu
            20                  25                  30

Gly Phe Tyr Pro Ala Glu Ile Thr Leu Thr Trp Gln Arg Asp Gly Glu
        35                  40                  45

Asp Gln Thr Gln Asp Thr Glu Leu Val Glu Thr Arg Pro Ala Gly Asp
    50                  55                  60

Arg Thr Phe Gln Lys Trp Ala Ala Val Val Val Pro Ser Gly Glu Glu
65                  70                  75                  80

Gln Arg Tyr Thr Cys His Val Gln His Glu Gly Leu Pro Lys Pro Leu
                85                  90                  95

Thr Leu Arg Trp Glu Pro
            100

<210> SEQ ID NO 8
<211> LENGTH: 106
<212> TYPE: PRT
<213> ORGANISM: Homo sapiens

<400> SEQUENCE: 8

Gly Arg Ile Pro Val Ser Arg Gly Phe Pro Ile Ala Glu Val Phe Thr
1               5                   10                  15

Leu Lys Pro Leu Glu Phe Gly Lys Pro Asn Thr Leu Val Cys Phe Val
            20                  25                  30

Ser Asn Leu Phe Pro Pro Met Leu Thr Val Asn Trp His Asp His Ser
        35                  40                  45

Val Pro Val Glu Gly Phe Gly Pro Thr Phe Val Ser Ala Val Asp Gly
    50                  55                  60

Leu Ser Phe Gln Ala Phe Ser Tyr Leu Asn Phe Thr Pro Glu Pro Ser
65                  70                  75                  80

Asp Ile Phe Ser Cys Ile Val Thr His Glu Pro Asp Arg Tyr Thr Ala
                85                  90                  95

Ile Ala Tyr Trp Val Pro Arg Asn Ala Leu
            100                 105

<210> SEQ ID NO 9
<211> LENGTH: 108

```
<212> TYPE: PRT
<213> ORGANISM: Homo sapiens

<400> SEQUENCE: 9

Trp Gly Ser Leu Thr Asn Arg Thr Arg Pro Ser Val Gln Val Ala
1               5                   10                  15

Lys Thr Thr Pro Phe Asn Thr Arg Glu Pro Val Met Leu Ala Cys Tyr
                20                  25                  30

Val Trp Gly Phe Tyr Pro Ala Glu Val Thr Ile Thr Trp Arg Lys Asn
            35                  40                  45

Gly Lys Leu Val Met His Ser Ser Ala His Lys Thr Ala Gln Pro Asn
        50                  55                  60

Gly Asp Trp Thr Tyr Gln Thr Leu Ser His Leu Ala Leu Thr Pro Ser
65                  70                  75                  80

Tyr Gly Asp Thr Tyr Thr Cys Val Val Glu His Ile Gly Ala Pro Glu
                85                  90                  95

Pro Ile Leu Arg Asp Trp Thr Pro Gly Leu Ser Pro
            100                 105

<210> SEQ ID NO 10
<211> LENGTH: 4
<212> TYPE: PRT
<213> ORGANISM: Homo sapiens

<400> SEQUENCE: 10

Thr Val Ser Ser
1

<210> SEQ ID NO 11
<211> LENGTH: 3
<212> TYPE: PRT
<213> ORGANISM: Homo sapiens

<400> SEQUENCE: 11

Thr Val Leu
1

<210> SEQ ID NO 12
<211> LENGTH: 2
<212> TYPE: PRT
<213> ORGANISM: Homo sapiens

<400> SEQUENCE: 12

Ile Lys
1

<210> SEQ ID NO 13
<211> LENGTH: 562
<212> TYPE: PRT
<213> ORGANISM: Homo sapiens

<400> SEQUENCE: 13

Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
                20                  25                  30

Ala Met Ser Trp Val Arg Gln Ala Pro Gly Lys Gly Leu Glu Trp Val
            35                  40                  45

Ser Gly Ile Asn Trp Gln Gly Gly Ser Thr Gly Tyr Ala Asp Ser Val
        50                  55                  60
```

```
Lys Gly Arg Val Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Lys Ile Leu Gly Ala Gly Arg Gly Trp Tyr Phe Asp Tyr Trp Gly
            100                 105                 110

Lys Gly Thr Thr Val Thr Val Ser Ser Gly Gly Gly Ser Ser Glu
            115                 120                 125

Leu Thr Gln Asp Pro Ala Val Ser Val Ala Leu Gly Gln Thr Val Arg
            130                 135                 140

Ile Thr Cys Ser Gly Asp Ser Leu Arg Ser Tyr Tyr Ala Ser Trp Tyr
145                 150                 155                 160

Gln Gln Lys Pro Gly Gln Ala Pro Val Leu Val Ile Tyr Gly Ala Asn
                165                 170                 175

Asn Arg Pro Ser Gly Ile Pro Asp Arg Phe Ser Gly Ser Ser Ser Gly
                180                 185                 190

Asn Thr Ala Ser Leu Thr Ile Thr Gly Ala Gln Ala Glu Asp Glu Ala
                195                 200                 205

Asp Tyr Tyr Cys Asn Ser Ala Asp Ser Ser Gly Asn His Val Val Phe
210                 215                 220

Gly Gly Gly Thr Lys Leu Thr Val Leu Ala Ser Thr Lys Gly Pro Ser
225                 230                 235                 240

Val Phe Pro Leu Ala Pro Ser Ser Lys Ser Thr Ser Gly Gly Thr Ala
                245                 250                 255

Ala Leu Gly Cys Leu Val Lys Asp Tyr Phe Pro Glu Pro Val Thr Val
                260                 265                 270

Ser Trp Asn Ser Gly Ala Leu Thr Ser Gly Val His Thr Phe Pro Ala
                275                 280                 285

Val Leu Gln Ser Ser Gly Leu Tyr Ser Leu Ser Ser Val Val Thr Val
                290                 295                 300

Pro Ser Ser Ser Leu Gly Thr Gln Thr Tyr Ile Cys Asn Val Asn His
305                 310                 315                 320

Lys Pro Ser Asn Thr Lys Val Asp Lys Lys Val Glu Pro Lys Ser Cys
                325                 330                 335

Asp Lys Thr His Thr Cys Pro Pro Cys Pro Ala Pro Pro Val Ala Gly
            340                 345                 350

Pro Ser Val Phe Leu Phe Pro Pro Lys Pro Lys Asp Thr Leu Met Ile
            355                 360                 365

Ser Arg Thr Pro Glu Val Thr Cys Val Val Val Asp Val Ser His Glu
370                 375                 380

Asp Pro Glu Val Lys Phe Asn Trp Tyr Val Asp Gly Val Glu Val His
385                 390                 395                 400

Asn Ala Lys Thr Lys Pro Arg Glu Glu Gln Tyr Asn Ser Thr Tyr Arg
            405                 410                 415

Val Val Ser Val Leu Thr Val Leu His Gln Asp Trp Leu Asn Gly Lys
            420                 425                 430

Glu Tyr Lys Cys Lys Val Ser Asn Lys Gly Leu Pro Ser Ser Ile Glu
            435                 440                 445

Lys Thr Ile Ser Lys Ala Lys Gly Gln Pro Arg Glu Pro Gln Val Tyr
            450                 455                 460

Thr Leu Pro Pro Ser Arg Asp Glu Leu Thr Lys Asn Gln Val Ser Leu
465                 470                 475                 480

Thr Cys Leu Val Lys Gly Phe Tyr Pro Ser Asp Ile Ala Val Glu Trp
```

```
                        485                 490                 495
Glu Ser Asn Gly Gln Pro Glu Asn Asn Tyr Lys Thr Thr Pro Pro Val
                    500                 505                 510

Leu Asp Ser Asp Gly Ser Phe Phe Leu Tyr Ser Lys Leu Thr Val Asp
                515                 520                 525

Lys Ser Arg Trp Gln Gln Gly Asn Val Phe Ser Cys Ser Val Met His
            530                 535                 540

Glu Ala Leu His Asn His Tyr Thr Gln Lys Ser Leu Ser Leu Ser Pro
545                 550                 555                 560

Gly Lys

<210> SEQ ID NO 14
<211> LENGTH: 340
<212> TYPE: PRT
<213> ORGANISM: Homo sapiens

<400> SEQUENCE: 14

Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Asn Trp Gln Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Tyr Trp Gly
            100                 105                 110

Lys Gly Thr Thr Val Thr Val Ser Ser Gly Gly Gly Ser Ser Glu
        115                 120                 125

Leu Thr Gln Asp Pro Ala Val Ser Val Ala Leu Gly Gln Thr Val Arg
    130                 135                 140

Ile Thr Cys Ser Gly Asp Ser Leu Arg Ser Tyr Tyr Ala Ser Trp Tyr
145                 150                 155                 160

Gln Gln Lys Pro Gly Gln Ala Pro Val Leu Val Ile Tyr Gly Ala Asn
                165                 170                 175

Asn Arg Pro Ser Gly Ile Pro Arg Phe Ser Gly Ser Ser Gly
            180                 185                 190

Asn Thr Ala Ser Leu Thr Ile Thr Gly Ala Gln Ala Glu Asp Glu Ala
        195                 200                 205

Asp Tyr Tyr Cys Asn Ser Ala Asp Ser Ser Gly Asn His Val Val Phe
    210                 215                 220

Gly Gly Gly Thr Lys Leu Thr Val Leu Arg Thr Val Ala Ala Pro Ser
225                 230                 235                 240

Val Phe Ile Phe Pro Pro Ser Asp Glu Gln Leu Lys Ser Gly Thr Ala
                245                 250                 255

Ser Val Val Cys Leu Leu Asn Asn Phe Tyr Pro Arg Glu Ala Lys Val
            260                 265                 270

Gln Trp Lys Val Asp Asn Ala Leu Gln Ser Gly Asn Ser Gln Glu Ser
        275                 280                 285

Val Thr Glu Gln Asp Ser Lys Asp Ser Thr Tyr Ser Leu Ser Ser Thr
```

```
            290                 295                 300
Leu Thr Leu Ser Lys Ala Asp Tyr Glu Lys His Lys Val Tyr Ala Cys
305                 310                 315                 320

Glu Val Thr His Gln Gly Leu Ser Ser Pro Val Thr Lys Ser Phe Asn
                325                 330                 335

Arg Gly Glu Cys
            340

<210> SEQ ID NO 15
<211> LENGTH: 563
<212> TYPE: PRT
<213> ORGANISM: Homo sapiens

<400> SEQUENCE: 15

Gln Val Gln Leu Gln Gln Ser Gly Ala Glu Val Lys Lys Pro Gly Ser
1               5                   10                  15

Ala Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Gly Asp Ala Phe Asp Ile Trp Gly Gln Gly Thr
            100                 105                 110

Met Val Thr Val Ser Ser Gly Gly Gly Ser Gln Ser Ala Leu Thr
        115                 120                 125

Gln Pro Arg Ser Val Ser Gly Ser Pro Gly Gln Ser Ile Thr Ile Ser
    130                 135                 140

Cys Thr Gly Thr Ser Ser Asp Val Gly Gly Tyr Asn Tyr Val Ser Trp
145                 150                 155                 160

Tyr Gln Gln His Pro Gly Lys Ala Pro Lys Leu Met Ile Tyr Asp Val
                165                 170                 175

Ser Asn Arg Pro Ser Gly Val Ser Asn Arg Phe Ser Gly Ser Lys Ser
            180                 185                 190

Gly Asn Thr Ala Ser Leu Thr Ile Ser Gly Leu Gln Ala Glu Asp Glu
        195                 200                 205

Ala Asp Tyr Tyr Cys Ser Ser Tyr Thr Ser Ser Thr Leu Val Val
    210                 215                 220

Phe Gly Gly Gly Thr Lys Leu Thr Val Leu Ala Ser Thr Lys Gly Pro
225                 230                 235                 240

Ser Val Phe Pro Leu Ala Pro Ser Ser Lys Ser Thr Ser Gly Gly Thr
                245                 250                 255

Ala Ala Leu Gly Cys Leu Val Lys Asp Tyr Phe Pro Glu Pro Val Thr
            260                 265                 270

Val Ser Trp Asn Ser Gly Ala Leu Thr Ser Gly Val His Thr Phe Pro
        275                 280                 285

Ala Val Leu Gln Ser Ser Gly Leu Tyr Ser Leu Ser Ser Val Val Thr
    290                 295                 300

Val Pro Ser Ser Ser Leu Gly Thr Gln Thr Tyr Ile Cys Asn Val Asn
305                 310                 315                 320
```

```
His Lys Pro Ser Asn Thr Lys Val Asp Lys Lys Val Glu Pro Lys Ser
            325                 330                 335

Cys Asp Lys Thr His Thr Cys Pro Pro Cys Pro Ala Pro Pro Val Ala
        340                 345                 350

Gly Pro Ser Val Phe Leu Phe Pro Pro Lys Pro Lys Asp Thr Leu Met
        355                 360                 365

Ile Ser Arg Thr Pro Glu Val Thr Cys Val Val Val Asp Val Ser His
370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
                405                 410                 415

Arg Val Val Ser Val Leu Thr Val Leu His Gln Asp Trp Leu Asn Gly
            420                 425                 430

Lys Glu Tyr Lys Cys Lys Val Ser Asn Lys Gly Leu Pro Ser Ser Ile
        435                 440                 445

Glu Lys Thr Ile Ser Lys Ala Lys Gly Gln Pro Arg Glu Pro Gln Val
    450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
                485                 490                 495

Trp Glu Ser Asn Gly Gln Pro Glu Asn Asn Tyr Lys Thr Thr Pro Pro
            500                 505                 510

Val Leu Asp Ser Asp Gly Ser Phe Phe Leu Tyr Ser Lys Leu Thr Val
        515                 520                 525

Asp Lys Ser Arg Trp Gln Gln Gly Asn Val Phe Ser Cys Ser Val Met
    530                 535                 540

His Glu Ala Leu His Asn His Tyr Thr Gln Lys Ser Leu Ser Leu Ser
545                 550                 555                 560

Pro Gly Lys

<210> SEQ ID NO 16
<211> LENGTH: 341
<212> TYPE: PRT
<213> ORGANISM: Homo sapiens

<400> SEQUENCE: 16

Gln Val Gln Leu Gln Gln Ser Gly Ala Glu Val Lys Lys Pro Gly Ser
1               5                   10                  15

Ala Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Gly Asp Ala Phe Asp Ile Trp Gly Gln Gly Thr
            100                 105                 110

Met Val Thr Val Ser Ser Gly Gly Gly Gly Ser Gln Ala Leu Thr
        115                 120                 125
```

```
Gln Pro Arg Ser Val Ser Gly Ser Pro Gly Gln Ser Ile Thr Ile Ser
        130                 135                 140

Cys Thr Gly Thr Ser Ser Asp Val Gly Gly Tyr Asn Tyr Val Ser Trp
145                 150                 155                 160

Tyr Gln Gln His Pro Gly Lys Ala Pro Lys Leu Met Ile Tyr Asp Val
                165                 170                 175

Ser Asn Arg Pro Ser Gly Val Ser Asn Arg Phe Ser Gly Ser Lys Ser
            180                 185                 190

Gly Asn Thr Ala Ser Leu Thr Ile Ser Gly Leu Gln Ala Glu Asp Glu
        195                 200                 205

Ala Asp Tyr Tyr Cys Ser Ser Tyr Thr Ser Ser Ser Thr Leu Val Val
210                 215                 220

Phe Gly Gly Gly Thr Lys Leu Thr Val Leu Arg Thr Val Ala Ala Pro
225                 230                 235                 240

Ser Val Phe Ile Phe Pro Pro Ser Asp Glu Gln Leu Lys Ser Gly Thr
                245                 250                 255

Ala Ser Val Val Cys Leu Leu Asn Asn Phe Tyr Pro Arg Glu Ala Lys
            260                 265                 270

Val Gln Trp Lys Val Asp Asn Ala Leu Gln Ser Gly Asn Ser Gln Glu
        275                 280                 285

Ser Val Thr Glu Gln Asp Ser Lys Asp Ser Thr Tyr Ser Leu Ser Ser
290                 295                 300

Thr Leu Thr Leu Ser Lys Ala Asp Tyr Glu Lys His Lys Val Tyr Ala
305                 310                 315                 320

Cys Glu Val Thr His Gln Gly Leu Ser Ser Pro Val Thr Lys Ser Phe
                325                 330                 335

Asn Arg Gly Glu Cys
            340

<210> SEQ ID NO 17
<211> LENGTH: 564
<212> TYPE: PRT
<213> ORGANISM: Homo sapiens

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Thr Val Thr Val Ser Ser Gly Gly Gly Gly Ser Gln Ser Ala Leu
        115                 120                 125

Thr Gln Pro Ala Ser Val Ser Gly Ser Pro Gly Gln Ser Ile Thr Ile
    130                 135                 140

Ser Cys Thr Gly Thr Ser Ser Asp Val Gly Ser Tyr Asn Val Val Ser
145                 150                 155                 160
```

```
Trp Tyr Gln Gln His Pro Gly Lys Ala Pro Lys Leu Ile Ile Tyr Glu
            165                 170                 175

Val Ser Gln Arg Pro Ser Gly Val Ser Asn Arg Phe Ser Gly Ser Lys
        180                 185                 190

Ser Gly Asn Thr Ala Ser Leu Thr Ile Ser Gly Leu Gln Thr Glu Asp
        195                 200                 205

Glu Ala Asp Tyr Tyr Cys Ser Ser Tyr Ala Gly Ser Ser Ile Phe Val
        210                 215                 220

Ile Phe Gly Gly Gly Thr Lys Val Thr Val Leu Ala Ser Thr Lys Gly
225                 230                 235                 240

Pro Ser Val Phe Pro Leu Ala Pro Ser Ser Lys Ser Thr Ser Gly Gly
                245                 250                 255

Thr Ala Ala Leu Gly Cys Leu Val Lys Asp Tyr Phe Pro Glu Pro Val
                260                 265                 270

Thr Val Ser Trp Asn Ser Gly Ala Leu Thr Ser Gly Val His Thr Phe
            275                 280                 285

Pro Ala Val Leu Gln Ser Ser Gly Leu Tyr Ser Leu Ser Ser Val Val
        290                 295                 300

Thr Val Pro Ser Ser Leu Gly Thr Gln Thr Tyr Ile Cys Asn Val
305                 310                 315                 320

Asn His Lys Pro Ser Asn Thr Lys Val Asp Lys Lys Val Glu Pro Lys
                325                 330                 335

Ser Cys Asp Lys Thr His Thr Cys Pro Pro Cys Pro Ala Pro Pro Val
                340                 345                 350

Ala Gly Pro Ser Val Phe Leu Phe Pro Pro Lys Pro Lys Asp Thr Leu
            355                 360                 365

Met Ile Ser Arg Thr Pro Glu Val Thr Cys Val Val Val Asp Val Ser
        370                 375                 380

His Glu Asp Pro Glu Val Lys Phe Asn Trp Tyr Val Asp Gly Val Glu
385                 390                 395                 400

Val His Asn Ala Lys Thr Lys Pro Arg Glu Glu Gln Tyr Asn Ser Thr
                405                 410                 415

Tyr Arg Val Val Ser Val Leu Thr Val Leu His Gln Asp Trp Leu Asn
            420                 425                 430

Gly Lys Glu Tyr Lys Cys Lys Val Ser Asn Lys Gly Leu Pro Ser Ser
        435                 440                 445

Ile Glu Lys Thr Ile Ser Lys Ala Lys Gly Gln Pro Arg Glu Pro Gln
        450                 455                 460

Val Tyr Thr Leu Pro Pro Ser Arg Asp Glu Leu Thr Lys Asn Gln Val
465                 470                 475                 480

Ser Leu Thr Cys Leu Val Lys Gly Phe Tyr Pro Ser Asp Ile Ala Val
                485                 490                 495

Glu Trp Glu Ser Asn Gly Gln Pro Glu Asn Asn Tyr Lys Thr Thr Pro
            500                 505                 510

Pro Val Leu Asp Ser Asp Gly Ser Phe Phe Leu Tyr Ser Lys Leu Thr
        515                 520                 525

Val Asp Lys Ser Arg Trp Gln Gln Gly Asn Val Phe Ser Cys Ser Val
        530                 535                 540

Met His Glu Ala Leu His Asn His Tyr Thr Gln Lys Ser Leu Ser Leu
545                 550                 555                 560

Ser Pro Gly Lys
```

<210> SEQ ID NO 18
<211> LENGTH: 338
<212> TYPE: PRT
<213> ORGANISM: Homo sapiens

<400> SEQUENCE: 18

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Val Met Ala Trp Val Arg Gln Ala Pro Gly Lys Gly Leu Glu Trp Val
        35                  40                  45

Ser Ser Ile Ser Ser Ser Gly Gly Trp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Leu Lys Met Ala Thr Ile Phe Asp Tyr Trp Gly Gln Gly
            100                 105                 110

Thr Leu Val Thr Val Ser Ser Gly Gly Gly Gly Ser Asp Ile Gln Leu
        115                 120                 125

Thr Gln Ser Pro Ser Phe Leu Ser Ala Ser Val Gly Asp Arg Val Thr
    130                 135                 140

Ile Thr Cys Arg Ala Ser Gln Ser Ile Gly Thr Asn Ile His Trp Tyr
145                 150                 155                 160

Gln Gln Lys Pro Gly Lys Ala Pro Lys Leu Leu Ile Lys Tyr Ala Ser
                165                 170                 175

Glu Ser Ile Ser Gly Val Pro Ser Arg Phe Ser Gly Ser Gly Ser Gly
            180                 185                 190

Thr Glu Phe Thr Leu Thr Ile Ser Ser Leu Gln Pro Glu Asp Phe Ala
        195                 200                 205

Thr Tyr Tyr Cys Gln Gln Asn Asn Asn Trp Pro Thr Thr Phe Gly Ala
    210                 215                 220

Gly Thr Lys Leu Glu Ile Lys Arg Thr Val Ala Ala Pro Ser Val Phe
225                 230                 235                 240

Ile Phe Pro Pro Ser Asp Glu Gln Leu Lys Ser Gly Thr Ala Ser Val
                245                 250                 255

Val Cys Leu Leu Asn Asn Phe Tyr Pro Arg Glu Ala Lys Val Gln Trp
            260                 265                 270

Lys Val Asp Asn Ala Leu Gln Ser Gly Asn Ser Gln Glu Ser Val Thr
        275                 280                 285

Glu Gln Asp Ser Lys Asp Ser Thr Tyr Ser Leu Ser Ser Thr Leu Thr
    290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
                325                 330                 335

Glu Cys
```

<210> SEQ ID NO 19
<211> LENGTH: 561
<212> TYPE: PRT
<213> ORGANISM: Homo sapiens

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Phe Thr Ile Ser Arg Asp Asn Ser Lys Asn Thr Leu Tyr Leu
65                      70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Thr Val Thr Val Ser Ser Gly Gly Gly Ser Gln Ala Gly Leu
            115                 120                 125

Thr Gln Pro Pro Ala Val Ser Val Ala Pro Gly Gln Thr Ala Ser Ile
    130                 135                 140

Thr Cys Gly Arg Asp Asn Ile Gly Ser Arg Ser Val His Trp Tyr Gln
145                 150                 155                 160

Gln Lys Pro Gly Gln Ala Pro Val Leu Val Val Tyr Asp Asp Ser Asp
                165                 170                 175

Arg Pro Ala Gly Ile Pro Glu Arg Phe Ser Gly Ser Asn Tyr Glu Asn
            180                 185                 190

Thr Ala Thr Leu Thr Ile Ser Arg Val Glu Ala Gly Asp Glu Ala Asp
            195                 200                 205

Tyr Tyr Cys Gln Val Trp Gly Ile Thr Ser Asp His Val Val Phe Gly
210                 215                 220

Gly Gly Thr Lys Leu Thr Val Leu Ala Ser Thr Lys Gly Pro Ser Val
225                 230                 235                 240

Phe Pro Leu Ala Pro Ser Ser Lys Ser Thr Ser Gly Gly Thr Ala Ala
                245                 250                 255

Leu Gly Cys Leu Val Lys Asp Tyr Phe Pro Glu Pro Val Thr Val Ser
            260                 265                 270

Trp Asn Ser Gly Ala Leu Thr Ser Gly Val His Thr Phe Pro Ala Val
            275                 280                 285

Leu Gln Ser Ser Gly Leu Tyr Ser Leu Ser Ser Val Val Thr Val Pro
    290                 295                 300

Ser Ser Ser Leu Gly Thr Gln Thr Tyr Ile Cys Asn Val Asn His Lys
305                 310                 315                 320

Pro Ser Asn Thr Lys Val Asp Lys Lys Val Glu Pro Lys Ser Cys Asp
            325                 330                 335

Lys Thr His Thr Cys Pro Pro Cys Pro Ala Pro Pro Val Ala Gly Pro
            340                 345                 350

Ser Val Phe Leu Phe Pro Pro Lys Pro Lys Asp Thr Leu Met Ile Ser
        355                 360                 365

Arg Thr Pro Glu Val Thr Cys Val Val Val Asp Val Ser His Glu Asp
370                 375                 380

Pro Glu Val Lys Phe Asn Trp Tyr Val Asp Gly Val Glu Val His Asn
385                 390                 395                 400

Ala Lys Thr Lys Pro Arg Glu Glu Gln Tyr Asn Ser Thr Tyr Arg Val
                405                 410                 415
```

```
Val Ser Val Leu Thr Val Leu His Gln Asp Trp Leu Asn Gly Lys Glu
            420                 425                 430

Tyr Lys Cys Lys Val Ser Asn Lys Gly Leu Pro Ser Ser Ile Glu Lys
        435                 440                 445

Thr Ile Ser Lys Ala Lys Gly Gln Pro Arg Glu Pro Gln Val Tyr Thr
    450                 455                 460

Leu Pro Pro Ser Arg Asp Glu Leu Thr Lys Asn Gln Val Ser Leu Thr
465                 470                 475                 480

Cys Leu Val Lys Gly Phe Tyr Pro Ser Asp Ile Ala Val Glu Trp Glu
                485                 490                 495

Ser Asn Gly Gln Pro Glu Asn Asn Tyr Lys Thr Thr Pro Pro Val Leu
            500                 505                 510

Asp Ser Asp Gly Ser Phe Phe Leu Tyr Ser Lys Leu Thr Val Asp Lys
        515                 520                 525

Ser Arg Trp Gln Gln Gly Asn Val Phe Ser Cys Ser Val Met His Glu
    530                 535                 540

Ala Leu His Asn His Tyr Thr Gln Lys Ser Leu Ser Leu Ser Pro Gly
545                 550                 555                 560

Lys

<210> SEQ ID NO 20
<211> LENGTH: 342
<212> TYPE: PRT
<213> ORGANISM: Homo sapiens

<400> SEQUENCE: 20

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Gln Ser Leu Lys Ser Arg Ile Thr Ile Asn Pro Asp Thr Pro Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gly Gln Leu Gly Leu Asp Ala Leu Asp Ile
            100                 105                 110

Trp Gly Gln Gly Thr Met Val Thr Val Ser Ser Gly Gly Gly Gly Ser
        115                 120                 125

Asp Ile Gln Leu Thr Gln Ser Pro Ser Phe Leu Ser Ala Ser Val Gly
    130                 135                 140

Asp Arg Val Thr Ile Thr Cys Arg Ala Ser Gln Ser Ile Gly Thr Asn
145                 150                 155                 160

Ile His Trp Tyr Gln Gln Lys Pro Gly Lys Ala Pro Lys Leu Leu Ile
                165                 170                 175

Lys Tyr Ala Ser Glu Ser Ile Ser Gly Val Pro Ser Arg Phe Ser Gly
            180                 185                 190

Ser Gly Ser Gly Thr Glu Phe Thr Leu Thr Ile Ser Ser Leu Gln Pro
        195                 200                 205

Glu Asp Phe Ala Thr Tyr Tyr Cys Gln Gln Asn Asn Asn Trp Pro Thr
    210                 215                 220
```

```
Thr Phe Gly Ala Gly Thr Lys Leu Glu Ile Lys Arg Thr Val Ala Ala
225                 230                 235                 240

Pro Ser Val Phe Ile Phe Pro Pro Ser Asp Glu Gln Leu Lys Ser Gly
                245                 250                 255

Thr Ala Ser Val Val Cys Leu Leu Asn Asn Phe Tyr Pro Arg Glu Ala
            260                 265                 270

Lys Val Gln Trp Lys Val Asp Asn Ala Leu Gln Ser Gly Asn Ser Gln
        275                 280                 285

Glu Ser Val Thr Glu Gln Asp Ser Lys Asp Ser Thr Tyr Ser Leu Ser
290                 295                 300

Ser Thr Leu Thr Leu Ser Lys Ala Asp Tyr Glu Lys His Lys Val Tyr
305                 310                 315                 320

Ala Cys Glu Val Thr His Gln Gly Leu Ser Ser Pro Val Thr Lys Ser
                325                 330                 335

Phe Asn Arg Gly Glu Cys
                340

<210> SEQ ID NO 21
<211> LENGTH: 566
<212> TYPE: PRT
<213> ORGANISM: Homo sapiens

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Thr Val Thr Val Ser Ser Gly Gly Gly Gly Ser Gln Ala Gly Leu
        115                 120                 125

Thr Gln Pro Pro Ala Val Ser Val Ala Pro Gly Gln Thr Ala Ser Ile
130                 135                 140

Thr Cys Gly Arg Asp Asn Ile Gly Ser Arg Ser Val His Trp Tyr Gln
145                 150                 155                 160

Gln Lys Pro Gly Gln Ala Pro Val Leu Val Val Tyr Asp Asp Ser Asp
                165                 170                 175

Arg Pro Ala Gly Ile Pro Glu Arg Phe Ser Gly Ser Asn Tyr Glu Asn
            180                 185                 190

Thr Ala Thr Leu Thr Ile Ser Arg Val Glu Ala Gly Asp Glu Ala Asp
        195                 200                 205

Tyr Tyr Cys Gln Val Trp Gly Ile Thr Ser Asp His Val Val Phe Gly
    210                 215                 220

Gly Gly Thr Lys Leu Thr Val Leu Ala Ser Asp Phe Thr Pro Pro Thr
225                 230                 235                 240

Val Lys Ile Leu Gln Ser Ser Cys Asp Gly Gly His Phe Pro Pro
                245                 250                 255
```

```
Thr Ile Gln Leu Leu Cys Leu Val Ser Gly Tyr Pro Gly Thr Ile
            260                 265                 270

Asn Ile Thr Trp Leu Glu Asp Gly Gln Val Met Asp Val Asp Leu Ser
            275                 280                 285

Thr Ala Ser Thr Thr Gln Glu Gly Glu Leu Ala Ser Thr Gln Ser Glu
        290                 295                 300

Leu Thr Leu Ser Gln Lys His Trp Leu Ser Asp Arg Thr Tyr Thr Cys
305                 310                 315                 320

Gln Val Thr Tyr Gln Gly His Thr Phe Glu Asp Ser Thr Lys Lys Cys
                325                 330                 335

Ala Asp Ser Asn Asp Lys Thr His Thr Cys Pro Pro Cys Pro Ala Pro
            340                 345                 350

Pro Val Ala Gly Pro Ser Val Phe Leu Phe Pro Pro Lys Pro Lys Asp
            355                 360                 365

Thr Leu Met Ile Ser Arg Thr Pro Glu Val Thr Cys Val Val Val Asp
    370                 375                 380

Val Ser His Glu Asp Pro Glu Val Lys Phe Asn Trp Tyr Val Asp Gly
385                 390                 395                 400

Val Glu Val His Asn Ala Lys Thr Lys Pro Arg Glu Glu Gln Tyr Asn
                405                 410                 415

Ser Thr Tyr Arg Val Val Ser Val Leu Thr Val Leu His Gln Asp Trp
            420                 425                 430

Leu Asn Gly Lys Glu Tyr Lys Cys Lys Val Ser Asn Lys Gly Leu Pro
        435                 440                 445

Ser Ser Ile Glu Lys Thr Ile Ser Lys Ala Lys Gly Gln Pro Arg Glu
450                 455                 460

Pro Gln Val Tyr Thr Leu Pro Pro Ser Arg Asp Glu Leu Thr Lys Asn
465                 470                 475                 480

Gln Val Ser Leu Thr Cys Leu Val Lys Gly Phe Tyr Pro Ser Asp Ile
                485                 490                 495

Ala Val Glu Trp Glu Ser Asn Gly Gln Pro Glu Asn Asn Tyr Lys Thr
            500                 505                 510

Thr Pro Pro Val Leu Asp Ser Asp Gly Ser Phe Phe Leu Tyr Ser Lys
        515                 520                 525

Leu Thr Val Asp Lys Ser Arg Trp Gln Gln Gly Asn Val Phe Ser Cys
    530                 535                 540

Ser Val Met His Glu Ala Leu His Asn His Tyr Thr Gln Lys Ser Leu
545                 550                 555                 560

Ser Leu Ser Pro Gly Lys
                565

<210> SEQ ID NO 22
<211> LENGTH: 343
<212> TYPE: PRT
<213> ORGANISM: Homo sapiens

<400> SEQUENCE: 22

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
```

```
                50              55              60
Gln Ser Leu Lys Ser Arg Ile Thr Ile Asn Pro Asp Thr Pro Lys Asn
 65              70              75              80

Gln Phe Ser Leu Gln Leu Asn Ser Val Thr Pro Glu Asp Thr Ala Val
                85              90              95

Tyr Tyr Cys Ala Arg Asp Gly Gln Leu Gly Leu Asp Ala Leu Asp Ile
               100             105             110

Trp Gly Gln Gly Thr Met Val Thr Val Ser Ser Gly Gly Gly Gly Ser
               115             120             125

Asp Ile Gln Leu Thr Gln Ser Pro Ser Phe Leu Ser Ala Ser Val Gly
               130             135             140

Asp Arg Val Thr Ile Thr Cys Arg Ala Ser Gln Ser Ile Gly Thr Asn
145             150             155             160

Ile His Trp Tyr Gln Gln Lys Pro Gly Lys Ala Pro Lys Leu Leu Ile
               165             170             175

Lys Tyr Ala Ser Glu Ser Ile Ser Gly Val Pro Ser Arg Phe Ser Gly
               180             185             190

Ser Gly Ser Gly Thr Glu Phe Thr Leu Thr Ile Ser Ser Leu Gln Pro
               195             200             205

Glu Asp Phe Ala Thr Tyr Tyr Cys Gln Gln Asn Asn Asn Trp Pro Thr
               210             215             220

Thr Phe Gly Ala Gly Thr Lys Leu Glu Ile Lys Arg Thr Asp Phe Thr
225             230             235             240

Pro Pro Thr Val Lys Ile Leu Gln Ser Ser Cys Asp Gly Gly Gly His
               245             250             255

Phe Pro Pro Thr Ile Gln Leu Leu Cys Leu Val Ser Gly Tyr Thr Pro
               260             265             270

Gly Thr Ile Asn Ile Thr Trp Leu Glu Asp Gly Gln Val Met Asp Val
               275             280             285

Asp Leu Ser Thr Ala Ser Thr Thr Gln Glu Gly Glu Leu Ala Ser Thr
               290             295             300

Gln Ser Glu Leu Thr Leu Ser Gln Lys His Trp Leu Ser Asp Arg Thr
305             310             315             320

Tyr Thr Cys Gln Val Thr Tyr Gln Gly His Thr Phe Glu Asp Ser Thr
               325             330             335

Lys Lys Cys Ala Asp Ser Asn
               340

<210> SEQ ID NO 23
<211> LENGTH: 566
<212> TYPE: PRT
<213> ORGANISM: Homo sapiens

<400> SEQUENCE: 23

Glu Val Gln Leu Val Glu Ser Gly Gly Gly Leu Val Gln Pro Gly Gly
 1               5              10              15

Ser Leu Arg Leu Ser Cys Ala Ala Ser Gly Phe Ser Leu Thr Asn Tyr
                20              25              30

Gly Val His Trp Val Arg Gln Ala Pro Gly Lys Gly Leu Glu Trp Leu
                35              40              45

Gly Val Ile Trp Ser Gly Gly Asn Thr Asp Tyr Asn Thr Pro Phe Thr
                50              55              60

Ser Arg Phe Thr Ile Ser Arg Asp Asn Ser Lys Asn Thr Leu Tyr Leu
 65              70              75              80
```

```
Gln Met Asn Ser Leu Arg Ala Glu Asp Thr Ala Val Tyr Tyr Cys Ala
                85                  90                  95
Arg Ala Leu Thr Tyr Tyr Asp Tyr Glu Phe Ala Tyr Trp Gly Gln Gly
            100                 105                 110
Thr Thr Val Thr Val Ser Ser Gly Gly Gly Gly Ser Gln Ala Gly Leu
        115                 120                 125
Thr Gln Pro Pro Ala Val Ser Val Ala Pro Gly Gln Thr Ala Ser Ile
    130                 135                 140
Thr Cys Gly Arg Asp Asn Ile Gly Ser Arg Ser Val His Trp Tyr Gln
145                 150                 155                 160
Gln Lys Pro Gly Gln Ala Pro Val Leu Val Val Tyr Asp Asp Ser Asp
                165                 170                 175
Arg Pro Ala Gly Ile Pro Glu Arg Phe Ser Gly Ser Asn Tyr Glu Asn
            180                 185                 190
Thr Ala Thr Leu Thr Ile Ser Arg Val Glu Ala Gly Asp Glu Ala Asp
        195                 200                 205
Tyr Tyr Cys Gln Val Trp Gly Ile Thr Ser Asp His Val Val Phe Gly
    210                 215                 220
Gly Gly Thr Lys Leu Thr Val Leu Ala Ser Asp Phe Thr Pro Pro Thr
225                 230                 235                 240
Val Lys Ile Leu Gln Ser Ser Cys Asp Gly Gly Gly His Phe Pro Pro
                245                 250                 255
Thr Ile Gln Leu Leu Cys Leu Val Ser Gly Tyr Thr Pro Gly Thr Ile
            260                 265                 270
Asn Ile Thr Trp Leu Glu Asp Gly Gln Val Met Asp Val Asp Leu Ser
        275                 280                 285
Thr Ala Ser Thr Thr Gln Glu Gly Glu Leu Ala Ser Thr Gln Ser Glu
    290                 295                 300
Leu Thr Leu Ser Gln Lys His Trp Leu Ser Asp Arg Thr Tyr Thr Cys
305                 310                 315                 320
Gln Val Thr Tyr Gln Gly His Thr Phe Glu Asp Ser Thr Lys Lys Ser
                325                 330                 335
Ala Asp Ser Asn Asp Lys Thr His Thr Cys Pro Pro Cys Pro Ala Pro
            340                 345                 350
Pro Val Ala Gly Pro Ser Val Phe Leu Phe Pro Pro Lys Pro Lys Asp
        355                 360                 365
Thr Leu Met Ile Ser Arg Thr Pro Glu Val Thr Cys Val Val Val Asp
    370                 375                 380
Val Ser His Glu Asp Pro Glu Val Lys Phe Asn Trp Tyr Val Asp Gly
385                 390                 395                 400
Val Glu Val His Asn Ala Lys Thr Lys Pro Arg Glu Glu Gln Tyr Asn
                405                 410                 415
Ser Thr Tyr Arg Val Val Ser Val Leu Thr Val Leu His Gln Asp Trp
            420                 425                 430
Leu Asn Gly Lys Glu Tyr Lys Cys Lys Val Ser Asn Lys Gly Leu Pro
        435                 440                 445
Ser Ser Ile Glu Lys Thr Ile Ser Lys Ala Lys Gly Gln Pro Arg Glu
    450                 455                 460
Pro Gln Val Tyr Thr Leu Pro Pro Ser Arg Asp Glu Leu Thr Lys Asn
465                 470                 475                 480
Gln Val Ser Leu Thr Cys Leu Val Lys Gly Phe Tyr Pro Ser Asp Ile
                485                 490                 495
Ala Val Glu Trp Glu Ser Asn Gly Gln Pro Glu Asn Asn Tyr Lys Thr
```

```
                500                 505                 510
Thr Pro Pro Val Leu Asp Ser Asp Gly Ser Phe Phe Leu Tyr Ser Lys
            515                 520                 525

Leu Thr Val Asp Lys Ser Arg Trp Gln Gln Gly Asn Val Phe Ser Cys
        530                 535                 540

Ser Val Met His Glu Ala Leu His Asn His Tyr Thr Gln Lys Ser Leu
545                 550                 555                 560

Ser Leu Ser Pro Gly Lys
                565

<210> SEQ ID NO 24
<211> LENGTH: 343
<212> TYPE: PRT
<213> ORGANISM: Homo sapiens

<400> SEQUENCE: 24

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Gln Ser Leu Lys Ser Arg Ile Thr Ile Asn Pro Asp Thr Pro Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gly Gln Leu Gly Leu Asp Ala Leu Asp Ile
            100                 105                 110

Trp Gly Gln Gly Thr Met Val Thr Val Ser Ser Gly Gly Gly Gly Ser
        115                 120                 125

Asp Ile Gln Leu Thr Gln Ser Pro Ser Phe Leu Ser Ala Ser Val Gly
    130                 135                 140

Asp Arg Val Thr Ile Thr Cys Arg Ala Ser Gln Ser Ile Gly Thr Asn
145                 150                 155                 160

Ile His Trp Tyr Gln Gln Lys Pro Gly Lys Ala Pro Lys Leu Leu Ile
                165                 170                 175

Lys Tyr Ala Ser Glu Ser Ile Ser Gly Val Pro Ser Arg Phe Ser Gly
            180                 185                 190

Ser Gly Ser Gly Thr Glu Phe Thr Leu Thr Ile Ser Ser Leu Gln Pro
        195                 200                 205

Glu Asp Phe Ala Thr Tyr Tyr Cys Gln Gln Asn Asn Asn Trp Pro Thr
    210                 215                 220

Thr Phe Gly Ala Gly Thr Lys Leu Glu Ile Lys Arg Thr Asp Phe Thr
225                 230                 235                 240

Pro Pro Thr Val Lys Ile Leu Gln Ser Ser Ser Asp Gly Gly Gly His
                245                 250                 255

Phe Pro Pro Thr Ile Gln Leu Leu Cys Leu Val Ser Gly Tyr Thr Pro
            260                 265                 270

Gly Thr Ile Gln Ile Thr Trp Leu Glu Asp Gly Gln Val Met Asp Val
        275                 280                 285

Asp Leu Ser Thr Ala Ser Thr Thr Gln Glu Gly Glu Leu Ala Ser Thr
    290                 295                 300
```

```
Gln Ser Glu Leu Thr Leu Ser Gln Lys His Trp Leu Ser Asp Arg Thr
305                 310                 315                 320

Tyr Thr Cys Gln Val Thr Tyr Gln Gly His Thr Phe Glu Asp Ser Thr
                325                 330                 335

Lys Lys Cys Ala Asp Ser Asn
            340

<210> SEQ ID NO 25
<211> LENGTH: 571
<212> TYPE: PRT
<213> ORGANISM: Homo sapiens

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Ala Leu Thr Tyr Tyr Asp Tyr Glu Phe Ala Tyr Trp Gly Gln Gly
            100                 105                 110

Thr Thr Val Thr Val Ser Ser Gly Gly Gly Ser Gln Ala Gly Leu
        115                 120                 125

Thr Gln Pro Pro Ala Val Ser Val Ala Pro Gly Gln Thr Ala Ser Ile
    130                 135                 140

Thr Cys Gly Arg Asp Asn Ile Gly Ser Arg Ser Val His Trp Tyr Gln
145                 150                 155                 160

Gln Lys Pro Gly Gln Ala Pro Val Leu Val Val Tyr Asp Asp Ser Asp
            165                 170                 175

Arg Pro Ala Gly Ile Pro Glu Arg Phe Ser Gly Ser Asn Tyr Glu Asn
            180                 185                 190

Thr Ala Thr Leu Thr Ile Ser Arg Val Glu Ala Gly Asp Glu Ala Asp
        195                 200                 205

Tyr Tyr Cys Gln Val Trp Gly Ile Thr Ser Asp His Val Val Phe Gly
    210                 215                 220

Gly Gly Thr Lys Leu Thr Val Leu Ala Ser Ala Glu Leu Pro Pro Lys
225                 230                 235                 240

Val Ser Val Phe Val Pro Pro Arg Asp Gly Phe Phe Gly Asn Pro Arg
            245                 250                 255

Lys Ser Lys Leu Ile Cys Gln Ala Thr Gly Phe Ser Pro Arg Gln Ile
            260                 265                 270

Gln Val Ser Trp Leu Arg Glu Gly Lys Gln Val Gly Ser Gly Val Thr
        275                 280                 285

Thr Asp Gln Val Gln Ala Glu Ala Lys Glu Ser Gly Pro Thr Thr Tyr
    290                 295                 300

Lys Val Thr Ser Thr Leu Thr Ile Lys Glu Ser Asp Trp Leu Gly Gln
305                 310                 315                 320

Ser Met Phe Thr Cys Arg Val Asp His Arg Gly Leu Thr Phe Gln Gln
            325                 330                 335
```

```
Asn Ala Ser Ser Met Cys Val Pro Asp Asp Lys Thr His Thr Cys Pro
                340                 345                 350

Pro Cys Pro Ala Pro Val Ala Gly Pro Ser Val Phe Leu Phe Pro
            355                 360                 365

Pro Lys Pro Lys Asp Thr Leu Met Ile Ser Arg Thr Pro Glu Val Thr
370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
                420                 425                 430

Leu His Gln Asp Trp Leu Asn Gly Lys Glu Tyr Lys Cys Lys Val Ser
                435                 440                 445

Asn Lys Gly Leu Pro Ser Ser Ile Glu Lys Thr Ile Ser Lys Ala Lys
            450                 455                 460

Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
            515                 520                 525

Phe Leu Tyr Ser Lys Leu Thr Val Asp Lys Ser Arg Trp Gln Gln Gly
530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 26
<211> LENGTH: 348
<212> TYPE: PRT
<213> ORGANISM: Homo sapiens

<400> SEQUENCE: 26

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Gln Ser Leu Lys Ser Arg Ile Thr Ile Asn Pro Asp Thr Pro Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gly Gln Leu Gly Leu Asp Ala Leu Asp Ile
            100                 105                 110

Trp Gly Gln Gly Thr Met Val Thr Val Ser Ser Gly Gly Gly Gly Ser
        115                 120                 125

Asp Ile Gln Leu Thr Gln Ser Pro Ser Phe Leu Ser Ala Ser Val Gly
```

```
          130                 135                 140
Asp Arg Val Thr Ile Thr Cys Arg Ala Ser Gln Ser Ile Gly Thr Asn
145                 150                 155                 160

Ile His Trp Tyr Gln Gln Lys Pro Gly Lys Ala Pro Lys Leu Leu Ile
                165                 170                 175

Lys Tyr Ala Ser Glu Ser Ile Ser Gly Val Pro Ser Arg Phe Ser Gly
                180                 185                 190

Ser Gly Ser Gly Thr Glu Phe Thr Leu Thr Ile Ser Ser Leu Gln Pro
                195                 200                 205

Glu Asp Phe Ala Thr Tyr Tyr Cys Gln Gln Asn Asn Asn Trp Pro Thr
210                 215                 220

Thr Phe Gly Ala Gly Thr Lys Leu Glu Ile Lys Arg Thr Ala Glu Leu
225                 230                 235                 240

Pro Pro Lys Val Ser Val Phe Val Pro Pro Arg Asp Gly Phe Phe Gly
                245                 250                 255

Asn Pro Arg Lys Ser Lys Leu Ile Cys Gln Ala Thr Gly Phe Ser Pro
                260                 265                 270

Arg Gln Ile Gln Val Ser Trp Leu Arg Glu Gly Lys Gln Val Gly Ser
                275                 280                 285

Gly Val Thr Thr Asp Gln Val Gln Ala Glu Ala Lys Glu Ser Gly Pro
                290                 295                 300

Thr Thr Tyr Lys Val Thr Ser Thr Leu Thr Ile Lys Glu Ser Asp Trp
305                 310                 315                 320

Leu Gly Gln Ser Met Phe Thr Cys Arg Val Asp His Arg Gly Leu Thr
                325                 330                 335

Phe Gln Gln Asn Ala Ser Ser Met Cys Val Pro Asp
                340                 345

<210> SEQ ID NO 27
<211> LENGTH: 569
<212> TYPE: PRT
<213> ORGANISM: Homo sapiens

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Gly Tyr
                20                  25                  30

Thr Met Asn Trp Val Arg Gln Ala Pro Gly Gln Gly Leu Glu Trp Met
                35                  40                  45

Gly Leu Ile Asn Pro Tyr Lys Gly Val Ser Thr Tyr Asn Gly Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Tyr Gly Asp Ser Asp Trp Tyr Phe Asp Val Trp
                100                 105                 110

Gly Gln Gly Thr Leu Val Thr Val Ser Ser Gly Gly Gly Gly Ser Gln
                115                 120                 125

Ala Gly Leu Thr Gln Pro Pro Ala Val Ser Val Ala Pro Gly Gln Thr
                130                 135                 140

Ala Ser Ile Thr Cys Gly Arg Asp Asn Ile Gly Ser Arg Ser Val His
145                 150                 155                 160
```

-continued

```
Trp Tyr Gln Gln Lys Pro Gly Gln Ala Pro Val Leu Val Val Tyr Asp
                165                 170                 175
Asp Ser Asp Arg Pro Ala Gly Ile Pro Glu Arg Phe Ser Gly Ser Asn
            180                 185                 190
Tyr Glu Asn Thr Ala Thr Leu Thr Ile Ser Arg Val Glu Ala Gly Asp
        195                 200                 205
Glu Ala Asp Tyr Tyr Cys Gln Val Trp Gly Ile Thr Ser Asp His Val
    210                 215                 220
Val Phe Gly Gly Gly Thr Lys Leu Thr Val Leu Ala Ser Asp Phe Thr
225                 230                 235                 240
Pro Pro Thr Val Lys Ile Leu Gln Ser Ser Cys Asp Gly Gly His
                245                 250                 255
Phe Pro Pro Thr Ile Gln Leu Leu Cys Leu Val Ser Gly Tyr Thr Pro
            260                 265                 270
Gly Thr Ile Asn Ile Thr Trp Leu Glu Asp Gly Gln Val Met Asp Val
        275                 280                 285
Asp Leu Ser Thr Ala Ser Thr Thr Gln Glu Gly Glu Leu Ala Ser Thr
    290                 295                 300
Gln Ser Glu Leu Thr Leu Ser Gln Lys His Trp Leu Ser Asp Arg Thr
305                 310                 315                 320
Tyr Thr Cys Gln Val Thr Tyr Gln Gly His Thr Phe Glu Asp Ser Thr
                325                 330                 335
Lys Lys Cys Ala Asp Ser Asn Asp Lys Thr His Thr Cys Pro Pro Cys
            340                 345                 350
Pro Ala Pro Pro Val Ala Gly Pro Ser Val Phe Leu Phe Pro Pro Lys
        355                 360                 365
Pro Lys Asp Thr Leu Met Ile Ser Arg Thr Pro Glu Val Thr Cys Val
    370                 375                 380
Val Val Asp Val Ser His Glu Asp Pro Glu Val Lys Phe Asn Trp Tyr
385                 390                 395                 400
Val Asp Gly Val Glu Val His Asn Ala Lys Thr Lys Pro Arg Glu Glu
                405                 410                 415
Gln Tyr Asn Ser Thr Tyr Arg Val Val Ser Val Leu Thr Val Leu His
            420                 425                 430
Gln Asp Trp Leu Asn Gly Lys Glu Tyr Lys Cys Lys Val Ser Asn Lys
        435                 440                 445
Gly Leu Pro Ser Ser Ile Glu Lys Thr Ile Ser Lys Ala Lys Gly Gln
    450                 455                 460
Pro Arg Glu Pro Gln Val Cys Thr Leu Pro Pro Ser Arg Asp Glu Leu
465                 470                 475                 480
Thr Lys Asn Gln Val Ser Leu Ser Cys Ala Val Lys Gly Phe Tyr Pro
                485                 490                 495
Ser Asp Ile Ala Val Glu Trp Glu Ser Asn Gly Gln Pro Glu Asn Asn
            500                 505                 510
Tyr Lys Thr Thr Pro Pro Val Leu Asp Ser Asp Gly Ser Phe Phe Leu
        515                 520                 525
Val Ser Lys Leu Thr Val Asp Lys Ser Arg Trp Gln Gln Gly Asn Val
    530                 535                 540
Phe Ser Cys Ser Val Met His Glu Ala Leu His Asn His Tyr Thr Gln
545                 550                 555                 560
Lys Ser Leu Ser Leu Ser Pro Gly Lys
                565
```

<210> SEQ ID NO 28
<211> LENGTH: 343
<212> TYPE: PRT
<213> ORGANISM: Homo sapiens

<400> SEQUENCE: 28

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Gln Ser Leu Lys Ser Arg Ile Thr Ile Asn Pro Asp Thr Pro Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gly Gln Leu Gly Leu Asp Ala Leu Asp Ile
            100                 105                 110

Trp Gly Gln Gly Thr Met Val Thr Val Ser Ser Gly Gly Gly Gly Ser
        115                 120                 125

Asp Ile Gln Met Thr Gln Ser Pro Ser Ser Leu Ser Ala Ser Val Gly
    130                 135                 140

Asp Arg Val Thr Ile Thr Cys Arg Ala Ser Gln Asp Ile Arg Asn Tyr
145                 150                 155                 160

Leu Asn Trp Tyr Gln Gln Lys Pro Gly Lys Ala Pro Lys Leu Leu Ile
                165                 170                 175

Tyr Tyr Thr Ser Arg Leu His Ser Gly Val Pro Ser Arg Phe Ser Gly
            180                 185                 190

Ser Gly Ser Gly Thr Asp Phe Thr Phe Thr Ile Ser Ser Leu Gln Pro
        195                 200                 205

Glu Asp Ile Ala Thr Tyr Tyr Cys Gln Gln Gly Asn Thr Leu Pro Trp
    210                 215                 220

Thr Phe Gly Gln Gly Thr Lys Leu Glu Ile Lys Arg Thr Asp Phe Thr
225                 230                 235                 240

Pro Pro Thr Val Lys Ile Leu Gln Ser Ser Cys Asp Gly Gly Gly His
                245                 250                 255

Phe Pro Pro Thr Ile Gln Leu Leu Cys Leu Val Ser Gly Tyr Thr Pro
            260                 265                 270

Gly Thr Ile Asn Ile Thr Trp Leu Glu Asp Gly Gln Val Met Asp Val
        275                 280                 285

Asp Leu Ser Thr Ala Ser Thr Thr Gln Glu Gly Glu Leu Ala Ser Thr
    290                 295                 300

Gln Ser Glu Leu Thr Leu Ser Gln Lys His Trp Leu Ser Asp Arg Thr
305                 310                 315                 320

Tyr Thr Cys Gln Val Thr Tyr Gln Gly His Thr Phe Glu Asp Ser Thr
                325                 330                 335

Lys Lys Cys Ala Asp Ser Asn
            340
```

<210> SEQ ID NO 29
<211> LENGTH: 454
<212> TYPE: PRT
<213> ORGANISM: Homo sapiens

<400> SEQUENCE: 29

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
50                  55                  60

Gln Ser Leu Lys Ser Arg Ile Thr Ile Asn Pro Asp Thr Pro Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gly Gln Leu Gly Leu Asp Ala Leu Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Gly Thr Asp Lys Thr His Thr Cys Pro Pro Cys Pro Ala Pro
225                 230                 235                 240

Pro Val Ala Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Cys Arg Asp Glu Leu Thr Lys Asn
        355                 360                 365

Gln Val Ser Leu Trp Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415
```

```
Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 30
<211> LENGTH: 214
<212> TYPE: PRT
<213> ORGANISM: Homo sapiens

<400> SEQUENCE: 30

Gln Ala Gly Leu Thr Gln Pro Pro Ala Val Ser Val Ala Pro Gly Gln
1               5                   10                  15

Thr Ala Ser Ile Thr Cys Gly Arg Asp Asn Ile Gly Ser Arg Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ala Gly Ile Pro Glu Arg Phe Ser Gly Ser
50                  55                  60

Asn Tyr Glu Asn Thr Ala Thr Leu Thr Ile Ser Arg Val Glu Ala Gly
65                  70                  75                  80

Asp Glu Ala Asp Tyr Tyr Cys Gln Val Trp Gly Ile Thr Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 31
<211> LENGTH: 475
<212> TYPE: PRT
<213> ORGANISM: Homo sapiens

<400> SEQUENCE: 31

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60
```

```
Gln Ser Leu Lys Ser Arg Ile Thr Ile Asn Pro Asp Thr Pro Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gly Gln Leu Gly Leu Asp Ala Leu Asp Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Ser Gln Ala Gly Leu Thr Gln
130                 135                 140

Pro Pro Ala Val Ser Val Ala Pro Gly Gln Thr Ala Ser Ile Thr Cys
145                 150                 155                 160

Gly Arg Asp Asn Ile Gly Ser Arg Ser Val His Trp Tyr Gln Gln Lys
                165                 170                 175

Pro Gly Gln Ala Pro Val Leu Val Val Tyr Asp Asp Ser Asp Arg Pro
            180                 185                 190

Ala Gly Ile Pro Glu Arg Phe Ser Gly Ser Asn Tyr Glu Asn Thr Ala
        195                 200                 205

Thr Leu Thr Ile Ser Arg Val Glu Ala Gly Asp Glu Ala Asp Tyr Tyr
    210                 215                 220

Cys Gln Val Trp Gly Ile Thr Ser Asp His Val Val Phe Gly Gly Gly
225                 230                 235                 240

Thr Lys Leu Thr Val Leu Ala Ala Ala Asp Lys Thr His Thr Cys Pro
                245                 250                 255

Pro Cys Pro Ala Pro Val Ala Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Gly Leu Pro Ser Ser Ile Glu Lys Thr Ile Ser Lys Ala Lys
        355                 360                 365

Gly Gln Pro Arg Glu Pro Gln Val Tyr Thr Leu Pro Pro Cys Arg Asp
    370                 375                 380

Glu Leu Thr Lys Asn Gln Val Ser Leu Trp Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475
```

```
<210> SEQ ID NO 32
<211> LENGTH: 564
<212> TYPE: PRT
<213> ORGANISM: Homo sapiens

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Ser Gln Ala Gly
        115                 120                 125

Leu Thr Gln Pro Pro Ala Val Ser Val Ala Pro Gly Gln Thr Ala Ser
    130                 135                 140

Ile Thr Cys Gly Arg Asp Asn Ile Gly Ser Arg Ser Val His Trp Tyr
145                 150                 155                 160

Gln Gln Lys Pro Gly Gln Ala Pro Val Leu Val Tyr Asp Asp Ser
                165                 170                 175

Asp Arg Pro Ala Gly Ile Pro Glu Arg Phe Ser Gly Ser Asn Tyr Glu
            180                 185                 190

Asn Thr Ala Thr Leu Thr Ile Ser Arg Val Glu Ala Gly Asp Glu Ala
        195                 200                 205

Asp Tyr Tyr Cys Gln Val Trp Gly Ile Thr Ser Asp His Val Val Phe
    210                 215                 220

Gly Gly Gly Thr Lys Leu Thr Val Leu Ala Ser Thr Lys Gly Pro Ser
225                 230                 235                 240

Val Phe Pro Leu Ala Pro Ser Ser Lys Ser Thr Ser Gly Gly Thr Ala
                245                 250                 255

Ala Leu Gly Cys Leu Val Lys Asp Tyr Phe Pro Glu Pro Val Thr Val
            260                 265                 270

Ser Trp Asn Ser Gly Ala Leu Thr Ser Gly Val His Thr Phe Pro Ala
        275                 280                 285

Val Leu Gln Ser Ser Gly Leu Tyr Ser Leu Ser Ser Val Val Thr Val
    290                 295                 300

Pro Ser Ser Ser Leu Gly Thr Gln Thr Tyr Ile Cys Asn Val Asn His
305                 310                 315                 320

Lys Pro Ser Asn Thr Lys Val Asp Lys Lys Val Glu Pro Lys Ser Cys
                325                 330                 335

Gly Thr Asp Lys Thr His Thr Cys Pro Pro Cys Pro Ala Pro Pro Val
            340                 345                 350

Ala Gly Pro Ser Val Phe Leu Phe Pro Pro Lys Pro Lys Asp Thr Leu
        355                 360                 365

Met Ile Ser Arg Thr Pro Glu Val Thr Cys Val Val Val Asp Val Ser
    370                 375                 380
```

```
His Glu Asp Pro Glu Val Lys Phe Asn Trp Tyr Val Asp Gly Val Glu
385                 390                 395                 400

Val His Asn Ala Lys Thr Lys Pro Arg Glu Glu Gln Tyr Asn Ser Thr
            405                 410                 415

Tyr Arg Val Val Ser Val Leu Thr Val Leu His Gln Asp Trp Leu Asn
        420                 425                 430

Gly Lys Glu Tyr Lys Cys Lys Val Ser Asn Lys Gly Leu Pro Ser Ser
    435                 440                 445

Ile Glu Lys Thr Ile Ser Lys Ala Lys Gly Gln Pro Arg Glu Pro Gln
450                 455                 460

Val Cys Thr Leu Pro Pro Ser Arg Asp Glu Leu Thr Lys Asn Gln Val
465                 470                 475                 480

Ser Leu Ser Cys Ala Val Lys Gly Phe Tyr Pro Ser Asp Ile Ala Val
            485                 490                 495

Glu Trp Glu Ser Asn Gly Gln Pro Glu Asn Asn Tyr Lys Thr Thr Pro
        500                 505                 510

Pro Val Leu Asp Ser Asp Gly Ser Phe Phe Leu Val Ser Lys Leu Thr
    515                 520                 525

Val Asp Lys Ser Arg Trp Gln Gln Gly Asn Val Phe Ser Cys Ser Val
530                 535                 540

Met His Glu Ala Leu His Asn His Tyr Thr Gln Lys Ser Leu Ser Leu
545                 550                 555                 560

Ser Pro Gly Lys

<210> SEQ ID NO 33
<211> LENGTH: 570
<212> TYPE: PRT
<213> ORGANISM: Homo sapiens

<400> SEQUENCE: 33

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Gln Ser Leu Lys Ser Arg Ile Thr Ile Asn Pro Asp Thr Pro Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gly Gln Leu Gly Leu Asp Ala Leu Asp Ile
            100                 105                 110

Trp Gly Gln Gly Thr Met Val Thr Val Ser Ser Gly Gly Gly Gly Ser
        115                 120                 125

Asp Ile Gln Met Thr Gln Ser Pro Ser Ser Leu Ser Ala Ser Val Gly
    130                 135                 140

Asp Arg Val Thr Ile Thr Cys Arg Ala Ser Gln Asp Val Asn Thr Ala
145                 150                 155                 160

Val Ala Trp Tyr Gln Gln Lys Pro Gly Lys Ala Pro Lys Leu Leu Ile
                165                 170                 175

Tyr Ser Ala Ser Phe Leu Tyr Ser Gly Val Pro Ser Arg Phe Ser Gly
            180                 185                 190
```

Ser Arg Ser Gly Thr Asp Phe Thr Leu Thr Ile Ser Ser Leu Gln Pro
            195                 200                 205

Glu Asp Phe Ala Thr Tyr Tyr Cys Gln Gln His Tyr Thr Thr Pro Pro
210                 215                 220

Thr Phe Gly Gln Gly Thr Lys Val Glu Ile Lys Arg Thr Val Ala Ala
225                 230                 235                 240

Pro Ser Val Phe Ile Phe Pro Pro Ser Asp Glu Gln Leu Lys Ser Gly
                245                 250                 255

Thr Ala Ser Val Val Cys Leu Leu Asn Asn Phe Tyr Pro Arg Glu Ala
            260                 265                 270

Lys Val Gln Trp Lys Val Asp Asn Ala Leu Gln Ser Gly Asn Ser Gln
            275                 280                 285

Glu Ser Val Thr Glu Gln Asp Ser Lys Asp Ser Thr Tyr Ser Leu Ser
290                 295                 300

Ser Thr Leu Thr Leu Ser Lys Ala Asp Tyr Glu Lys His Lys Val Tyr
305                 310                 315                 320

Ala Cys Glu Val Thr His Gln Gly Leu Ser Ser Pro Val Thr Lys Ser
                325                 330                 335

Phe Asn Arg Gly Glu Cys Gly Thr Asp Lys Thr His Thr Cys Pro Pro
            340                 345                 350

Cys Pro Ala Pro Pro Val Ala Gly Pro Ser Val Phe Leu Phe Pro Pro
            355                 360                 365

Lys Pro Lys Asp Thr Leu Met Ile Ser Arg Thr Pro Glu Val Thr Cys
370                 375                 380

Val Val Val Asp Val Ser His Glu Asp Pro Glu Val Lys Phe Asn Trp
385                 390                 395                 400

Tyr Val Asp Gly Val Glu Val His Asn Ala Lys Thr Lys Pro Arg Glu
                405                 410                 415

Glu Gln Tyr Asn Ser Thr Tyr Arg Val Val Ser Val Leu Thr Val Leu
            420                 425                 430

His Gln Asp Trp Leu Asn Gly Lys Glu Tyr Lys Cys Lys Val Ser Asn
            435                 440                 445

Lys Gly Leu Pro Ser Ser Ile Glu Lys Thr Ile Ser Lys Ala Lys Gly
            450                 455                 460

Gln Pro Arg Glu Pro Gln Val Tyr Thr Leu Pro Pro Cys Arg Asp Glu
465                 470                 475                 480

Leu Thr Lys Asn Gln Val Ser Leu Trp Cys Leu Val Lys Gly Phe Tyr
                485                 490                 495

Pro Ser Asp Ile Ala Val Glu Trp Glu Ser Asn Gly Gln Pro Glu Asn
                500                 505                 510

Asn Tyr Lys Thr Thr Pro Pro Val Leu Asp Ser Asp Gly Ser Phe Phe
            515                 520                 525

Leu Tyr Ser Lys Leu Thr Val Asp Lys Ser Arg Trp Gln Gln Gly Asn
530                 535                 540

Val Phe Ser Cys Ser Val Met His Glu Ala Leu His Asn His Tyr Thr
545                 550                 555                 560

Gln Lys Ser Leu Ser Leu Ser Pro Gly Lys
                565                 570

<210> SEQ ID NO 34
<211> LENGTH: 106
<212> TYPE: PRT
<213> ORGANISM: Homo sapiens

<400> SEQUENCE: 34

Asp Phe Thr Pro Pro Thr Val Lys Ile Leu Gln Ser Ser Cys Asp Gly
1               5                   10                  15

Gly Gly His Phe Pro Pro Thr Ile Gln Leu Leu Cys Leu Val Ser Gly
                20                  25                  30

Tyr Thr Pro Gly Thr Ile Asn Ile Thr Trp Leu Glu Asp Gly Gln Val
            35                  40                  45

Met Asp Val Asp Leu Ser Thr Ala Ser Thr Thr Gln Glu Gly Glu Leu
50                  55                  60

Ala Ser Thr Gln Ser Glu Leu Thr Leu Ser Gln Lys His Trp Leu Ser
65                  70                  75                  80

Asp Arg Thr Tyr Thr Cys Gln Val Thr Tyr Gln Gly His Thr Phe Glu
                85                  90                  95

Asp Ser Thr Lys Lys Cys Ala Asp Ser Asn
            100                 105

<210> SEQ ID NO 35
<211> LENGTH: 111
<212> TYPE: PRT
<213> ORGANISM: Homo sapiens

<400> SEQUENCE: 35

Ala Glu Leu Pro Pro Lys Val Ser Val Phe Val Pro Pro Arg Asp Gly
1               5                   10                  15

Phe Phe Gly Asn Pro Arg Lys Ser Lys Leu Ile Cys Gln Ala Thr Gly
                20                  25                  30

Phe Ser Pro Arg Gln Ile Gln Val Ser Trp Leu Arg Glu Gly Lys Gln
            35                  40                  45

Val Gly Ser Gly Val Thr Thr Asp Gln Val Gln Ala Glu Ala Lys Glu
50                  55                  60

Ser Gly Pro Thr Thr Tyr Lys Val Thr Ser Thr Leu Thr Ile Lys Glu
65                  70                  75                  80

Ser Asp Trp Leu Gly Gln Ser Met Phe Thr Cys Arg Val Asp His Arg
                85                  90                  95

Gly Leu Thr Phe Gln Gln Asn Ala Ser Ser Met Cys Val Pro Asp
            100                 105                 110

<210> SEQ ID NO 36
<211> LENGTH: 226
<212> TYPE: PRT
<213> ORGANISM: Homo sapiens

<400> SEQUENCE: 36

Asp Lys Thr His Thr Cys Pro Pro Cys Pro Ala Pro Val Ala Gly
1               5                   10                  15

Pro Ser Val Phe Leu Phe Pro Pro Lys Pro Lys Asp Thr Leu Met Ile
                20                  25                  30

Ser Arg Thr Pro Glu Val Thr Cys Val Val Val Asp Val Ser His Glu
            35                  40                  45

Asp Pro Glu Val Lys Phe Asn Trp Tyr Val Asp Gly Val Glu Val His
50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Gly Leu Pro Ser Ser Ile Glu

-continued

```
                100             105             110
Lys Thr Ile Ser Lys Ala Lys Gly Gln Pro Arg Glu Pro Gln Val Tyr
        115             120             125

Thr Leu Pro Pro Ser Arg Asp Glu Leu Thr Lys Asn Gln Val Ser Leu
    130             135             140

Thr Cys Leu Val Lys Gly Phe Tyr Pro Ser Asp Ile Ala Val Glu Trp
145             150             155             160

Glu Ser Asn Gly Gln Pro Glu Asn Asn Tyr Lys Thr Thr Pro Pro Val
            165             170             175

Leu Asp Ser Asp Gly Ser Phe Phe Leu Tyr Ser Lys Leu Thr Val Asp
        180             185             190

Lys Ser Arg Trp Gln Gln Gly Asn Val Phe Ser Cys Ser Val Met His
        195             200             205

Glu Ala Leu His Asn His Tyr Thr Gln Lys Ser Leu Ser Leu Ser Pro
    210             215             220

Gly Lys
225
```